US011821003B2

(12) United States Patent
Colas et al.

(10) Patent No.: US 11,821,003 B2
(45) Date of Patent: Nov. 21, 2023

(54) CARDIOGENIC MESODERM FORMATION REGULATORS

(71) Applicant: Sanford Burnham Prebys Medical Discovery Institute, La Jolla, CA (US)

(72) Inventors: Alexandre Romain Colas, La Jolla, CA (US); Mark Mercola, Los Altos, CA (US); Wesley Lawrence McKeithan, Palo Alto, CA (US); Michael Shenghan Yu, San Diego, CA (US)

(73) Assignee: Sanford Burnham Prebys Medical Discovery Institute, La Jolla, CA (US)

(*) Notice: Subject to any disclaimer, the term of this patent is extended or adjusted under 35 U.S.C. 154(b) by 588 days.

Patent file contains an affidavit/declaration under 37 CFR 1.130(b).

(21) Appl. No.: 16/638,918

(22) PCT Filed: Aug. 13, 2018

(86) PCT No.: PCT/US2018/046536
§ 371 (c)(1),
(2) Date: Feb. 13, 2020

(87) PCT Pub. No.: WO2019/036375
PCT Pub. Date: Feb. 21, 2019

(65) Prior Publication Data
US 2020/0332260 A1    Oct. 22, 2020

Related U.S. Application Data

(60) Provisional application No. 62/545,310, filed on Aug. 14, 2017.

(51) Int. Cl.
C12N 5/077 (2010.01)
A61P 9/00 (2006.01)
C07K 14/47 (2006.01)

(52) U.S. Cl.
CPC ............ *C12N 5/0657* (2013.01); *A61P 9/00* (2018.01); *C07K 14/4702* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| 4,522,811 | A  | 6/1985  | Eppstein et al. |
| 6,168,587 | B1 | 1/2001  | Bellhouse et al. |
| 6,194,389 | B1 | 2/2001  | Johnston et al. |
| 6,468,798 | B1 | 10/2002 | Debs et al. |
| 6,471,996 | B1 | 10/2002 | Sokoll et al. |
| 6,472,375 | B1 | 10/2002 | Hoon et al. |
| 6,849,272 | B1 | 2/2005  | Langer et al. |
| 8,058,065 | B2 | 11/2011 | Yamanaka et al. |
| 9,624,471 | B2 | 4/2017  | Ruohola-Baker et al. |
| 2007/0191294 | A1 | 8/2007  | Elmen et al. |
| 2008/0249039 | A1 | 10/2008 | Elmen et al. |
| 2009/0181914 | A1 | 7/2009  | Rosenbohm et al. |
| 2010/0234451 | A1 | 9/2010  | Work |
| 2010/0249052 | A1 | 9/2010  | Benson et al. |
| 2010/0317718 | A1 | 12/2010 | Marcusson et al. |
| 2010/0330044 | A1 | 12/2010 | Blanpain et al. |
| 2011/0318775 | A1 | 12/2011 | Mercola et al. |
| 2013/0130387 | A1 | 5/2013  | Itskovitz-Eldor et al. |
| 2014/0093486 | A1 | 4/2014  | Chiou et al. |
| 2015/0099690 | A1 | 4/2015  | Pellois |

FOREIGN PATENT DOCUMENTS

| WO | WO 2010/040112 | 4/2010 |
| WO | WO 2010/094757 | 8/2010 |
| WO | WO 2010/129746 | 11/2010 |
| WO | WO 2011/044253 | 4/2011 |

OTHER PUBLICATIONS

Cunningham (Genes Dev, 31(3): 1325-1338, 2017). (Year: 2017).*
Altschul et al., "Basic Local Alignment Search Tool," *J. Mol. Biol.*, 1990, 215(3): 403-410.
Benezra et al., "The protein Id: a negative regulator of helix-loop-helix DNA binding proteins," *Cell*, 1990, 61(1): 49-59.
Beppu et al., "BMP type II receptor is required for gastrulation and early development of mouse embryos," *Developmental Biology*, 2000, 221(1):249-258.
Birket et al., "Expansion and patterning of cardiovascular progenitors derived from human pluripotent stem cells," *Nature Biotechnology*, 2015, 33(9):970-979.
Blin et al., "A Purified Population of Multipotent Cardiovascular Progenitors Derived From Primate Pluripotent Stem Cells Engrafts in Postmyocardial Infarcted Nonhuman Primates," *J Clin Invest*, 2010, 120(4):1125-1139.
Bondue et al., "Mesp1 acts as a master regulator of multipotent cardiovascular progenitor specification," *Cell Stem Cell*, 2008, 3(1):69-84.
Bruneau, "Signaling and transcriptional networks m heart development and regeneration," *Cold Spring Harb Perspect Biol*, 2013, 5(3):a008292.
Buckingham et al., "Building the mammalian heart from hvo sources of myocardial cells," *Nature Reviews Genetics*, 2005, 6(11):826-835.
Burridge et al., "Chemically defined generation of human cardiomyocytes," *Nature Methods*, 2014, 11(8):855-860.
Cai et al., "ISL1 identifies a cardiac progenitor population that proliferates prior to differentiation and contributes a majority of cells to the heart," *Developmental Cell*, 2003, 5(6):877-889.
Chan et al., "Mesp1 patterns mesoderm into cardiac, hematopoietic, or skeletal myogenic progenitors in a context-dependent manner," *Cell Stem Cell*, 2012, 12:587-601.

(Continued)

*Primary Examiner* — Emily A Cordas
(74) *Attorney, Agent, or Firm* — Fish & Richardson P.C.

(57) ABSTRACT

This disclosure relates to cardiogenic mesoderm formation regulators and methods of use thereof, e.g., generating a multipotent cardiovascular progenitor cell by overexpressing Id1, Id2, Id3, Id4, Evx1, and/or Grrp1 in a stem cell.

7 Claims, 39 Drawing Sheets

Specification includes a Sequence Listing.

(56) References Cited

OTHER PUBLICATIONS

Chiapparo et al., "Mesp1 controls the speed, polarity, and directionality of cardiovascular progenitor migration," *J Cell Biol*, 2016, 213(4):463-477.

Christoforou et al., "Implantation of Mouse Embryonic Stem Cell-Derived Cardiac Progenitor Cells Preserves Function of Infarcted Murine Hearts," *PLoS One*, 2010, 5(7):e11536, 14 pages.

Colas et al., "Mix. 1/2-dependent control of FGF availability during gastrulation is essential for pronephros development in Xenopus," *Developmental Biology*, 2008, 320(2):351-365.

Colas et al., "Whole-genome microRNA screening identifies let-7 and mir-18 as regulators of germ layer formation during early embryogenesis," *Genes & Development*, 2012, 26(23):2567-2579.

Collop et al., "Retinoic acid signaling is essential for formation of the heart tube in Xenopus," *Developmental Biology*, 2006, 291(1):96-109.

Costello et al., "The T-box transcription factor Eomesodermin acts upstream of Mesp1 to specify cardiac mesoderm during mouse gastrulation," *Nature Cell Biology*, 2011, 13(9):1084-1091.

Czarnik, "Encoding Methods for Combinatorial Chemistry," Curr. Opin. Chem Biol, 1997, 1(1):60-6.

David et al., "MesP1 drives vertebrate cardiovascular differentiation through Dkk-1-mediated blockade of Wnt-signalling," *Nature Cell Biology*, 2008, 10:338-345.

Devine et al., "Early patterning and specification of cardiac progenitors in gastrulating mesoderm," *Elife*, 2014, 3:e03848, 23 pages.

Djiane et al., "Role of frizzled 7 in the regulation of convergent extension movements during gastrulation in Xenopus laevis," *Development*, 2000, 127(14):3091-3100.

Ekins et al., "Microarrays: Their Origins and Applications," *Trends in Biotechnology*, 1999, 17(6):217-218.

Ema et al., "Deletion of the selection cassette, but not cis-acting elements, in targeted Flk1-lacZ allele reveals Flk1 expression in multipotent mesodermal progenitors," *Blood*, 2006, 107(1):111-117.

Foley et al., "Multiple functions of Cerberus cooperate to induce heart downstream of Nodal," *Developmental Biology*, 2007, 303(1):57-65.

Fraidenraich et al., "Rescue of cardiac defects in id knockout embryos by injection of embryonic stem cells," *Science*, 2004, 306(5694):247-252.

Gadue et al., "Wnt and TGF-beta signaling are required for the induction of an in vitro model of primitive streak formation using embryonic stem cells," *Proc Natl Acad Sci USA*, 2006, 103(45):16806-16811.

Galvin et al., "Nodal signaling regulates the bone morphogenic protein pluripotency pathway in mouse embryonic stem cells," *The Journal of Biological Chemistry*, 2010, 285(26):19747-19756.

Hamajima et al., "Intranasal Administration of HIV-DNA Vaccine Formulated With a Polymer, Carboxymethylcellulose, Augments Mucosal Antibody Production and Cell-Mediated Immune Response," *Clin. Immunol. Immunopathol.*, 1998, 88(2):205-10.

Hollnagel et al., "Id genes are direct targets of bone morphogenetic protein induction in embryonic stem cells," *The Journal of Biological Chemistry*, 1999, 274(28):19838-19845.

Huang et al., "Induction of functional hepatocyte-like cells from mouse fibroblasts by defined factors," *Nature*, 2011, 475(7356):386-389.

Katagiri et al., "Identification of a BMP-responsive element in Id1, the gene for inhibition of myogenesis," *Gene Cells*, 2002, 7(9):949-960.

Kattman et al., "Multipotent flk-1 + cardiovascular progenitor cells give rise to the cardiomyocyte, endothelial, and vascular smooth muscle lineages," *Developmental Cell*, 2006, 11(5):723-732.

Kee et al., "E and ID proteins branch out," Nature Reviews Immunology, 2009, 9(3):175-184.

Kee et al., "To proliferate or to die: role of Id3 in cell cycle progression and survival of neural crest progenitors," *Genes & Development*, 2005, 19(6):744-755.

Kelly et al, "Heart fields and cardiac morphogenesis," *Cold Spring Harb Perspect Med*, 2014, 4(10):a015750, 10 pages.

Kelly et al., "The arterial pole of the mouse heart forms from Fgf10-expressing cells in pharyngeal mesoderm," Developmental Cell, 2001, 1(3):435-440.

Korchynskyi et al., "Identification and functional characterization of distinct critically important bone morphogenetic protein-specific response elements in the Id1 promoter," *The Journal of Biological Chemistry*, 2002, 277(7):4883-4891.

Laflamme et al., "Cardiomyocytes derived from human embryonic stem cells in pro-survival factors enhance function of infarcted rat hearts," *Nature Biotechnology*, 2007, 25(9):1015-1024.

Lescroart et al., "Early lineage restriction in temporally distinct populations of Mesp 1 progenitors during mammalian heart development," Nature Cell Biology, 2014, 16:829-840.

Lian et al., "Directed cardiomyocyte differentiation from human pluripotent stem cells by modulating Wnt/beta-catenin signaling under fully defined conditions," *Nature Protocols*, 2013, 8(1):162-175.

Liang et al., "Drug screening using a library of human induced pluripotent stem cell-derived cardiomyocytes reveals disease specific patterns of cardiotoxicity," *Circulation*, 2013, 127:1677-91.

Lopez-Rovira et al., "Direct binding of Smad1 and Smad4 to two distinct motifs mediates bone morphogenetic protein-specific transcriptional activation of Id1 gene," *The Journal of Biological Chemistry*, 2002, 277(5):3176-3185.

Lyden et al., "Id1 and Id3 are required for neurogenesis, angiogenesis and vascularization of tumour xenografts," *Nature*, 1999, 401(6754):670-677.

MacBeath et al., "Printing Proteins as Microarrays for High-Throughput Function Determination," *Science*, 2000, 289(5485):1760-1763.

Marvin et al., "Inhibition of Wnt activity induces heart formation from posterior mesoderm," *Genes & Development*, 2001, 15(3):316-327.

McKeithan et al., "An Automated Platform for Assessment of Congenital and Drug-Induced Arrhythmia with hiPSC-Derived Cardiomyocytes," *Frontiers in Physiology*, 2017, 8:766, 12 pages.

McKeithan et al., "Serum-free generation of multipotent mesoderm (Kdr+) progenitor cells in mouse embryonic stem cells for functional genomics screening," Current Protocols in Stem Cell Biology, 2012, Chapter 1, Unit 1F 13, 17 pages.

Meilhac et al., "Cardiac cell lineages that form the heart," *Cold Spring Harb Perspect Med*, 2015, 5(2):a026344, 14 pages.

Meilhac et al., "The clonal origin of myocardial cells in different regions of the embryonic mouse heart," *Developmental Cell*, 2004, 6(5):685-698.

Menard et al., "Transplantation of Cardiac-Committed Mouse Embryonic Stem Cells to Infarcted Sheep Myocardium: A Preclinical Study," Lancet, 2005, 366(9490):1005-1012.

Menasche et al., "Towards a clinical use of human embryonic stem cell-derived cardiac progenitors: a translational experience," *Eur Heart J*, 2015, 36(12):743-750.

Mercola et al., "Induced pluripotent stem cells in cardiovascular drug discovery," *Circulation Research*, 2013, 112(3):534-548.

Miller et al., "Optically monitoring voltage in neurons by photo-induced electron transfer through molecular wires," *Proceedings of the National Academy of Sciences of the United States of America*, 2012, 109(6):2114-2119.

Moretti et al., "Pluripotent stem cell models of human heart disease," *Cold Spring Harb Perspect Med*, 2013, 3(11):a014027, 20 pages.

Nieuwkoop et al., "The "organization centre". 3. Segregation and pattern formation in morphogenetic fields," *Acta Biotheor*, 1967, 17(4):178-194.

Niola et al., "Id proteins synchronize stemness and anchorage to the niche of neural stem cells," *Nature Cell Biology*, 2012, 14(5):477-487.

Niola et al., "Mesenchymal high-grade glioma is maintained by the ID-RAP1 axis," The Journal of Clinical Investigation, 2013, 123(1):405-417.

Olson, "Gene regulatory networks in the evolution and development of the heart," *Science*, 2006, 313(5795):1922-1927.

(56) References Cited

OTHER PUBLICATIONS

Paige et al., "A temporal 5 chromatin signature in human embryonic stem cells identifies regulators of cardiac development," *Cell*, 2012, 151(1):221-232.
Pandur et al., "Wnt-11 activation of a non-canonical Wnt signalling pathway is required for cardiogenesis," *Nature*, 2002, 418(6898):636-641.
PCT International Search Report and Written Opinion in International Appln. No. PCT/US2018/046536, dated Nov. 12, 2018, 1 pages.
Peng, "Xenopus laevis: Practical uses in cell and molecular biology. Solutions and Protocols," *Methods Cell Biol*, 1991, 36:657-662.
Raffin et al., "Subdivision of the cardiac Nkx2.5 expression domain into myogenic and nonmyogenic compartments," *Developmental Biology*, 2000, 218(2):326-340.
Roschger et al., "The Id-protein family in developmental and cancer-associated pathways," *Cell Commun Signal*, 2017, 15(1):7, 26 pages.
Saga et al., "Mespl expression is the earliest sign of cardiovascular development," *Trends in Cardiovascular Medicine*, 2000, 10(8):345-352.
Saga et al., "MesP1: a novel basic helix-loop-helix protein expressed in the nascent mesodermal cells during mouse gastrulation," *Development*, 1996, 122:2769-2778.
Schneider et al., "Wnt antagonism initiates cardiogenesis in Xenopus laevis," *Genes & Development*, 2001, 15(3):304-315.
Schultheiss et al., "A role for bone morphogenetic proteins in the induction of cardiac myogenesis," *Genes & Development*, 1997, 11(4):451-462.
Sekiya et al., "Direct conversion of mouse fibroblasts to hepatocyte-like cells by defined factors," *Nature*, 2011, 475(7356):390-393.
Stainier, "A glimpse into the molecular entrails of endoderm formation," *Genes & Development*, 2002, 16(8):893-907.
Tomescot et al., "Differentiation in Vivo of Cardiac Committed Human Embryonic Stem Cells in Postmyocardial Infarcted Rats," *Stem Cells*, 2007, 25(9):2200-2205.
Viotti et al., "SOX17 Links Gut Endoderm Morphogenesis and Germ Layer Segregation," Nature Cell Biology, 2014, 16(12):1146-1156.
Wilkinson et al., "Detection of messenger RNA by in situ hybridization to tissue sections and whole mounts," *Methods in Enzymology*, 1993, 225:361-373.
Yang et al., "Human cardiovascular progenitor cells develop from a KDR+ embryonic-stem-cell-derived population," *Nature*, 2008, 453(7194):524-528.
Yang et al., "Id proteins in the vasculature: from molecular biology to cardiopulmonary medicine," *Cardiovascular Research*, 2014, 104(3):388-398.
Yoon et al., "HEB and E2A function as SMAD/FOXH1 cofactors," *Genes Dev*, 2011, 25(15):1654-1661.
Yoshida et al., "Cell lineage in mammalian craniofacial mesenchyme," *Mech Dev*, 2008, 125(9-10):797-808.
Yu et al., "Generation of First Heart Field-like Cardiac Progenitors and Ventricular-like Cardiomyocytes from Human Pluripotent Stem Cells," J Vis Exp., 2018, 136:57688, 9 pages.
Zhang et al., "PowerBLAST: A New Network BLAST Application for Interactive or Automated Sequence Analysis and Annotation," *Genome Res.*, 1997, 7(6):649-656.
Zhao et al., "Loss of both GAT A4 and GAT A6 blocks cardiac myocyte differentiation and results in acardiain mice," *Developmental Biology*, 2008, 317(2):614-619.
Thomas Cunningham et al., "Id genes are essential for early heart formation", Genes and Development, vol. 31, No. 13, Jul. 1, 2017, pp. 1325-1338.
International Application No. PCT/US2018/046536, International Preliminary Report on Patentability and Written Opinion of the International Searching Authority, dated Feb. 27, 2020, 9 pages.

\* cited by examiner siAcvr1b + siCandidate

Day 6

Kdr-eGFP Foxa2

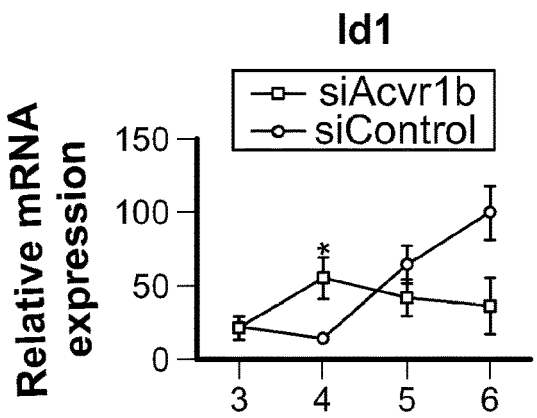
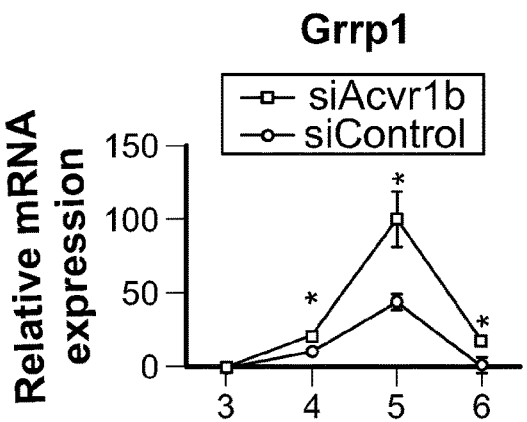
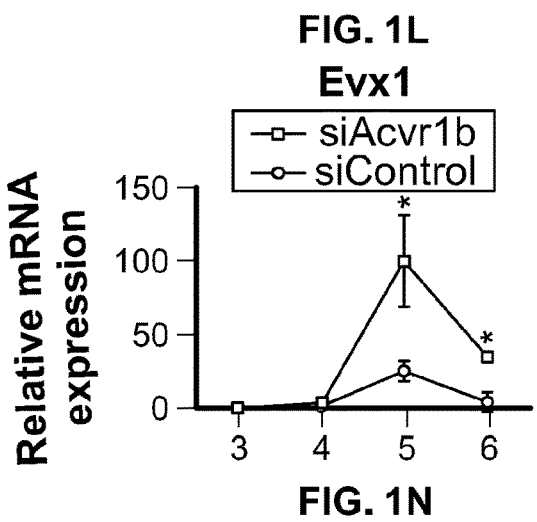
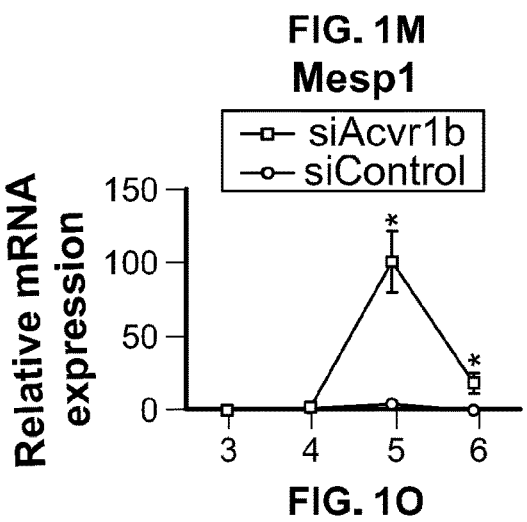
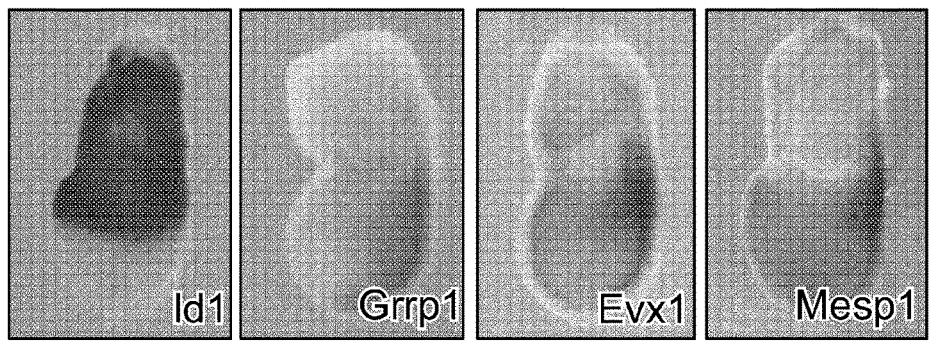
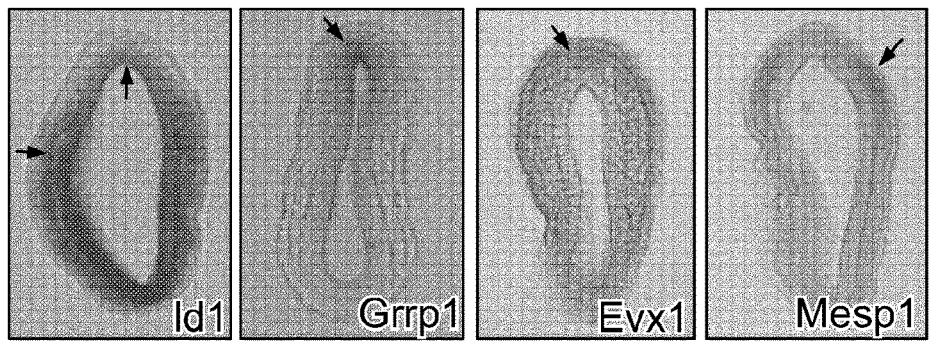
FIG. 1L  FIG. 1M  FIG. 1N  FIG. 1O
FIG. 1P  FIG. 1Q  FIG. 1R  FIG. 1S
FIG. 1T  FIG. 1U  FIG. 1V  FIG. 1W

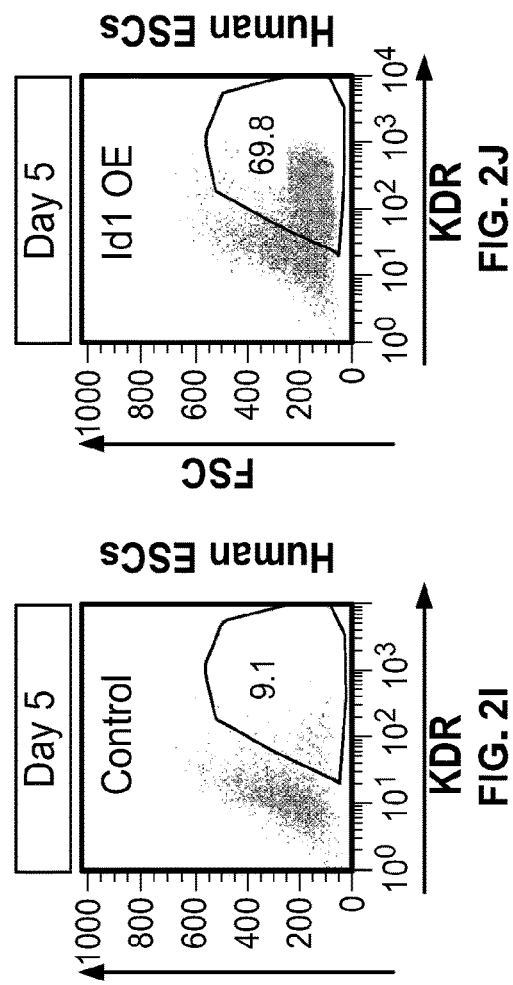
FIG. 2G
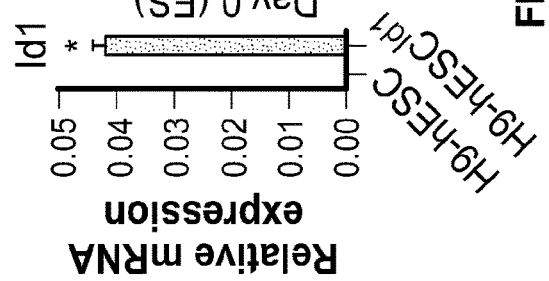
FIG. 2H
FIG. 2I
FIG. 2J

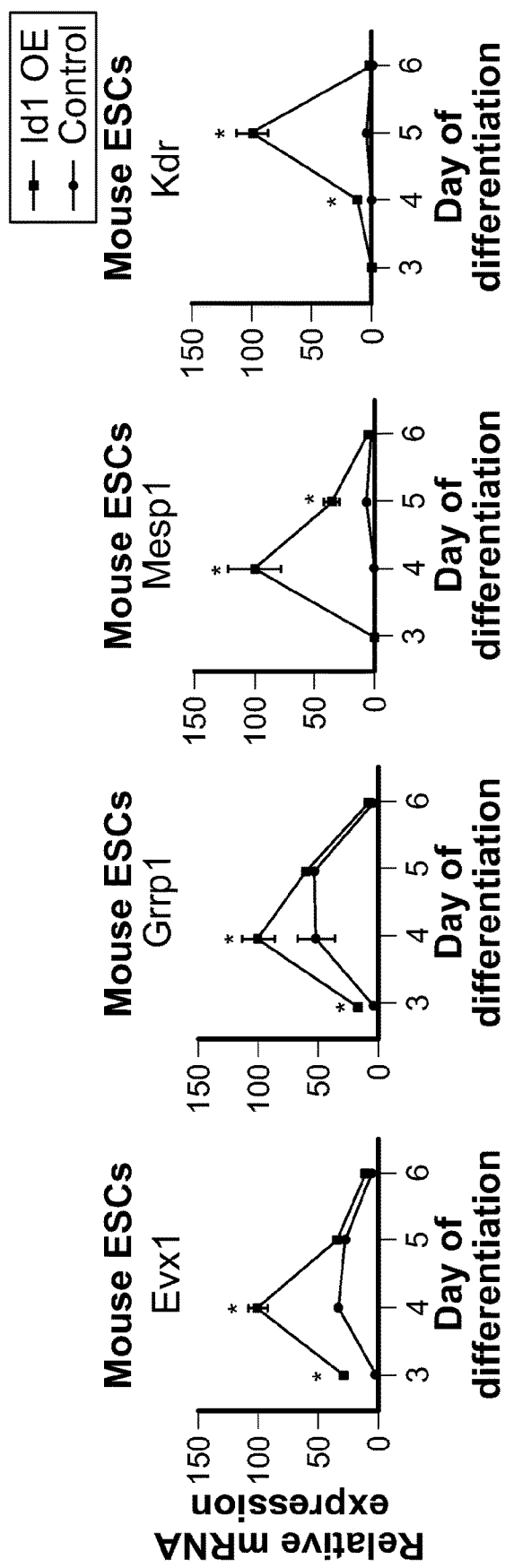
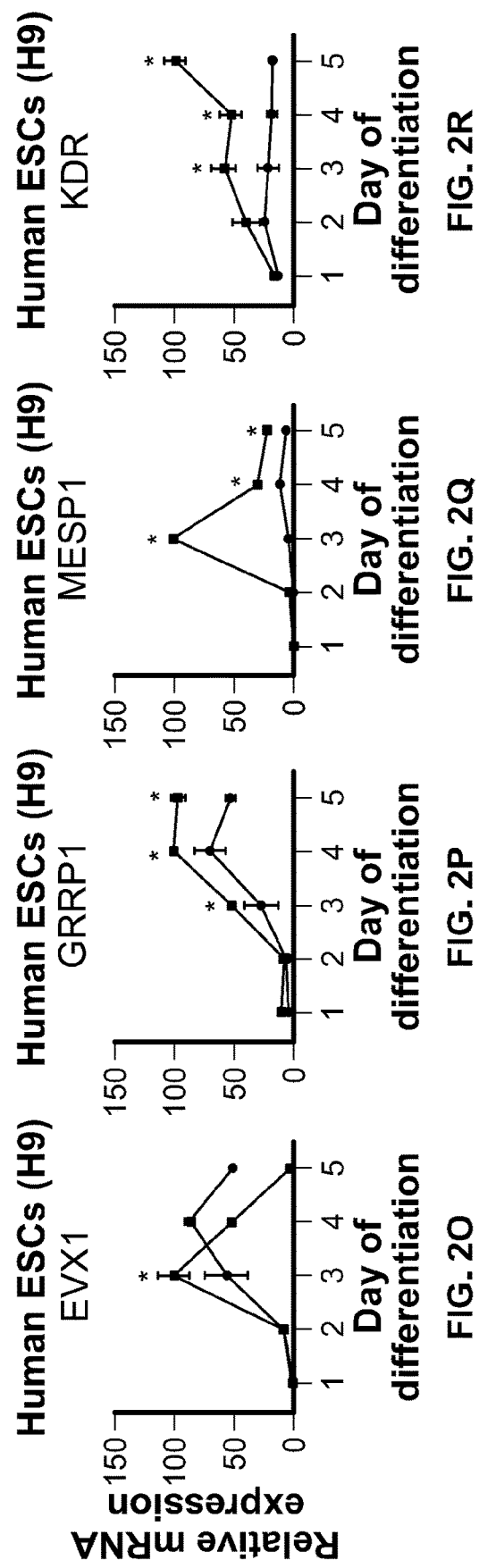

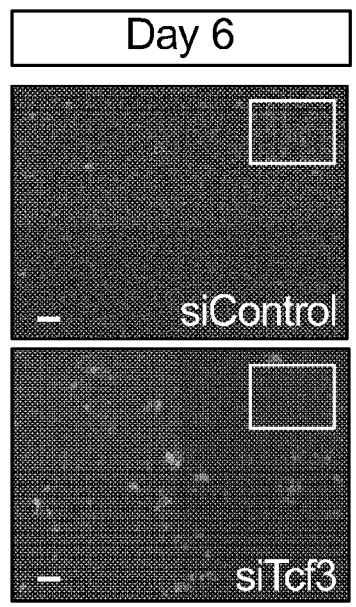
FIG. 4C
FIG. 4D
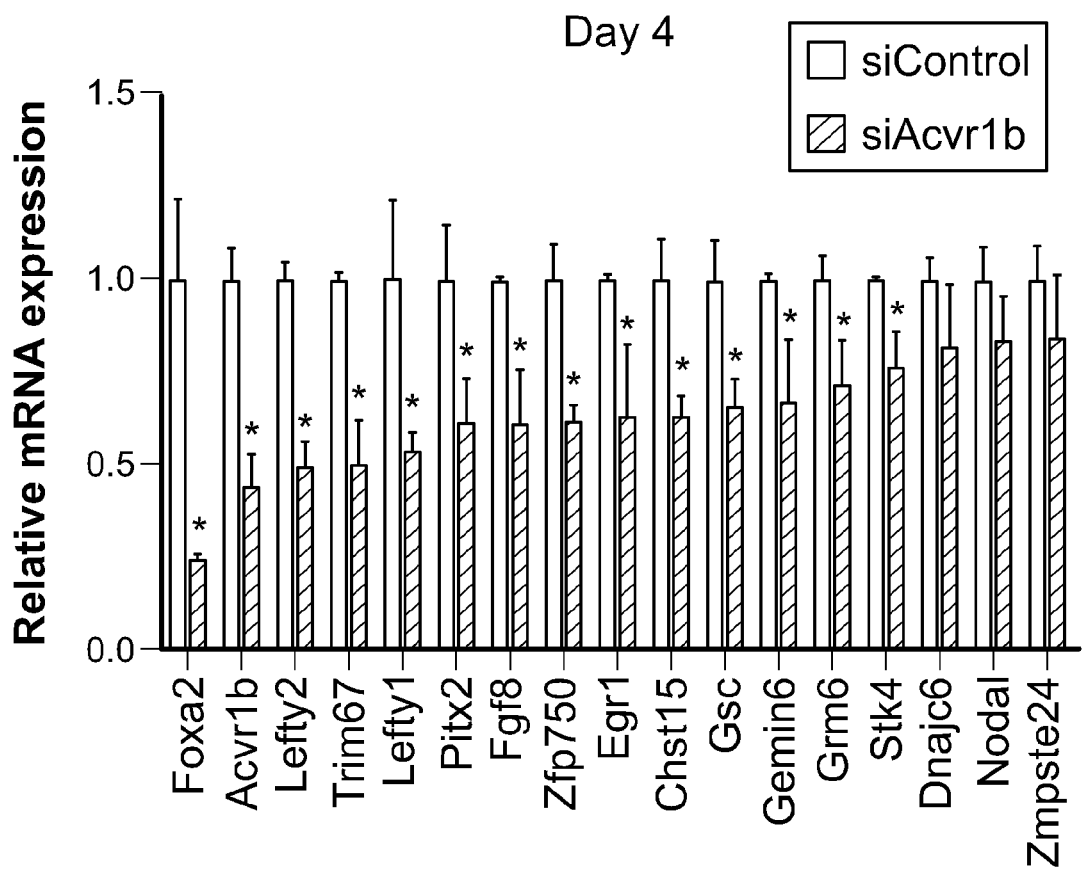
FIG. 4E

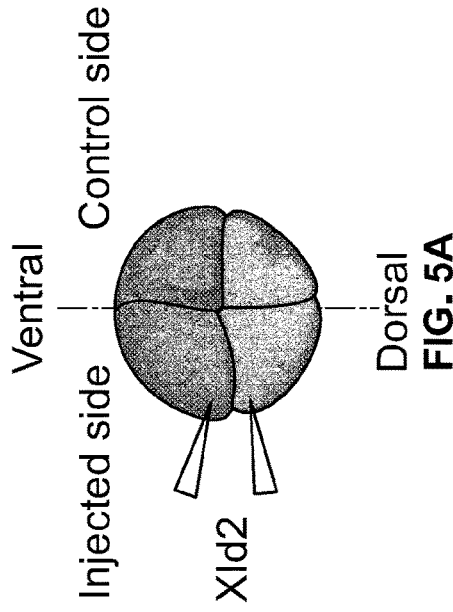

FIG. 5A

```
          HLH domain
   (79% identical, 93% positives)
Xid2 14 SLTEHSLGIAR---SKTP--VDDPMS--LLYNMNDCYSKLKEL VPSIPQNKKVSKMEILQ 66
         L+E  S+ I+R    ++ P   +D+     LLY+MN CYS+LKE LVP++PQN+KVSK+EILQ
mld1 30 GLSEQSVAISRCAGTRLPALLDEQQVNVLLYDMNGCYSRLKELVPTLPQNRKVSKVEILQ 89

Xid2 67 HVIDYILDLQLTLDSHPSIVSLHHLPRVGGNT--SRTPLDPLNTDISILSLQAA 118
         HVIDYI DLQL L+S        +    +       R PL  LN +IS L+ +AA
mld1 90 HVIDYIRDLQLELNSESEVGT-----TGGRGLPVRAPLSTLNGEISALAAEAA 137
```

FIG. 5B

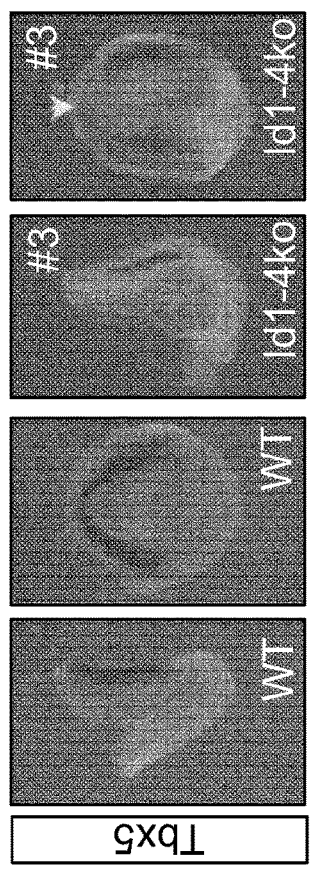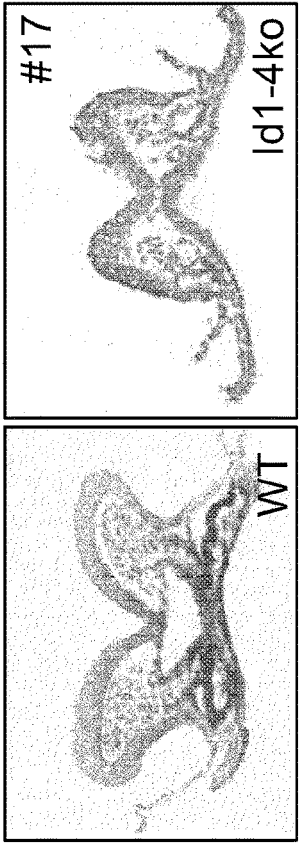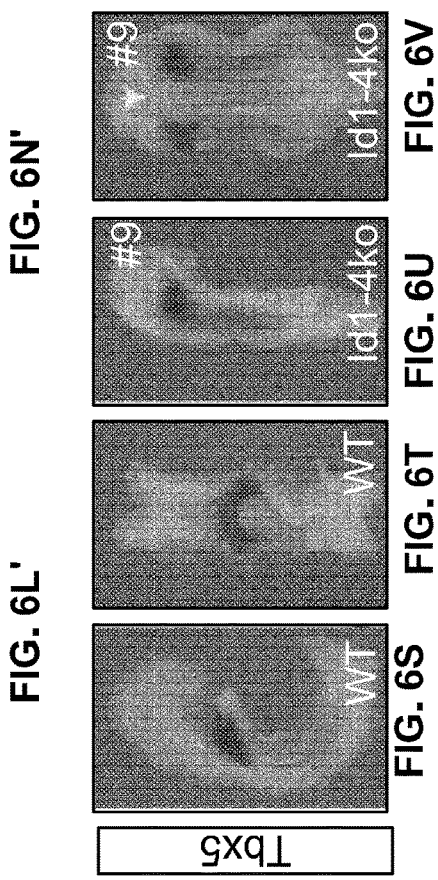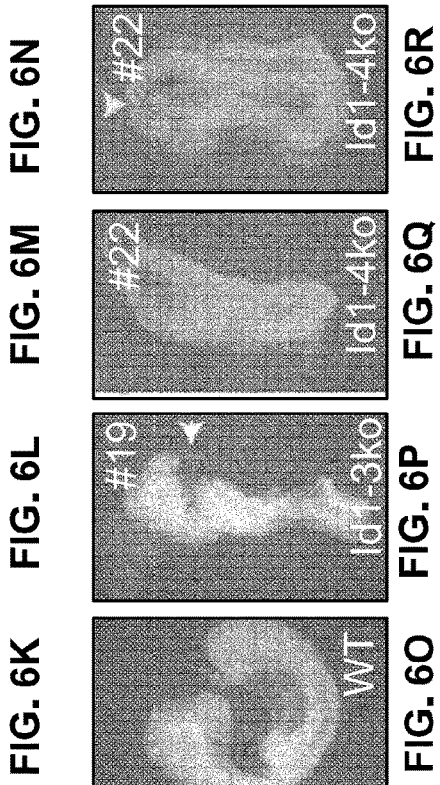

Kdr-eGFP, DAPI

SEQ ID NO: 1
Id1; human (NP_851998.1)

```
  1 MKVASGSTAT AAAGPSCALK AGKTASGAGE VVRCLSEQSV AISRCAGGAG ARLPALLDEQ
 61 QVNVLLYDMN GCYSRLKELV PTLPQNRKVS KVEILQHVID YIRDLQLELN SESEVGTPGG
121 RGLPVRAPLS TLNGEISALT AEVRSRSDH
```

SEQ ID NO: 2
Id2; human (Q02363-1)

```
            10         20         30         40         50
    MKAFSPVRSV RKNSLSDHSL GISRSKTPVD DPMSLLYNMN DCYSKLKELV
            60         70         80         90        100
    PSIPQNKKVS KMEILQHVID YILDLQIALD SHPTIVSLHH QRPGQNQASR
           110        120        130
    TPLTTLNTDI SILSLQASEF PSELMSNDSK ALCG
```

SEQ ID NO: 3
Id3; human (Q02535-1)

```
            10         20         30         40         50
    MKALSPVRGC YEAVCCLSER SLAIARGRGK GPAAEEPLSL LDDMNHCYSR
            60         70         80         90        100
    LRELVPGVPR GTQLSQVEIL QRVIDYILDL QVVLAEPAPG PPDGPHLPIQ
           110
    TAELTPELVI SNDKRSFCH
```

SEQ ID NO: 4
Id4; human (P47928-1)

```
            10         20         30         40         50
    MKAVSPVRPS GRKAPSGCGG GELALRCLAE HGHSLGGSAA AAAAAAAARC
            60         70         80         90        100
    KAAEAAADEP ALCLQCDMND CYSRLRRLVP TIPPNKKVSK VEILQHVIDY
           110        120        130        140        150
    ILDLQLALET HPALLRQPPP PAPPHHPAGT CPAAPPRTPL TALNTDPAGA
           160
    VNKQGDSILC R
```

SEQ ID NO: 5
Evx1; human (P49640-1)

```
            10         20         30         40         50
    MESRKDMVVF LDGGQLGTLV GKRVSNLSEA VGSPLPEPPE KMVPRGCLSP
            60         70         80         90        100
    RAVPPATRER GGGGPEEEPV DGLAGSAAGP GAEPQVAGAA MLGPGPPAPS
           110        120        130        140        150
    VDSLSGQGQP SSSDTESDFY EEIEVSCTPD CATGNAEYQH SKGSGSEALV
           160        170        180        190        200
    GSPNGGSETP KSNGGSGGGG SQGTLACSAS DQMRRYRTAF TREQIARLEK
           210        220        230        240        250
    EFYRENYVSR PRRCELAAAL NLPETTIKVW FQNRRMKDKR QRLAMTWPHP
           260        270        280        290        300
    ADPAFYTYMM SHAAAGGLP YPFPSHLPLP YYSPVGLGAA SAASAAASPF
           310        320        330        340        350
    SGSLRPLDTF RVLSQPYPRP ELLCAFRHPP LYPGPAHGLG ASAGGPCSCL
```

FIG. 14

```
                360        370        380        390        400
         ACHSGPANGL APRAAAASDF TCASTSRSDS FLTFAPSVLS KASSVALDQR
         EEVPLTR
```

SEQ ID NO: 6
Grrp1; human (Q8TAY7-1)
```
                 10         20         30         40         50
         MLLAPPSTPS RGRTPSAVER LEADKAKYVK THQVIARRQE PALRGSPGPL
                 60         70         80         90        100
         TPHPCNELGP PASPRTPRPV RRGSGRRLPR PDSLIFYRQK RDCKASVNKE
                110        120        130        140        150
         NAKGQGLVRR LFLGAPRDAA PSSPASTERP AASGGWAAPQ DAPEAAGKRA
                160        170        180        190        200
         LCPTCSLPLS EKERFFNYCG LERALVEVLG AERFSPQSWG ADASPQAGTS
                210        220        230        240        250
         PPPGSGDASD WTSSDRGVDS PGGAGGGGGS EAAGSARDRR PPVSVVERNA
                260        270
         RVIQWLYGCQ RARGPPRESE V
```

SEQ ID NO: 7.
Mesp1; human (Q9BRJ9-1)
```
                 10         20         30         40         50
         MAQPLCPPLS ESWMLSAAWG PTRRPPPSDK DCGRSLVSSP DSWGSTPADS
                 60         70         80         90        100
         PVASPARPGT LRDPRAPSVG RRGARSSRLG SGQRQSASER EKLRMRTLAR
                110        120        130        140        150
         ALHELRRFLP PSVAPAGQSL TKIETLRLAI RYIGHLSAVL GLSEESLQRR
                160        170        180        190        200
         CRQRGDAGSP RGCPLCPDDC PAQMQTRTQA EGQGQGRGLG LVSAVRAGAS
                210        220        230        240        250
         WGSPPACPGA RAAPEPRDPP ALFAEAACPE GQAMEPSPPS PLLPGDVLAL
                260
         LETWMPLSPL EWLPEEPK
```

SEQ ID NO: 8
Foxa2; human (Q9Y261-1)
```
                 10         20         30         40         50
         MLGAVKMEGH EPSDWSSYYA EPEGYSSVSN MNAGLGMNGM NTYMSMSAAA
                 60         70         80         90        100
         MGSGSGNMSA GSMNMSSYVG AGMSPSLAGM SPGAGAMAGM GGSAGAAGVA
                110        120        130        140        150
         GMGPHLSPSL SPLGGQAAGA MGGLAPYANM NSMSPMYGQA GLSRARDPKT
                160        170        180        190        200
         YRRSYTHAKP PYSYISLITM AIQQSPNKML TLSEIYQWIM DLFPFYRQNQ
                210        220        230        240        250
         QRWQNSIRHS LSFNDCFLKV PRSPDKPGKG SFWTLHPDSG NMFENGCYLR
                260        270        280        290        300
         RQKRFKCEKQ LALKEAAGAA GSGKKAAAGA QASQAQLGEA AGPASETPAG
                310        320        330        340        350
         TESPHSSASP CQEHKRGGLG ELKGTPAAAL SPPEPAPSPG QQQQAAAHLL
                360        370        380        390        400
         GPPHHPGLPP EAHLKPEHHY AFNHPFSINN LMSSEQQHHH SHHHHQPHKM
                410        420        430        440        450
         DLKAYEQVMH YPGYGSPMPG SLAMGPVTNK TGLDASPLAA DTSYYQGVYS
```

FIG. 14 (Cont.)

RPIMNSS

SEQ ID NO: 9
Tcf3; human (P15923-1)

```
         10         20         30         40         50
MNQPQRMAPV GTDKELSDLL DFSMMFPLPV TNGKGRPASL AGAQFGGSGL
         60         70         80         90        100
EDRPSSGSWG SGDQSSSSFD PSRTFSEGTH FTESHSSLSS STFLGPGLGG
        110        120        130        140        150
KSGERGAYAS FGRDAGVGGL TQAGFLSGEL ALNSPGPLSP SGMKGTSQYY
        160        170        180        190        200
PSYSGSSRRR AADGSLDTQP KKVRKVPPGL PSSVYPPSSG EDYGRDATAY
        210        220        230        240        250
PSAKTPSSTY PAPFYVADGS LHPSAELWSP PGQAGFGPML GGGSSPLPLP
        260        270        280        290        300
PGSGPVGSSG SSSTFGGLHQ HERMGYQLHG AEVNGGLPSA SSFSSAPGAT
        310        320        330        340        350
YGGVSSHTPP VSGADSLLGS RGTTAGSSGD ALGKALASIY SPDHSSNNFS
        360        370        380        390        400
SSPSTPVGSP QGLAGTSQWP RAGAPGALSP SYDGGLHGLQ SKIEDHLDEA
        410        420        430        440        450
IHVLRSHAVG TAGDMHTLLP GHGALASGFT GPMSLGGRHA GLVGGSHPED
        460        470        480        490        500
GLAGSTSLMH NHAALPSQPG TLPDLSRPPD SYSGLGRAGA TAAASEIKRE
        510        520        530        540        550
EKEDEENTSA ADHSEEEKKE LKAPRARTSP DEDEDDLLPP EQKAEREKER
        560        570        580        590        600
RVANNARERL RVRDINEAFK ELGRMCQLHL NSEKPQTKLL ILHQAVSVIL
        610        620        630        640        650
NLEQQVRERN LNPKAACLKR REEEKVSGVV GDPQMVLSAP HPGLSEAHNP
```

AGHM

SEQ ID NO: 10
Id1; mouse (NP_034625.1)

```
  1 MKVASGSAAA AAGPSCSLKA GRTAGEVVLG LSEQSVAISR CAGTRLPALL DEQQVNVLLY
 61 DMNGCYSRLK ELVPTLPQNR KVSKVEILQH VIDYIRDLQL ELNSESEVGT TGGRGLPVRA
121 PLSTLNGEIS ALAAEAACVP ADDRILCR
```

SEQ ID NO: 11
Id1; human (NM_181353)

```
  1 ACTCTCATTC CACGTTCTTA ACTGTTCCAT TTTCCGTATC TGCTTCGGGC TTCCACCTCA
 61 TTTTTTTCGC TTTGCCCATT CTGTTTCAGC CAGTCGCCAA GAATCATGAA AGTCGCCAGT
121 GGCAGCACCG CCACCGCCGC CGCGGGCCCC AGCTGCGCGC TGAAGGCCGG CAAGACAGCG
181 AGCGGTGCGG GCGAGGTGGT GCGCTGTCTG TCTGAGCAGA GCGTGGCCAT CTCGCGCTGC
241 GCCGGGGGCG CCGGGGCGCG CCTGCCTGCC CTGCTGGACG AGCAGCAGGT AAACGTGCTG
301 CTCTACGACA TGAACGGCTG TTACTCACGC CTCAAGGAGC TGGTGCCCAC CCTGCCCCAG
361 AACCGCAAGG TGAGCAAGGT GGAGATTCTC CAGCACGTCA TCGACTACAT CAGGGACCTT
421 CAGTTGGAGC TGAACTCGGA ATCCGAAGTT GGAACCCCCG GGGCCGAGG GCTGCCGGTC
481 CGGGCTCCGC TCAGCACCCT CAACGGCGAG ATCAGCGCCC TGACGGCCGA GGTGAGATCC
541 AGATCCGACC ACTAGATCAT CCTTATACCG ACGGGGAAAC GGAGGCCAGA GAGGGCGTGG
601 GCGCTTGCAC CACTTCCGTC CCATCCTTGC GGGTACCTGG CTATGCGGGG GTGCCTAAGG
661 AGCCTGGAAA AAGCGCTCCC CGTCGTGCT TCCTGGGGAA GGGGCGTTC GCTGCGCTCG
721 GAGCGGCGTC CCTTCCAACC CGCCGGTCTC ATTTCTTCTC GTTTTCACAG GCGGCATGCG
781 TTCCTGCGGA CGATCGCATC TTGTGTCGCT GAAGCGCCTC CCCCAGGGAC GGCGGACCC
841 CAGCCATCCA GGGGGCAAGA GGAATTACGT GCTCTGTGGG TCTCCCCAA CGCGCCTCGC
901 CGGATCTGAG GGAGAACAAG ACCGATCGGC GGCCACTGCG CCCTTAACTG CATCCAGCCT
961 GGGGCTGAGG CTGAGGCACT GGCGAGGAGA GGGCGCTCCT CTCTGCACAC CTACTAGTCA
```

FIG. 14 (Cont.)

```
1021 CCAGAGACTT TAGGGGGTGG GATTCCACTC GTGTGTTTCT ATTTTTTGAA AAGCAGACAT
1081 TTTAAAAAAT GGTCACGTTT GGTGCTTCTC AGATTTCTGA GGAAATTGCT TTGTATTGTA
1141 TATTACAATG ATCACCGACT GAAAATATTG TTTTACAATA GTTCTGTGGG GCTGTTTTTT
1201 TGTTATTAAA CAAATAATTT AGATGGTGGT AAAAAAAAA
```

SEQ ID NO: 12 Id2
Id2; HUMAN NM_002166.4

```
   1 GGGGACGAAG GGAAGCTCCA GCGTGTGGCC CCGGCGAGTG CGGATAAAAG CCGCCCCGCC
  61 GGGCTCGGGC TTCATTCTGA GCCGAGCCCG GTGCCAAGCG CAGCTAGCTC AGCAGGCGGC
 121 AGCGGCGGCC TGAGCTTCAG GGCAGCCAGC TCCCTCCCGG TCTCGCCTTC CCTCGCGGTC
 181 AGCATGAAAG CCTTCAGTCC CGTGAGGTCC GTTAGGAAAA ACAGCCTGTC GGACCACAGC
 241 CTGGGCATCT CCCGGAGCAA AACCCCTGTG GACGACCCGA TGAGCCTGCT ATACAACATG
 301 AACGACTGCT ACTCCAAGCT CAAGGAGCTG GTGCCCAGCA TCCCCAGAA CAAGAAGGTG
 361 AGCAAGATGG AAATCCTGCA GCACGTCATC GACTACATCT TGGACCTGCA GATCGCCCTG
 421 GACTCGCATC CCACTATTGT CAGCCTGCAT CACCAGAGAC CCGGGCAGAA CCAGGCGTCC
 481 AGGACGCCGC TGACCACCCT CAACACGGAT ATCAGCATCC TGTCCTTGCA GGCTTCTGAA
 541 TTCCCTTCTG AGTTAATGTC AAATGACAGC AAAGCACTGT GTGGCTGAAT AAGCGGTGTT
 601 CATGATTTCT TTTATTCTTT GCACAACAAC AACAACAACA AATTCACGGA ATCTTTTAAG
 661 TGCTGAACTT ATTTTTCAAC CATTTCACAA GGAGGACAAG TTGAATGGAC CTTTTTAAAA
 721 AGAAAAAAAA AATGGAAGGA AAACTAAGAA TGATCATCTT CCCAGGGTGT TCTCTTACTT
 781 GGACTGTGAT ATTCGTTATT TATGAAAAAG ACTTTTAAAT GCCCTTTCTG CAGTTGGAAG
 841 GTTTTCTTTA TATACTATTC CCACCATGGG GAGCGAAAAC GTTAAAATCA CAAGGAATTG
 901 CCCAATCTAA GCAGACTTTG CCTTTTTTCA AAGGTGGAGC GTGAATACCA GAAGGATCCA
 961 GTATTCAGTC ACTTAAATGA AGTCTTTTGG TCAGAAATTA CCTTTTTGAC ACAAGCCTAC
1021 TGAATGCTGT GTATATATTT ATATATAAAT ATATCTATTT GAGTGAAACC TTGTGAACTC
1081 TTTAATTAGA GTTTTCTTGT ATAGTGGCAG AGATGTCTAT TTCTGCATTC AAAAGTGTAA
1141 TGATGTACTT ATTCATGCTA AACTTTTTAT AAAAGTTTAG TTGTAAACTT AACCCTTTTA
1201 TACAAAATAA ATCAAGTGTG TTTATTGAAT GGTGATTGCC TGCTTTATTT CAGAGGACCA
1261 GTGCTTTGAT TTTTATTATG CTATGTTATA ACTGAACCCA AATAAATACA AGTTCAAATT
1321 TATGTAGACT GTATAAGATT ATAATAAAAC ATGTCTGAAG TCAAAAAAAA AAAAAAAAA
1381 AAAAAAAAAA AAAAAAAAA AA
```

SEQ ID NO: 13 Id3
Id3; HUMAN NM_002167.4

```
   1 GATCTGGGGT GCTGCCAGGA AAAAGCAAAT TCTGGAAGTT AATGGTTTTG AGTGATTTTT
  61 AAATCCTTGC TGGCGGAGAG GCCCGCCTCT CCCCGGTATC AGCGCTTCCT CATTCTTTGA
 121 ATCCGCGGCT CCGCGGTCTT CGGCGTCAGA CCAGCCGGAG GAAGCCTGTT TGCAATTTAA
 181 GCGGGCTGTG AACGCCCAGG GCCGGCGGGG GCAGGGCCGA GGCGGGCCAT TTTGAATAAA
 241 GAGGCGTGCC TTCCAGGCAG GCTCTATAAG TGACCGCCGC GGCGAGCGTG CGCGCGTTGC
 301 AGGTCACTGT AGCGGGACTT CTTTTGGTTT TCTTTCTCTT TGGGCACCT CTGGACTCAC
 361 TCCCCAGCAT GAAGGCGCTG AGCCCGGTGC GCGGCTGCTA CGAGGCGGTG TGCTGCCTGT
 421 CGGAACGCAG TCTGGCCATC GCCCGGGGCC GAGGGAAGGG CCCGGCAGCT GAGGAGCCGC
 481 TGAGCTTGCT GGACGACATG AACCACTGCT ACTCCCGCCT GCGGGAACTG GTACCCGGAG
 541 TCCCGAGAGG CACTCAGCTT AGCCAGGTGG AAATCCTACA GCGCGTCATC GACTACATTC
 601 TCGACCTGCA GGTAGTCCTG GCCGAGCCAG CCCTGGACC CCTGATGGC CCCCACCTTC
 661 CCATCCAGAC AGCCGAGCTC ACTCCGGAAC TTGTCATCTC CAACGACAAA AGGAGCTTTT
 721 GCCACTGACT CGGCCGTGTC CTGACACCTC CAGAACGCAG GTGCTGGCGC CCGTTCTGCC
 781 TGGGACCCCG GGAACCTCTC CTGCCGGAAG CCGGACGGCA GGGATGGGCC CCAACTTCGC
 841 CCTGCCCACT TGACTTCACC AAATCCCTTC CTGGAGACTA AACCTGGTGC TCAGGAGCGA
 901 AGGACTGTGA ACTTGTGGCC TGAAGAGCCA GAGCTAGCTC TGGCCACCAG CTGGGCGACG
 961 TCACCCTGCT CCCACCCCAC CCCCAAGTTC TAAGGTCTCT TCAGAGCGTG GAGGTGTGGA
1021 AGGAGTGGCT GCTCTCCAAA CTATGCCAAG GCGGCGGCAG AGCTGGTCTT CTGGTCTCCT
1081 TGGAGAAAGG TTCTGTTGCC CTGATTTATG AACTCTATAA TAGAGTATAT AGGTTTTGTA
1141 CCTTTTTTAC AGGAAGGTGA CTTTCTGTAA CAATGCGATG TATATTAAAC TTTTTTATAAA
1201 AGTTAACATT TTGCATAATA AACGATTTTT AAACACTTGA AAAAAAAAA AA
```

SEQ ID NO: 14 Id4
Id4; HUMAN NM_001546.3

```
   1 GAGAGCGTAG TGGAGGAGGC GCGGTTGTGA GTAGTACCGG GAGTGGGGTG ATCCCGGGCT
  61 AGGGGAGCGC GGCGGCCGCG ATCGGGCTTA GTCGGAGCTC CGAAGGGAGT GACTAGGACA
 121 CCCGGGTGGG CTACTTTTCT TCCGGTGCTT TTGCTTTTTT TTTCCTTTGG GCTCGGGCTG
```

```
 181 AGTGTCGCCC ACTGAGCAAA GATTCCCTCG TAAAACCCAG AGCGACCCTC CCGTCAATTG
 241 TTGGGCTCGG GAGTGTCGCG GTGCCCCGAG CGCGCCGGGC GCGGAGGCAA AGGGAGCGGA
 301 GCCGGCCGCG GACGGGGCCC GGAGCTTGCC TGCCTCCCTC GCTCGCCCCA GCGGGTTCGC
 361 TCGCGTAGAG CGCAGGGCGC GCGCGATGAA GGCGGTGAGC CCGGTGCGCC CCTCGGGCCG
 421 CAAGGCGCCG TCGGGCTGCG GCGGCGGGGA GCTGGCGCTG CGCTGCCTGG CCGAGCACGG
 481 CCACAGCCTG GGTGGCTCCG CAGCCGCGGC GGCGGCGGCG GCGGCAGCGC GCTGTAAGGC
 541 GGCCGAGGCG GCGGCCGACG AGCCGGCGCT GTGCCTGCAG TGCGATATGA ACGACTGCTA
 601 TAGCCGCCTG CGGAGGCTGG TGCCCACCAT CCCGCCCAAC AAGAAAGTCA GCAAAGTGGA
 661 GATCCTGCAG CACGTTATCG ACTACATCCT GGACCTGCAG CTGGCGCTGG AGACGCACCC
 721 GGCCCTGCTG AGGCAGCCAC CACCGCCCGC GCCGCCACAC CACCCGGCCG GGACCTGTCC
 781 AGCCGCGCCG CCGCGGACCC CGCTCACTGC GCTCAACACC GACCCGGCCG GCGCGGTGAA
 841 CAAGCAGGGC GACAGCATTC TGTGCCGCTG AGCCGCGCTG TCCAGGTGTG CGGCCGCCTG
 901 AGCCCGAGCC AGGAGCACTA GAGAGGGAGG GGGAAGAGCA GAAGTTAGAG AAAAAAAGCC
 961 ACCGGAGGAA AGGAAAAAAC ATCGGCCAAC CTAGAAACGT TTTCATTCGT CATTCCAAGA
1021 GAGAGAGAGG AAAGAAAAAT ACAACTTTCA TTCTTTCTTT GCACGTTCAT AAACATTCTA
1081 CATACGTATT CTCTTTTGTC TCTTCATTTA TAACTGCTGT GAATTGTACA TTTCTGTGTT
1141 TTTTGGAGGT GCAGTTAAAC TTTTAAGCTT AAGTGTGACA GGACTGATAA ATAGAAGATC
1201 AAGAGTAGAT CCGACTTTAG AAGCCTACTT TGTGACCAAG GAGCTCAATT TTTGTTTTGA
1261 AGCTTTACTA ATCTACCAGA GCATTGTAGA TATTTTTTTT TTACATCTAT TGTTTAAAAT
1321 AGATGATTAT AACGGGGCAG AGAACTTTCT TTTCTCTGCA AGAATGTTAC ATATTGTATA
1381 GATAAATGAG TGACATTTCA TACCATGTAT ATATAGAGAT GTTCTATAAG TGTGAGAAAG
1441 TATATGCTTT AATAGATACT GTAATTATAA GATATTTTA ATTAAATATT TTTTTGTAAA
1501 TATTATGTGT GTGTTTTTTT TTAATCTATG GGAATATTTC TTTTGGAAAA TCATTTTTCA
1561 GCTCAATTAC AGAGCTCTTG ATATCTTGAA TGTCTTTTCT GTTTGGCCTG GCTCTTAATT
1621 TGCTTTTGTT TTGCCCAGTA TAGACTCGGA AGTAACAGTT ATAGCTAGTG GTCTTGCATG
1681 ATTGCATGAG ATGTTTAATC ACAAATTAAA CTTGTTCTGA GTCCATTCAA ATGTGTTTTT
1741 TTAAATGTAG ATTGAAATCT TTGTATTTGA AGCATACATG TTGAAAATAC ACCTTATCAG
1801 TTTTTAAGTA CAGGGTTTTA TAGTGTAATA TATACAGAGT AAGTGTTTGT TTTTGTTTTT
1861 CAACTGAGGT CAAAATGGAT TCTGAATGAT TTTGCATATG GGATGAGGAA ATGCTTGGAT
1921 CCTTAAGGAG TTTACGAAAT CTGCTGTTTT ATCAAAGTGA AAAAAAATTG CTTATTACTC
1981 TTCATTTTAC ACTAAAGCTT AATGTCACTA AGTTTCATGT CTGTACAGAT TATTTAAATC
2041 ATGGAAATGA AAAAAAATGTT CTCTGCTTGC TACCAAAGGA CAAACTCTTG GAAATGAACA
2101 CTTTCTGCTT TCCTTCCTCC AAAGAATTAA TAGGCAACAG TGGGAGAAAA AAAAGGCATA
2161 ATGGCAAATC CTTCAAGCAG GGATAAAAGT CGATCTTCAA ACATTAACTT AAGCAGACCA
2221 AAAATTCTGA TGACCGCATC TAGATTATTT TTTTATAAAA ATGATTTTCA CTATAGCTAT
2281 GTTACGCTAA GCTACTGTCC AATCTCTTGT GATGTGTAAC TTTTACATGT GAATATTAAA
2341 GTAGATTTCT CTGTCTTGTA CTGTGATTTC TGGTCTCATT TCTTTAAAAC CTTACTCTTA
2401 TTTTTCTTTT AAGGCTCTTT TTTCTCCTTA AGGAAGGTAA TATTTTCTAG GTTAGATAGG
2461 ACTATCAGGG TTTGTGAACA TTATGCATTT AATGTTATGG GTACTTTACA CACAAGTTAG
2521 ATGGAATTTT TAGAGTGAAA GAATTAAGTA GGATTTAATT GGGTGCTTTG TAAATAGTCA
2581 ACTGTGTGTA TAACGTGGTC TGTTTGATTT TTAAAAGGAA AGGATTTGTT TCAGATTATA
2641 CAAGAATAAA AGTATTATAG ACCCAAGGGA CTTCTTATGA GGTCAAATTC AGATATTTAT
2701 ATGAATATGA AATACCATGG TCCCTAGTAG TCAGTTGAAG TGGCAATGTC TAAACAGAAA
2761 TGAACAAAAC TAATGCTAGC AGGTTAAAAT CAATCAAAAT GTTTAAAAAT TGATTCTGTC
2821 CTCAGCATGT TATTTCCTCA GCTCTGATAA TTTACTGGTC TTGAGTATTT TGAGAATTTG
2881 ATGTTGAACG TTATAAAGTC AAAGAACTGC TTGTTTAGAT GAGGTTTATT TTTATTTTTG
2941 ATATTATTCA TTCTTGTCAC ACATCAAGAA GAAAACACTA GAGTGCTGCT GGAATTCCAA
3001 ATCTGAAGAA TTCTAACGAC TGCATTCTTT GTTATTAAAA AGGGCACAAT CCTTCCTTTT
3061 TATTTGGCAG TTTAATTTCA GTAGGAAGCA TGTCACATGT GCACTGTTGG TTAGAATTAT
3121 GCATCTGTCA TGCCTGACTG CTGAACCCTA CCTAAGCCTT TTGGCGCAGT TTAAAACTTA
3181 TACTCCTTGA CTGTGAACCT CAAAACAAAT GGGTATTTTT GGGTTTTGAG GATAGATGTT
3241 ACTCCTTAAA GTTTGTATTT GGGGCATGAA AAACTACTGA AAGAAGAAAA GTGCTACAGA
3301 TACTACATTT CAAAGAGTTG GCATTTTCCC TTTGGCCACT CAAGCAGCAT TTGATGTATC
3361 TAAAGAACA AAGTCATTGT TTATTTTTTA AAAAATTATA TGCAGTTGTA CAAGATACTA
3421 CATTCCATTG AAATGTTGGC TATGTCCTAA CCAGGCAACC AGATAACAAA AACATTTTGA
3481 GTCTTTTATC TAGGTAGTTC TAATTATTCA GCTACTTAGT TTAACAAAGG AAAATATCCT
3541 GACTTCTCTC ATTTCATTTG TAGACTTTTC ATTGTATAGG CACAACCAAA GAGTCAGACT
3601 GGTTTAAAAAC TCCAGAAGGA AAAAAAGTAT CCCACACAGT GGATGTTGTT TCTAAGAATG
3661 CTACAAAATC CTGACATCTC AGACATCTCA ATGTTAAAGG AAGAAAAAAA ATACCTTTTC
3721 ATTTCAAAGA ACTAATATAC TTTGATATTG TGTAAACCTT ACTCAAGTTT ATTGTCAAGC
3781 TTTAACTGCC TTTTTAGAAC TTTTTAAAAT TTCGAGCCCA CAAATCTATT GTATTAGTTG
```

FIG. 14 (Cont.)

3841 CCTTCTATAA CAATAAATCT TCACTGAGCA AAAGGCAAAA AAAAAAAAA A

SEQ ID NO: 15
Evx1; human (NM_001989)

```
   1 CTCTGCCTGG GTGTCTCCCT CTCTCAGTGT GTGTGTCTCT CTGTCTGTTT TCACACTCTC
  61 CTCCCCAATC GAGCGAGGCC CACACCTGGC GCATCACTGC CGAGCCATTA GCTGCGGGTT
 121 TCCTTTCATC TTCGCTGTGG CAGACGTTTC TATTTATCCA CTTGCGCTCG CCGAGTGGCG
 181 TCACCAGCGG TACTGTAATG ACGATTGCAG CAGGAGGATG ACAGCTTAGA AAGAAGAGGG
 241 CAATGGGGCT TCCTCCCAGA GGCGGTGCGG CACAGAGGAG CGCTCGCTTC ACAAGGTGAC
 301 CCTAGCTCCC ACCGCCACCG CCGCGGTCGC GGTCCAGACC GCGCTCCAGC AGCTCCGCGC
 361 CCTCCCAGGC ACCCGGCCTT TCTTTCTCCC TCTTGCAACC AAGATCCGTC CGGCCGCTGG
 421 AGACCCAGGG AGCCGGGGTT AGGAACTCAC TTGGGGCTTT CCCCTCCCCC ACCGGAGAGC
 481 CCCGGGATGG AGAGCCGAAA GGACATGGTT GTGTTTCTGG ATGGGGGTCA GCTTGGCACT
 541 CTGGTTGGCA AGAGAGTCTC AAATTTGTCC GAAGCCGTGG GCAGCCCGCT GCCGGAGCCG
 601 CCCGAGAAAA TGGTGCCCCG TGGTTGCCTG AGCCCTCGGG CCGTCCCTCC GGCCACCCGG
 661 GAGCGCGGCG GGGGAGGCCC GGAGGAGGAG CCGGTAGATG GACTCGCAGG CAGCGCGGCG
 721 GGGCCGGGCG CCGAGCCCCA GGTAGCTGGG GCGGCCATGC TCGGCCCAGG ACCCCCGGCC
 781 CCCTCAGTCG ACAGCCTCTC CGGACAGGGG CAACCCAGTA GCTCGGACAC CGAGTCGGAT
 841 TTCTATGAAG AAATCGAGGT GAGCTGCACC CCGGACTGCG CCACCGGGAA CGCCGAGTAC
 901 CAGCACAGCA AAGGGTCCGG CTCCGAGGCG CTGGTCGGCA GTCCGAACGG AGGGAGCGAG
 961 ACCCCCAAGA GCAACGGCGG CAGTGGTGGG GGCGGCTCGC AAGGCACCCT GGCGTGCAGC
1021 GCCAGTGACC AGATGCGTCG TTACCGCACC GCCTTCACCC GAGAGCAGAT TGCGCGGCTG
1081 GAGAAGGAAT TCTACCGGGA GAACTACGTA TCCAGGCCGC GGAGATGTGA GCTGGCGGCC
1141 GCCCTAAACC TGCCGGAAAC CACCATCAAG GTGTGGTTCC AGAACCGGCG CATGAAGGAC
1201 AAGCGGCAGC GCCTGGCCAT GACGTGGCCG CACCCGGCGG ACCCGCCTT CTACACTTAC
1261 ATGATGAGCC ATGCGGCGGC CGCGGGCGGC CTGCCCTACC CCTTCCCATC GCACCTGCCC
1321 CTGCCCTACT ACTCGCCGGT GGGCCTGGGC GCCGCATCCG CCGCCTCCGC CGCCGCCTCG
1381 CCCTTCAGCG GCTCGCTGCG CCCGCTCGAC ACGTTCCGCG TGCTGTCGCA GCCCTACCCG
1441 CGGCCCGAAC TGCTGTGCGC CTTCCGCCAC CCGCCGCTCT ACCCCGGGCC CGCGCACGGA
1501 CTGGGCGCCT CTGCCGGCGG CCCCTGCTCC TGCCTCGCCT GTCACAGCGG CCCGGCCAAC
1561 GGGCTGGCGC CCCGGGCTGC CGCCGCCTCG GACTTCACCT GTGCCTCCAC CTCCCGCTCG
1621 GACTCCTTCC TCACCTTCGC GCCCTCGGTG CTCAGCAAGG CCTCCTCCGT CGCGCTGGAC
1681 CAGAGGGAGG AGGTGCCCCT CACTAGATAA GGGGCCGCCG GCTGGCTGCC GGCTCCATGA
1741 CGCCCGTGGG GTCACCCCCC GGCCCCGGGA CTCAGCCAGC CTCGCTCCTC GCTCCTCGCT
1801 CCTCGCCCCT AGGACGCCAA GGGGGAAAGG AGAGGGCGGA AAAGGACCAG CGGGATCCGG
1861 CCGCAAGAAT TGGAAAGCCT AGGAAGTGGC GGTGGCTGGC GCGTTTGGGG AGCAGGAGTG
1921 GGGATAGGGA AGCAGAGCTT GAGAGACCTT CCTCCGGGGC AGCCTCCGGA CCCACCGCCC
1981 CCCACCAGGG TCGAGGCTGT AGCTCCAAAG CTAAACAAAA CTTAGCAGCA ACAGCAACCA
2041 ATATCCAGTC CCTCGGCCCC TCGGCCCCTC ACCCTCCACC TCACACTCCC TTCTCACCGG
2101 GCCCCCTCTC CCCAGCCAAG GCCCAAGCAC TGGAAAGGGA AATTGCTGTC TCTCTGAACA
2161 AAATGCTGTG TATGCAGAGC AGGTAGAGAT TAATCTTTGC CAGCTTTTCC AAGGCATGAC
2221 AAGGGGCTGG TGGATGGCAA CATACCAGTC ATTTGGAGGA GAGAGTGAGA GATGATTTAC
2281 TACCAGGGAG AATCCAGCCC CTTGGCATGG GACCTGGAGC CTCGACTACA CAGCATCTTC
2341 TGGGTCTGGC GTCTGCCAGC ACCTGATCTC TTTCCTCATT CCCAGCTTTG TGACACTTCT
2401 CAACTTGCGG CTCCATCTCT CCCTGCCCCC ACTTTTTTGT TGGCCAGGGA GGCTGCAGAT
2461 GCCCCAGGAG CCCTTTGCCG CTTCTATGAG GCCAAGCCTT TTTTCCCTGG GCCCAGCACA
2521 CACCCTGATT AGCAAGTGAT GTGTGCGAGG AGGGTTTGTG AATGTTGAAT GTGTAATAAT
2581 GATCACCATG GAGCTGGCCA CTGACCCCAG AGCTGAGCTG TTAACAAGGC GCCCAGGGAA
2641 GAGCTTAGGG AGTGGGAACT TCACCTCCCT CTCTCGGTAT CTGGCGGTAA ATTAGAGGCA
2701 ATTTTCATCC TTTGCTTGTT CACCTTCACT TCACCAGGAA CTTTCTGGCC CTACCCTTTG
2761 CATTGGGTAT TTTACAACTT TCTCTCATTT TCTTCCCAAG CTACCACTGG AGCTTGACTT
2821 TCAGATACCA GTGGGAGCCT TCTGTCCCTT TTGGGGACCC TGTCTGTGGC CTCCACCAGG
2881 GTTTGTTTAG AGCCACTCCC AAATCCTCAC TCCCACACTC ATCCTTGCAG CCAGTTTTTG
2941 AGGAAGAGGA GAACGTGTAA CCCCAATGCA AGCTTCACCC TGACTGAGAG GGAGTGGTTC
3001 TTCCTGTAGG GAATGAATTT GGTTTGATTT GGGGTTTTCC TTTGAAGCCC AAAGAACTTG
3061 CTGTTATGAT TCGTTAACCA TATTGCAATA AAAGCTGGAC ATAA
```

SEQ ID NO: 16
Grrp1; human (NM_024869)

```
   1 GAGTGAGGTT TGGCTGCCAC CAAAGTTACT TCTAGTCCTT GCTGTCCACT CCTGCCCTCA
  61 GTCTGGACCT GCCCAAGGAC CCCTGCAATT AGGCCTCCCA TGCAGAGGTC AGTGAGAGCC
```

```
 121 CAAGCCAATT GCTCTAGGCC CCGTGGCTGG CTACTTATGG GGCACTGTCC TGACCAGCTC
 181 TGCTAAGATG CTCCTGGCCC CTCCCTCCAC CCCGTCCAGA GGACGGACCC CCAGCGCCGT
 241 GGAGAGGCTG GAAGCCGACA AAGCCAAGTA TGTCAAGACG CACCAGGTGA TAGCTAGGCG
 301 ACAGGAGCCA GCCCTGCGTG GGAGTCCTGG GCCGCTCACG CCGCACCCCT GCAACGAGCT
 361 GGGGCCCCCT GCATCGCCCA GGACGCCCAG GCCGGTCCGC CGGGGAAGCG GCAGGCGGCT
 421 GCCGAGGCCT GATTCCCTCA TCTTCTACCG CCAGAAGCGG GACTGCAAGG CTTCGGTGAA
 481 CAAAGAGAAC GCCAAGGGCC AGGGTCTGGT GCGGCGCCTC TTTCTGGGTG CCCCGCGGGA
 541 CGCTGCCCCG AGCAGCCCGG CCTCCACAGA GCGACCTGCG GCTTCAGGGG GTTGGGCTGC
 601 GCCCCAGGAT GCCCCGGAAG CGGCGGGAAA GCGGGCGCTG TGTCCCACGT GCTCGCTGCC
 661 CCTGTCGGAG AAGGAGCGCT TCTTCAACTA CTGCGGCCTG GAGCGCGCGC TGGTGGAGGT
 721 GCTGGGCGCA GAGCGCTTCT CCCCGCAGAG CTGGGGAGCC GACGCCAGCC CGCAGGCCGG
 781 AACTTCGCCG CCGCCCGGCT CCGGGGACGC CAGCGACTGG ACATCCAGCG ACAGGGGCGT
 841 GGACAGCCCG GGCGGCGCGG GCGGCGGCGG CGGCTCGGAG GCAGCGGGCT CGGCGCGGGA
 901 CCGGCGCCCC CCGGTGTCGG TGGTGGAGCG CAACGCGCGC GTCATCCAGT GGCTGTACGG
 961 CTGCCAGCGC GCCCGCGGAC CGCCGCGCGA GTCCGAGGTG TGACCGCCGC GGCTCCGGAC
1021 TGGCCCCGGG ACTGGCCCCG GGCACGGAAA AGGACACCCC TCTTCTGGCG CGCTGGGTGC
1081 CTTTGCGTAA GCCCTTCCTT CTGGAACTCA GTTTCGCGTC TGAACCTTGG GGAGGTGGAA
1141 CAAGTTGCTG CCGAAGGCCC TTCCCTGCTC CCGCGGCGAA GGGGGAGGGA GAGGCCTCTT
1201 GGTCCCTGTG GAGACCCGGT CTGGGGAGTC ACGATTGGGG TGGGAGATGA GCAAACCTGC
1261 TGAATAAAGT TAAAACGTTA TTTAAATGGG GAGCTGAGGA AGGAGCAAAC GGGTTTTCGC
1321 GGTTAAACCC GTGGGTTTTG GAATGTGTGT TCCCGGCTGT GTGATCCTGG GCAAGAACTT
1381 GACCTCCCTG GACGCAGCGG CACCCCTCGG TTATTAAGGA GGGAGGAGTA GGGGATAGAA
1441 GTATTTCAAA ATAGTTGTAA TGCGCATGGC AAAGTGCCCA GCATATAGAA AGTGCTCAAT
1501 AAACGATAAC TGCTGTGACT TCTAAAAAAA AAAAAAAAAA AAAAAAAAAA AAAAAAAAA
1561 AAAAAAAA
```
SEQ ID NO: 17
Mesp1; HUMAN NM_018670.3
```
    1 TGGAAGGGGC CACTTCACAC CTCGGGCTCG GCATAAAGCG GCCGCCGGCC
GCCGGCCCCC
   61 AGACGCGCCG CCGCTGCCAT GGCCCAGCCC CTGTGCCCGC CGCTCTCCGA GTCCTGGATG
  121 CTCTCTGCGG CCTGGGGCCC AACTCGGCGG CCGCCGCCCT CCGACAAGGA CTGCGGCCGC
  181 TCCCTCGTCT CGTCCCCAGA CTCATGGGGC AGCACCCCAG CCGACAGCCC CGTGGCGAGC
  241 CCCGCGCGGC CAGGCACCCT CCGGGACCCC CGCGCCCCCT CCGTAGGTAG GCGCGGCGCG
  301 CGCAGCAGCC GCCTGGGCAG CGGGCAGAGG CAGAGCGCCA GTGAGCGGGA GAAACTGCGC
  361 ATGCGCACGC TGGCCCGCGC CCTGCACGAG CTGCGCCGCT TCTACCGCCC GTCCGTGGCG
  421 CCCGCGGGCC AGAGCCTGAC CAAGATCGAG ACGCTGCGCC TGGCTATCCG CTATATCGGC
  481 CACCTGTCGG CCGTGCTAGG CCTCAGCGAG GAGAGTCTCC AGCGCCGGTG CCGGCAGCGC
  541 GGTGACGCGG GGTCCCCTCG GGGCTGCCCG CTGTGCCCCG ACGACTGCCC CGCGCAGATG
  601 CAGACACGGA CGCAGGCTGA GGGGCAGGGG CAGGGGCGCG GCTGGGCCT GGTATCCGCC
  661 GTCCGCGCCG GGGCGTCCTG GGGATCCCCG CCTGCCTGCC CCGGAGCCCG AGCTGCACCC
  721 GAGCCGCGCG ACCCGCCTGC GCTGTTCGCC GAGGCGGCGT GCCCTGAAGG GCAGGCGATG
  781 GAGCCAAGCC CACCGTCCCC GCTCCTTCCG GGCGACGTGC TGGCTCTGTT GGAGACCTGG
  841 ATGCCCCTCT CGCCTCTGGA GTGGCTGCCT GAGGAGCCCA AGTGACAAGG ACAACTGAC
  901 GCCGTCTCTG TGAGCACCGA GGCTTTTTGG CCTCAGCACC TTCGAAGTGG TTCCTTGGCA
  961 GACTGCCTTT CCTGGAAGAG GGCACGGGCG ATCCCGACGG GGGCATTCCT GCGGGTGAGA
 1021 GCCGTCCCCA CCGCGGCGGC CCTTCTCAGC CCCTCCCTCC ATGGAGGGAC CCATAGGGCT
 1081 AGACACTTTG AGGCAAGCAG GAGGCTCTGC CTAATGTGAA TTTATTTATT TGTGAATAAA
 1141 CTGTACTGGT GTCAGTTGGC AAAAAAAAAA AAAAAAAAAA AAAA
```
SEQ ID NO: 18
Foxa2; HUMAN NM_021784.4
```
   1 CCCGCCCACT TCCAACTACC GCCTCCGGCC TGCCCAGGGA GAGAGAGGGA GTGGAGCCCA
  61 GGGAGAGGGA GCGCGAGAGA GGGAGGGAGG AGGGGACGGT GCTTTGGCTG ACTTTTTTTT
 121 AAAAGAGGGT GGGGGTGGGG GGTGATTGCT GGTCGTTTGT TGTGGCTGTT AAATTTTAAA
 181 CTGCCATGCA CTCGGCTTCC AGTATGCTGG GAGCGGTGAA GATGGAAGGG CACGAGCCGT
 241 CCGACTGGAG CAGCTACTAT GCAGAGCCCG AGGGCTACTC CTCCGTGAGC AACATGAACG
 301 CCGGCCTGGG GATGAACGGC ATGAACACGT ACATGAGCAT GTCGGCGGCC GCCATGGGCA
 361 GCGGCTCGGG CAACATGAGC GCGGGCTCCA TGAACATGTC GTCGTACGTG GGCGCTGGCA
 421 TGAGCCCGTC CCTGGCGGGG ATGTCCCCCG GCGCGGGCGC CATGGCGGGC ATGGGCGGCT
 481 CGGCCGGGGC GGCCGGCGTG GCGGGCATGG GCCGCACTT GAGTCCCAGC CTGAGCCCGC
```
FIG. 14 (Cont.)

```
 541 TCGGGGGGCA GGCGGCCGGG GCCATGGGCG GCCTGGCCCC CTACGCCAAC ATGAACTCCA
 601 TGAGCCCCAT GTACGGGCAG GCGGGCCTGA GCCGCGCCCG CGACCCCAAG ACCTACAGGC
 661 GCAGCTACAC GCACGCAAAG CCGCCCTACT CGTACATCTC GCTCATCACC ATGGCCATCC
 721 AGCAGAGCCC CAACAAGATG CTGACGCTGA GCGAGATCTA CCAGTGGATC ATGGACCTCT
 781 TCCCCTTCTA CCGGCAGAAC CAGCAGCGCT GGCAGAACTC CATCCGCCAC TCGCTCTCCT
 841 TCAACGACTG TTTCCTGAAG GTGCCCCGCT CGCCCGACAA GCCCGGCAAG GGCTCCTTCT
 901 GGACCCTGCA CCCTGACTCG GGCAACATGT TCGAGAACGG CTGCTACCTG CGCCGCCAGA
 961 AGCGCTTCAA GTGCGAGAAG CAGCTGGCGC TGAAGGAGGC CGCAGGCGCC GCCGGCAGCG
1021 GCAAGAAGGC GGCCGCCGGA GCCCAGGCCT CACAGGCTCA ACTCGGGGAG GCCGCCGGGC
1081 CGGCCTCCGA GACTCCGGCG GGCACCGAGT CGCCTCACTC GAGCGCCTCC CCGTGCCAGG
1141 AGCACAAGCG AGGGGGCCTG GGAGAGCTGA AGGGACGCC GGCTGCGGCG CTGAGCCCCC
1201 CAGAGCCGGC GCCCTCTCCC GGGCAGCAGC AGCAGGCCGC GGCCCACCTG CTGGGCCCGC
1261 CCCACCACCC GGGCCTGCCG CCTGAGGCCC ACCTGAAGCC GGAACACCAC TACGCCTTCA
1321 ACCACCCGTT CTCCATCAAC AACCTCATGT CCTCGGAGCA GCAGCACCAC CACAGCCACC
1381 ACCACCACCA ACCCACAAA ATGGACCTCA AGGCCTACGA ACAGGTGATG CACTACCCCG
1441 GCTACGGTTC CCCCATGCCT GGCAGCTTGG CCATGGGCCC GGTCACGAAC AAAACGGGCC
1501 TGGACGCCTC GCCCCTGGCC GCAGATACCT CCTACTACCA GGGGGTGTAC TCCCGGCCCA
1561 TTATGAACTC CTCTTAAGAA GACGACGGCT TCAGGCCCGG CTAACTCTGG CACCCCGGAT
1621 CGAGGACAAG TGAGAGAGCA AGTGGGGGTC GAGACTTTGG GGAGACGGTG TTGCAGAGAC
1681 GCAAGGGAGA AGAAATCCAT AACACCCCA CCCCAACACC CCCAAGACAG CAGTCTTCTT
1741 CACCCGCTGC AGCCGTTCCG TCCCAAACAG AGGGCCACAC AGATACCCCA CGTTCTATAT
1801 AAGGAGGAAA ACGGGAAAGA ATATAAAGTT AAAAAAAAGC CTCCGGTTTC CACTACTGTG
1861 TAGACTCCTG CTTCTTCAAG CACCTGCAGA TTCTGATTTT TTTGTTGTTG TTGTTCTCCT
1921 CCATTGCTGT TGTTGCAGGG AAGTCTTACT TAAAAAAAAA AAAAATTTT GTGAGTGACT
1981 CGGTGTAAAA CCATGTAGTT TTAACAGAAC CAGAGGGTTG TACTATTGTT TAAAAACAGG
2041 AAAAAAAATA ATGTAAGGGT CTGTTGTAAA TGACCAAGAA AAAGAAAAAA AAAGCATTCC
2101 CAATCTTGAC ACGGTGAAAT CCAGGTCTCG GGTCCGATTA ATTTATGGTT TCTGCGTGCT
2161 TTATTTATGG CTTATAAATG TGTATTCTGG CTGCAAGGGC CAGAGTTCCA CAAATCTATA
2221 TTAAAGTGTT ATACCCGGTT TTATCCCTTG AATCTTTTCT TCCAGATTTT TCTTTTCTTT
2281 ACTTGGCTTA CAAAATATAC AGGCTTGGAA ATTATTTCAA GAAGGAGGGA GGGATACCCT
2341 GTCTGGTTGC AGGTTGTATT TTATTTTGGC CCAGGGAGTG TTGCTGTTTT CCCAACATTT
2401 TATTAATAAA ATTTTCAGAC ATAAAAAA
```

SEQ ID NO: 19
TCF3; HUMAN NM_001136139.3

```
   1 GGTTTCCAGG CCTGAGGTGC CCGCCCTGGC CCCAGGAGAA TGAACCAGCC GCAGAGGATG
  61 GCGCCTGTGG GCACAGACAA GGAGCTCAGT GACCTCCTGG ACTTCAGCAT GATGTTCCCG
 121 CTGCCTGTCA CCAACGGGAA GGGCCGGCCC GCCTCCCTGG CCGGGGCGCA GTTCGGAGGT
 181 TCAGGTCTTG AGGACCGGCC CAGCTCAGGC TCCTGGGGCA GCGGCGACCA GAGCAGCTCC
 241 TCCTTTGACC CCAGCCGGAC CTTCAGCGAG GCACCCACT TCACTGAGTC GCACAGCAGC
 301 CTCTCTTCAT CCACATTCCT GGGACCGGGA CTCGGAGGCA AGAGCGGTGA GCGGGGCGCC
 361 TATGCCTCCT TCGGGAGAGA CGCAGGCGTG GGCGGCCTGA CTCAGGCTGG CTTCCTGTCA
 421 GGCGAGCTGG CCCTCAACAG CCCCGGGCCC CTGTCCCCTT CGGGCATGAA GGGGACCTCC
 481 CAGTACTACC CCTCCTACTC CGGCAGCTCC GGCGGAGAG CGGCAGACGG CAGCCTAGAC
 541 ACGCAGCCCA AGAAGGTCCG GAAGGTCCCG CCGGGTCTTC CATCCTCGGT GTACCCACCC
 601 AGCTCAGGTG AGGACTACGG CAGGGATGCC ACCGCCTACC CGTCCGCCAA GACCCCAGC
 661 AGCACCTATC CCGCCCCCTT CTACGTGGCA GATGGCAGCC TGCACCCCTC AGCCGAGCTC
 721 TGGAGTCCCC CGGGCCAGGC GGGCTTCGGG CCCATGCTGG GTGGGGCTC ATCCCCGCTG
 781 CCCCTCCCGC CCGGTAGCGG CCCGGTGGGC AGCAGTGGAA GCAGCAGCAC GTTTGGTGGC
 841 CTGCACCAGC ACGAGCGTAT GGGCTACCAG CTGCATGGAG CAGAGGTGAA CGGTGGGCTC
 901 CCATCTGCAT CCTCCTTCTC CTCAGCCCCC GGAGCCACGT ACGGCGGCGT CTCCAGCCAC
 961 ACGCCGCCTG TCAGCGGGGC CGACAGCCTC TGGGCTCCC GAGGGACCAC AGCTGGCAGC
1021 TCCGGGGATG CCCTCGGCAA AGCACTGGCC TCGATCTACT CCCCGGATCA CTCAAGCAAT
1081 AACTTCTCGT CCAGCCCTTC TACCCCCGTG GGCTCCCCC AGGGCCTGGC AGGAACGTCA
1141 CAGTGGCCTC GAGCAGGAGC CCCGGTGCC TTATCGCCCA GCTACGACGG GGGTCTCCAC
1201 GGCCTGCAGA GTAAGATAGA AGACCACCTG GACGAGGCCA TCCACGTGCT CCGCAGCCAC
1261 GCCGTGGGCA CAGCCGGCGA CATGCACACG CTGCTGCCTG GCACGGGGGC GCTGGCCTCA
1321 GGTTTCACCG GCCCCATGTC ACTGGGCGGG CGGCACGCAG GCCTGGTTGG AGGCAGCCAC
1381 CCCGAGGACG GCCTCGCAGG CAGCACCAGC CTCATGCACA ACCACGCGGC CCTCCCCAGC
1441 CAGCCAGGCA CCCTCCCTGA CCTGTCTCGG CCTCCCGACT CCTACAGTGG GCTAGGGCGA
1501 GCAGGTGCCA CGGCGGCCGC CAGCGAGATC AAGCGGGAGG AGAAGGAGGA CGAGGAGAAC
```

FIG. 14 (Cont.)

```
1561 ACGTCAGCGG CTGACCACTC GGAGGAGGAG AAGAAGGAGC TGAAGGCCCC CCGGGCCCGG
1621 ACCAGCAGTA CGGACGAGGT GCTGTCCCTG GAGGAGAAAG ACCTGAGGGA CCGGGAGAGG
1681 CGCATGGCCA ATAACGCGCG GGAGCGGGTG CGCGTGCGGG ATATTAACGA GGCCTTCCGG
1741 GAGCTGGGGC GCATGTGCCA GATGCACCTC AAGTCGGACA AAGCGCAGAC CAAGCTGCTC
1801 ATCCTGCAGC AGGCCGTGCA GGTCATCCTG GGGCTGGAGC AGCAGGTGCG AGAGCGGAAC
1861 CTGAATCCCA AAGCAGCCTG TTTGAAACGG CGAGAAGAGG AAAAGGTGTC AGGTGTGGTT
1921 GGAGACCCCC AGATGGTGCT TTCAGCTCCC CACCCAGGCC TGAGCGAAGC CCACAACCCC
1981 GCCGGGCACA TGTGAAAGTA AACAAAACCT GAAAGCAAGC AACAAAACAT ACACTTTGTC
2041 AGAGAAGAAA AAAATGCCTT AACTATAAAA AGCGGAGAAA TGGAAACATA TCACTCAAGG
2101 GGGATGCTGT GGAAACCTGG CTTATTCTTC TAAAGCCACC AGCAAATTGT GCCTAAGCGA
2161 AATATTTTTT TTAAGGAAAA TAAAAACATT AGTTACAAGA TTTTTTTTTT CTTAATGTAG
2221 ATGAAAATTA GCAAGGATGC TGCCTTTGGT CTCTGGTTTT TTTAAGCTTT TTTTGCATAT
2281 GTTTTGTAAG CAACAAATTT TTTTGTATAA AAGTCCCGTG TCTCTCGCTA TTTCTGCTGC
2341 TGTTCCTAGA CTGAGCATTG CATTTCTTGA TCAACCAGAT GATTAAACGT TGTATTAAAA
2401 AGACCCCGTG TAAACCTGAG CCCCCCCGTC CCCCCCCCCC CCGGAAGCC ACTGCACACA
2461 GACAGAACGG GGACAGGCGG CGGGTCTTTT GTTTTTTTGA TGTTGGGGGT TCTCTTGGTT
2521 TTGTCATGTG GAAAGTGATG CGTGGGCGTT CCCTGATGAA GGCACCTTGG GGCTTCCCTG
2581 CCGCATCCTC TCCCCTCAGG AAGGGGACTG ACCTGGGCTT GGGGAAGGG ACGTCAGCAA
2641 GGTGGCTCTG ACCCTCCCAG GTGACTCTGC CAAGCAGCTG TGGCCCCAG GGCTACCCTA
2701 CACAACGCCC TCCCCAGGCC CCCTAAGCT GCTCTCCCTT GGAACCTGCA CAGCTCTCTG
2761 AAATGGGGCA TTTTGTTGGG ACCAGTGACC CCTGGCATGG GGACCACACC CTGGAGCCCG
2821 GTGCTGGGGA CCTCCTGGAC ACCCTGTCCT TCACTCCTTT GCCCAGGGA CCCAGGCTCA
2881 TGCTCTGAAC TCTGGCTGAG AGGATGCTGC TCAGGAGCCA GCACAGGACA CCCCCCACCC
2941 CACCCCACCA TGTCCCCATT ACACCAGAGG GCCATCGTGA CGTAGACAGG ATGCCAGGGG
3001 CCTGGCCAGC CTCCCCCAAT GCTGGGAGC ATCCCTGGGC CTGGGGCCAC ACCTGCTGCC
3061 CTCCCTCTGT GTGGTCCAAG GGCAAGAGTG GCTGGAGCCG GGGGACTGTG CTGGTCTGAG
3121 CCCCACGAAG GCCTTGGGCT GTGCGTCCGA CCCTGCTGCA GAACCAGCAG GGTGTCCCCT
3181 CGGGCCCATC TGTGTCCCAT GTCCCAGCAC CCAGGCCTCT CTCCAGGTCT CCTTTTCTGG
3241 TCTTTTGCCA TGAGGGTAAC CAGCTCTTCC CAGCTGGCTG GGGACTGTCT TGGGTTTAAA
3301 ACTGCAAGTC TCCTACCCTG GGATCCCATC CAGTTCCACA CGAACTAGGG CAGTGGTCAC
3361 TGTGGCACCC AGGTGTGGGC CTGGCTAGCT GGGGGCCTTC ATGTGCCCTT CATGCCCCTC
3421 CCTGCATTGA GGCCTTGTGG ACCCCTGGGC TGGCTGTGTT CATCCCCGCT GCAGGTCGGG
3481 CGTCTCCCCC CGTGCCACTC CTGAGACTCC CACCGTTACC CCCAGGAGAT CCTGGACTGC
3541 CTGACTCCCC TCCCCAGACT GGCTTGGGAG CCTGGGCCCC ATGGTAGATG CAAGGGAAAC
3601 CTCAAGGCCA GCTCAATGCC TGGTATCTGC CCCCAGTCCA GGCCAGGCGG AGGGGAGGGG
3661 CTGTCCGGCT GCCTCTCCCT TCTCGGTGGC TTCCCCTACG CCCTGGGAGT TTGATCTCTT
3721 AAGGGAACTT GCCTCTCCCT CTTGTTTTGC TCCTGGCCCT GCCCCTAGGT CTGGGTGGGC
3781 AGTGGCCCCA TAGCCTCTGG AACTGTGCGT TCTGCATAGA ATTCAAACGA GATTCACCCA
3841 GCGCGAGGAG GAAGAAACAG CAGTTCCTGG GAACCACAAT TATGGGGGT GGGGGGTGTG
3901 ATCTGAGTGC CTCAAGATGG TTTTCAAAAA AATTTTTTTA AAGAAAATAA TTGTATACGT
3961 GTCAACACAG CTGGCTGGAT GATTGGGACT TTAAAACGAC CCTCTTTCAG GTGGATTCAG
4021 AGACCTGTCC TGTATATAAC AGCACTGTAG CAATAAACGT GACATTTTAT AACGATGCCC
4081 TGCA
```

SEQ ID NO: 20
ID1;HUMAN NM_002165.3

```
  1 ACTCTCATTC CACGTTCTTA ACTGTTCCAT TTTCCGTATC TGCTTCGGGC TTCCACCTCA
 61 TTTTTTTCGC TTTGCCCATT CTGTTTCAGC CAGTCGCCGA GAATCATGAA AGTCGCCAGT
121 GGCAGCACCG CCACCGCCGC CGCCGCCCGA AGCTGCCGCC TGAAGCCGG CAAGACAGCG
181 AGCGGTGCGG GCGAGGTGGT GCGCTGTCTG TCTGAGCAGA GCGTGGCCAT CTCGCGCTGC
241 GCCGGGGGCG CCGGGGCGCG CCTGCCTGCC CTGCTGGACG AGCAGCAGGT AAACGTGCTG
301 CTCTACGACA TGAACGGCTG TTACTCACGC CTCAAGGAGC TGGTGCCCAC CCTGCCCCAG
361 AACCGCAAGG TGAGCAAGGT GGAGATTCTC CAGCACGTCA TCGACTACAT CAGGGACCTT
421 CAGTTGGAGC TGAACTCGGA ATCCGAAGTT GGAACCCCG GGGGCCGAGG GCTGCCGGTC
481 CGGGCTCCGC TCAGCACCCT CAACGGCGAG ATCAGCGCCC TGACGGCCGA GGCGGCATGC
541 GTTCCTGCGG ACGATCGCAT CTTGTGTCGC TGAAGCGCCT CCCCCAGGGA CCGGCGGACC
601 CCAGCCATCC AGGGGGCAAG AGGAATTACG TGCTCTGTGG GTCTCCCCCA ACGCGCCTCG
661 CCGGATCTGA GGGAGAACAA GACCGATCGG CGGCCACTGC GCCCTTAACT GCATCCAGCC
721 TGGGGCTGAG GCTGAGGCAC TGGCGAGGAG AGGGCGCTCC TCTCTGCACA CCTACTAGTC
781 ACCAGAGACT TTAGGGGGTG GGATTCCACT CGTGTGTTTC TATTTTTTGA AAAGCAGACA
841 TTTTAAAAAA TGGTCACGTT TGGTGCTTCT CAGATTTCTG AGGAAATTGC TTTGTATTGT
```

```
 901 ATATTACAAT GATCACCGAC TGAAAATATT GTTTTACAAT AGTTCTGTGG GGCTGTTTTT
 961 TTGTTATTAA ACAAATAATT TAGATGGTGG TAAAAAAAAA
```

SEQ ID NO: 21
FOXA2; HUMAN NM_153675.2

```
   1 CGGCCGCTGC TAGAGGGGCT GCTTGCGCCA GGCGCCGGCC GCCCCACTGC GGGTCCCTGG
  61 CGGCCGGTGT CTGAGGAGTC GGAGAGCCGA GGCGGCCAGA CCGTGCGCCC CGCGCTTCTC
 121 CCGAGGCCGT TCCGGGTCTG AACTGTAACA GGGAGGGGCC TCGCAGGAGC AGCAGCGGGC
 181 GAGTTAAAGT ATGCTGGGAG CGGTGAAGAT GGAAGGGCAC GAGCCGTCCG ACTGGAGCAG
 241 CTACTATGCA GAGCCCGAGG GCTACTCCTC CGTGAGCAAC ATGAACGCCG GCCTGGGGAT
 301 GAACGGCATG AACACGTACA TGAGCATGTC GGCGGCCGCC ATGGGCAGCG GCTCGGGCAA
 361 CATGAGCGCG GGCTCCATGA ACATGTCGTC GTACGTGGGG CTGGCATGA GCCCGTCCCT
 421 GGCGGGGATG TCCCCCGGCG CGGGCGCCAT GGCGGGCATG GGCGGCTCGG CCGGGGCGGC
 481 CGGCGTGGCG GGCATGGGGC CGCACTTGAG TCCCAGCCTG AGCCGCTCG GGGGGCAGGC
 541 GGCCGGGGCC ATGGGCGGCC TGGCCCCCTA CGCCAACATG AACTCCATGA GCCCCATGTA
 601 CGGGCAGGCG GGCCTGAGCC GCGCCCGCGA CCCCAAGACC TACAGGCGCA GCTACACGCA
 661 CGCAAAGCCG CCCTACTCGT ACATCTCGCT CATCACCATG GCCATCCAGC AGAGCCCCAA
 721 CAAGATGCTG ACGCTGAGCG AGATCTACCA GTGGATCATG GACCTCTTCC CCTTCTACCG
 781 GCAGAACCAG CAGCGCTGGC AGAACTCCAT CCGCCACTCG CTCTCCTTCA CGACTGTTT
 841 CCTGAAGGTG CCCCGCTCGC CGACAAGCC CGGCAAGGGC TCCTTCTGGA CCCTGCACCC
 901 TGACTCGGGC AACATGTTCG AGAACGGCTG CTACCTGCGC CGCCAGAAGC GCTTCAAGTG
 961 CGAGAAGCAG CTGGCGCTGA AGGAGGCCGC AGGCGCCGCC GGCAGCGGCA AGAAGGCGGC
1021 CGCCGGAGCC CAGGCCTCAC AGGCTCAACT CGGGGAGGCC GCGGGCCGG CCTCCGAGAC
1081 TCCGGCGGGC ACCGAGTCGC CTCACTCGAG CGCCTCCCCG TGCCAGGAGC ACAAGCGAGG
1141 GGGCCTGGGA GAGCTGAAGG GGACGCCGGC TGCGGCGCTG AGCCCCCAG AGCCGGCGCC
1201 CTCTCCCGGG CAGCAGCAGC AGGCCGCGGC CCACCTGCTG GGCCCGCCCC ACCACCCGGG
1261 CCTGCCGCCT GAGGCCCACC TGAAGCCGGA ACACCACTAC GCCTTCAACC ACCCGTTCTC
1321 CATCAACAAC CTCATGTCCT CGGAGCAGCA GCACCACCAC AGCCACCACC ACCACCAACC
1381 CCACAAAATG GACCTCAAGG CCTACGAACA GGTGATGCAC TACCCCGGCT ACGGTTCCCC
1441 CATGCCTGGC AGCTTGGCCA TGGGCCCGGT CACGAACAAA ACGGGCCTGG ACGCCTCGCC
1501 CCTGGCCGCA GATACCTCCT ACTACCAGGG GGTGTACTCC CGGCCCATTA TGAACTCCTC
1561 TTAAGAAGAC GACGGCTTCA GGCCCGGCTA ACTCTGGCAC CCCGGATCGA GGACAAGTGA
1621 GAGAGCAAGT GGGGGTCGAG ACTTTGGGGA GACGGTGTTG CAGAGACGCA AGGGAGAAGA
1681 AATCCATAAC ACCCCCACCC CAACACCCCC AAGACAGCAG TCTTCTTCAC CCGCTGCAGC
1741 CGTTCCGTCC CAAACAGAGG GCCACACAGA TACCCCACGT TCTATATAAG GAGGAAAACG
1801 GGAAAGAATA TAAAGTTAAA AAAAAGCCTC CGGTTTCCAC TACTGTGTAG ACTCCTGCTT
1861 CTTCAAGCAC CTGCAGATTC TGATTTTTT GTTGTTGTTG TTCTCCTCCA TTGCTGTTGT
1921 TGCAGGGAAG TCTTACTTAA AAAAAAAAA AAATTTTGTG AGTGACTCGG TGTAAAACCA
1981 TGTAGTTTTA ACAGAACCAG AGGGTTGTAC TATTGTTTAA AAACAGGAAA AAAAATAATG
2041 TAAGGGTCTG TTGTAAATGA CCAAGAAAAA GAAAAAAAAA GCATTCCCAA TCTTGACACG
2101 GTGAAATCCA GGTCTCGGGT CCGATTAATT TATGGTTTCT GCGTGCTTTA TTTATGGCTT
2161 ATAAATGTGT ATTCTGGCTG CAAGGGCCAG AGTTCCACAA ATCTATATTA AAGTGTTATA
2221 CCCGGTTTTA TCCCTTGAAT CTTTTCTTCC AGATTTTTCT TTTCTTTACT TGGCTTACAA
2281 AATATACAGG CTTGGAAATT ATTTCAAGAA GGAGGGAGGG ATACCCTGTC TGGTTGCAGG
2341 TTGTATTTTA TTTTGGCCCA GGGAGTGTTG CTGTTTTCCC AACATTTTAT TAATAAAATT
2401 TCAGACATA AAAAA
```

SEQ ID NO: 22
TCF3; HUMAN NM_001351778.1

```
   1 ACGCGCCGCG TGCCCGGCCG CGCCCAGCAG GGTTTCCAGG CCTGAGGTGC CCGCCCTGGC
  61 CCCAGGAGAA TGAACCAGCC GCAGAGGATG GCGCCTGTGG GCACAGACAA GGAGCTCAGT
 121 GACCTCCTGG ACTTCAGCAT GATGTTCCCG CTGCCTGTCA CCAACGGGAA GGGCCGGCCC
 181 GCCTCCCTGG CCGGGGCGCA GTTCGGAGGT TCAGGTCTTG AGGACCGGCC CAGCTCAGGC
 241 TCCTGGGGCA GCGGCGACCA GAGCAGCTCC TCCTTTGACC CCAGCCGGAC CTTCAGCGAG
 301 GGCACCCACT TCACTGAGTC GCACAGCAGC CTCTCTTCAT CCACATTCCT GGGACCGGGA
 361 CTCGGAGGCA AGAGCGGTGA GCGGGGCGCC TATGCCTCCT TCGGGAGAGA CGCAGGCGTG
 421 GGCGGCCTGA CTCAGGCTGG CTTCCTGTCA GGCGAGCTGG CCCTCAACAG CCCCGGGCCC
 481 CTGTCCCCTT CGGGCATGAA GGGGACCTCC CAGTACTACC CCTCCTACTC CGGCAGCTCC
 541 CGGCGGAGAG CGGCAGACGG CAGCCTAGAC ACGCAGCCCA AGAAGGTCCG GAAGGTCCCG
 601 CCGGGTCTTC CATCCTCGGT GTACCCACCC AGCTCAGGTG AGGACTACGG CAGGGATGCC
 661 ACCGCCTACC CGTCCGCCAA GACCCCAGC AGCACCTATC CGCCCCCTT CTACGTGGCA
```

FIG. 14 (Cont.)

```
 721 GATGGCAGCC TGCACCCCTC AGCCGAGCTC TGGAGTCCCC CGGGCCAGGC GGGCTTCGGG
 781 CCCATGCTGG GTGGGGGCTC ATCCCCGCTG CCCCTCCCGC CCGGTAGCGG CCCGGTGGGC
 841 AGCAGTGGAA GCAGCAGCAC GTTTGGTGGC CTGCACCAGC ACGAGCGTAT GGGCTACCAG
 901 CTGCATGGAG CAGAGGTGAA CGGTGGGCTC CCATCTGCAT CCTCCTTCTC CTCAGCCCCC
 961 GGAGCCACGT ACGGCGGCGT CTCCAGCCAC ACGCCGCCTG TCAGCGGGGC CGACAGCCTC
1021 CTGGGCTCCC GAGGGACCAC AGCTGGCAGC TCCGGGGATG CCCTCGGCAA AGCACTGGCC
1081 TCGATCTACT CCCCGGATCA CTCAAGCAAT AACTTCTCGT CCAGCCCTTC TACCCCCGTG
1141 GGCTCCCCCC AGGGCCTGGC AGGAACGTCA CAGTGGCCTC GAGCAGGAGC CCCCGGTGCC
1201 TTATCGCCCA GCTACGACGG GGGTCTCCAC GGCCTGAGTA AGATAGAAGA CCACCTGGAC
1261 GAGGCCATCC ACGTGCTCCG CAGCCACGCC GTGGGCACAG CCGGCGACAT GCACACGCTG
1321 CTGCCTGGCC ACGGGGCGCT GGCCTCAGGT TTCACCGGCC CCATGTCACT GGGCGGGCGG
1381 CACGCAGGCC TGGTTGGAGG CAGCCACCCC GAGGACGGCC TCGCAGGCAG CACCAGCCTC
1441 ATGCACAACC ACGCGGCCCT CCCCAGCCAG CCAGGCACCC TCCTGACCT GTCTCGGCCT
1501 CCCGACTCCT ACAGTGGGCT AGGGCGAGCA GGTGCCACGG CGGCCGCCAG CGAGATCAAG
1561 CGGGAGGAGA AGGAGGACGA GGAGAACACG TCAGCGGCTG ACCACTCGGA GGAGGAGAAG
1621 AAGGAGCTGA AGGCCCCCG GGCCCGGACC AGCCCAGACG AGGACGAGGA CGACCTTCTC
1681 CCCCAGAGC AGAAGGCCGA GCGGGAGAAG GAGCGCCGGG TGGCCAATAA CGCCCGGGAG
1741 CGGCTGCGGG TCCGTGACAT CAACGAGGCC TTTAAGGAGC TGGGGCGCAT GTGCCAACTG
1801 CACCTCAACA GCGAGAAGCC CCAGACCAAA CTGCTCATCC TGCACCAGGC TGTCTCGGTC
1861 ATCCTGAACT TGGAGCAGCA AGTGCGAGAG CGGAACCTGA ATCCCAAAGC AGCCTGTTTG
1921 AAACGGCGAG AAGAGGAAAA GGTGTCAGGT GTGGTTGGAG ACCCCAGAT GGTGCTTTCA
1981 GCTCCCCACC CAGGCCTGAG CGAAGCCCAC AACCCCGCCG GGCACATGTG AAAGGTCTGG
2041 GTGGGCAGTG GCCCATAGC CTCTGGAACT GTGCGTTCTG CATAGAATTC AAACGAGATT
2101 CACCCAGCGC GAGGAGGAAG AAACAGCAGT TCCTGGGAAC CACAATTATG GGGGGTGGGG
2161 GGTGTGATCT GAGTGCCTCA AGATGGTTTT CAAAAAAATT TTTTAAAGA AAATAATTGT
2221 ATACGTGTCA ACACAGCTGG CTGGATGATT GGGACTTTAA AACGACCCTC TTTCAGGTGG
2281 ATTCAGAGAC CTGTCCTGTA TATAACAGCA CTGTAGCAAT AAACGTGACA TTTTATAACG
2341 ATGCCCTGCA
```

SEQ ID NO: 23
TCF3; HUMAN NM_001351779.1

```
   1 ACGCGCCGCG TGCCCGGCCG CGCCCAGCAG GGTTTCCAGG CCTGAGGTGC CCGCCCTGGC
  61 CCCAGGAGAA TGAACCAGCC GCAGAGGATG GCGCCTGTGG GCACAGACAA GGAGCTCAGT
 121 GACCTCCTGG ACTTCAGCAT GATGTTCCCG CTGCCTGTCA CCAACGGGAA GGGCCGGCCC
 181 GCCTCCCTGG CCGGGGCGCA GTTCGGAGGT TCAGGTCTTG AGGACCGGCC CAGCTCAGGC
 241 TCCTGGGGCA GCGGCGACCA GAGCAGCTCC TCCTTTGACC CCAGCCGGAC CTTCAGCGAG
 301 GGCACCCACT TCACTGAGTC GCACAGCAGC CTCTCTTCAT CCACATTCCT GGGACCGGGA
 361 CTCGGAGGCA AGAGCGGTGA GCGGGGCGCC TATGCCTCCT TCGGAGAGA CGCAGGCGTG
 421 GGCGGCCTGA CTCAGGCTGG CTTCCTGTCA GGCGAGCTGG CCCTCAACAG CCCCGGGCCC
 481 CTGTCCCCTT CGGGCATGAA GGGGACCTCC CAGTACTACC CCTCCTACTC CGGCAGCTCC
 541 CGGCGGAGAG CGGCAGACGG CAGCCTAGAC ACGCAGCCCA AGAAGGTCCG GAAGGTCCCG
 601 CCGGGTCTTC CATCCTCGGT GTACCCACCC AGCTCAGGTG AGGACTACGG CAGGGATGCC
 661 ACCGCCTACC CGTCCGCCAA GACCCCCAGC AGCACCTATC CCGCCCCCTT CTACGTGGCA
 721 GATGGCAGCC TGCACCCCTC AGCCGAGCTC TGGAGTCCCC CGGGCCAGGC GGGCTTCGGG
 781 CCCATGCTGG GTGGGGGCTC ATCCCCGCTG CCCCTCCCGC CCGGTAGCGG CCCGGTGGGC
 841 AGCAGTGGAA GCAGCAGCAC GTTTGGTGGC CTGCACCAGC ACGAGCGTAT GGGCTACCAG
 901 CTGCATGGAG CAGAGGTGAA CGGTGGGCTC CCATCTGCAT CCTCCTTCTC CTCAGCCCCC
 961 GGAGCCACGT ACGGCGGCGT CTCCAGCCAC ACGCCGCCTG TCAGCGGGGC CGACAGCCTC
1021 CTGGGCTCCC GAGGGACCAC AGCTGGCAGC TCCGGGGATG CCCTCGGCAA AGCACTGGCC
1081 TCGATCTACT CCCCGGATCA CTCAAGCAAT AACTTCTCGT CCAGCCCTTC TACCCCCGTG
1141 GGCTCCCCCC AGGGCCTGGC AGGAACGTCA CAGTGGCCTC GAGCAGGAGC CCCCGGTGCC
1201 TTATCGCCCA GCTACGACGG GGGTCTCCAC GGCCTGCAGA GTAAGATAGA AGACCACCTG
1261 GACGAGGCCA TCCACGTGCT CCGCAGCCAC GCCGTGGGCA CAGCCGGCGA CATGCACACG
1321 CTGCTGCCTG GCCACGGGGC GCTGGCCTCA GGTTTCACCG GCCCCATGTC ACTGGGCGGG
1381 CGGCACGCAG GCCTGGTTGG AGGCAGCCAC CCCGAGGACG GCCTCGCAGG CAGCACCAGC
1441 CTCATGCACA ACCACGCGGC CCTCCCCAGC CAGCCAGGCA CCCTCCCTGA CCTGTCTCGG
1501 CCTCCCGACT CCTACAGTGG GCTAGGGCGA GCAGGTGCCA CGGCGGCCGC CAGCGAGATC
1561 AAGCGGGAGG AGAAGGAGGA CGAGGAGAAC ACGTCAGCGG CTGACCACTC GGAGGAGGAG
1621 AAGAAGGAGC TGAAGGCCCC CGGGCCCGG ACCAGCAGTA CGGACGAGGT GCTGTCCCTG
1681 GAGGAGAAAG ACCTGAGGGA CCGGGAGAGG CGCATGGCCA ATAACGCGCG GGAGCGGGTG
1741 CGCGTGCGGG ATATTAACGA GGCCTTCCGG GAGCTGGGGC GCATGTGCCA GATGCACCTC
```

```
1801 AAGTCGGACA AAGCGCAGAC CAAGCTGCTC ATCCTGCAGC AGGCCGTGCA GGTCATCCTG
1861 GGGCTGGAGC AGCAGGTGCG AGAGCGGAAC CTGAATCCCA AAGCAGCCTG TTTGAAACGG
1921 CGAGAAGAGG AAAAGGTGTC AGGTGTGGTT GGAGACCCCC AGATGGTGCT TTCAGCTCCC
1981 CACCCAGGCC TGAGCGAAGC CCACAACCCC GCCGGGCACA TGTGAAAGGT ATGCCTCCGT
2041 GGGACGAGCC ACCCGCTTTC AGCCCTGTGC TCTGGCCCCA GAACGGCCAC TCGAGACCCC
2101 GGGCTTCATC CACATCCACA CCTCACACAC CTGTTGTCAG CATCGAGCCA ACACCAACCT
2161 GACAAGGTTC GGAGTGATGG GGGCGGCCAA GGTGACACTG GGTCCAGGAG CTCCCTGGGG
2221 CCCTGGCCTA CCACTCACTG GCCTCGCTCC CCTGTCCCC GAATCTCAGC CACCGTGTCA
2281 CTCTGTGACC TGTCCCATGG ATCCTGAAAC TGCATCTTGG CCCTGTTGCC TGGGCTGACA
2341 GGAGCATTTT TTTTTTTTCC AGTAAACAAA ACCTGAAAGC AAGCAACAAA ACATACACTT
2401 TGTCAGAGAA GAAAAAAATG CCTTAACTAT AAAAAGCGGA GAAATGGAAA CATATCACTC
2461 AAGGGGGATG CTGTGGAAAC CTGGCTTATT CTTCTAAAGC CACCAGCAAA TTGTGCCTAA
2521 GCGAAATATT TTTTTAAGG AAAATAAAAA CATTAGTTAC AAGATTTTTT TTTTCTTAAT
2581 GTAGATGAAA ATTAGCAAGG ATGCTGCCTT TGGTCTCTGG TTTTTTTAAG CTTTTTTTGC
2641 ATATGTTTTG TAAGCAACAA ATTTTTTTGT ATAAAAGTCC CGTGTCTCTC GCTATTTCTG
2701 CTGCTGTTCC TAGACTGAGC ATTGCATTTC TTGATCAACC AGATGATTAA ACGTTGTATT
2761 AAAAAGACCC CGTGTAAACC TGAGCCCCCC CGTCCCCCCC CCCCCCCGGA AGCCACTGCA
2821 CACAGACAGA ACGGGGACAG GCGGCGGGTC TTTTGTTTTT TTGATGTTGG GGGTTCTCTT
2881 GGTTTTGTCA TGTGGAAAGT GATGCGTGGG CGTTCCCTGA TGAAGGCACC TTGGGGCTTC
2941 CCTGCCGCAT CCTCTCCCCT CAGGAAGGGG ACTGACCTGG GCTTGGGGGA AGGGACGTCA
3001 GCAAGGTGGC TCTGACCCTC CAGGTGACT CTGCCAAGCA GCTGTGGCCC CCAGGGCTAC
3061 CCTACACAAC GCCCTCCCCA GGCCCCCCTA AGCTGCTCTC CCTTGGAACC TGCACAGCTC
3121 TCTGAAATGG GGCATTTTGT TGGGACCAGT GACCCCTGGC ATGGGGACCA CACCCTGGAG
3181 CCCGGTGCTG GGGACCTCCT GGACACCCTG TCCTTCACTC CTTTGCCCCA GGGACCCAGG
3241 CTCATGCTCT GAACTCTGGC TGAGAGGATG CTGCTCAGGA GCCAGCACAG GACACCCCCC
3301 ACCCCACCCC ACCATGTCCC CATTACACCA GAGGGCATC GTGACGTAGA CAGGATGCCA
3361 GGGGCCTGGC CAGCCTCCCC CAATGCTGGG GAGCATCCCT GGGCCTGGGG CCACACCTGC
3421 TGCCCTCCCT CTGTGTGGTC CAAGGGCAAG AGTGGCTGGA GCCGGGGGAC TGTGCTGGTC
3481 TGAGCCCCAC GAAGGCCTTG GGCTGTGCGT CCGACCCTGC TGCAGAACCA GCAGGGTGTC
3541 CCCTCGGGCC CATCTGTGTC CCATGTCCCA GCACCCAGGC CTCTCTCCAG GTCTCCTTTT
3601 CTGGTCTTTT GCCATGAGGG TAACCAGCTC TTCCCAGCTG GCTGGGGACT GTCTTGGGTT
3661 TAAAACTGCA AGTCTCCTAC CCTGGGATCC CATCCAGTTC CACACGAACT AGGGCAGTGG
3721 TCACTGTGGC ACCCAGGTGT GGGCCTGGCT AGCTGGGGGC CTTCATGTGC CCTTCATGCC
3781 CCTCCCTGCA TTGAGGCCTT GTGGACCCT GGGCTGGCTG TGTTCATCCC CGCTGCAGGT
3841 CGGGCGTCTC CCCCCGTGCC ACTCCTGAGA CTCCCACCGT TACCCCCAGG AGATCCTGGA
3901 CTGCCTGACT CCCCTCCCCA GACTGGCTTG GGAGCCTGGG CCCCATGGTA GATGCAAGGG
3961 AAACCTCAAG GCCAGCTCAA TGCCTGGTAT CTGCCCCCAG TCCAGGCCAG GCGGAGGGGA
4021 GGGGCTGTCC GGCTGCCTCT CCCTTCTCGG TGGCTTCCCC TACGCCCTGG GAGTTTGATC
4081 TCTTAAGGGA ACTTGCCTCT CCCTCTTGTT TTGCTCCTGG CCCTGCCCCT AGGTCTGGGT
4141 GGGCAGTGGC CCCATAGCCT CTGGAACTGT GCGTTCTGCA TAGAATTCAA ACGAGATTCA
4201 CCCAGCGCGA GGAGGAAGAA ACAGCAGTTC CTGGGAACCA CAATTATGGG GGGTGGGGGG
4261 TGTGATCTGA GTGCCTCAAG ATGGTTTTCA AAAAAATTTT TTTAAAGAAA ATAATTGTAT
4321 ACGTGTCAAC ACAGCTGGCT GGATGATTGG GACTTTAAAA CGACCCTCTT TCAGGTGGAT
4381 TCAGAGACCT GTCCTGTATA TAACAGCACT GTAGCAATAA ACGTGACATT TTATAACGAT
4441 GCCCTGCA
```

SEQ ID NO: 24
TCF3 HUMAN NM_003200.4

```
   1 ACGCGCCGCG TGCCCGGCCG CGCCCAGCAG GGTTTCCAGG CCTGAGGTGC CCGCCCTGGC
  61 CCCAGGAGAA TGAACCAGCC GCAGAGGATG GCGCCTGTGG GCACAGACAA GGAGCTCAGT
 121 GACCTCCTGG ACTTCAGCAT GATGTTCCCG CTGCCTGTCA CCAACGGGAA GGGCCGGCCC
 181 GCCTCCCTGG CCGGGGCGCA GTTCGGAGGT TCAGGTCTTG AGGACCGGCC CAGCTCAGGC
 241 TCCTGGGGCA GCGGCGACCA GAGCAGCTCC TCCTTTGACC CCAGCCGGAC CTTCAGCGAG
 301 GGCACCCACT TCACTGAGTC GCACAGCAGC CTCTCTTCAT CCACATTCCT GGGACCGGGA
 361 CTCGGAGGCA AGAGCGGTGA GCGGGGCGCC TATGCCTCCT TCGGGAGAGA CGCAGGCGTG
 421 GGCGGCCTGA CTCAGGCTGG CTTCCTGTCA GGCGAGCTGG CCCTCAACAG CCCCGGGCCC
 481 CTGTCCCCTT CGGGCATGAA GGGGACCTCC CAGTACTACC CCTCCTACTC CGGCAGCTCC
 541 CGGCGGAGAG CGGCAGACGG CAGCCTAGAC ACGCAGCCCA AGAAGGTCCG GAAGGTCCCG
 601 CCGGGTCTTC CATCCTCGGT GTACCCACCC AGCTCAGGTG AGGACTACGG CAGGGATGCC
 661 ACCGCCTACC CGTCCGCCAA GACCCCAGC AGCACCTATC CGGCCCCCTT CTACGTGCCA
 721 GATGGCAGCC TGCACCCCTC AGCCGAGCTC TGGAGTCCCC CGGGCCAGGC GGGCTTCGGG
```

FIG. 14 (Cont.)

```
 781 CCCATGCTGG GTGGGGGCTC ATCCCCGCTG CCCCTCCCGC CCGGTAGCGG CCCGGTGGGC
 841 AGCAGTGGAA GCAGCAGCAC GTTTGGTGGC CTGCACCAGC ACGAGCGTAT GGGCTACCAG
 901 CTGCATGGAG CAGAGGTGAA CGGTGGGCTC CCATCTGCAT CCTCCTTCTC CTCAGCCCCC
 961 GGAGCCACGT ACGGCGGCGT CTCCAGCCAC ACGCCGCCTG TCAGCGGGGC CGACAGCCTC
1021 CTGGGCTCCC GAGGGACCAC AGCTGGCAGC TCCGGGGATG CCCTCGGCAA AGCACTGGCC
1081 TCGATCTACT CCCCGGATCA CTCAAGCAAT AACTTCTCGT CCAGCCCTTC TACCCCGTG
1141 GGCTCCCCCC AGGGCCTGGC AGGAACGTCA CAGTGGCCTC GAGCAGGAGC CCCCGGTGCC
1201 TTATCGCCCA GCTACGACGG GGGTCTCCAC GGCCTGCAGA GTAAGATAGA AGACCACCTG
1261 GACGAGGCCA TCCACGTGCT CCGCAGCCAC GCCGTGGGCA CAGCCGGCGA CATGCACACG
1321 CTGCTGCCTG GCCACGGGGC GCTGGCCTCA GGTTTCACCG GCCCCATGTC ACTGGGCGGG
1381 CGGCACGCAG GCCTGGTTGG AGGCAGCCAC CCCGAGGACG GCCTCGCAGG CAGCACCAGC
1441 CTCATGCACA ACCACGCGGC CCTCCCCAGC CAGCCAGGCA CCCTCCCTGA CCTGTCTCGG
1501 CCTCCCGACT CCTACAGTGG GCTAGGGCGA GCAGGTGCCA CGGCGGCCGC CAGCGAGATC
1561 AAGCGGGAGG AGAAGGAGGA CGAGGAGAAC ACGTCAGCGG CTGACCACTC GGAGGAGGAG
1621 AAGAAGGAGC TGAAGGCCCC CCGGGCCCGG ACCAGCCCAG ACGAGGACGA GGACGACCTT
1681 CTCCCCCCAG AGCAGAAGGC CGAGCGGGAG AAGGAGCGCC GGGTGGCCAA TAACGCCCGG
1741 GAGCGGCTGC GGGTCCGTGA CATCAACGAG GCCTTTAAGG AGCTGGGGCG CATGTGCCAA
1801 CTGCACCTCA ACAGCGAGAA GCCCCAGACC AAACTGCTCA TCCTGCACCA GGCTGTCTCG
1861 GTCATCCTGA ACTTGGAGCA GCAAGTGCGA GAGCGGAACC TGAATCCCAA AGCAGCCTGT
1921 TTGAAACGGC GAGAAGAGGA AAAGGTGTCA GGTGTGGTTG AGACCCCCA GATGGTGCTT
1981 TCAGCTCCCC ACCCAGGCCT GAGCGAAGCC CACAACCCCG CCGGGCACAT GTGAAAGGTA
2041 TGCCTCCGTG GGACGAGCCA CCCGCTTTCA GCCCTGTGCT CTGGCCCAG AACGGCCACT
2101 CGAGACCCCG GGCTTCATCC ACATCCACAC CTCACACACC TGTTGTCAGC ATCGAGCCAA
2161 CACCAACCTG ACAAGGTTCG GAGTGATGGG GGCGGCCAAG GTGACACTGG GTCCAGGAGC
2221 TCCCTGGGGC CCTGGCCTAC CACTCACTGG CCTCGCTCCC CCTGTCCCCG AATCTCAGCC
2281 ACCGTGTCAC TCTGTGACCT GTCCCATGGA TCCTGAAACT GCATCTTGGC CCTGTTGCCT
2341 GGGCTGACAG GAGCATTTTT TTTTTTTCCA GTAAACAAAA CCTGAAAGCA AGCAACAAAA
2401 CATACACTTT GTCAGAGAAG AAAAAAATGC CTTAACTATA AAAAGCGGAG AAATGGAAAC
2461 ATATCACTCA AGGGGGATGC TGTGGAAACC TGGCTTATTC TTCTAAAGCC ACCAGCAAAT
2521 TGTGCCTAAG CGAAATATTT TTTTTAAGGA AAATAAAAAC ATTAGTTACA AGATTTTTTT
2581 TTTCTTAATG TAGATGAAAA TTAGCAAGGA TGCTGCCTTT GGTCTCTGGT TTTTTTAAGC
2641 TTTTTTTGCA TATGTTTTGT AAGCAACAAA TTTTTTTGTA TAAAAGTCCC GTGTCTCTCG
2701 CTATTTCTGC TGCTGTTCCT AGACTGAGCA TTGCATTTCT TGATCAACCA GATGATTAAA
2761 CGTTGTATTA AAAAGACCCC GTGTAAACCT GAGCCCCCCC GTCCCCCCCC CCCCCCGGAA
2821 GCCACTGCAC ACAGACAGAA CGGGGACAGG CGGCGGGTCT TTTGTTTTTT TGATGTTGGG
2881 GGTTCTCTTG GTTTTGTCAT GTGGAAAGTG ATGCGTGGGC GTTCCCTGAT GAAGGCACCT
2941 TGGGGCTTCC CTGCCGCATC CTCTCCCCTC AGGAAGGGGA CTGACCTGGG CTTGGGGGAA
3001 GGGACGTCAG CAAGGTGGCT CTGACCCTCC CAGGTGACTC TGCCAAGCAG CTGTGGCCCC
3061 CAGGGCTACC CTACACAACG CCCTCCCCAG GCCCCCTAA GCTGCTCTCC CTTGGAACCT
3121 GCACAGCTCT CTGAAATGGG GCATTTTGTT GGGACCAGTG ACCCCTGGCA TGGGGACCAC
3181 ACCCTGGAGC CCGGTGCTGG GGACCTCCTG GACACCCTGT CCTTCACTCC TTTGCCCCAG
3241 GGACCCAGGC TCATGCTCTG AACTCTGGCT GAGAGGATGC TGCTCAGGAG CCAGCACAGG
3301 ACACCCCCCA CCCCACCCCA CCATGTCCCC ATTACACCAG AGGGCCATCG TGACGTAGAC
3361 AGGATGCCAG GGGCCTGGCC AGCCTCCCCC AATGCTGGGG AGCATCCCTG GGCCTGGGGC
3421 CACACCTGCT GCCCTCCCTC TGTGTGGTCC AAGGGCAAGA GTGGCTGGAG CCGGGGGACT
3481 GTGCTGGTCT GAGCCCCACG AAGGCCTTGG GCTGTGCGTC CGACCCTGCT GCAGAACCAG
3541 CAGGGTGTCC CCTCGGGCCC ATCTGTGTCC CATGTCCCAG CACCCAGGCC TCTCTCCAGG
3601 TCTCCTTTTC TGGTCTTTTG CCATGAGGGT AACCAGCTCT TCCCAGCTGG CTGGGGACTG
3661 TCTTGGGTTT AAAACTGCAA GTCTCCTACC CTGGGATCCC ATCCAGTTCC ACACGAACTA
3721 GGGCAGTGGT CACTGTGGCA CCCAGGTGTG GGCCTGGCTA GCTGGGGGCC TTCATGTGCC
3781 CTTCATGCCC CTCCCTGCAT TGAGGCCTTG TGGACCCCTG GGCTGGCTGT GTTCATCCCC
3841 GCTGCAGGTC GGGCGTCTCC CCCCGTGCCA CTCCTGAGAC TCCCACCGTT ACCCCCAGGA
3901 GATCCTGGAC TGCCTGACTC CCCTCCCCAG ACTGGCTTGG GAGCCTGGGC CCCATGGTAG
3961 ATGCAAGGGA AACCTCAAGG CCAGCTCAAT GCCTGGTATC TGCCCCAGT CCAGGCCAGG
4021 CGGAGGGGAG GGGCTGTCCG GCTGCCTCTC CCTTCTCGGT GGCTTCCCCT ACGCCCTGGG
4081 AGTTTGATCT CTTAAGGGAA CTTGCCTCTC CCTCTTGTTT TGCTCCTGGC CCTGCCCCTA
4141 GGTCTGGGTG GGCAGTGGCC CCATAGCCTC TGGAACTGTG CGTTCTGCAT AGAATTCAAA
4201 CGAGATTCAC CCAGCGCGAG GAGGAAGAAA CAGCAGTTCC TGGAACCAC AATTATGGGG
4261 GGTGGGGGGT GTGATCTGAG TGCCTCAAGA TGGTTTTCAA AAAAATTTTT TTAAAGAAAA
4321 TAATTGTATA CGTGTCAACA CAGCTGGCTG GATGATTGGG ACTTTAAAAC GACCCTCTTT
4381 CAGGTGGATT CAGAGACCTG TCCTGTATAT AACAGCACTG TAGCAATAAA CGTGACATTT
4441 TATAACGATG CCCTGCA
```

FIG. 14 (Cont.)

SEQUENCE LISTING

```
<160> NUMBER OF SEQ ID NOS: 137

<210> SEQ ID NO 1
<211> LENGTH: 149
<212> TYPE: PRT
<213> ORGANISM: Homo sapiens

<400> SEQUENCE: 1

Met Lys Val Ala Ser Gly Ser Thr Ala Thr Ala Ala Ala Gly Pro Ser
1               5                   10                  15

Cys Ala Leu Lys Ala Gly Lys Thr Ala Ser Gly Ala Gly Glu Val Val
            20                  25                  30
```

```
Arg Cys Leu Ser Glu Gln Ser Val Ala Ile Ser Arg Cys Ala Gly Gly
         35                  40                  45

Ala Gly Ala Arg Leu Pro Ala Leu Leu Asp Glu Gln Gln Val Asn Val
 50                  55                  60

Leu Leu Tyr Asp Met Asn Gly Cys Tyr Ser Arg Leu Lys Glu Leu Val
 65                  70                  75                  80

Pro Thr Leu Pro Gln Asn Arg Lys Val Ser Lys Val Glu Ile Leu Gln
                 85                  90                  95

His Val Ile Asp Tyr Ile Arg Asp Leu Gln Leu Glu Leu Asn Ser Glu
             100                 105                 110

Ser Glu Val Gly Thr Pro Gly Gly Arg Gly Leu Pro Val Arg Ala Pro
         115                 120                 125

Leu Ser Thr Leu Asn Gly Glu Ile Ser Ala Leu Thr Ala Glu Val Arg
     130                 135                 140

Ser Arg Ser Asp His
145

<210> SEQ ID NO 2
<211> LENGTH: 134
<212> TYPE: PRT
<213> ORGANISM: Homo sapiens

<400> SEQUENCE: 2

Met Lys Ala Phe Ser Pro Val Arg Ser Val Arg Lys Asn Ser Leu Ser
 1               5                  10                  15

Asp His Ser Leu Gly Ile Ser Arg Ser Lys Thr Pro Val Asp Asp Pro
                 20                  25                  30

Met Ser Leu Leu Tyr Asn Met Asn Asp Cys Tyr Ser Lys Leu Lys Glu
             35                  40                  45

Leu Val Pro Ser Ile Pro Gln Asn Lys Lys Val Ser Lys Met Glu Ile
         50                  55                  60

Leu Gln His Val Ile Asp Tyr Ile Leu Asp Leu Gln Ile Ala Leu Asp
 65                  70                  75                  80

Ser His Pro Thr Ile Val Ser Leu His His Gln Arg Pro Gly Gln Asn
                 85                  90                  95

Gln Ala Ser Arg Thr Pro Leu Thr Thr Leu Asn Thr Asp Ile Ser Ile
             100                 105                 110

Leu Ser Leu Gln Ala Ser Glu Phe Pro Ser Glu Leu Met Ser Asn Asp
         115                 120                 125

Ser Lys Ala Leu Cys Gly
     130

<210> SEQ ID NO 3
<211> LENGTH: 119
<212> TYPE: PRT
<213> ORGANISM: Homo sapiens

<400> SEQUENCE: 3

Met Lys Ala Leu Ser Pro Val Arg Gly Cys Tyr Glu Ala Val Cys Cys
 1               5                  10                  15

Leu Ser Glu Arg Ser Leu Ala Ile Ala Arg Gly Arg Gly Lys Gly Pro
                 20                  25                  30

Ala Ala Glu Glu Pro Leu Ser Leu Leu Asp Asp Met Asn His Cys Tyr
             35                  40                  45

Ser Arg Leu Arg Glu Leu Val Pro Gly Val Pro Arg Gly Thr Gln Leu
         50                  55                  60
```

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
            85                  90                  95

Leu Pro Ile Gln Thr Ala Glu Leu Thr Pro Glu Leu Val Ile Ser Asn
        100                 105                 110

Asp Lys Arg Ser Phe Cys His
        115

<210> SEQ ID NO 4
<211> LENGTH: 161
<212> TYPE: PRT
<213> ORGANISM: Homo sapiens

<400> SEQUENCE: 4

Met Lys Ala Val Ser Pro Val Arg Pro Ser Gly Arg Lys Ala Pro Ser
1               5                   10                  15

Gly Cys Gly Gly Gly Glu Leu Ala Leu Arg Cys Leu Ala Glu His Gly
            20                  25                  30

His Ser Leu Gly Gly Ser Ala Ala Ala Ala Ala Ala Ala Ala Ala Ala
        35                  40                  45

Arg Cys Lys Ala Ala Glu Ala Ala Ala Asp Glu Pro Ala Leu Cys Leu
50                  55                  60

Gln Cys Asp Met Asn Asp Cys Tyr Ser Arg Leu Arg Arg Leu Val Pro
65                  70                  75                  80

Thr Ile Pro Pro Asn Lys Lys Val Ser Lys Val Glu Ile Leu Gln His
            85                  90                  95

Val Ile Asp Tyr Ile Leu Asp Leu Gln Leu Ala Leu Glu Thr His Pro
        100                 105                 110

Ala Leu Leu Arg Gln Pro Pro Pro Ala Pro Pro His His Pro Ala
            115                 120                 125

Gly Thr Cys Pro Ala Ala Pro Arg Thr Pro Leu Thr Ala Leu Asn
        130                 135                 140

Thr Asp Pro Ala Gly Ala Val Asn Lys Gln Gly Asp Ser Ile Leu Cys
145                 150                 155                 160

Arg

<210> SEQ ID NO 5
<211> LENGTH: 407
<212> TYPE: PRT
<213> ORGANISM: Homo sapiens

<400> SEQUENCE: 5

Met Glu Ser Arg Lys Asp Met Val Val Phe Leu Asp Gly Gly Gln Leu
1               5                   10                  15

Gly Thr Leu Val Gly Lys Arg Val Ser Asn Leu Ser Glu Ala Val Gly
            20                  25                  30

Ser Pro Leu Pro Glu Pro Glu Lys Met Val Pro Arg Gly Cys Leu
        35                  40                  45

Ser Pro Arg Ala Val Pro Ala Thr Arg Glu Arg Gly Gly Gly Gly
50                  55                  60

Pro Glu Glu Glu Pro Val Asp Gly Leu Ala Ser Ala Ala Gly Pro
65                  70                  75                  80

Gly Ala Glu Pro Gln Val Ala Gly Ala Ala Met Leu Gly Pro Gly Pro
            85                  90                  95

Pro Ala Pro Ser Val Asp Ser Leu Ser Gly Gln Gly Gln Pro Ser Ser

```
                100                 105                 110
        Ser Asp Thr Glu Ser Asp Phe Tyr Glu Glu Ile Glu Val Ser Cys Thr
                    115                 120                 125

Pro Asp Cys Ala Thr Gly Asn Ala Glu Tyr Gln His Ser Lys Gly Ser
            130                 135                 140

Gly Ser Glu Ala Leu Val Gly Ser Pro Asn Gly Ser Glu Thr Pro
        145                 150                 155                 160

Lys Ser Asn Gly Ser Gly Gly Gly Ser Gln Gly Thr Leu Ala
                        165                 170                 175

Cys Ser Ala Ser Asp Gln Met Arg Arg Tyr Arg Thr Ala Phe Thr Arg
                        180                 185                 190

Glu Gln Ile Ala Arg Leu Glu Lys Glu Phe Tyr Arg Glu Asn Tyr Val
                    195                 200                 205

Ser Arg Pro Arg Arg Cys Glu Leu Ala Ala Ala Leu Asn Leu Pro Glu
            210                 215                 220

Thr Thr Ile Lys Val Trp Phe Gln Asn Arg Arg Met Lys Asp Lys Arg
        225                 230                 235                 240

Gln Arg Leu Ala Met Thr Trp Pro His Pro Ala Asp Pro Ala Phe Tyr
                        245                 250                 255

Thr Tyr Met Met Ser His Ala Ala Ala Gly Gly Leu Pro Tyr Pro
                    260                 265                 270

Phe Pro Ser His Leu Pro Leu Pro Tyr Tyr Ser Pro Val Gly Leu Gly
                    275                 280                 285

Ala Ala Ser Ala Ala Ser Ala Ala Ser Pro Phe Ser Gly Ser Leu
            290                 295                 300

Arg Pro Leu Asp Thr Phe Arg Val Leu Ser Gln Pro Tyr Pro Arg Pro
        305                 310                 315                 320

Glu Leu Leu Cys Ala Phe Arg His Pro Pro Leu Tyr Pro Gly Pro Ala
                        325                 330                 335

His Gly Leu Gly Ala Ser Ala Gly Gly Pro Cys Ser Cys Leu Ala Cys
                    340                 345                 350

His Ser Gly Pro Ala Asn Gly Leu Ala Pro Arg Ala Ala Ala Ala Ser
                    355                 360                 365

Asp Phe Thr Cys Ala Ser Thr Ser Arg Ser Asp Ser Phe Leu Thr Phe
            370                 375                 380

Ala Pro Ser Val Leu Ser Lys Ala Ser Ser Val Ala Leu Asp Gln Arg
        385                 390                 395                 400

Glu Glu Val Pro Leu Thr Arg
                        405

<210> SEQ ID NO 6
<211> LENGTH: 271
<212> TYPE: PRT
<213> ORGANISM: Homo sapiens

<400> SEQUENCE: 6

Met Leu Leu Ala Pro Pro Ser Thr Pro Ser Arg Gly Arg Thr Pro Ser
1               5                   10                  15

Ala Val Glu Arg Leu Glu Ala Asp Lys Ala Lys Tyr Val Lys Thr His
            20                  25                  30

Gln Val Ile Ala Arg Arg Gln Glu Pro Ala Leu Arg Gly Ser Pro Gly
        35                  40                  45

Pro Leu Thr Pro His Pro Cys Asn Glu Leu Gly Pro Pro Ala Ser Pro
    50                  55                  60
```

```
Arg Thr Pro Arg Pro Val Arg Gly Ser Gly Arg Leu Pro Arg
 65                  70                  75                  80

Pro Asp Ser Leu Ile Phe Tyr Arg Gln Lys Arg Asp Cys Lys Ala Ser
                     85                  90                  95

Val Asn Lys Glu Asn Ala Lys Gly Gln Gly Leu Val Arg Arg Leu Phe
                100                 105                 110

Leu Gly Ala Pro Arg Asp Ala Ala Pro Ser Ser Pro Ala Ser Thr Glu
            115                 120                 125

Arg Pro Ala Ala Ser Gly Gly Trp Ala Ala Pro Gln Asp Ala Pro Glu
        130                 135                 140

Ala Ala Gly Lys Arg Ala Leu Cys Pro Thr Cys Ser Leu Pro Leu Ser
145                 150                 155                 160

Glu Lys Glu Arg Phe Phe Asn Tyr Cys Gly Leu Glu Arg Ala Leu Val
                165                 170                 175

Glu Val Leu Gly Ala Glu Arg Phe Ser Pro Gln Ser Trp Gly Ala Asp
            180                 185                 190

Ala Ser Pro Gln Ala Gly Thr Ser Pro Pro Gly Ser Gly Asp Ala
        195                 200                 205

Ser Asp Trp Thr Ser Ser Asp Arg Gly Val Asp Ser Pro Gly Gly Ala
210                 215                 220

Gly Gly Gly Gly Gly Ser Glu Ala Ala Gly Ser Ala Arg Asp Arg Arg
225                 230                 235                 240

Pro Pro Val Ser Val Val Glu Arg Asn Ala Arg Val Ile Gln Trp Leu
                245                 250                 255

Tyr Gly Cys Gln Arg Ala Arg Gly Pro Pro Arg Glu Ser Glu Val
                260                 265                 270

<210> SEQ ID NO 7
<211> LENGTH: 268
<212> TYPE: PRT
<213> ORGANISM: Homo sapiens

<400> SEQUENCE: 7

Met Ala Gln Pro Leu Cys Pro Pro Leu Ser Glu Ser Trp Met Leu Ser
 1               5                  10                  15

Ala Ala Trp Gly Pro Thr Arg Arg Pro Pro Ser Asp Lys Asp Cys
             20                  25                  30

Gly Arg Ser Leu Val Ser Ser Pro Asp Ser Trp Gly Ser Thr Pro Ala
             35                  40                  45

Asp Ser Pro Val Ala Ser Pro Ala Arg Pro Gly Thr Leu Arg Asp Pro
 50                  55                  60

Arg Ala Pro Ser Val Gly Arg Arg Gly Ala Arg Ser Ser Arg Leu Gly
 65                  70                  75                  80

Ser Gly Gln Arg Gln Ser Ala Ser Glu Arg Glu Lys Leu Arg Met Arg
                 85                  90                  95

Thr Leu Ala Arg Ala Leu His Glu Leu Arg Arg Phe Leu Pro Pro Ser
             100                 105                 110

Val Ala Pro Ala Gly Gln Ser Leu Thr Lys Ile Glu Thr Leu Arg Leu
             115                 120                 125

Ala Ile Arg Tyr Ile Gly His Leu Ser Ala Val Leu Gly Leu Ser Glu
 130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
                 165                 170                 175
```

```
Arg Thr Gln Ala Glu Gly Gln Gly Arg Gly Leu Gly Leu Val
            180                 185                 190

Ser Ala Val Arg Ala Gly Ala Ser Trp Gly Ser Pro Pro Ala Cys Pro
            195                 200                 205

Gly Ala Arg Ala Ala Pro Glu Pro Arg Asp Pro Pro Ala Leu Phe Ala
            210                 215                 220

Glu Ala Ala Cys Pro Glu Gly Gln Ala Met Glu Pro Ser Pro Pro Ser
225                 230                 235                 240

Pro Leu Leu Pro Gly Asp Val Leu Ala Leu Leu Glu Thr Trp Met Pro
                245                 250                 255

Leu Ser Pro Leu Glu Trp Leu Pro Glu Glu Pro Lys
            260                 265

<210> SEQ ID NO 8
<211> LENGTH: 457
<212> TYPE: PRT
<213> ORGANISM: Homo sapiens

<400> SEQUENCE: 8

Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
            35                  40                  45

Ala Ala Met Gly Ser Gly Ser Gly Asn Met Ser Ala Gly Ser Met Asn
        50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Gly Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
            115                 120                 125

Asn Met Asn Ser Met Ser Pro Met Tyr Gly Gln Ala Gly Leu Ser Arg
        130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
            195                 200                 205

His Ser Leu Ser Phe Asn Asp Cys Phe Leu Lys Val Pro Arg Ser Pro
        210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Gly Ser
            260                 265                 270

Gly Lys Lys Ala Ala Ala Gly Ala Gln Ala Ser Gln Ala Gln Leu Gly
```

```
                275                 280                 285
Glu Ala Ala Gly Pro Ala Ser Glu Thr Pro Ala Gly Thr Glu Ser Pro
        290                 295                 300
His Ser Ser Ala Ser Pro Cys Gln Glu His Lys Arg Gly Gly Leu Gly
305                 310                 315                 320
Glu Leu Lys Gly Thr Pro Ala Ala Leu Ser Pro Glu Pro Ala
                325                 330                 335
Pro Ser Pro Gly Gln Gln Gln Ala Ala His Leu Leu Gly Pro
            340                 345                 350
Pro His His Pro Gly Leu Pro Pro Glu Ala His Leu Lys Pro Glu His
            355                 360                 365
His Tyr Ala Phe Asn His Pro Phe Ser Ile Asn Asn Leu Met Ser Ser
        370                 375                 380
Glu Gln Gln His His His Ser His His His Gln Pro His Lys Met
385                 390                 395                 400
Asp Leu Lys Ala Tyr Glu Gln Val Met His Tyr Pro Gly Tyr Gly Ser
                405                 410                 415
Pro Met Pro Gly Ser Leu Ala Met Gly Pro Val Thr Asn Lys Thr Gly
            420                 425                 430
Leu Asp Ala Ser Pro Leu Ala Ala Asp Thr Ser Tyr Tyr Gln Gly Val
            435                 440                 445
Tyr Ser Arg Pro Ile Met Asn Ser Ser
450                 455

<210> SEQ ID NO 9
<211> LENGTH: 654
<212> TYPE: PRT
<213> ORGANISM: Homo sapiens

<400> SEQUENCE: 9

Met Asn Gln Pro Gln Arg Met Ala Pro Val Gly Thr Asp Lys Glu Leu
1               5                   10                  15
Ser Asp Leu Leu Asp Phe Ser Met Met Phe Pro Leu Pro Val Thr Asn
                20                  25                  30
Gly Lys Gly Arg Pro Ala Ser Leu Ala Gly Ala Gln Phe Gly Gly Ser
            35                  40                  45
Gly Leu Glu Asp Arg Pro Ser Ser Gly Ser Trp Gly Ser Gly Asp Gln
        50                  55                  60
Ser Ser Ser Ser Phe Asp Pro Ser Arg Thr Phe Ser Glu Gly Thr His
65                  70                  75                  80
Phe Thr Glu Ser His Ser Ser Leu Ser Ser Ser Thr Phe Leu Gly Pro
                85                  90                  95
Gly Leu Gly Gly Lys Ser Gly Glu Arg Gly Ala Tyr Ala Ser Phe Gly
            100                 105                 110
Arg Asp Ala Gly Val Gly Gly Leu Thr Gln Ala Gly Phe Leu Ser Gly
            115                 120                 125
Glu Leu Ala Leu Asn Ser Pro Gly Pro Leu Ser Pro Ser Gly Met Lys
        130                 135                 140
Gly Thr Ser Gln Tyr Tyr Pro Ser Tyr Ser Gly Ser Ser Arg Arg Arg
145                 150                 155                 160
Ala Ala Asp Gly Ser Leu Asp Thr Gln Pro Lys Lys Val Arg Lys Val
                165                 170                 175
Pro Pro Gly Leu Pro Ser Ser Val Tyr Pro Pro Ser Ser Gly Glu Asp
            180                 185                 190
```

```
Tyr Gly Arg Asp Ala Thr Ala Tyr Pro Ser Ala Lys Thr Pro Ser Ser
            195                 200                 205

Thr Tyr Pro Ala Pro Phe Tyr Val Ala Asp Gly Ser Leu His Pro Ser
        210                 215                 220

Ala Glu Leu Trp Ser Pro Gly Gln Ala Gly Phe Gly Pro Met Leu
225                 230                 235                 240

Gly Gly Gly Ser Ser Pro Leu Pro Leu Pro Pro Gly Ser Gly Pro Val
                245                 250                 255

Gly Ser Ser Gly Ser Ser Ser Thr Phe Gly Gly Leu His Gln His Glu
            260                 265                 270

Arg Met Gly Tyr Gln Leu His Gly Ala Glu Val Asn Gly Gly Leu Pro
        275                 280                 285

Ser Ala Ser Ser Phe Ser Ser Ala Pro Gly Ala Thr Tyr Gly Gly Val
    290                 295                 300

Ser Ser His Thr Pro Pro Val Ser Gly Ala Asp Ser Leu Leu Gly Ser
305                 310                 315                 320

Arg Gly Thr Thr Ala Gly Ser Ser Gly Asp Ala Leu Gly Lys Ala Leu
                325                 330                 335

Ala Ser Ile Tyr Ser Pro Asp His Ser Ser Asn Asn Phe Ser Ser Ser
            340                 345                 350

Pro Ser Thr Pro Val Gly Ser Pro Gln Gly Leu Ala Gly Thr Ser Gln
        355                 360                 365

Trp Pro Arg Ala Gly Ala Pro Gly Ala Leu Ser Pro Ser Tyr Asp Gly
    370                 375                 380

Gly Leu His Gly Leu Gln Ser Lys Ile Glu Asp His Leu Asp Glu Ala
385                 390                 395                 400

Ile His Val Leu Arg Ser His Ala Val Gly Thr Ala Gly Asp Met His
                405                 410                 415

Thr Leu Leu Pro Gly His Gly Ala Leu Ala Ser Gly Phe Thr Gly Pro
            420                 425                 430

Met Ser Leu Gly Gly Arg His Ala Gly Leu Val Gly Gly Ser His Pro
        435                 440                 445

Glu Asp Gly Leu Ala Gly Ser Thr Ser Leu Met His Asn His Ala Ala
450                 455                 460

Leu Pro Ser Gln Pro Gly Thr Leu Pro Asp Leu Ser Arg Pro Pro Asp
465                 470                 475                 480

Ser Tyr Ser Gly Leu Gly Arg Ala Gly Ala Thr Ala Ala Ala Ser Glu
                485                 490                 495

Ile Lys Arg Glu Glu Lys Glu Asp Glu Glu Asn Thr Ser Ala Ala Asp
            500                 505                 510

His Ser Glu Glu Glu Lys Lys Glu Leu Lys Ala Pro Arg Ala Arg Thr
        515                 520                 525

Ser Pro Asp Glu Asp Glu Asp Asp Leu Leu Pro Pro Glu Gln Lys Ala
530                 535                 540

Glu Arg Glu Lys Glu Arg Arg Val Ala Asn Asn Ala Arg Glu Arg Leu
545                 550                 555                 560

Arg Val Arg Asp Ile Asn Glu Ala Phe Lys Glu Leu Gly Arg Met Cys
                565                 570                 575

Gln Leu His Leu Asn Ser Glu Lys Pro Gln Thr Lys Leu Leu Ile Leu
            580                 585                 590

His Gln Ala Val Ser Val Ile Leu Asn Leu Glu Gln Gln Val Arg Glu
        595                 600                 605

Arg Asn Leu Asn Pro Lys Ala Ala Cys Leu Lys Arg Arg Glu Glu Glu
```

```
                    610                  615                  620
Lys Val Ser Gly Val Val Gly Asp Pro Gln Met Val Leu Ser Ala Pro
625                 630                  635                  640

His Pro Gly Leu Ser Glu Ala His Asn Pro Ala Gly His Met
                    645                  650

<210> SEQ ID NO 10
<211> LENGTH: 148
<212> TYPE: PRT
<213> ORGANISM: Mus musculus

<400> SEQUENCE: 10

Met Lys Val Ala Ser Gly Ser Ala Ala Ala Ala Gly Pro Ser Cys
1               5                   10                  15

Ser Leu Lys Ala Gly Arg Thr Ala Gly Glu Val Val Leu Gly Leu Ser
                20                  25                  30

Glu Gln Ser Val Ala Ile Ser Arg Cys Ala Gly Thr Arg Leu Pro Ala
            35                  40                  45

Leu Leu Asp Glu Gln Gln Val Asn Val Leu Leu Tyr Asp Met Asn Gly
        50                  55                  60

Cys Tyr Ser Arg Leu Lys Glu Leu Val Pro Thr Leu Pro Gln Asn Arg
65                  70                  75                  80

Lys Val Ser Lys Val Glu Ile Leu Gln His Val Ile Asp Tyr Ile Arg
                85                  90                  95

Asp Leu Gln Leu Glu Leu Asn Ser Glu Ser Glu Val Gly Thr Thr Gly
            100                 105                 110

Gly Arg Gly Leu Pro Val Arg Ala Pro Leu Ser Thr Leu Asn Gly Glu
        115                 120                 125

Ile Ser Ala Leu Ala Ala Glu Ala Ala Cys Val Pro Ala Asp Asp Arg
    130                 135                 140

Ile Leu Cys Arg
145

<210> SEQ ID NO 11
<211> LENGTH: 1239
<212> TYPE: DNA
<213> ORGANISM: Homo sapiens

<400> SEQUENCE: 11
actctcattc cacgttctta actgttccat tttccgtatc tgcttcgggc ttccacctca      60 ttttttttcgc tttgcccatt ctgtttcagc cagtcgccaa gaatcatgaa agtcgccagt    120
ggcagcaccg ccaccgccgc cgcgggcccc agctgcgcgc tgaaggccgg caagacagcg    180
agcggtgcgg cgaggtggt gcgctgtctg tctgagcaga gcgtggccat ctcgcgctgc     240
gccgggggcg ccggggcgcg cctgcctgcc ctgctggacg agcagcaggt aaacgtgctg    300
ctctacgaca tgaacggctg ttactcacgc ctcaaggagc tggtgcccac cctgccccag    360
aaccgcaagg tgagcaaggt ggagattctc cagcacgtca tcgactacat cagggacctt    420
cagttggagc tgaactcgga atccgaagtt ggaaccccg ggggccgagg gctgccggtc    480
cgggctccgc tcagcaccct caacggcgag atcagcgccc tgacggccga ggtgagatcc    540
agatccgacc actagatcat ccttataccg acggggaaac ggaggccaga gagggcgtgg    600
gcgcttgcac cacttccgtc ccatccttgc gggtacctgg ctatgcgggg gtgcctaagg    660
agcctggaaa aagcgctccc ccgtcgtgct tcctggggaa gggggcgttc gctgcgctcg    720
gagcggcgtc ccttccaacc cgccggtctc atttcttctc gttttcacag gcggcatgcg    780
```

| | | |
|---|---|---|
| ttcctgcgga cgatcgcatc ttgtgtcgct gaagcgcctc ccccagggac cggcggaccc | 840 | |
| cagccatcca gggggcaaga ggaattacgt gctctgtggg tctcccccaa cgcgcctcgc | 900 | |
| cggatctgag ggagaacaag accgatcggc ggccactgcg cccttaactg catccagcct | 960 | |
| ggggctgagg ctgaggcact ggcgaggaga gggcgctcct ctctgcacac ctactagtca | 1020 | |
| ccagagactt taggggtgg gattccactc gtgtgtttct attttttgaa aagcagacat | 1080 | |
| tttaaaaaat ggtcacgttt ggtgcttctc agatttctga ggaaattgct ttgtattgta | 1140 | |
| tattacaatg atcaccgact gaaaatattg ttttacaata gttctgtggg gctgtttttt | 1200 | |
| tgttattaaa caaataattt agatggtggt aaaaaaaaa | 1239 | |

<210> SEQ ID NO 12
<211> LENGTH: 1402
<212> TYPE: DNA
<213> ORGANISM: Homo sapiens

<400> SEQUENCE: 12

| | | |
|---|---|---|
| ggggacgaag ggaagctcca gcgtgtggcc ccggcgagtg cggataaaag ccgccccgcc | 60 | |
| gggctcgggc ttcattctga gccgagcccg gtgccaagcg cagctagctc agcaggcggc | 120 | |
| agcggcggcc tgagcttcag ggcagccagc tccctcccgg tctcgccttc cctcgcggtc | 180 | |
| agcatgaaag ccttcagtcc cgtgaggtcc gttaggaaaa acagcctgtc ggaccacagc | 240 | |
| ctgggcatct cccggagcaa aaccctgtg gacgacccga tgagcctgct atacaacatg | 300 | |
| aacgactgct actccaagct caaggagctg gtgcccagca tccccagaa caagaaggtg | 360 | |
| agcaagatgg aaatcctgca gcacgtcatc gactacatct tggacctgca gatcgccctg | 420 | |
| gactcgcatc ccactattgt cagcctgcat caccagagac ccgggcagaa ccaggcgtcc | 480 | |
| aggacgccgc tgaccaccct caacacggat atcagcatcc tgtccttgca ggcttctgaa | 540 | |
| ttcccttctg agttaatgtc aaatgacagc aaagcactgt gtggctgaat aagcggtgtt | 600 | |
| catgatttct tttattcttt gcacaacaac aacaacaaca aattcacgga atcttttaag | 660 | |
| tgctgaactt attttttcaac catttcacaa ggaggacaag ttgaatggac cttttttaaaa | 720 | |
| agaaaaaaaa aatggaagga aaactaagaa tgatcatctt cccagggtgt tctcttactt | 780 | |
| ggactgtgat attcgttatt tatgaaaaag actttttaaat gccccttctg cagttggaag | 840 | |
| gttttctttta tatactattc ccaccatggg gagcgaaaac gttaaaatca aaggaattg | 900 | |
| cccaatctaa gcagactttg cctttttttca aggtggagc gtgaatacca gaaggatcca | 960 | |
| gtattcagtc acttaaatga agtctttggg tcagaaatta ccttttttgac acaagcctac | 1020 | |
| tgaatgctgt gtatatattt atatataaat atatctatttt gagtgaaacc ttgtgaactc | 1080 | |
| tttaattaga gttttcttgt atagtggcag agatgtctat ttctgcattc aaaagtgtaa | 1140 | |
| tgatgtactt attcatgcta aacttttat aaaagtttag ttgtaaactt aacccttta | 1200 | |
| tacaaaataa atcaagtgtg tttattgaat ggtgattgcc tgctttattt cagaggacca | 1260 | |
| gtgctttgat ttttattatg ctatgttata actgaaccca aataaataca agttcaaatt | 1320 | |
| tatgtagact gtataagatt ataataaaac atgtctgaag tcaaaaaaaa aaaaaaaaa | 1380 | |
| aaaaaaaaaa aaaaaaaaaa aa | 1402 | |

<210> SEQ ID NO 13
<211> LENGTH: 1252
<212> TYPE: DNA
<213> ORGANISM: Homo sapiens

<400> SEQUENCE: 13

```
gatctggggt gctgccagga aaaagcaaat tctggaagtt aatggttttg agtgatttt        60
aaatccttgc tggcggagag gcccgcctct ccccggtatc agcgcttcct cattctttga      120
atccgcggct ccgcggtctt cggcgtcaga ccagccggag gaagcctgtt tgcaatttaa      180
gcgggctgtg aacgcccagg gccggcgggg gcagggccga ggcgggccat tttgaataaa      240
gaggcgtgcc ttccaggcag gctctataag tgaccgccgc ggcgagcgtg cgcgcgttgc      300
aggtcactgt agcgggactt cttttggttt tctttctctt tggggcacct ctggactcac      360
tccccagcat gaaggcgctg agccggtgc gcggctgcta cgaggcggtg tgctgcctgt       420
cggaacgcag tctggccatc gcccggggcc gagggaaggg cccggcagct gaggagccgc      480
tgagcttgct ggacgacatg aaccactgct actcccgcct gcgggaactg gtacccggag      540
tcccgagagg cactcagctt agccaggtgg aaatcctaca gcgcgtcatc gactacattc      600
tcgacctgca ggtagtcctg gccgagccac ccctggacc ccctgatggc ccccaccttc       660
ccatccagac agccgagctc actccggaac ttgtcatctc caacgacaaa aggagctttt      720
gccactgact cggccgtgtc ctgacacctc cagaacgcag gtgctggcgc ccgttctgcc      780
tgggaccccg ggaacctctc ctgccggaag ccggacggca gggatgggcc caacttcgc       840
cctgccact tgacttcacc aaatcccttc ctggagacta aacctggtgc tcaggagcga       900
aggactgtga acttgtggcc tgaagagcca gagctagctc tggccaccag ctgggcgacg      960
tcaccctgct cccaccccac ccccaagttc taaggtctct tcagagcgtg gaggtgtgga     1020
aggagtggct gctctccaaa ctatgccaag gcggcggcag agctggtctt ctggtctcct     1080
tggagaaagg ttctgttgcc ctgatttatg aactctataa tagagtatat aggttttgta     1140
ccttttttac aggaaggtga ctttctgtaa caatgcgatg tatattaaac ttttattaaa     1200
agttaacatt ttgcataata aacgattttt aaacacttga aaaaaaaaaa aa             1252
```

<210> SEQ ID NO 14
<211> LENGTH: 3891
<212> TYPE: DNA
<213> ORGANISM: Homo sapiens

<400> SEQUENCE: 14

```
gagagcgtag tggaggaggc gcggttgtga gtagtaccgg gagtgggtg atcccgggct         60
aggggagcgc ggcggccgcg atcgggctta gtcggagctc cgaagggagt gactaggaca      120
cccgggtggg ctactttct tccggtgctt ttgcttttt tttcctttgg gctcgggctg        180
agtgtcgccc actgagcaaa gattccctcg taaaacccag agcgaccctc ccgtcaattg      240
ttgggctcgg gagtgtcgcg gtgccccgag cgcgccgggc gcggaggcaa agggagcgga     300
gccggccgcg gacggggccc ggagcttgcc tgcctccctc gctcgcccca gcgggttcgc      360
tcgcgtagag cgcagggcgc gcgcgatgaa ggcggtgagc ccggtgcgcc cctcgggccg     420
caaggcgccg tcgggctgcg gcggcgggga gctggcgctg cgctgcctgg ccgagcacgg      480
ccacagcctg ggtggctccg cagccgcggc ggcggcggcg gcgcagcgc gctgtaaggc      540
ggccgaggcg gcggccgacg agccggcgct gtgcctgcag tgcgatatga acgactgcta      600
tagccgcctg cggaggctgg tgcccaccat cccgcccaac aagaaagtca gcaaagtgga      660
gatcctgcag cacgttatcg actacatcct ggacctgcag ctggcgctgg agacgcaccc      720
ggccctgctg aggcagccac caccgccgc gccgccacac cacccggccg ggacctgtcc       780
agccgcgccg ccgcggaccc cgctcactgc gctcaacacc gacccggccg gcgcggtgaa      840
```

```
caagcagggc gacagcattc tgtgccgctg agccgcgctg tccaggtgtg cggccgcctg    900
agcccgagcc aggagcacta gagagggagg gggaagagca aagttagag aaaaaaagcc    960 accggaggaa aggaaaaaac atcggccaac ctagaaacgt tttcattcgt cattccaaga   1020
gagagagagg aaagaaaaat acaactttca ttctttcttt gcacgttcat aaacattcta   1080
catacgtatt ctcttttgtc tcttcattta taactgctgt gaattgtaca tttctgtgtt   1140
ttttggaggt gcagttaaac ttttaagctt aagtgtgaca ggactgataa atagaagatc   1200
aagagtagat ccgactttag aagcctactt tgtgaccaag agctcaatt tttgttttga    1260 agctttacta atctaccaga gcattgtaga tattttttt ttacatctat tgtttaaaat    1320
agatgattat aacggggcag agaactttct tttctctgca agaatgttac atattgtata   1380
gataaatgag tgacatttca taccatgtat atatagagat gttctataag tgtgagaaag   1440
tatatgcttt aatagatact gtaattataa gatatttta ttaaatatt ttttttgtaaa    1500 tattatgtgt gtgtttttt taatctatg ggaatatttc ttttggaaaa tcattttca     1560 gctcaattac agagctcttg atatcttgaa tgtcttttct gtttggcctg gctcttaatt   1620
tgcttttgtt ttgcccagta tagactcgga agtaacagtt atagctagtg gtcttgcatg   1680
attgcatgag atgtttaatc acaaattaaa cttgttctga gtccattcaa atgtgttttt   1740
ttaaatgtag attgaaatct ttgtatttga agcatacatg ttgaaaatac acctatcag    1800 tttttaagta cagggtttta tagtgtaata tatacagagt aagtgtttgt ttttgttttt   1860
caactgaggt caaaatggat tctgaatgat tttgcatatg ggatgaggaa atgcttggat   1920
ccttaaggag tttacgaaat ctgctgtttt atcaaagtga aaaaaaattg cttattactc   1980
ttcattttac actaaagctt aatgtcacta agtttcatgt ctgtacagat tatttaaatc   2040
atggaaatga aaaaaatgtt ctctgcttgc taccaaagga caaactcttg gaaatgaaca   2100
ctttctgctt tccttcctcc aaagaattaa taggcaacag tggggagaaaa aaaaggcata  2160 atggcaaatc cttcaagcag ggataaaagt cgatcttcaa acattaactt aagcagacca   2220
aaaattctga tgaccgcatc tagattattt ttttataaaa atgattttca ctatagctat   2280
gttacgctaa gctactgtcc aatctcttgt gatgtgtaac ttttacatgt gaatattaaa   2340
gtagatttct ctgtcttgta ctgtgatttc tggtctcatt tctttaaaac cttactctta   2400
tttttctttt aaggctcttt tttctcctta aggaaggtaa tattttctag gttagatagg   2460
actatcaggg tttgtgaaca ttatgcattt aatgttatgg gtactttaca cacaagttag   2520
atggaatttt tagagtgaaa gaattaagta ggatttaatt gggtgctttg taaatagtca   2580
actgtgtgta taacgtggtc tgtttgattt ttaaaggaa aggatttgtt tcagattata    2640
caagaataaa agtattatag acccaaggga cttcttatga ggtcaaattc agatatttat   2700
atgaatatga aataccatgg tccctagtag tcagttgaag tggcaatgtc taaacagaaa   2760
tgaacaaaac taatgctagc aggttaaaat caatcaaaat gtttaaaaat tgattctgtc   2820
ctcagcatgt tatttcctca gctctgataa tttactggtc ttgagtattt tgagaatttg   2880
atgttgaacg ttataaagtc aaagaactgc ttgtttagat gaggtttatt tttattttg    2940 atattattca ttccttgtcac acatcaagaa gaaaacacta gagtgctgct ggaattccaa   3000
atctgaagaa ttctaacgac tgcattcttt gttattaaaa agggcacaat ccttcctttt   3060
tatttggcag tttaatttca gtaggaagca tgtcacatgt gcactgttgg ttagaattat   3120
gcatctgtca tgcctgactg ctgaacccta cctaagcctt ttggcgcagt ttaaaactta   3180
```

-continued

| | |
|---|---|
| tactggtgga ctgtgaacct caaaacaaat gggtattttt gggttttgag gatagatgtt | 3240 |
| actccttaaa gtttgtattt ggggcatgaa aaactactga agaagaaaaa gtgctacaga | 3300 |
| tactacattt caaagagttg gcatttttccc tttggccact caagcagcat ttgatgtatc | 3360 |
| taaagaaaca aagtcattgt ttattttttta aaaaattata tgcagttgta caagatacta | 3420 |
| cattccattg aaatgttggc tatgtcctaa ccaggcaacc agataacaaa acatttttga | 3480 |
| gtcttttatc taggtagttc taattattca gctacttagt ttaacaaagg aaaatatcct | 3540 |
| gacttctctc atttcatttg tagacttttc attgtatagg cacaaccaaa gagtcagact | 3600 |
| ggtttaaaac tccagaagga aaaaagtat cccacacagt ggatgttgtt tctaagaatg | 3660 |
| ctacaaaatc ctgacatctc agacatctca atgttaaagg aagaaaaaa ataccttttc | 3720 |
| atttcaaaga actaatatac tttgatattg tgtaaacctt actcaagttt attgtcaagc | 3780 |
| tttaactgcc ttttttagaac ttttttaaaat ttcgagccca caaatctatt gtattagttg | 3840 |
| ccttctataa caataaatct tcactgagca aaggcaaaa aaaaaaaaaa a | 3891 |

<210> SEQ ID NO 15
<211> LENGTH: 3104
<212> TYPE: DNA
<213> ORGANISM: Homo sapiens

<400> SEQUENCE: 15

| | |
|---|---|
| ctctgcctgg gtgtctccct ctctcagtgt gtgtgtctct ctgtctgttt tcacactctc | 60 |
| ctccccaatc gagcgaggcc cacacctggc gcatcactgc cgagccatta gctgcgggtt | 120 |
| tcctttcatc ttcgctgtgg cagacgtttc tatttatcca cttgcgctcg ccgagtggcg | 180 |
| tcaccagcgg tactgtaatg acgattgcag caggaggatg acagcttaga agaagaggg | 240 |
| caatggggct tcctcccaga ggcggtgcgc cacagaggag cgctcgcttc acaaggtgac | 300 |
| cctagctccc accgccaccg ccgcggtcgc ggtccagacc gcgctccagc agctccgcgc | 360 |
| cctcccaggc acccggcctt tctttctccc tcttgcaacc aagatccgtc cggccgctgg | 420 |
| agacccaggg agccggggtt aggaactcac ttggggcttt cccctccccc accggagagc | 480 |
| cccgggatgg agagccgaaa ggacatggtt gtgtttctgg atgggggtca gcttggcact | 540 |
| ctggttggca agagagtctc aaatttgtcc gaagccgtgg gcagcccgct gccggagccg | 600 |
| cccgagaaaa tggtgccccg tggttgcctg agccctcggg ccgtcccctcc ggccacccgg | 660 |
| gagcgcggcg ggggaggccc ggaggaggag ccggtagatg gactcgcagg cagcgcggcg | 720 |
| gggccgggcg ccgagcccca ggtagctggg gcggccatgc tcggcccagg accccggcc | 780 |
| ccctcagtcg acagcctctc cggacagggg caacccagta gctcggacac cgagtcggat | 840 |
| ttctatgaag aaatcgaggt gagctgcacc ccggactgcg ccaccgggaa cgccgagtac | 900 |
| cagcacagca aagggtccgg ctccgaggcg ctggtcggca gtccgaacgg agggagcgag | 960 |
| accccccaaga gcaacggcgg cagtggtggg ggcggctcgc aaggcaccct ggcgtgcagc | 1020 |
| gccagtgacc agatgcgtcg ttaccgcacc gccttcaccc gagagcagat tgcgcggctg | 1080 |
| gagaaggaat ctaccgggga gaactacgta tccaggccgc ggagatgtga gctggcggcc | 1140 |
| gccctaaacc tgccggaaac caccatcaag gtgtggttcc agaaccggcg catgaaggac | 1200 |
| aagcggcagc gcctggccat gacgtggccg caccggcgg accccgcctt ctacacttac | 1260 |
| atgatgagcc atggcggc cgcgggcggc ctgcctaacc ccttcccatc gcacctgccc | 1320 |
| ctgcccactact actcgccggt gggcctgggc gccgcatccg ccgcctccgc cgccgcctcg | 1380 |
| cccttcagcg gctcgctgcg cccgctcgac acgttccgcg tgctgtcgca gccctacccg | 1440 |

```
cggccccgaac tgctgtgcgc cttccgccac ccgccgctct acccccgggcc cgcgcacgga    1500 ctgggcgcct ctgccggcgg cccctgctcc tgcctcgcct gtcacagcgg cccggccaac    1560
gggctggcgc cccgggctgc cgccgcctcg gacttcacct gtgcctccac ctcccgctcg    1620
gactccttcc tcaccttcgc gccctcggtg ctcagcaagg cctcctccgt cgcgctggac    1680
cagagggagg aggtgcccct cactagataa ggggccgccg gctggctgcc ggctccatga    1740
cgcccgtggg gtcaccccc ggcccggga ctcagccagc ctcgctcctc gctcctcgct    1800
cctcgcccct aggacgccaa gggggaaagg agagggcgga aaaggaccag cgggatccgg    1860
ccgcaagaat tggaaagcct aggaagtggc ggtggctggc gcgtttgggg agcaggagtg    1920
gggataggga agcagagctt gagagacctt cctccggggc agcctccgga cccaccgccc    1980
cccaccaggg tcgaggctgt agctccaaag ctaaacaaaa cttagcagca acagcaacca    2040
atatccagtc cctcggcccc tcggcccctc accctccacc tcacactccc ttctcaccgg    2100
gccccctctc cccagccaag gcccaagcac tggaaaggga aattgctgtc tctctgaaca    2160
aaatgctgtg tatgcagagc aggtagagat taatctttgc cagcttttcc aaggcatgac    2220
aaggggctgg tggatggcaa cataccagtc atttggagga gagagtgaga gatgatttac    2280
taccagggag aatccagccc cttggcatgg gacctggagc ctcgactaca cagcatcttc    2340
tgggtctggc gtctgccagc acctgatctc tttcctcatt cccagctttg tgacacttct    2400
caacttgcgg ctccatctct ccctgccccc acttttttgt tggccaggga ggctgcagat    2460
gccccaggag ccctttgccg cttctatgag gccaagcctt ttttccctgg gcccagcaca    2520
caccctgatt agcaagtgat gtgtgcgagg agggtttgtg aatgttgaat gtgtaataat    2580
gatcaccatg gagctggcca ctgacccccag agctgagctg ttaacaaggc gcccagggaa    2640
gagcttaggg agtgggaact tcacctccct ctctcggtat ctggcggtaa attagaggca    2700
attttcatcc tttgcttgtt caccttcact tcaccaggaa cttttctgcc ctacccttg    2760 cattgggtat tttacaactt tctctcattt tcttcccaag ctaccactgg agcttgactt    2820
tcagatacca gtgggagcct tctgtcccctt ttggggaccc tgtctgtggc ctccaccagg    2880
gtttgtttag agccactccc aaatcctcac tcccacactc atccttgcag ccagtttttg    2940
aggaagagga gaacgtgtaa ccccaatgca agcttcaccc tgactgagag ggagtggttc    3000
ttcctgtagg gaatgaattt ggtttgattt gggttttcc tttgaagccc aaagaacttg    3060
ctgttatgat tcgttaacca tattgcaata aaagctggac ataa                     3104
```

<210> SEQ ID NO 16
<211> LENGTH: 1568
<212> TYPE: DNA
<213> ORGANISM: Homo sapiens

<400> SEQUENCE: 16

```
gagtgaggtt tggctgccac caaagttact tctagtcctt gctgtccact cctgccctca      60
gtctggacct gcccaaggac ccctgcaatt aggcctccca tgcagaggtc agtgagagcc     120
caagccaatt gctctaggcc ccgtggctgg ctacttatgg ggcactgtcc tgaccagctc     180
tgctaagatg ctcctggccc ctccctccac cccgtccaga ggacggaccc ccagcgccgt     240
ggagaggctg gaagccgaca aagccaagta tgtcaagacg caccaggtga tagctaggcg     300
acaggagcca gccctgcgtg ggagtcctgg gccgctcacg ccgcacccct gcaacgagct     360 ggggcccccct gcatcgccca ggacgcccag gccggtccgc cggggaagcg gcaggcggct     420
```

```
gccgaggcct gattccctca tcttctaccg ccagaagcgg gactgcaagg cttcggtgaa    480
caaagagaac gccaagggcc agggtctggt gcggcgcctc tttctgggtg ccccgcggga    540
cgctgccccg agcagcccgg cctccacaga gcgacctgcg gcttcagggg gttgggctgc    600
gccccaggat gccccggaag cggcgggaaa gcgggcgctg tgtcccacgt gctcgctgcc    660
cctgtcggag aaggagcgct tcttcaacta ctgcggcctg gagcgcgcgc tggtggaggt    720
gctgggcgca gagcgcttct ccccgcagag ctggggagcc gacgcagcc cgcaggccgg     780
aacttcgccg ccgcccggct ccggggacgc cagcgactgg acatccagcg acaggggcgt    840
ggacagcccg ggcggcgcgg gcggcggcgg cggctcggag gcagcgggct cggcgcggga    900
ccggcgcccc ccggtgtcgg tggtggagcg caacgcgcgc gtcatccagt ggctgtacgg    960
ctgccagcgc gcccgcggac cgccgcgcga gtccgaggtg tgaccgccgc ggctccggac   1020
tggccccggg actgccccg gcacggaaa aggacacccc tcttctggcg cgctgggtgc     1080
cttttgcgtaa gccttccctt ctggaactca gtttcgcgtc tgaaccttgg ggaggtggaa   1140
caagttgctg ccgaaggccc ttccctgctc ccgcggcgaa gggggaggga gaggcctctt   1200
ggtccctgtg gagacccggt ctggggagtc acgattgggg tgggagatga gcaaacctgc   1260
tgaataaagt taaaacgtta tttaaatggg gagctgagga aggagcaaac gggttttcgc   1320
ggttaaaccc gtgggttttg gaatgtgtgt tcccggctgt gtgatcctgg gcaagaactt   1380
gacctccctg gacgcagcgg caccctcgg ttattaagga gggaggagta ggggatagaa    1440
gtatttcaaa atagttgtaa tgcgcatggc aaagtgccca gcatatagaa agtgctcaat   1500
aaacgataac tgctgtgact tctaaaaaaa aaaaaaaaa aaaaaaaaaa aaaaaaaaa     1560
aaaaaaaa                                                            1568

<210> SEQ ID NO 17
<211> LENGTH: 1184
<212> TYPE: DNA
<213> ORGANISM: Homo sapiens

<400> SEQUENCE: 17
tggaaggggc cacttcacac ctcgggctcg gcataaagcg gccgccggcc gccggccccc     60
agacgcgccg ccgctgccat ggcccagccc ctgtgcccgc cgctctccga gtcctggatg    120
ctctctgcgg cctggggccc aactcggcgg ccgccgccct ccgacaagga ctgcggccgc    180
tccctcgtct cgtccccaga ctcatggggc agcacccag ccgacagccc cgtggcgagc     240
cccgcgcggc caggcaccct ccgggacccc gcgccccct ccgtaggtag gcgcggcgcg    300
cgcagcagcc gcctgggcag cgggcagagg cagagcgcca gtgagcggga gaaactgcgc    360
atgcgcacgc tggcccgcgc cctgcacgag ctgcgcgct tctctaccgcc gtccgtggcg    420
cccgcgggcc agagcctgac caagatcgag acgctgcgcc tggctatccg ctatatcggc    480
cacctgtcgg ccgtgctagg cctcagcgag gagagtctcc agcgccggtg ccggcagcgc    540
ggtgacgcgc ggtcccctcg gggctgcccg ctgtgccccg acgactgccc cgcgcagatg    600
cagacacgga cgcaggctga ggggcagggg caggggcgcg ggctgggcct ggtatccgcc    660
gtccgcgccg gggcgtcctg gggatccccg cctgcctgcc ccgagcccg agctgcaccc     720
gagccgcgcg accgcctgc gctgttcgcc gaggcggcgt gccctgaagg gcaggcgatg    780
gagccaagcc caccgtcccc gctccttccg ggcgacgtgc tggctctgtt ggagacctgg    840
atgcccctct cgcctctgga gtggctgcct gaggagccca agtgacaagg gacaactgac    900
gccgtctctg tgagcaccga ggcttttttgg cctcagcacc ttcgaagtgg ttccttggca   960
```

```
gactgccttt cctggaagag ggcacgggcg atcccgacgg gggcattcct gcgggtgaga    1020
gccgtcccca ccgcggcggc ccttctcagc ccctccctcc atggagggac ccatagggct    1080
agacactttg aggcaagcag gaggctctgc ctaatgtgaa tttatttatt tgtgaataaa    1140
ctgtactggt gtcagttggc aaaaaaaaaa aaaaaaaaa aaaa                      1184

<210> SEQ ID NO 18
<211> LENGTH: 2428
<212> TYPE: DNA
<213> ORGANISM: Homo sapiens

<400> SEQUENCE: 18
cccgcccact tccaactacc gcctccggcc tgcccaggga gagagaggga gtggagccca     60
gggagaggga gcgcgagaga gggagggagg aggggacggt gctttggctg acttttttt    120 aaaagagggt gggggtgggg ggtgattgct ggtcgtttgt tgtggctgtt aaatttaaa    180 ctgccatgca ctcggcttcc agtatgctgg gagcggtgaa gatggaaggg cacgagccgt    240
ccgactggag cagctactat gcagagcccg agggctactc ctccgtgagc aacatgaacg    300
ccggcctggg gatgaacggc atgaacacgt acatgagcat gtcggcggcc gccatgggca    360
gcggctcggg caacatgagc gcgggctcca tgaacatgtc gtcgtacgtg ggcgctggca    420
tgagcccgtc cctggcgggg atgtcccccg gcgcgggcgc catggcgggc atgggcggct    480
cggccggggc ggccggcgtg gcgggcatgg ggccgcactt gagtcccagc ctgagcccgc    540
tcggggggca ggcggccggg gccatgggcg gcctggcccc ctacgccaac atgaactcca    600
tgagccccat gtacgggcag gcgggcctga gccgcgcccg cgaccccaag acctacaggc    660
gcagctacac gcacgcaaag ccgccctact cgtacatctc gctcatcacc atggccatcc    720
agcagagccc caacaagatg ctgacgctga gcgagatcta ccagtggatc atggacctct    780 tcccttcta ccggcagaac cagcagcgct ggcagaactc catccgccac tcgctctcct    840
tcaacgactg tttcctgaag gtgccccgct cgcccgacaa gccggcaag ggctccttct    900 ggacctgca ccctgactcg gcaacatgt tcgagaacgg ctgctacctg cgccgccaga    960
agcgcttcaa gtgcgagaag cagctggccg ctgaaggagc cgcaggcgcc gccggcagcg    1020
gcaagaaggc ggccgccgga gcccaggcct cacaggctca actcgggag gccgccgggc    1080 cggcctccga gactccggcg gcaccgagt cgcctcactc gagcgcctcc ccgtgccagg    1140
agcacaagcg agggggcctg ggagagctga aggggacgcc ggctgcggcg ctgagccccc    1200
cagagccggc gccctctccc gggcagcagc agcaggccgc ggcccacctg ctgggccccc    1260 cccaccacc gggcctgccg cctgaggccc acctgaagcc ggaacaccac tacgccttca    1320 accaccgtt ctccatcaac aacctcatgt cctcggagca gcagcaccac cacagccacc    1380
accaccacca accccacaaa atggacctca aggcctacga caggtgatg cactacccg    1440 gctacggttc cccatgcct ggcagcttgg ccatgggccc ggtcacgaac aaaacgggcc    1500
tggacgcctc gccctggcc gcagatacct cctactacca gggggtgtac tcccggccca    1560
ttatgaactc ctcttaagaa gacgacggct tcaggcccgg ctaactctgg caccccggat    1620
cgaggacaag tgagagagca agtggggtc gagactttgg ggagacggtg ttgcagagac    1680
gcaagggaga agaaatccat aacaccccca ccccaacacc cccaagacag cagtcttctt    1740
cacccgctgc agccgttccg tcccaaacag agggccacac agatacccca cgttctatat    1800
aaggaggaaa acgggaaaga atataaagtt aaaaaaaagc ctccggtttc cactactgtg    1860
```

| | |
|---|---:|
| tagactcctg cttcttcaag cacctgcaga ttctgatttt tttgttgttg ttgttctcct | 1920 |
| ccattgctgt tgttgcaggg aagtcttact taaaaaaaaa aaaaaattttt gtgagtgact | 1980 |
| cggtgtaaaa ccatgtagtt ttaacagaac cagagggttg tactattgtt taaaaacagg | 2040 |
| aaaaaaaata atgtaagggt ctgttgtaaa tgaccaagaa aaagaaaaaa aaagcattcc | 2100 |
| caatcttgac acggtgaaat ccaggtctcg ggtccgatta atttatggtt tctgcgtgct | 2160 |
| ttatttatgg cttataaatg tgtattctgg ctgcaagggc cagagttcca caaatctata | 2220 |
| ttaaagtgtt ataccccggtt ttatcccttg aatcttttct tccagatttt tcttttcttt | 2280 |
| acttggctta caaatatac aggcttggaa attatttcaa gaaggaggga gggatacccct | 2340 |
| gtctggttgc aggttgtatt ttatttttggc ccagggagtg ttgctgtttt cccaacatttt | 2400 |
| tattaataaa attttcagac ataaaaaa | 2428 |

<210> SEQ ID NO 19
<211> LENGTH: 4084
<212> TYPE: DNA
<213> ORGANISM: Homo sapiens

<400> SEQUENCE: 19

| | |
|---|---:|
| ggtttccagg cctgaggtgc ccgccctggc cccaggagaa tgaaccagcc gcagaggatg | 60 |
| gcgcctgtgg gcacagacaa ggagctcagt gacctcctgg acttcagcat gatgttcccg | 120 |
| ctgcctgtca ccaacgggaa gggccggccc gcctccctgg ccggggcgca gttcggaggt | 180 |
| tcaggtcttg aggaccggcc cagctcaggc tcctggggca gcggcgacca gagcagctcc | 240 |
| tcctttgacc ccagccggac cttcagcgag ggcaccccact tcactgagtc gcacagcagc | 300 |
| ctctcttcat ccacattcct gggaccggga ctcggaggca agagcggtga gcggggcgcc | 360 |
| tatgcctcct tcgggagaga cgcaggcgtg gcggcctga tcaggctggg cttcctgtca | 420 |
| ggcgagctgg ccctcaacag ccccgggccc ctgtcccctt cgggcatgaa ggggacctcc | 480 |
| cagtactacc cctcctactc cggcagctcc ggcggagag cggcagacgg cagcctagac | 540 |
| acgcagccca agaaggtccg gaaggtcccg ccgggtcttc catcctcggt gtacccaccc | 600 |
| agctcaggtg aggactacgg cagggatgcc accgcctacc cgtccgccaa gacccccagc | 660 |
| agcacctatc ccgcccccctt ctacgtggca gatggcagcc tgcaccccct cagccgagctc | 720 |
| tggagtcccc cggccaggc gggcttcggg cccatgctgg gtggggggctc atccccgctg | 780 |
| ccccctcccgc ccggtagcgg cccggtgggc agcagtggaa gcagcagcac gtttggtggc | 840 |
| ctgcaccagc acgagcgtat gggctaccag ctgcatggag cagaggtgaa cggtgggctc | 900 |
| ccatctgcat cctccttctc ctcagccccc ggagccacgt acggcggcgt ctccagccac | 960 |
| acgccgcctg tcagcgggc cgacagcctc tgggctccc gagggaccac agctggcagc | 1020 |
| tccggggatg ccctcggcaa agcactggcc tcgatctact cccccggatca ctcaagcaat | 1080 |
| aacttctcgt ccagcccttc tacccccgtg ggctccccccc agggcctggc aggaacgtca | 1140 |
| cagtggcctc gagcaggagc ccccggtgcc ttatcgccca gctacgacgg gggtctccac | 1200 |
| ggcctgcaga gtaagataga agaccacctg gacgaggcca tccacgtgct ccgcagccac | 1260 |
| gccgtgggca cagccggcga catgcacacg ctgctgcctg ccacggggc gctggcctca | 1320 |
| ggtttcaccg gccccatgtc actgggcggg cggcacgcag gcctggttgg aggcagccac | 1380 |
| cccgaggacg gcctcgcagg cagcaccagc ctcatgcaca accacgcggc cctccccagc | 1440 |
| cagccaggca ccctccctga cctgtctcgg cctcccgact cctacagtgg gctagggcga | 1500 |
| gcaggtgcca cggcggccgc cagcgagatc aagcgggagg agaaggagga cgaggagaac | 1560 |

```
acgtcagcgg ctgaccactc ggaggaggag aagaaggagc tgaaggcccc ccgggcccgg    1620
accagcagta cggacgaggt gctgtccctg gaggagaaag acctgaggga ccgggagagg    1680
cgcatggcca ataacgcgcg ggagcgggtg cgcgtgcggg atattaacga ggccttccgg    1740
gagctggggc gcatgtgcca gatgcacctc aagtcggaca aagcgcagac caagctgctc    1800
atcctgcagc aggccgtgca ggtcatcctg gggctggagc agcaggtgcg agagcggaac    1860
ctgaatccca aagcagcctg tttgaaacgg cgagaagagg aaaaggtgtc aggtgtggtt    1920
ggagaccccc agatggtgct ttcagctccc cacccaggcc tgagcgaagc ccacaacccc    1980
gccgggcaca tgtgaaagta aacaaaacct gaaagcaagc aacaaaacat acactttgtc    2040
agagaagaaa aaaatgcctt aactataaaa agcggagaaa tggaaacata tcactcaagg    2100
gggatgctgt ggaaacctgg cttattcttc taaagccacc agcaaattgt gcctaagcga    2160
aatatttttt ttaaggaaaa taaaaacatt agttacaaga ttttttttt cttaatgtag     2220 atgaaaatta gcaaggatgc tgcctttggt ctctggtttt tttaagcttt ttttgcatat    2280
gttttgtaag caacaaattt ttttgtataa aagtcccgtg tctctcgcta tttctgctgc    2340
tgttcctaga ctgagcattg catttcttga tcaaccagat gattaaacgt tgtattaaaa    2400
agaccccgtg taaacctgag ccccccgtc ccccccccc ccggaagcc actgcacaca       2460 gacagaacgg ggacaggcgg cgggtctttt gttttttga tgttgggggt tctcttggtt     2520
ttgtcatgtg gaaagtgatg cgtgggcgtt ccctgatgaa ggcaccttgg ggcttccctg    2580
ccgcatcctc tcccctcagg aaggggactg acctgggctt gggggaaggg acgtcagcaa    2640
ggtggctctg accctcccag gtgactctgc caagcagctg tggcccccag ggctacccta    2700
cacaacgccc tccccaggcc cccctaagct gctctccctt ggaacctgca cagctctctg    2760
aaatggggca ttttgttggg accagtgacc cctggcatgg ggaccacacc ctggagcccg    2820
gtgctgggga cctcctggac accctgtcct tcactccttt gccccaggga cccaggctca    2880
tgctctgaac tctggctgag aggatgctgc tcaggagcca gcacaggaca ccccccaccc    2940
caccccacca tgtccccatt acaccagagg gccatcgtga cgtagacagg atgccagggg    3000
cctggccagc ctccccaat gctggggagc atccctgggc ctggggccac acctgctgcc     3060
ctccctctgt gtggtccaag ggcaagagtg gctggagccg ggggactgtg ctggtctgag    3120
ccccacgaag gccttgggct gtgcgtccga ccctgctgca gaaccagcag ggtgtccct    3180 cgggcccatc tgtgtcccat gtcccagcac ccaggcctct ctccaggtct ccttttctgg    3240
tcttttgcca tgagggtaac cagctcttcc cagctggctg gggactgtct tgggtttaaa    3300
actgcaagtc tcctaccctg ggatcccatc cagttccaca cgaactaggg cagtggtcac    3360
tgtggcaccc aggtgtgggc ctggctagct gggggccttc atgtgccctt catgcccctc    3420
cctgcattga ggccttgtgg acccctgggc tggctgtgtt catccccgct gcaggtcggg    3480
cgtctccccc cgtgccactc ctgagactcc accgttacc cccaggagat cctggactgc     3540
ctgactcccc tccccagact ggcttgggag cctgggcccc atggtagatg caagggaaac    3600
ctcaaggcca gctcaatgcc tggtatctgc ccccagtcca ggccaggcgg aggggagggg    3660
ctgtccggct gcctctccct tctcggtggc ttccctacg ccctgggagt ttgatctctt     3720
aagggaactt gcctctccct cttgttttgc tcctggccct gccctaggt ctgggtgggc     3780 agtgccccca tagcctctgg aactgtgcgt tctgcataga attcaaacga gattcaccca    3840
gcgcgaggag gaagaaacag cagttcctgg gaaccacaat tatgggggt gggggtgtg     3900
```

```
atctgagtgc ctcaagatgg tttttcaaaaa aatttttttta aagaaaataa ttgtatacgt    3960
gtcaacacag ctggctggat gattgggact ttaaaacgac cctctttcag gtggattcag    4020
agacctgtcc tgtatataac agcactgtag caataaacgt gacattttat aacgatgccc    4080
tgca                                                                  4084
```

<210> SEQ ID NO 20
<211> LENGTH: 1000
<212> TYPE: DNA
<213> ORGANISM: Homo sapiens

<400> SEQUENCE: 20

```
actctcattc cacgttctta actgttccat tttccgtatc tgcttcgggc ttccacctca      60 ttttttttcgc tttgcccatt ctgtttcagc cagtcgccaa gaatcatgaa agtcgccagt    120
ggcagcaccg ccaccgccgc cgcgggcccc agctgcgcgc tgaaggccgg caagacagcg    180
agcggtgcgg gcgaggtggt gcgctgtctg tctgagcaga gcgtggccat ctcgcgctgc    240
gccgggggcg ccggggcgcg cctgcctgcc ctgctggacg agcagcaggt aaacgtgctg    300
ctctacgaca tgaacggctg ttactcacgc ctcaaggagc tggtgcccac cctgccccag    360
aaccgcaagg tgagcaaggt ggagattctc cagcacgtca tcgactacat cagggacctt    420
cagttggagc tgaactcgga atccgaagtt ggaaccccccg ggggccgagg gctgccggtc    480
cgggctccgc tcagcaccct caacggcgag atcagcgccc tgacgccga ggcggcatgc    540 gttcctgcgg acgatcgcat cttgtgtcgc tgaagcgcct ccccccaggga ccggcggacc    600 ccagccatcc aggggcaag aggaattacg tgctctgtgg gtctccccca acgcgcctcg    660
ccggatctga gggagaacaa gaccgatcgg cggccactgc gcccttaact gcatccagcc    720
tggggctgag gctgaggcac tggcgaggag agggcgctcc tctctgcaca cctactagtc    780
accagagact ttaggggtg ggattccact cgtgtgtttc tatttttga aaagcagaca      840 ttttaaaaaa tggtcacgtt tggtgcttct cagatttctg aggaaattgc tttgtattgt    900
atattacaat gatcaccgac tgaaaatatt gttttacaat agttctgtgg ggctgttttt    960
ttgttattaa acaaataatt tagatggtgg taaaaaaaaa                          1000
```

<210> SEQ ID NO 21
<211> LENGTH: 2415
<212> TYPE: DNA
<213> ORGANISM: Homo sapiens

<400> SEQUENCE: 21

```
cggccgctgc tagaggggct gcttgcgcca ggcgccggcc gccccactgc gggtccctgg      60
cggccggtgt ctgaggagtc ggagagccga ggcggccaga ccgtgcgccc cgcgcttctc    120
ccgaggccgt tccgggtctg aactgtaaca gggaggggcc tcgcaggagc agcagcgggc    180
gagttaaagt atgctgggag cggtgaagat ggaagggcac gagccgtccg actggagcag    240
ctactatgca gagcccgagg gctactcctc cgtgagcaac atgaacgccg gcctggggat    300
gaacggcatg aacacgtaca tgagcatgtc ggcggccgcc atgggcagcg gctcgggcaa    360
catgagcgcg ggctccatga acatgtcgtc gtacgtgggc gctggcatga gcccgtccct    420
ggcggggatg tcccccggcg cgggcgccat ggcgggcatg ggcggctcgg ccggggcggc    480
ggccgtggcg gcatggggc cgcacttgag tcccagcctg agccgctcg gggggcaggc    540 ggccggggc atgggcggcc tggcccccta cgccaacatg aactccatga gccccatgta    600
cgggcaggcg ggcctgagcc gcgcccgcga ccccaagacc tacaggcgca gctacacgca    660
```

```
cgcaaagccg ccctactcgt acatctcgct catcaccatg gccatccagc agagccccaa    720
caagatgctg acgctgagcg agatctacca gtggatcatg gacctcttcc ccttctaccg    780
gcagaaccag cagcgctggc agaactccat ccgccactcg ctctccttca cgactgttt     840 cctgaaggtg ccccgctcgc ccgacaagcc cggcaagggc tccttctgga ccctgcaccc    900
tgactcgggc aacatgttcg agaacggctg ctacctgcgc cgccagaagc gcttcaagtg    960
cgagaagcag ctggcgctga aggaggccga aggcgccgcc ggcagcggca agaaggcggc   1020
cgccggagcc caggcctcac aggctcaact cggggaggcc gccgggccgg cctccgagac   1080
tccggcgggc accgagtcgc ctcactcgag cgcctccccg tgccaggagc acaagcgagg   1140
gggcctggga gagctgaagg ggacgccggc tgcggcgctg agccccccag agccggcgcc   1200
ctctcccggg cagcagcagc aggccgcggc ccacctgctg ggcccgcccc accccggg     1260 cctgccgcct gaggcccacc tgaagccgga acaccactac gccttcaacc cccgttctc    1320 catcaacaac ctcatgtcct cggagcagca gcaccaccac agccaccacc accaccaacc   1380
ccacaaaatg gacctcaagg cctacgaaca ggtgatgcac taccccggct acggttcccc   1440
catgcctggc agcttggcca tgggcccggt cacgaacaaa acgggcctgg acgcctcgcc   1500
cctggccgca gatacctcct actaccaggg ggtgtactcc cggcccatta tgaactcctc   1560
ttaagaagac gacggcttca ggcccggcta actctggcac cccggatcga ggacaagtga   1620
gagagcaagt gggggtcgag actttgggga gacggtgttg cagagacgca agggagaaga   1680
aatccataac ccccaccc caacacccc aagacagcag tcttcttcac ccgctgcagc      1740
cgttccgtcc caaacagagg gccacacaga taccccacgt tctatataag gaggaaaacg   1800
ggaaagaata taagttaaaa aaaaagcctc cggtttccac tactgtgtag actcctgctt   1860
cttcaagcac ctgcagattc tgattttttt gttgttgttg ttctcctcca ttgctgttgt   1920
tgcagggaag tcttacttaa aaaaaaaaaa aatttgtg agtgactcgg tgtaaaacca     1980
tgtagtttta acagaaccag agggttgtac tattgtttaa aaacaggaaa aaaataatg    2040 taagggtctg ttgtaaatga ccaagaaaaa gaaaaaaaaa gcattcccaa tcttgacacg   2100
gtgaaatcca ggtctcgggt ccgattaatt tatggtttct gcgtgcttta tttatggctt   2160
ataaatgtgt attctggctg caagggccag agttccacaa atctatatta aagtgttata   2220
cccgttttta tcccttgaat cttttcttcc agatttttct tttctttact ggcttacaa    2280 aatatacagg cttggaaatt atttcaagaa ggagggaggg ataccctgtc tggttgcagg   2340
ttgtatttta ttttggccca gggagtgttg ctgttttccc aacatttat taataaaatt    2400 ttcagacata aaaaa                                                    2415
```

<210> SEQ ID NO 22
<211> LENGTH: 2350
<212> TYPE: DNA
<213> ORGANISM: Homo sapiens

<400> SEQUENCE: 22

```
acgcgccgcg tgcccggccg cgcccagcag ggtttccagg cctgaggtgc ccgccctggc     60
cccaggagaa tgaaccagcc gcagaggatg gcgcctgtgg gcacagacaa ggagctcagt    120
gacctcctgg acttcagcat gatgttcccg ctgcctgtca ccaacgggaa gggccggccc    180
gcctccctgg ccggggcgca gttcggaggt tcaggtcttg aggaccggcc cagctcaggc    240
tcctggggca gcggcgacca gagcagctcc tcctttgacc ccagccggac cttcagcgag    300
```

```
ggcacccact tcactgagtc gcacagcagc ctctcttcat ccacattcct gggaccggga    360
ctcggaggca agagcggtga gcggggcgcc tatgcctcct cgggagaga cgcaggcgtg    420 ggcggcctga ctcaggctgg cttcctgtca ggcgagctgg ccctcaacag ccccgggccc    480 ctgtccccctt cgggcatgaa ggggacctcc cagtactacc cctcctactc cggcagctcc    540
cggcggagag cggcagacgg cagcctagac acgcagccca agaaggtccg gaaggtcccg    600
ccgggtcttc catcctcggt gtacccaccc agctcaggtg aggactacgg cagggatgcc    660
accgcctacc cgtccgccaa gaccccccagc agcacctatc ccgcccccctt ctacgtggca    720 gatggcagcc tgcacccctc agccgagctc tggagtcccc cgggccaggc gggcttcggg    780
cccatgctgg gtgggggctc atccccgctg ccctcccgc ccggtagcgg cccggtgggc    840
agcagtggaa gcagcagcac gtttggtggc ctgcaccagc acgagcgtat gggctaccag    900
ctgcatggag cagaggtgaa cggtgggctc ccatctgcat cctccttctc ctcagccccc    960
ggagccacgt acggcggcgt ctccagccac acgccgcctg tcagcggggc cgacagcctc   1020
ctgggctccc gagggaccac agctggcagc tccggggatg ccctcggcaa agcactggcc   1080
tcgatctact ccccggatca ctcaagcaat aacttctcgt ccagcccttc taccccgtg   1140 ggctcccccc agggcctggc aggaacgtca cagtggcctc gagcaggagc cccggtgcc   1200 ttatcgccca gctacgacgg gggtctccac ggcctgagta agatagaaga ccacctggac   1260
gaggccatcc acgtgctccg cagccacgcc gtgggcacag ccggcgacat gcacgctg   1320 ctgcctggcc acggggcgct ggcctcaggt ttcaccggcc ccatgtcact gggcgggcgg   1380
cacgcaggcc tggttggagg cagccacccc gaggacggcc tcgcaggcag caccagcctc   1440
atgcacaacc acgcggccct ccccagccag ccaggcaccc tccctgacct gtctcggcct   1500
cccgactcct acagtgggct agggcgagca ggtgccacgg cggccgccag cgagatcaag   1560
cgggaggaga aggaggacga ggagaacacg tcagcggctg accactcgga ggaggagaag   1620
aaggagctga aggccccccg ggcccggacc agcccagacg aggacgagga cgaccttctc   1680
cccccagagc agaaggccga gcgggagaag gagcgccggg tggccaataa cgcccgggag   1740
cggctgcggg tccgtgacat caacgaggcc tttaaggagc tggggcgcat gtgccaactg   1800
cacctcaaca gcgagaagcc ccagaccaaa ctgctcatcc tgcaccaggc tgtctcggtc   1860
atcctgaact tggagcagca agtgcgagag cggaacctga atcccaaagc agcctgtttg   1920
aaacggcgag aagaggaaaa ggtgtcaggt gtggttggag accccagat ggtgctttca   1980 gctccccacc caggcctgag cgaagccac aaccccgccg ggcacatgtg aaaggtctgg   2040
gtgggcagtg gccccatagc ctctggaact gtgcgttctg catagaattc aaacgagatt   2100
cacccagcgc gaggaggaag aaacagcagt tcctgggaac cacaattatg ggggtgggg   2160 ggtgtgatct gagtgcctca agatggtttt caaaaaaatt tttttaaaga aaataattgt   2220
atacgtgtca acacagctgg ctggatgatt gggactttaa aacgaccctc tttcaggtgg   2280
attcagagac ctgtcctgta tataacagca ctgtagcaat aaacgtgaca ttttataacg   2340
atgccctgca                                                          2350
```

<210> SEQ ID NO 23  
<211> LENGTH: 4448  
<212> TYPE: DNA  
<213> ORGANISM: Homo sapiens

<400> SEQUENCE: 23

```
acgcgccgcg tgcccggccg cgcccagcag ggtttccagg cctgaggtgc ccgccctggc     60
```

```
cccaggagaa tgaaccagcc gcagaggatg gcgcctgtgg gcacagacaa ggagctcagt      120
gacctcctgg acttcagcat gatgttcccg ctgcctgtca ccaacgggaa gggccggccc      180
gcctccctgg ccggggcgca gttcggaggt tcaggtcttg aggaccggcc cagctcaggc      240
tcctggggca gcgcgaccca gagcagctcc tcctttgacc ccagccggac cttcagcgag      300
ggcacccact tcactgagtc gcacagcagc ctctcttcat ccacattcct gggaccggga      360
ctcggaggca gagcggtga gcggggcgcc tatgcctcct tcgggagaga cgcaggcgtg       420
ggcggcctga ctcaggctgg cttcctgtca ggcgagctgg ccctcaacag ccccgggccc      480 ctgtccccctt cgggcatgaa ggggacctcc cagtactacc cctcctactc cggcagctcc     540
cggcggagag cggcagacgg cagcctagac acgcagccca agaaggtccg gaaggtcccg      600
ccgggtcttc catcctcggt gtacccaccc agctcaggtg aggactacgg cagggatgcc      660
accgcctacc cgtccgccaa gaccccccagc agcacctatc ccgccccctt ctacgtggca     720
gatggcagcc tgcaccccte agccgagctc tggagtcccc cgggccaggc gggcttcggg      780
cccatgctgg gtggggcctc atccccgctg ccctcccgc ccggtagcgg cccggtgggc       840
agcagtggaa gcagcagcac gtttggtggc ctgcaccagc acgagcgtat gggctaccag      900
ctgcatggag cagaggtgaa cggtgggctc ccatctgcat cctccttctc ctcagccccc      960
ggagccacgt acggcggcgt ctccagccac acgccgcctg tcagcggggc cgacagcctc     1020
ctgggctccc gagggaccac agctggcagc tccggggatg ccctcggcaa agcactggcc     1080
tcgatctact ccccggatca ctcaagcaat aacttctcgt ccagccccttc tacccccgtg    1140 ggctccccccc agggcctggc aggaacgtca cagtggcctc gagcaggagc cccggtgcc     1200 ttatcgccca gctacgacgg gggtctccac ggcctgcaga gtaagataga agaccacctg     1260
gacgaggcca tccacgtgct ccgcagccac gccgtgggca cagccggcga catgcacacg     1320
ctgctgcctg ccacggggc gctggcctca ggtttcaccg gccccatgtc actgggcggg      1380
cggcacgcag gcctggttgg aggcagccac cccgaggacg gcctcgcagg cagcaccagc     1440
ctcatgcaca accacgcggc cctccccagc cagccaggca ccctccctga cctgtctcgg     1500
cctcccgact cctacagtgg gctagggcga gcaggtgcca cggcggccgc cagcgagatc     1560
aagcgggagg agaaggagga cgaggagaac acgtcagcgg ctgaccactc ggaggaggag     1620
aagaaggagc tgaaggcccc ccgggcccgg accagcagta cggacgaggt gctgtccctg     1680
gaggagaaag acctgaggga ccgggagagg cgcatggcca ataacgcgcg ggagcgggtg     1740
cgcgtgcggg atattaacga ggccttccgg gagctggggc gcatgtgcca gatgcacctc     1800
aagtcggaca agcgcagac caagctgctc atcctgcagc aggccgtgca ggtcatcctg     1860
gggctggagc agcaggtgcg agagcggaac ctgaatccca agcagcctg tttgaaacgg      1920 cgagaagagg aaaaggtgtc aggtgtggtt ggagacccccc agatggtgct ttcagctccc    1980
cacccaggcc tgagcgaagc ccacaacccc gccgggcaca tgtgaaaggt atgcctccgt     2040
gggacgagcc acccgctttc agccctgtgc tctggcccca gaacggccac tcgagacccc    2100
gggcttcatc cacatccaca cctcacacac ctgttgtcag catcgagcca acaccaacct    2160
gacaaggttc ggagtgatgg gggcggccaa ggtgacactg ggtccaggag ctccctgggg    2220 cctggccta ccactcactg gcctcgctcc cctgtccccc gaatctcagc caccgtgtca     2280
ctctgtgacc tgtcccatgg atcctgaaac tgcatcttgg ccctgttgcc tgggctgaca    2340
ggagcatttt tttttttttcc agtaaacaaa acctgaaagc aagcaacaaa acatacactt    2400
```

```
tgtcagagaa gaaaaaaatg ccttaactat aaaaagcgga gaaatggaaa catatcactc    2460
aagggggatg ctgtggaaac ctggcttatt cttctaaagc caccagcaaa ttgtgcctaa    2520
gcgaaatatt ttttttaagg aaaataaaaa cattagttac aagattttt  ttttcttaat    2580 gtagatgaaa attagcaagg atgctgcctt tggtctctgg ttttttttaag cttttttttgc   2640 atatgttttg taagcaacaa attttttttgt ataaaagtcc cgtgtctctc gctatttctg    2700
ctgctgttcc tagactgagc attgcatttc ttgatcaacc agatgattaa acgttgtatt    2760
aaaaagaccc cgtgtaaacc tgagcccccc cgtcccccccc ccccccgga agccactgca    2820 cacagacaga acggggacag gcggcgggtc ttttgttttt ttgatgttgg gggttctctt    2880
ggttttgtca tgtggaaagt gatgcgtggg cgttccctga tgaaggcacc ttggggcttc    2940
cctgccgcat cctctcccct caggaagggg actgacctgg gcttgggga agggacgtca    3000 gcaaggtggc tctgaccctc ccaggtgact ctgccaagca gctgtggccc ccagggctac    3060
cctacacaac gccctcccca ggcccccccta agctgctctc ccttggaacc tgcacagctc    3120
tctgaaatgg ggcattttgt tgggaccagt gacccctggc atgggaccac accctggag     3180 cccggtgctg gggacctcct ggacaccctg tccttcactc ctttgcccca gggacccagg    3240
ctcatgctct gaactctggc tgagaggatg ctgctcagga gccagcacag gacaccccc     3300 accccacccc accatgtccc cattacacca gagggccatc gtgacgtaga caggatgcca    3360
ggggcctggc cagcctcccc caatgctggg gagcatccct gggcctgggg ccacacctgc    3420
tgccctccct ctgtgtggtc caagggcaag agtggctgga gccggggac tgtgctggtc     3480 tgagccccac gaaggccttg ggctgtgcgt ccgaccctgc tgcagaacca gcaggtgtc    3540 ccctcgggcc catctgtgtc ccatgtccca gcacccaggc ctctctccag gtctccttt    3600 ctggtctttt gccatgaggg taaccagctc ttcccagctg gctggggact gtcttgggtt    3660
taaaactgca agtctcctac cctgggatcc catccagttc cacacgaact agggcagtgg    3720
tcactgtggc acccaggtgt gggcctggct agctgggggc cttcatgtgc ccttcatgcc    3780
cctccctgca ttgaggcctt gtggaccct gggctggctg tgttcatccc cgctgcaggt     3840
cgggcgtctc ccccgtgcc actcctgaga ctcccaccgt tacccccagg agatcctgga    3900
ctgcctgact cccctcccca gactggcttg ggagcctggg cccatggta gatgcaaggg    3960 aaacctcaag gccagctcaa tgcctggtat ctgcccccag tccaggccag gcggagggga   4020
ggggctgtcc ggctgcctct cccttctcgg tggcttcccc tacgccctgg gagtttgatc    4080
tcttaaggga acttgcctct ccctcttgtt ttgctcctgg ccctgcccct aggtctgggt    4140
gggcagtggc cccatagcct ctggaactgt gcgttctgca tagaattcaa acgagattca    4200
cccagcgcga ggaggaagaa acagcagttc ctgggaacca caattatggg gggtgggggg    4260
tgtgatctga gtgcctcaag atggttttca aaaaatttt tttaaagaaa ataattgtat    4320
acgtgtcaac acagctggct ggatgattgg gactttaaaa cgaccctctt tcaggtggat    4380
tcagagacct gtcctgtata taacagcact gtagcaataa acgtgacatt ttataacgat    4440
gccctgca                                                             4448
```

<210> SEQ ID NO 24
<211> LENGTH: 4457
<212> TYPE: DNA
<213> ORGANISM: Homo sapiens

<400> SEQUENCE: 24

```
acgcgccgcg tgcccggccg cgcccagcag ggtttccagg cctgaggtgc ccgccctggc      60
```

```
cccaggagaa tgaaccagcc gcagaggatg gcgcctgtgg gcacagacaa ggagctcagt    120
gacctcctgg acttcagcat gatgttcccg ctgcctgtca ccaacgggaa gggccggccc    180
gcctccctgg ccggggcgca gttcggaggt tcaggtcttg aggaccggcc cagctcaggc    240
tcctggggca gcgcgaccca gagcagctcc tcctttgacc ccagccggac cttcagcgag    300
ggcacccact tcactgagtc gcacagcagc ctctcttcat ccacattcct gggaccggga    360
ctcggaggca gagcggtga gcggggcgcc tatgcctcct tcgggagaga cgcaggcgtg    420
ggcggcctga ctcaggctgg cttcctgtca ggcgagctgg ccctcaacag ccccgggccc    480
ctgtcccctt cgggcatgaa ggggacctcc cagtactacc cctcctactc cggcagctcc    540
cggcggagag cggcagacgg cagcctagac acgcagccca agaaggtccg gaaggtcccg    600
ccgggtcttc catcctcggt gtacccaccc agctcaggtg aggactacgg cagggatgcc    660
accgcctacc cgtccgccaa gaccccccagc agcacctatc ccgccccctt ctacgtggca    720
gatggcagcc tgcaccccct cagccgagctc tggagtcccc cgggccaggc gggcttcggg    780
cccatgctgg gtggggctc atccccgctg cccctcccgc ccggtagcgg cccggtgggc    840
agcagtggaa gcagcagcac gtttggtggc ctgcaccagc acgagcgtat gggctaccag    900
ctgcatggag cagaggtgaa cggtgggctc ccatctgcat cctccttctc ctcagccccc    960
ggagccacgt acggcggcgt ctccagccac acgccgcctg tcagcggggc cgacagcctc    1020
ctgggctccc gagggaccac agctggcagc tccggggatg ccctcggcaa agcactggcc    1080
tcgatctact ccccggatca ctcaagcaat aacttctcgt ccagcccttc taccccgtg    1140 ggctccccc agggcctggc aggaacgtca cagtggcctc gagcaggagc ccccggtgcc    1200
ttatcgccca gctacgacgg gggtctccac ggcctgcaga gtaagataga agaccacctg    1260
gacgaggcca tccacgtgct ccgcagccac gccgtgggca cagccggcga catgcacacg    1320
ctgctgcctg ccacggggc gctggcctca ggtttcaccg gccccatgtc actgggcggg    1380
cggcacgcag gcctggttgg aggcagccac cccgaggacg gcctcgcagg cagcaccagc    1440
ctcatgcaca accacgcggc cctccccagc cagccaggca ccctcccctga cctgtctcgg    1500 cctcccgact cctacagtgg gctagggcga gcaggtgcca cggcggccgc cagcgagatc    1560
aagcgggagg agaaggagga cgaggagaac acgtcagcgg ctgaccactc ggaggaggag    1620
aagaaggagc tgaaggcccc ccgggcccgg accagcccag acgaggacga ggacgacctt    1680
ctccccccag agcagaaggc cgagcgggag aaggagcgcc gggtggccaa taacgcccgg    1740
gagcggctgc gggtccgtga catcaacgag gcctttaagg agctggggcg catgtgccaa    1800
ctgcacctca cagcgagaa gccccagacc aaactgctca tcctgcacca ggctgtctcg    1860
gtcatcctga acttggagca gcaagtgcga gagcggaacc tgaatcccaa agcagcctgt    1920
ttgaaacggc gagaagagga aaaggtgtca ggtgtggttg agacccccca gatggtgctt    1980
tcagctcccc acccaggcct gagcgaagcc acaacccccg ccgggcacat gtgaaaggta    2040
tgcctccgtg ggacgagcca cccgctttca gccctgtgct ctggccccag aacggccact    2100
cgagaccccg ggcttcatcc acatccacac ctcacacacc tgttgtcagc atcgagccaa    2160
caccaacctg acaaggttcg gagtgatggg ggcggccaag gtgacactgg gtccaggagc    2220
tccctggggc cctggcctac cactcactgg cctcgctccc cctgtccccg aatctcagcc    2280
accgtgtcac tctgtgacct gtcccatgga tcctgaaact gcatcttggc cctgttgcct    2340
gggctgacag gagcattttt ttttttttcca gtaaacaaaa cctgaaagca agcaacaaaa    2400
```

-continued

| | |
|---|---|
| catacacttt gtcagagaag aaaaaaatgc cttaactata aaaagcggag aaatggaaac | 2460 |
| atatcactca agggggatgc tgtggaaacc tggcttattc ttctaaagcc accagcaaat | 2520 |
| tgtgcctaag cgaaatattt tttttaagga aaataaaaac attagttaca agatttttttt | 2580 |
| tttcttaatg tagatgaaaa ttagcaagga tgctgccttt ggtctctggt ttttttaagc | 2640 |
| ttttttttgca tatgttttgt aagcaacaaa ttttttttgta taaaagtccc gtgtctctcg | 2700 |
| ctatttctgc tgctgttcct agactgagca ttgcatttct tgatcaacca gatgattaaa | 2760 |
| cgttgtatta aaaagacccc gtgtaaacct gagccccccc gtcccccccc ccccccggaa | 2820 |
| gccactgcac acagacagaa cggggacagg cggcgggtct tttgtttttt tgatgttggg | 2880 |
| ggttctcttg gttttgtcat gtggaaagtg atgcgtgggc gttccctgat gaaggcacct | 2940 |
| tggggcttcc ctgccgcatc ctctcccctc aggaagggga ctgacctggg cttggggga | 3000 |
| gggacgtcag caaggtggct ctgaccctcc caggtgactc tgccaagcag ctgtggcccc | 3060 |
| cagggctacc ctacacaacg ccctcccag gccccctaa gctgctctcc cttggaacct | 3120 |
| gcacagctct ctgaaatggg gcattttgtt gggaccagtg acccctggca tggggaccac | 3180 |
| accctggagc ccggtgctgg ggacctcctg gacaccctgt ccttcactcc tttgccccag | 3240 |
| ggacccaggc tcatgctctg aactctggct gagaggatgc tgctcaggag ccagcacagg | 3300 |
| acaccccca ccccacccca ccatgtcccc attacaccag agggccatcg tgacgtagac | 3360 |
| aggatgccag gggcctggcc agcctccccc aatgctgggg agcatccctg ggcctggggc | 3420 |
| cacacctgct gccctccctc tgtgtggtcc aagggcaaga gtggctggag ccggggact | 3480 |
| gtgctggtct gagccccacg aaggccttgg gctgtgcgtc cgaccctgct gcagaaccag | 3540 |
| cagggtgtcc cctcgggccc atctgtgtcc catgtcccag cacccaggcc tctctccagg | 3600 |
| tctccttttc tggtcttttg ccatgagggt aaccagctct tcccagctgg ctggggactg | 3660 |
| tcttgggttt aaaactgcaa gtctcctacc ctgggatccc atccagttcc acacgaacta | 3720 |
| gggcagtggt cactgtggca cccaggtgtg ggcctggcta gctgggggcc ttcatgtgcc | 3780 |
| cttcatgccc ctccctgcat tgaggccttg tggaccctg ggctggctgt gttcatcccc | 3840 |
| gctgcaggtc gggcgtctcc ccccgtgcca ctcctgagac tcccaccgtt acccccagga | 3900 |
| gatcctggac tgcctgactc ccctccccag actggcttgg gagcctgggc cccatggtag | 3960 |
| atgcaaggga aacctcaagg ccagctcaat gcctggtatc tgcccccagt ccaggccagg | 4020 |
| cggaggggag gggctgtccg gctgcctctc ccttctcggt ggcttcccct acgccctggg | 4080 |
| agtttgatct cttaagggaa cttgcctctc cctcttgttt tgctcctggc cctgccccta | 4140 |
| ggtctgggtg ggcagtggcc ccatagcctc tggaactgtg cgttctgcat agaattcaaa | 4200 |
| cgagattcac ccagcgcgag gaggaagaaa cagcagttcc tgggaaccac aattatgggg | 4260 |
| ggtgggggt gtgatctgag tgcctcaaga tggttttcaa aaaaattttt ttaaagaaaa | 4320 |
| taattgtata cgtgtcaaca cagctggctg gatgattggg actttaaaac gaccctcttt | 4380 |
| caggtggatt cagagacctg tcctgtatat aacagcactg tagcaataaa cgtgacattt | 4440 |
| tataacgatg ccctgca | 4457 |

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

```
<400> SEQUENCE: 25
ttcttccccc ttgttgtcct c                                              21

<210> SEQ ID NO 26
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
acaggtgtag ttggtctgta gg                                             22

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ctggattctg gcgatggtgt a                                              21

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
cggacaattt cacgttcagc a                                              21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
aacagcagcg gaaaaccttc a                                              21

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
ggctttattg acattggcga ttt                                            23

<210> SEQ ID NO 31
<211> LENGTH: 22
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ctgggtctgg aaccaattct tt                                            22

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gcctgagcca tcagtgtgta                                               20

<210> SEQ ID NO 33
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
cactgctttg ggagccttc                                                19

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ggggcagcga ttcatttttc t                                             21

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
ttccccgaag acacacacaa a                                             21

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ccccagtttt cattgccctc a                                             21
```

<210> SEQ ID NO 37
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
atgcctaact tttctggcaa ct                                              22

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gcacagtggt ggaggttttg a                                               21

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
tgcatcagtg acggtaaacc a                                               21

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
ttcttcagcc gtgcaacaat c                                               21

<210> SEQ ID NO 41
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
tgaaaataaa ggtgcctcgt ctc                                             23

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 42
tcaggttact gaatagcctc cc                                            22

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tcggctcctt tcctcactca                                               20

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
ctcatagggt tgttcgctcg g                                             21

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
tcctatgcac gtcccagttc t                                             21

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
tcgatcctct tgtcaaagcg g                                             21

<210> SEQ ID NO 47
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gagagccgaa aggacatggt t                                             21

<210> SEQ ID NO 48
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
ctgcctgcta gtccatcgac                                          20

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
ccgaggaggg atctaaggaa c                                        21

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
cttccaaaag tatcggtctc cac                                      23

<210> SEQ ID NO 51
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
ggtcgcttcg tgagtccag                                           19

<210> SEQ ID NO 52
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
agcagccgtc tccagtagt                                           19

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
```
ccctacgcca acatgaactc g                                      21

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
gttctgccgg tagaaaggga                                        20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
gggaaagcac tgcacgaact                                        20

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
agcacgcaaa aggtcacatt g                                      21

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
caacttcgac aaagccgagg                                        20

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
actcgtcttt cccttgccct                                        20

<210> SEQ ID NO 59
<211> LENGTH: 22
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 59
gccaacattg tcctcgtaaa ct                                              22

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
tgtggtcccc ttcacttatg g                                               21

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
gcagaaacat ctggtttgct g                                               21

<210> SEQ ID NO 62
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
cctcctgttc ataggtggag tc                                              22

<210> SEQ ID NO 63
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
agggaccact gcaactcag                                                  19

<210> SEQ ID NO 64
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
ccatacacag ttaaggacgc ac                                              22

<210> SEQ ID NO 65
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
cagatgctgc cctacatgaa c                                             21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
tctgggtact tcgtctcctg g                                             21

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
cctagctgtt cgctgaaggc                                               20

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
ctccgacaga ccaagtacca c                                             21

<210> SEQ ID NO 69
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
cgaccgagga gcctcttag                                                19

<210> SEQ ID NO 70
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
```

```
ggacgcgata gggaagacc                                                 19

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
tctgggtccc tatccaatgt g                                              21

<210> SEQ ID NO 72
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
ggtccccgaa ctggtactg                                                 19

<210> SEQ ID NO 73
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
tacagcacca gcgtcatttc g                                              21

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
gagcccacgt aagagaaggc                                                20

<210> SEQ ID NO 75
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
tttggcaaat acaacccttc aga                                            23

<210> SEQ ID NO 76
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 76
gcagaagata ctgtcaccac c                                              21

<210> SEQ ID NO 77
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
ccaaccgcac tgcccttat                                                 19

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
cgcgaaacga accaacttgt                                                20

<210> SEQ ID NO 79
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
cagccagaat tttcgagagg t                                              21

<210> SEQ ID NO 80
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
cagtgcgatt ggagccatc                                                 19

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
gtcactcggt cctggtttaa g                                              21
```

```
<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
acgatgggtc ccacgattct                                                   20

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gcccagtacc tccgaaagtc                                                   20

<210> SEQ ID NO 84
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
gccttaacat actcctcctt gtc                                               23

<210> SEQ ID NO 85
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
gagacatccc cctatttcta cca                                               23

<210> SEQ ID NO 86
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
gctcagtccg ctcatagcc                                                    19

<210> SEQ ID NO 87
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 87
ttcaagcctg ttgggctcta c                                          21

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
tccggtcacg tccacatctt                                            20

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
acgctggtgc tctatgcaag                                            20

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tcagttgctg cccattcatc a                                          21

<210> SEQ ID NO 91
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
gcagccgttg aatgtctctt c                                          21

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
gtccgtgaac tcgaccttt t                                           21

<210> SEQ ID NO 93
<211> LENGTH: 19
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 93
cacacgctgc cttgtgtct                                                    19

<210> SEQ ID NO 94
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
ggtcagcaaa agcacggtt                                                    19

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
gagccggatc tgaagaggga                                                   20

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
gcttgacgtg tggcttgttc                                                   20

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
tcattcggct acggaacaag a                                                 21

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
gacctgcgac tccaaagtct g                                                 21
```

```
<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
cagaggaggc caacgtagaa g                                              21

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
ctccatcggg gatcttgggt                                                20

<210> SEQ ID NO 101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
atgctcctga aagcaaacca g                                              21

<210> SEQ ID NO 102
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
ccttttaggg caagtccatt gt                                             22

<210> SEQ ID NO 103
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
ccactctctg cgagcaatg                                                 19

<210> SEQ ID NO 104
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 104
ggtggctgaa ctagccgat                                                19

<210> SEQ ID NO 105
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
atgagtctcc taaaggaacg ga                                            22

<210> SEQ ID NO 106
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
gggaatacga tcttgctctg ac                                            22

<210> SEQ ID NO 107
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
gcatcggtgg acgctatgt                                                19

<210> SEQ ID NO 108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
tgtgctagga aggtctccca a                                             21

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
gatgacccca tcggaaacct g                                             21

<210> SEQ ID NO 110
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
cttgcagatc ctgttggcag                                              20

<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
gtatcctcga aggacaaccc t                                            21

<210> SEQ ID NO 112
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
gacatcggtc agtgtgatcg t                                            21

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
aagcgtgagt cgcaagaatg                                              20

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
tctccaggtt ttcgccagtg                                              20

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
gaccagatgc gtcgttaccg                                              20
```

```
<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
gtggtttccg gcaggtttag                                              20

<210> SEQ ID NO 117
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
tcaagacgca ccaggtgata g                                            21

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
cggtagaaga tgagggaatc agg                                          23

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
ctgctctacg acatgaacgg                                              20

<210> SEQ ID NO 120
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
gaaggtccct gatgtagtcg at                                           22

<210> SEQ ID NO 121
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                        Synthetic primer"

<400> SEQUENCE: 121
gtgatcggaa atgacactgg ag                                              22

<210> SEQ ID NO 122
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
catgttggtc actaacagaa gca                                             23

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
ccaccgtccc cgctccttcc                                                 20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
cggtgctcac agagacggcg                                                 20

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
gctggtcacc aacaatccct a                                               21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
cgtcaaaggc actatcggtg g                                               21

<210> SEQ ID NO 127
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
ggggaaaact acctgcctgt c                                           21

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
aggcgctcga tgtactggat                                             20

<210> SEQ ID NO 129
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
ccaaggtggg atcgtgagg                                              19

<210> SEQ ID NO 130
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
tcggaaggat aaaacgcggt c                                           21

<210> SEQ ID NO 131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
tcggaagcct aactacagcg a                                           21

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
```

```
agatgagcat tggcagcgag                                                    20
```

<210> SEQ ID NO 133
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133

```
acagagcgga aaagtgggaa g                                                  21
```

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134

```
tcgttgatcc tgtttcggag a                                                  21
```

<210> SEQ ID NO 135
<211> LENGTH: 141
<212> TYPE: PRT
<213> ORGANISM: Homo sapiens

<400> SEQUENCE: 135

Pro Ser Cys Ala Leu Lys Ala Gly Lys Thr Ala Ser Gly Ala Gly Glu
1               5                   10                  15

Val Val Arg Cys Leu Ser Glu Gln Ser Val Ala Ile Ser Arg Cys Ala
            20                  25                  30

Gly Gly Ala Gly Ala Arg Leu Pro Ala Leu Leu Asp Glu Gln Gln Val
        35                  40                  45

Asn Val Leu Leu Tyr Asp Met Asn Gly Cys Tyr Ser Arg Leu Lys Glu
    50                  55                  60

Leu Val Pro Thr Leu Pro Gln Asn Arg Lys Val Ser Lys Val Glu Ile
65                  70                  75                  80

Leu Gln His Val Ile Asp Tyr Ile Arg Asp Leu Gln Leu Glu Leu Asn
                85                  90                  95

Ser Glu Ser Glu Val Gly Thr Pro Gly Gly Arg Gly Leu Pro Val Arg
            100                 105                 110

Ala Pro Leu Ser Thr Leu Asn Gly Glu Ile Ser Ala Leu Thr Ala Glu
        115                 120                 125

Ala Ala Cys Val Pro Ala Asp Asp Arg Ile Leu Cys Arg
    130                 135                 140

<210> SEQ ID NO 136
<211> LENGTH: 105
<212> TYPE: PRT
<213> ORGANISM: Xenopus laevis

<400> SEQUENCE: 136

Ser Leu Thr Glu His Ser Leu Gly Ile Ala Arg Ser Lys Thr Pro Val
1               5                   10                  15

Asp Asp Pro Met Ser Leu Leu Tyr Asn Met Asn Asp Cys Tyr Ser Lys
            20                  25                  30

-continued

```
Leu Lys Glu Leu Val Pro Ser Ile Pro Gln Asn Lys Lys Val Ser Lys
        35                  40                  45

Met Glu Ile Leu Gln His Val Ile Asp Tyr Ile Leu Asp Leu Gln Leu
    50                  55                  60

Thr Leu Asp Ser His Pro Ser Ile Val Ser Leu His His Leu Pro Arg
65                  70                  75                  80

Val Gly Gly Asn Thr Ser Arg Thr Pro Leu Asp Pro Leu Asn Thr Asp
                85                  90                  95

Ile Ser Ile Leu Ser Leu Gln Ala Ala
            100                 105

<210> SEQ ID NO 137
<211> LENGTH: 108
<212> TYPE: PRT
<213> ORGANISM: Mus musculus

<400> SEQUENCE: 137

Gly Leu Ser Glu Gln Ser Val Ala Ile Ser Arg Cys Ala Gly Thr Arg
1               5                   10                  15

Leu Pro Ala Leu Leu Asp Glu Gln Gln Val Asn Val Leu Leu Tyr Asp
            20                  25                  30

Met Asn Gly Cys Tyr Ser Arg Leu Lys Glu Leu Val Pro Thr Leu Pro
        35                  40                  45

Gln Asn Arg Lys Val Ser Lys Val Glu Ile Leu Gln His Val Ile Asp
    50                  55                  60

Tyr Ile Arg Asp Leu Gln Leu Glu Leu Asn Ser Glu Ser Glu Val Gly
65                  70                  75                  80

Thr Thr Gly Gly Arg Gly Leu Pro Val Arg Ala Pro Leu Ser Thr Leu
                85                  90                  95

Asn Gly Glu Ile Ser Ala Leu Ala Ala Glu Ala Ala
            100                 105
```

CARDIOGENIC MESODERM FORMATION REGULATORS

CROSS-REFERENCE TO RELATED APPLICATION

This application is a National Stage Application under 35 U.S.C. § 371 and claims the benefit of International Application No. PCT/US2018/046536, filed Aug. 13, 2018, which claims the benefit of priority of U.S. Provisional Appl. No. 62/545,310, filed Aug. 14, 2017, the contents of which are incorporated by reference herein in its entirety.

FEDERALLY SPONSORED RESEARCH OR DEVELOPMENT

This invention was made with government support under grant nos. R01 HL113601, R33 HL088266, P30 AR061303, R01 AR056712, R01 AR052779, F31 AR065923 and P30 CA030199 awarded by the National Institutes of Health. The government has certain rights in the invention.

TECHNICAL FIELD

This disclosure relates to cardiogenic mesoderm formation regulators.

BACKGROUND

Heart formation begins during gastrulation with the specification of multipotent cardiovascular progenitors (MCPs) that migrate anteriorly to form the cardiac primordium that assembles into the fully formed heart (Buckingham et al., 2005; Kelly et al., 2014; Meilhac et al., 2015). Intense research over the past two decades has led to the identification of extracellular signals that initiate cardiogenesis (Collop et al., 2006; Foley et al., 2007; Kaltman et al., 2006; Laflamme et al., 2007; Lian et al., 2013; Marvin et al., 2001; Pandur et al., 2002; Schneider and Mercola, 2001; Schultheiss et al., 1997; Yang et al., 2008). In contrast, current knowledge of the intra-cellular mediators controlling this process is very fragmentary. The most commonly used molecules rely on combinations of Wnt inhibitors, Activin, BMP and Wnt agonists, all of which were revealed originally by embryology studies in the 1990s to early 2000 s. However, the embryology studies never comprehensively probed the signaling pathways that induce heart but rather took a more hit and miss approach since large-scale approaches were not available at the time.

Discovering such factors by a comprehensive approach would have major implications (1) for appreciating how cardiogenesis is normally initiated, as embryos lacking cardiac progenitors fail to form a heart (Zhao et al., 2008), and (2) for informing the development of regenerative and disease modeling technologies (Mercola et al., 2013; Moretti et al., 2013). Therefore, there is a need to identify cardiogenic mesoderm formation regulators and develop methods of using these regulators for therapeutic and cardiac disease-modeling purposes.

SUMMARY

This disclosure relates to cardiogenic mesoderm formation regulators.

In one aspect, the disclosure relates to methods of generating a multipotent cardiovascular progenitor cell. The methods involve overexpressing one or more proteins selected from the group consisting of Id1 (Inhibitor of DNA binding 1, HLH protein), Id2 (Inhibitor of DNA Binding 2, HLH Protein), Id3 (Inhibitor of DNA Binding 3, HLH Protein), Id4 (Inhibitor of DNA Binding 4, HLH Protein), Evx1 (Even-Skipped Homeobox 1), and Grrp1 (glycine/arginine rich protein 1) in a stem cell, thereby generating a multipotent cardiovascular progenitor cell.

In some embodiments, the methods involve transfecting the stem cell with a nucleic acid comprising a sequence encoding one or more proteins selected from the group consisting of Id1, Id2, Id3, Id4, Evx1, and Grrp1.

In some embodiments, the protein is Id1, Id2, Id3, or Id4. In some embodiments, the protein is Id1.

In some embodiments, the methods involve overexpressing Mesp1 (Mesoderm posterior protein 1).

In some embodiments, the stem cell is an embryonic stem cell, or an induced pluripotent stem cell. In some embodiments, the stem cell is a human induced pluripotent stem cell, or a mouse induced pluripotent stem cell.

In some embodiments, the nucleic acid is a ribonucleic acid, or a deoxyribonucleic acid.

In one aspect, the disclosure also relates to methods of generating a multipotent cardiovascular progenitor cell. The methods involve delivering into a stem cell a composition comprising one or more proteins selected from the group consisting of Id1, Id2, Id3, Id4, Evx1, and Grrp1.

In some embodiments, the composition includes Id1, Id2, Id3, or Id4. In some embodiments, the composition includes Id1. In some embodiments, the composition further includes Mesp1.

In some embodiments, the composition includes an endosomolytic agent.

In some embodiments, the stem cell is an embryonic stem cell, or an induced pluripotent stem cell. In some embodiments, the stem cell is a human induced pluripotent stem cell, or a mouse induced pluripotent stem cell.

In another aspect, the disclosure relates to methods of generating a multipotent cardiovascular progenitor cell. The methods involve inhibiting the expression or activity of one or both Foxa2 (Forkhead Box A2) and Tcf3 (Transcription Factor 3) in a stem cell, thereby generating a multipotent cardiovascular progenitor cell.

In some embodiments, the methods involve inhibiting Tcf3. In some embodiments, the methods involve inhibiting Foxa2. In some embodiments, the methods involve contacting the stem cell with siTcf3. In some embodiments, the methods involve contacting the stem cell with siFoxa2.

In some embodiments, the stem cell is an embryonic stem cell or an induced pluripotent stem cell. In some embodiments, the stem cell is a human induced pluripotent stem cell or a mouse induced pluripotent stem cell.

In one aspect, the disclosure also relates to a plurality of in vitro multipotent cardiovascular progenitor cells, wherein the multipotent cardiovascular progenitor cells are generated by overexpressing one or more proteins selected from the group consisting of Id1, Id2, Id3, Id4, Evx1, and Grrp1 in a plurality of stem cells.

In some embodiments, the protein is Id1, Id2, Id3, or Id4. In some embodiments, the protein is Id1. In some embodiments, the multipotent cardiovascular progenitor cells are generated by further overexpressing Mesp1.

In some embodiments, the total number of cells is over $10^6$, $10^7$, or $10^8$.

In some embodiments, the stem cells are induced pluripotent stem cells.

The disclosure also relates to a plurality of in vitro multipotent cardiovascular progenitor cells, wherein the multipotent cardiovascular progenitor cells are generated by delivering into a plurality of stem cells a composition comprising one or more proteins selected from the group consisting of Id1, Id2, Id3, Id4, Evx1, and Grrp1.

In some embodiments, the composition includes Id1, Id2, Id3, or Id4. In some embodiments, the composition includes Id1. In some embodiments, the composition further includes Mesp1.

In some embodiments, the total number of cells is over $10^6$, $10^7$, or $10^8$.

In some embodiments, the stem cells are induced pluripotent stem cells.

In another aspect, the disclosure also relates to a plurality of in vitro multipotent cardiovascular progenitor cells, wherein the multipotent cardiovascular progenitor cells are generated by inhibiting the expression or activity of one or both proteins of Foxa2 and Tcf3 in a plurality of stem cells.

In some embodiments, the multipotent cardiovascular progenitor cells are generated by inhibiting Tcf3. In some embodiments, the multipotent cardiovascular progenitor cells are generated by inhibiting Foxa2.

In some embodiments, the total number of cells is over $10^6$, $10^7$, or $10^8$.

In some embodiments, the stem cells are induced pluripotent stem cells.

In another aspect, the disclosure relates to methods of screening for an agent that promotes multipotent cardiovascular progenitor cell formation. The methods involve contacting a cell with a test agent; determining that (1). the cell has an increased expression or activity of Id1;
(2). the cell has an increased expression or activity of Id2, Id3, or Id4;
(3). the cell has an increased expression or activity of Evx1, Grrp1, or Mesp1; or
(4). the cell has a decreased expression or activity of Foxa2 or Tcf3; identifying the test agent as an agent that promotes multipotent cardiovascular progenitor cell formation.

In some embodiments, the cell is from an embryonic stem cell line. In some embodiments, the cell is an embryonic stem cell, or an induced pluripotent stem cell. In some embodiments, the cell is a human induced pluripotent stem cell or a mouse induced pluripotent stem cell.

In some embodiments, the agent is a small molecule, a nucleic acid, a peptide, or a protein. In some embodiments, the agent is an oligonucleotide. In some embodiments, the agent is an antisense molecule, a small interfering RNA, or a small hairpin RNA. In some embodiments, the agent is an antibody or an antigen-binding fragment.

In some embodiments, the methods further involve formulating the agent with a pharmaceutically acceptable carrier as a pharmaceutical composition.

In another aspect, the disclosure relates to methods of preparing a pharmaceutical composition. The methods involve formulating an agent that promotes cardiac mesoderm progenitor formation with a pharmaceutically acceptable carrier, wherein the agent has been previously determined to:

(1). increase expression or activity of Id1 in a stem cell;
(2). increase expression or activity of Id2, Id3, or Id4 in a stem cell;
(3). increase expression or activity of Evx1, Grrp1, or Mesp1 in a stem cell; or
(4). decrease expression or activity of Foxa2 or Tcf3 in a stem cell.

In some embodiments, the stem cell is an embryonic stem cell or an induced pluripotent stem cell.

In some embodiments, the agent has been previously determined to increase expression of Id1 in a stem cell, or has been previously determined to increase expression of Evx1, Grrp1, or Mesp1 in a stem cell.

In some embodiments, the agent is a small molecule, a nucleic acid, a peptide, or a protein.

In some embodiments, the agent is an oligonucleotide. In some embodiments, the agent is an antisense molecule, a small interfering RNA, or a small hairpin RNA. In some embodiments, the agent is an antibody or an antigen-binding fragment.

In another aspect, the disclosure relates to methods of promoting cardiac regeneration in a subject in need thereof. The methods involve generating a plurality of multipotent cardiovascular progenitor cells from a plurality of stem cells; and delivering the plurality of multipotent cardiovascular progenitor cells to the subject.

In some embodiments, the multipotent cardiovascular progenitor cells are generated by overexpressing one or more proteins selected from the group consisting of Id1, Id2, Id3, Id4, Evx1, and Grrp1 in the plurality of stem cells.

In some embodiments, the multipotent cardiovascular progenitor cells are generated by overexpressing Id1 in the plurality of stem cells.

In some embodiments, the multipotent cardiovascular progenitor cells are generated by delivering into the plurality of stem cells a composition comprising one or more proteins selected from the group consisting of Id1, Id2, Id3, Id4, Evx1, and Grrp1.

In some embodiments, the composition includes Id1, Id2, Id3, or Id4. In some embodiments, the composition includes Id1.

In some embodiments, the multipotent cardiovascular progenitor cells are generated by inhibiting the expression or activity of one or both proteins of Foxa2 and Tcf3 in the plurality of stem cells.

In some embodiments, the methods involve inhibiting expression or activity of Tcf3.

In some embodiments, the multipotent cardiovascular progenitor cells are generated by contacting the plurality of stem cells an agent that promotes multipotent cardiovascular progenitor cell formation.

In some embodiments, the stem cells are induced pluripotent stem cells derived from the cells of the subject.

In some embodiments, the subject has myocardial infarction, ischemic heart disease, hypertrophic cardiomyopathy, or congenital cardiomyopathy.

As used herein, the term "effective amount" is an amount sufficient to effect beneficial or desired results (e.g., sufficient to promote multipotent cardiovascular progenitor (MCP) cell formation, or sufficient to provide symptom relief for cardiovascular disorders).

As used herein, the term "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1L-1O. Temporal expression profiles of Id1, Grrp1, Evx1 and Mesp1 in response to siAcvr1b or siControl from day 3 to day 6 of differentiation.

FIGS. 1P-1W. Endogenous expression of Id1, Grrp1, Evx1 and Mesp1 in E7 mouse embryos by in situ hybridization. Whole mount view (FIGS. 1P-1S). Transverse histological section of the proximal region of E7 embryos indicating Id1 (FIG. 1T) expression in the gastrulating epiblast (yellow arrow) and migrating mesoderm (white arrow), Grrp1 (FIG. 1U) expression in the gastrulating epiblast (yellow arrow), as well as Evx1 (FIG. 1V) and Mesp1 (FIG. 1W) expression in the primitive streak (yellow arrow).

FIGS. 1T'-1W'. Endogenous expression of Id1, Grrp1, Evx1 and Mesp1 in E7 mouse embryos by in situ hybridization. Transverse histological section of the proximal region of E7 embryos indicating Id1 (FIG. 1T') expression (partial view (upper)) in the gastrulating epiblast and migrating mesoderm, Grrp1 (FIG. 1U') expression (partial view (upper)) in the gastrulating epiblast, as well as Evx1 (FIG. 1V') (partial view (upper)) and Mesp1 (FIG. 1W') expression (partial view (upper)) in the primitive streak.

FIG. 2G. Alignment and comparison of the mouse (NP_034625.1; SEQ ID NO: 10) Id1 HLH domain to the human (NP_851998.1; SEQ ID NO: 1) Id1 HLH domain using Protein Blast tool reveals the amino acid sequence is 100% identical.

FIG. 2H. qRT-PCR analysis for expression of Id1 in control h9-hESCs vs. h9-hESCs stably overexpressing Id1 measured at day 0 of differentiation.

FIGS. 2I-2J Flow cytometry analysis reveals that 69.8% of Id1-overexpressing h9-hESCs differentiate into KDR+ mesoderm at day 5 of differentiation as compared to 9.1% for control h9-hESCs.

FIGS. 2K-2N. Temporal mRNA expression profile of pro-cardiogenic mesoderm genes (Evx1 (FIG. 2K), Grrp1 (FIG. 2L), Mesp1 (FIG. 2M), and Kdr (FIG. 2N)) in mESC lines overexpressing Id1 compared to control mESC lines illustrate that Evx1, Grrp1, and Mesp1 mRNA expression peaks at day 4 of differentiation while Kdr mRNA expression peaks at day 5 of differentiation.

FIGS. 2O-2R. Temporal mRNA expression profiles of EVX1 (FIG. 2O), GRRP1 (FIG. 2P), MESP1 (FIG. 2Q), and KDR (FIG. 2R) in h9-hESCs stably overexpressing Id1 compared to control h9-hESCs.

FIGS. 4C-4D. Representative immunofluorescence images of Kdr-eGFP at day 6 of differentiation from mESCs transfected at day 3 with siControl (FIG. 4C) and siTcf3 (FIG. 4D). Scale bar is 50 μm.

FIG. 4E. qRT-PCR validation showing that 17 genes are downregulated at day 4 in response to siAcvr1b as compared to siControl, 24 hours post transfection.

FIG. 5A. Xid2 mRNA was injected equatorially into two blastomeres on one side of four-cell stage embryos.

FIG. 5B. Mouse HLH domain of Id1 (NP_034625.1) was aligned and compared to all *Xenopus laevis* HLH (yellow) domains of id proteins using Protein Blast tool (blast.ncbi.nlm.nih.gov). With 79% of identical amino acids, Xid2, (NP_001081902.1) (A), is the closest ortholog to Id1.

FIGS. 6B-I and 6K-V. In situ hybridization results from the most severe Id1-4 mutants, compared to wild type (individual mutants are marked by a #), plus one lesser affected mutant (FIG. 6P); analyzing Smarcd3 at E7.75 (FIGS. 6B-6E), Tbx5 at E8.0 (FIGS. 6F-6I), Nkx2.5 at E8.25 (FIGS. 6K-6N; plus transverse sections through the heat tube forming region, FIG. 6L', FIG. 6N'), Nkx2.5 at E8.5 (FIGS. 6O-6R), and Tbx5 at E8.5 (FIGS. 6S-6V). Yellow arrowheads point to the missing heart tube (or missing heart tube forming region at cardiac crescent stages) in Id1-4 mutants; white arrowhead indicates a malformed heart tube; black arrows indicate the plane of transverse sectioning through the heart tube forming region; black dashed arrows point to posterior-lateral cardiac regions. See Supplemental methods for detailed sequencing results of mutant embryos.

FIG. 14 shows the sequences for several cardiogenic mesoderm formation regulators.

DETAILED DESCRIPTION

Figure 1A:
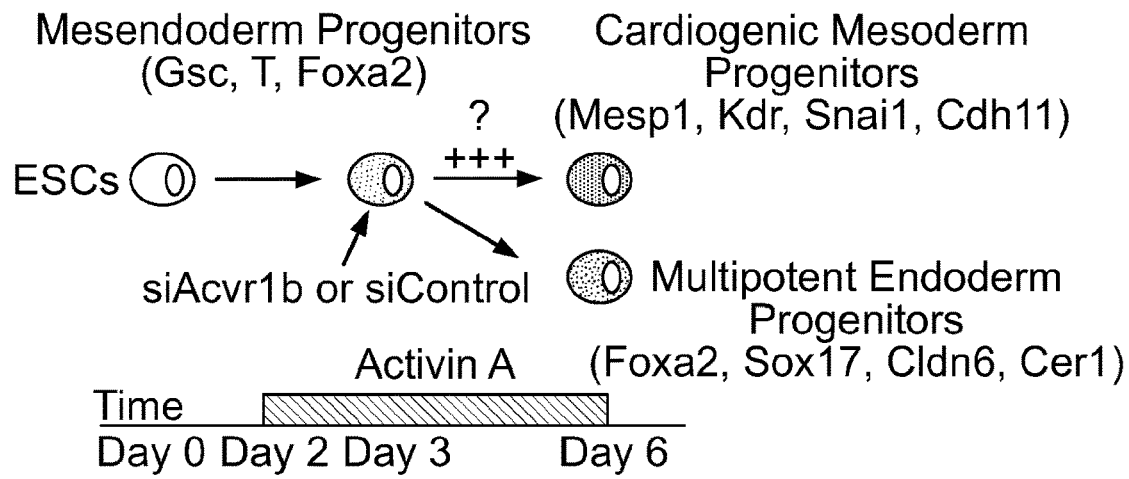
FIG. 1A. Schematic of screening strategy to identify new regulators of cardiogenic mesoderm differentiation.

This disclosure relates to cardiogenic mesoderm formation regulators. Basic helix-loop-helix (bHLH) transcription factors Mesp1 and Mesp2 (Saga et al., 2000) under the control of T-box factor Eomes (Costello et al., 2011), regulate at least part of this process in mesoderm cells by directing the expression of genes involved in cardiac specification (Hand2, Gata4, Nkx2.5, Myocd) and cellular migration (Prickle1 and RasGRP3), while actively repressing genes regulating pluripotency (Oct4, Nanog, Sox2), early mesoderm (T), and endoderm (Foxa2, Sox17) fates (Bondue et al., 2008; Chiapparo et al., 2016; Costello et al., 2011). Although these observations suggest that Mesp1/2 genes could act as master regulators of multipotent cardiovascular specification, retrospective lineage analysis (Saga et al., 2000; Yoshida et al., 2008) and in vitro differentiation studies (Chan et al., 2013) have shown that Mesp1-expressing cells also contribute to a wide range of non-cardiac derivatives, including hematopoietic precursors, skeletal muscle cells, and head mesenchyme. Therefore, additional effectors responsible for specifying cardiac cell fate remain to be discovered.

Attenuating Acvr1b signaling in mesendoderm segregates cardiogenic mesoderm from endoderm, whereas persistent Acvr1b signaling drives cells to form endoderm (Colas et al., 2012). Thus, it is hypothesized that genes induced in response to Acvr1b signaling inhibition might be key determinants of cardiogenic mesoderm formation. This disclosure took a systematic approach to functionally test the necessity and sufficiency of the genes modulated by Acvr1b signaling blockade. Unexpectedly, Id1, a helix-loop-helix transcriptional regulator, was identified as a single factor sufficient to control the emergence of $Kdr^+$ multipotent cardiovascular progenitors both in mouse and human embryonic stem cells. Mechanistically, Id proteins mediate their evolutionarily conserved role by activating the expression of agonists of cardiogenic mesoderm formation (Evx1, Grrp1 and Mesp1), while inhibiting antagonists' activity (Tcf3, Foxa2). Finally, CRISPR/Cas9-mediated deletion of all four Id family members in mouse blocked early cardiac progenitor formation, and yielded embryos without a heart. The heartless phenotype was unique to the quadruple knockout, indicating compensatory or redundant functions of the Id proteins in formation of cardiac mesoderm. These findings reveal an unexpected role for Id proteins as the earliest determinants of cardiac cell fate in vertebrates.

A number of studies showed that cardiac progenitor cells made from embryonic stem cells (ESCs) form new cardiomyocytes and improve cardiac function in rodent (Christoforou, N., et al. PLoS One 5, e11536 (2010); Tomescot, A., et al. Stem Cells 25, 2200-2205 (2007)), non-human primate (Blin, G., et al. J Clin Invest 120, 1125-1139 (2010)) and sheep MI models (Menard, C., et al. Lancet 366, 1005-1012 (2005)). These studies showed that the progenitor cells improved cardiac function and were safe. Despite these promising results, there has not been progress in developing stem cell-derived cardiac progenitors for human use, largely because there has not been a reproducible and robust means to produce such cells. Illustrating this point, a reference involving a small clinical trial using ESC-derived cardiac progenitor cells indicates that the challenges in producing enriched progenitors are, in part, that the cells used in the human clinical trial might not be as cardiac-committed as in the preceding animal studies (see Menasché et al., Eur Heart J (2015) 36: 743-750). This disclosure presents methods to overcome the roadblock to producing enriched populations of cardiac committed progenitors.

This disclosure demonstrates that simple overexpression of Id1 in hESCs (huma embryonic stem cell) or hiPSCs (human induced pluripotent stem cell) is sufficient to generate large amounts (>$10^8$ cells/batch) of cryopreservable and bona fide multipotent cardiovascular progenitors with remarkable abilities to spontaneously differentiate into beating cardiomyocytes (~70% efficiency). These combined properties enable at least two major applications for Id1-programmed progenitors: (1) as a promising transplantable cell population to test for cardiac regenerative purposes after myocardial injury, and (2) as a novel source of cells enabling large-scale production of hESC or hiPSC-derived cardiomyocytes suitable for in vitro studies of cardiomyocyte physiology.

Cardiogenic Mesoderm Formation Regulators

Figure 7:
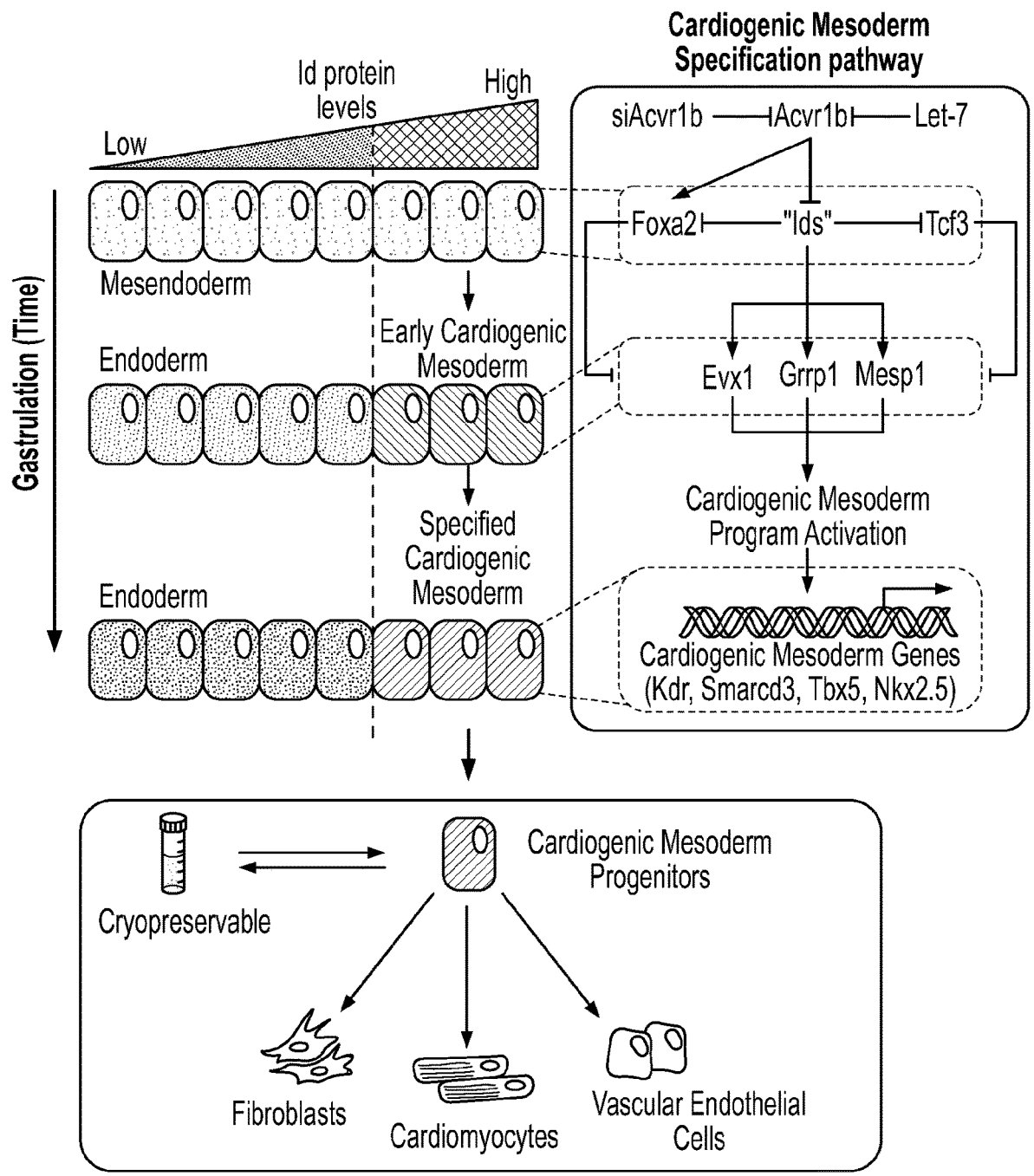
FIG. 7. Id1 orchestrates cardiogenic mesoderm differentiation in vertebrates. Id1 controls the activation of cardiogenic mesoderm differentiation program in mesendoderm progenitors by inhibiting the activity of repressors (Tcf3, Foxa2) while promoting the expression of activators of cardiogenic mesoderm differentiation (Evx1, Grrp1, Mesp1). The Id1-controlled network consistently induces robust cardiogenic mesoderm (Mesp1, Kdr) differentiation from pluripotent cells. Resulting multipotent cardiovascular progenitors spontaneously differentiate into contracting cardiomyocytes, vascular endothelial cells and fibroblasts both in mouse and human ESCs.

Unraveling the molecular mechanisms controlling cardiogenic mesoderm specification is crucial to understand how heart formation is normally initiated during embryonic development. This disclosure reveals that cardiogenic mesoderm specification is tightly regulated in bi-potent mesendoderm progenitors by an antagonistic interplay between Id proteins (Id1, Id2, Id3, Id4) and the Acvr1b (Activin A Receptor Type 1B) signaling pathway. Stereotypically, high Acvr1b signaling activity represses Id genes expression and biases mesendoderm progenitors to differentiate towards endoderm. Conversely, attenuation of Acvr1b signaling in these cells de-represses Id gene transcription that, in turn, promotes cardiogenic mesoderm specification (FIG. 7). A central finding in this disclosure is the ability of Id proteins to override pro-endoderm cues, induced by high Acvr1b signaling, and promote cardiogenic mesoderm differentiation instead. The functional dominance of Id proteins over Acvr1b signaling implies that molecules controlling the spatial and quantitative distribution of Id proteins are likely to be crucial regulators of cardiogenic mesoderm formation. FIG. 7 summarizes the function of each cardiogenic mesoderm formation regulator in multipotent cardiovascular progenitor cell formation. As shown in FIG. 7, Id1, Id2, Id3, Id4, Evx1, Grrp1, and Mesp1 are promotors of multipotent cardiovascular progenitor cell formation. In contrast, Foxa2 and Tcf3 inhibit multipotent cardiovascular progenitor cell formation. Therefore, inhibiting the expression or the activity of Foxa2 and Tcf3 can promote cardiogenic mesoderm differentiation.

Id1 (Inhibitor of DNA binding 1, HLH protein), Id2 (Inhibitor of DNA binding 2, HLH protein), Id3 (Inhibitor of DNA binding 3, HLH protein) and Id4 (Inhibitor of DNA binding 4, HLH protein) belong to the inhibitor of DNA binding (Id) family. Members of Id family are transcriptional regulators, and contain a helix-loop-helix (HLH) domain. Id proteins can inhibit the functions of basic helix-loop-helix transcription factors in a dominant-negative manner by suppressing their heterodimerization partners through the HLH domains.

Id1 is encoded by Id1 gene (NM_181353.2, SEQ ID NO: 11; NM_002165.3, SEQ ID NO: 20). The amino sequence (NP_851998.1) of Id1 is set forth in SEQ ID NO: 1. Id1 has no DNA binding activity and can inhibit the DNA binding and transcriptional activation ability of basic HLH proteins with which it interacts (Benezra R, Davis R L, Lockshon D, Turner D L, Weintraub H (1990). "The protein Id: a negative regulator of helix-loop-helix DNA binding proteins". Cell. 61 (1): 49-59). Id2 is encoded by Id2 gene (NM_002166.4; SEQ ID NO: 12). The amino sequence (Q02363-1) of Id2 is set forth in SEQ ID NO: 2. Id3 is encoded by Id3 gene (NM_002167.4; SEQ ID NO: 13). The amino sequence (Q02535-1) of Id3 is set forth in SEQ ID NO: 3. Id4 is encoded by Id4 gene (NM_001546.3; SEQ ID NO: 14). The amino sequence (P47928-1) of Id4 is set forth in SEQ ID NO: 4.

Evx1 (Even-Skipped Homeobox) is a homeobox transcription factor (NM_001989; SEQ ID NO: 15). It is a member of the even-skipped homeobox family characterized by the presence of a homeodomain closely related to the Drosophila even-skipped (eve) segmentation gene of the pair-rule class. Evx1 plays an important role as a transcriptional repressor during embryogenesis. The amino acid sequence of Evx1 (P49640-1) is set forth in SEQ ID NO: 5.

Grrp1 (glycine/arginine rich protein 1; NM_024869; SEQ ID NO: 16), also known as FAM110D (Family With Sequence Similarity 110 Member D), is a paralog of FAM110A. The amino acid sequence of Grrp1 (Q8TAY7-1) is set forth in SEQ ID NO: 6.

Mesp1 (Mesoderm posterior protein 1; NM_018670.3; SEQ ID NO: 17) plays an important role in the epithelialization of somitic mesoderm and in the development of cardiac mesoderm. The amino acid sequence of Mesp1 (Q9BRJ9-1) is set forth in SEQ ID NO: 7.

Foxa2 (Forkhead Box A2; NM_021784.4, SEQ ID NO: 18; NM_153675.2, SEQ ID NO: 21) is known to be involved in embryonic development, and is involved in the development of multiple endoderm-derived organ systems such as the liver, pancreas and lungs. The amino acid sequence of Foxa2 (Q9Y261-1) is set forth in SEQ ID NO: 8.

Tcf3 (Transcription Factor 3; NM_001136139.3, SEQ ID NO: 19; NM_001351778.1, SEQ ID NO: 22; NM_001351779.1, SEQ ID NO: 23; NM_003200.4, SEQ ID NO: 24), also known as E2A; E47. The amino acid sequence of Tcf3 (P15923-1) is set forth in SEQ ID NO: 9.

Positioning Id Genes in the Context of Mesp1 Pro-Cardiogenic Activity

Many transcription factors have been shown to be essential for cardiac development. Among them, Mesp1 is expressed the earliest and is sufficient to directly promote cardiac specification in mesoderm progenitors. Importantly, the gain of function experiments show that Id1/Xid2 is sufficient to direct Mesp1/Xmespb expression in both mouse and human ESCs as well as in Xenopus embryos, and subsequently promote cardiogenic mesoderm differentiation. These observations suggest that Id proteins exert at least part of their pro-cardiogenic effect through the upregulation of Mesp genes. Since Id proteins do not directly bind DNA to promote gene transcription, the Id-mediated upregulation of Mesp genes is likely to be indirect and may result from the inhibition of repressors of Mesp gene transcription. Indeed, the data in this disclosure shows that siRNA-mediated knock-down of canonical Id protein target Tcf3, and Id downstream target Foxa2, are sufficient to independently upregulate Mesp1 expression and promote cardiogenic mesoderm differentiation. Consistent with the model, previous studies have shown that Tcf3 agonistically interacts with Smad2/3 to upregulate Nodal (Activin) target genes in mesendoderm progenitors (Yoon et al 2011), while Foxa2 is the earliest known determinant of definitive endoderm (Stainier, 2002; Viotti et al., 2014) and is sufficient to induce hepatocyte-like cell differentiation in ESCs and adult fibroblasts (Huang et al., 2011; Sekiya and Suzuki, 2011). These functions suggest that the dual blockade of Tcf3 and Foxa2 in mesendoderm progenitors drives concomitant two processes: (1) the activation of cardiac specification via Mesp upregulation, and (2) the prevention of endoderm specification.

Figure 13A:
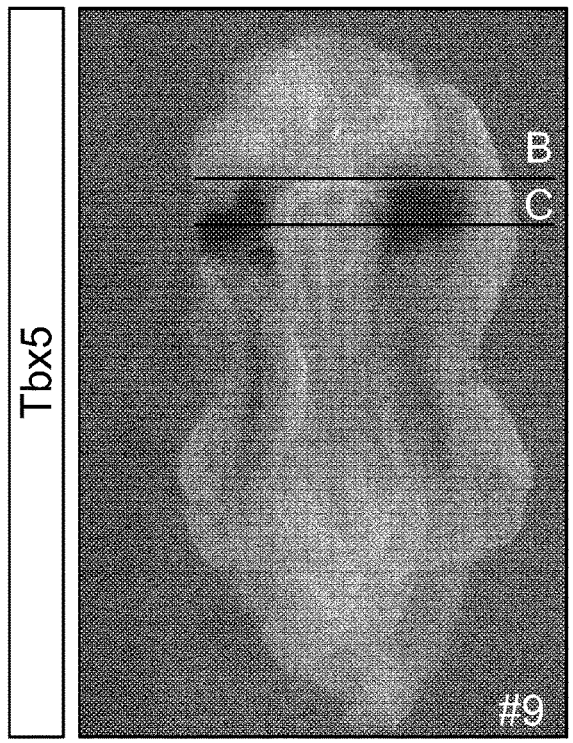
FIG. 13A. Ventral view of embryo #9 after Tbx5 in situ hybridization.
Figure 13B:
FIG. 13B. Transverse section at heart tube level confirms the absence of anatomical heart tube and mesoderm between neural tube and foregut.
Figure 13C:
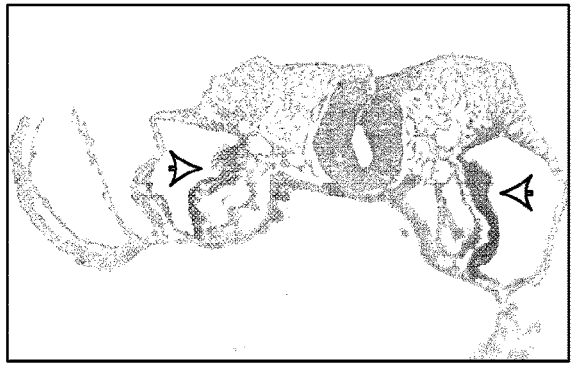
FIG. 13C. More posterior transverse section showing expression of Tbx5 expression in cardiac splanchnic mesoderm marked by yellow arrows.

It is well described that most of the heart myocardium in mammals derives from two distinct populations of cardiac progenitors, referred to as heart fields (Cai et al., 2003; Kelly et al., 2001; Meilhac et al., 2004; Meilhac et al., 2015). It is, however, not known whether similar or distinct molecular mechanisms regulate cardiac specification in these two cell populations. The loss of function results show that embryos lacking functional Id1-4 genes fail to express cardiogenic mesoderm markers (Smarcd3, Tbx5 and Nkx2.5) in the most anterior region of the cardiac crescent at E7.75, and subsequently develop without forming a heart tube. In contrast, posterior expression of these genes in the cardiac crescent is maintained and histological sectioning confirmed the presence of splanchnic cardiac mesoderm, posterior to the presumptive heart tube location (FIGS. 13A-13C). Collectively, these observations suggest that only the most anterior subset of cardiac progenitors require Id1-4 activity for their specification. Thus, Id genes normally specify first heart field progenitors that form the early heart tube. These findings also imply that cardiogenic mesoderm specification is not a singular process and can be initiated in an Id-dependent (first heart field progenitors) or Id-independent (posterior cardiac progenitors) manner during embryonic development.

Furthermore, BMP (Bone morphogenetic protein) signaling directly activates Id1 transcription (Hollnagel et al., 1999; Katagiri et al., 2002; Korchynskyi and ten Dijke, 2002; Lopez-Rovira et al., 2002). Conversely, the finding that Acvr1b signaling represses Id1/3 gene expression is consistent with the ability of a small molecule inhibitor of the Nodal receptor (SB431542) to upregulate Id1 transcripts in mESCs (Galvin et al., 2010), and reinforces the role of Acvr1b signaling in opposing cardiac cell fate acquisition during gastrulation. In summary, high Id protein levels in mesendoderm progenitors constitute a dominant molecular cue that is sufficient to trigger and orchestrate cardiogenic mesoderm specification in vertebrates.

Methods of Generating Multipotent Cardiovascular Progenitor Cells (MCP)

Mesoderm is one of the three primary germ layers in the very early embryo. It forms mesenchyme, mesothelium, non-epithelial blood cells and coelomocytes. Multipotent cardiovascular progenitor cells (or known as cardiogenic mesoderm progenitor cells) are differentiated from mesoderm cells. Multipotent cardiovascular progenitor cells resemble cells in the developing embryo that can develop into various cells of the heart, including cardiomyocytes, vascular endothelial cells, vascular smooth muscle cells and cardiac fibroblasts. Therefore, multipotent cardiovascular progenitor cells are in principle useful for regenerative medicine and disease-modeling.

The present disclosure provides methods of generating multipotent cardiovascular progenitor cells. In one aspect, the methods involve overexpressing one or more proteins (or protein variants thereof) selected from the group consisting of Id1, Id2, Id3, Id4, Evx1, Mesp1, and Grrp1 in a stem cell, thereby generating a multipotent cardiovascular progenitor cell. Overexpression can be achieved by various methods known in the art, e.g., by introducing nucleic acids into cells. Methods for introducing nucleic acids into cells include, but are not limited to, virus infection, transfection, electroporation, lipofection, and may other methods known in the art.

Viral vectors are often used to deliver genetic material into cells. This process can be performed inside a living organism (in vivo) or in cell culture (in vitro). Commonly used virus vectors include retrovirus, lentivirus (e.g., lentivectors such as pCDH-CMV), adenovirus, and adeno-associated virus, etc.

Overexpression can also be achieved by transfecting the cell with a nucleic acid (e.g., a ribonucleic acid, a deoxyribonucleic acid, a modified RNA, or a modified DNA). The nucleic acid can encode one or more proteins selected from the group consisting of Id1, Id2, Id3, Id4, Evx1, Mesp1, and Grrp1, or encode the protein variants of these cardiogenic mesoderm formation regulators. In addition, in some embodiments, inhibitory nucleic acids are used. For example, multipotent cardiovascular progenitor cells can be generated by contacting cells with Foxa2 and/or Tcf3 inhibitory nucleic acids. In some embodiments, the nucleic acid is a modified RNA.

In some embodiments, overexpression can be achieved by delivering an agent to a cell, wherein the agent stimulates the expression of endogenous Id1, Id2, Id3, Id4, Evx1, Mesp1, and/or Grrp1 (i.e. a compound that has the same effect as Id1, Id2, Id3, Id4, Evx1, Mesp1, and/or Grrp1 when administered to a subject).

Multipotent cardiovascular progenitor cells can also be generated by delivering a composition comprising one or more proteins (or protein variants thereof) selected from the group consisting of Id1, Id2, Id3, Id4, Evx1, Mesp1, and Grrp1 into a stem cell.

As used herein, a protein variant is a peptide that has a sequence that is at least 70%, 80%, 90%, 95%, 96%, 97%, 98%, 99% identical to the proteins described in this disclosure (e.g., Id1, Id2, Id3, Id4, Evx1, Mesp1, Grrp1, Foxa2, and Tcf3). To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5. Therefore, multipotent cardiovascular progenitor cells can be generated by delivering a composition comprising the protein variants of Id1, Id2, Id3, Id4, Evx1, Mesp1, and/or Grrp1 into a stem cell, or overexpressing the protein variants of Id1, Id2, Id3, Id4, Evx1, Mesp1, and/or Grrp1 in a stem cell. For example, multipotent cardiovascular progenitor cells can be generated by transfecting the cell with a nucleic acid encoding an Id1 protein variant. The Id1 protein variant can be at least 70%, 80%, 90%, 95%, 96%, 97%, 98%, 99% identical to SEQ ID NO: 1.

The composition that contains one or more proteins selected from the group consisting of Id1, Id2, Id3, Id4, Evx1, Mesp1, and Grrp1, or contains protein variants of Id1, Id2, Id3, Id4, Evx1, Mesp1, arm/or Grrp1 can further include an endosomolytic agent. Macromolecular delivery typically involves the endocytic pathway as a route of cellular entry. However, endosomal entrapment severely limits the efficiency with which macromolecules penetrate the cytosolic space of cells. Endosomolytic agents can facility the escape of macromolecular from endosomes. Some exemplary endosomolytic agents include one domain of the HIV transactivating transcriptional activator, or trans-activator of transcription ("the TAT domain"). By mediating endosomal leakage, these endosomolytic agents can deliver proteins into cells after a simple co-incubation procedure. Delivery does not require a binding interaction between TAT and a macromolecular. Multiple molecules can be delivered simultaneously. These methods of using the TAT endosomolytic agents are described, e.g., in US 20150099690, which is incorporated by reference in its entirety. Some other endosomolytic agents and cell delivery systems are described, e.g., in U.S. Pat. No. 6,849,272 B1, which is incorporated by reference herein in its entirety.

In some embodiments, the nucleic acid, the proteins, or any other agents or compositions as described in the present application are delivered through exosomal delivery. Exosomes are small intracellular membrane-based vesicles with different compositions that are involved in several biological and pathological processes, and can be used in drug delivery.

Multipotent cardiovascular progenitor cells can be generated from stem cells or mesoderm cells. Stem cells are undifferentiated biological cells that can differentiate into specialized cells and can divide (through mitosis) to produce more stem cells. The stem cell can come from a human or a non-human organism (e.g., a mouse, a rat, or a pig). In some embodiments, the stem cell is not a human embryonic stem cell. Stem cells can also be obtained from differentiated cells by induced pluripotent stem cell (iPSC) technique. Thus, as used herein, stem cells include embryonic stem cell and induced pluripotent stem cells. Methods of obtaining induced pluripotent stem cells are known in the art, e.g., U.S. Pat. No. 8,058,065, US 20130130387, and US 20140093486, each of which is incorporated by reference herein in its entirety.

The methods described herein can effectively produce a sufficient number of multipotent cardiovascular progenitor cells for therapeutic and cardiac disease-modeling purposes. The number of cells can range, e.g., from about $1 \times 10^4$ to about $1 \times 10^9$, or from about $1 \times 10^5$ to about $1 \times 10^7$ cells. In some embodiments, the number of multipotent cardiovascular progenitor cells is over $10^4$, $10^5$, $10^6$, $10^7$, $10^8$, or $10^9$. In some embodiments, the number of multipotent cardiovascular progenitor cells is less than $10^{10}$, $10^9$, $10^8$, $10^7$, $10^6$, or $10^5$. The methods described here can also generate homogenous multipotent cardiovascular progenitor cells. In some embodiments, the percentage of multipotent cardiovascular progenitor cells among all cultured cells is over 50%, 60%, 70%, 80%, 90%, 95%, or 99%. The cells can be further sorted, e.g., by flow cytometry, to increase homogeneity.

The multipotent cardiovascular progenitor cells are useful for various purposes, e.g., therapeutic use (treating cardiovascular disorders), screening compounds for treating various disorders (e.g., cardiovascular disorders), and disease modeling etc.

Inhibitory Nucleic Acids

The present disclosure also provides inhibitory nucleic acids for generating multipotent cardiovascular progenitors as described herein. In one aspect, the present disclosure provides methods of promoting multipotent cardiovascular progenitor cell formation. The methods involving contacting cells with Foxa2 and/or Tcf3 inhibitory nucleic acids (e.g., Foxa2 and Tcf3 siRNAs: siTcf3 and siFoxa2). In another aspect, the present disclosure provides methods of inhibiting multipotent cardiovascular progenitor cell formation, inhibiting mesoderm cell differentiation, or promoting endoderm cell generation. The methods involve contacting cells with Id1, Id2, Id3, Id4, Evx1, Grrp1, and/or Mesp1 inhibitory nucleic acids.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin.

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position 100% complementarity is not required.

Routine methods can be used to design an inhibitory nucleic acid that binds to the sequence of interest (e.g., Foxa2 or Tcf3 mRNA) with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids), each of which is incorporated by reference herein in its entirety.

Cardiovascular Regeneration

The present disclosure also provides methods of promoting cardiac regeneration or treating cardiovascular disorders in a subject. The methods involve generating a plurality of multipotent cardiovascular progenitor cells from a plurality of stem cells, and delivering an effective amount of multipotent cardiovascular progenitor cells to the subject.

A subject to be treated according to the methods described herein is one who has suffered an injury or has an illness or disorder that in need of cardiovascular regeneration. In certain cases, the subject has a cardiovascular disorder, e.g., myocardial infarction, ischemic heart disease, hypertrophic cardiomyopathy, congenital cardiomyopathy, cardiac injury etc. The injury can be an infarction that results in tissue necrosis, or a mechanical injury, Tissue can be torn, crushed, scarred, weakened, or lost as a result of the mechanical injury. Scar tissue may have formed at the site of damage. The heart may be reduced in size due to loss of healthy cells as a result of ischemia or other disease. Other types of damage and disease can be treated as well. Such damage and disease can be ameliorated by repopulating or replacing the affected area by healthy cells of the appropriate cell type, or augmenting/expanding the healthy tissue by adding healthy cells of the appropriate cell type to the affected site.

Repopulating or replacing the affected area by healthy cells or augmenting/expanding the healthy tissue is accomplished by introducing multipotent cardiovascular progenitor cells to the site of damage or disease. In some embodiments, multipotent cardiovascular progenitor cells are generated from induced pluripotent stem cells derived from the cells of the subject. The use of autologous cells eliminates the risk of rejection of the implanted cell/tissue by the recipient.

Alternatively, multipotent cardiovascular progenitor cells can be generated from embryonic stem cells, or induced pluripotent stem cells derived from cells of a cell line, or cells that are obtained from a donor subject. When allogeneic or xenogeneic cells are used, it is preferred that the donor and the subject be HLA-compatible to the extent possible. When allogeneic or xenogeneic cells are used, methods of suppressing the immune system of the recipient can be used, including, but not limited to, the administration of immunosuppressive drugs, radiation, chemotherapeutics, or antibody masking techniques or agents.

The amount of multipotent cardiovascular progenitor cells that is administered to a subject can vary depending on the need of the subject. The effective amount of multipotent cardiovascular progenitor cells can be determined by observing the effects of the treatment. The composition comprising multipotent cardiovascular progenitor cells can include a mixed population of different subpopulations of cells, e.g., undifferentiated stem cells, undifferentiated mesoderm cells, multipotent cardiovascular progenitor cells, cardiomyocytes, endothelial cells etc. Separation methods (e.g., fluorescence-activated cell sorting) can be employed to enrich for multipotent cardiovascular progenitor cells.

The multipotent cardiovascular progenitor cells can be used the same day or cryogenically stored for later use. Cryogenic preservation methods are known in the art. The cells can also be expanded ex vivo using methods known in the art. The cells can also be subjected to other manipulations including the introduction of exogenous nucleic acids. Methods for introducing nucleic acids to mammalian cells are known in the art and include, but are not limited to, transfection, electroporation, lipofection, and other methods. Nucleic acids can be introduced prior to or following expamultipotent cardiovascular progenitor cell generation.

The multipotent cardiovascular progenitor cells can be administered to the subject, or delivered to the heart or the specific site of the organ, using any methods known in the art. For example, the cells can be delivered to the tissue by intramuscular or intramyocardial injection using a needle or other delivery device. Alternatively, the cells can be delivered by a catheter, such as a Stilleto catheter (Boston Scientific, Natick MA). The cells can also be delivered using surgical procedures, or during surgical procedures if appropriate; or they can be delivered by intracoronary infusion, intraarterial infusion, intravenous infusion, or retrograde perfusion. While non-surgical methods are preferred when possible, the route and method of introduction can vary depending on the tissue to be treated as well as the size of the damaged or diseased area. The cells can be delivered in a single procedure, or in more than one procedure. The number of cells delivered to the site of damage or disease can vary depending on the size of the damaged or diseased area and the severity of damage or disease progression. The number of cells can range, e.g., from about $1\times10^4$ to about $1\times10^9$, or from about $1\times10^5$ to about $1\times10^7$ cells. In some embodiments, the number of multipotent cardiovascular progenitor cells is over $10^4$, $10^5$, $10^6$, $10^7$, $10^8$, or $10^9$. In some embodiments, the number of multipotent cardiovascular progenitor cells is less than $10^{10}$, $10^9$, $10^8$, $10^7$, $10^6$, or $10^5$.

The cells can be included in formulations suitable for administration directly into tissues or organs, or suitable for administration into the bloodstream. A suitable formation can be determined by a medical practitioner according to standard procedures. Thus, a pharmaceutical composition can include an effective amount of multipotent cardiovascular progenitor cells and a suitable pharmaceutically acceptable carrier. Suitable pharmaceutically acceptable carriers and their formulation are known in the art (see, e.g., Remington's Pharmaceutical Sciences 16th edition, Osol, A. Ed. 1980). Cells are preferably formulated in solution at a pH from about 6.5 to about 8.5. Excipients to bring the solution to isotonicity can also be added, for example, 4.5% mannitol or 0.9% sodium chloride, pH buffered with art-known buffer solutions, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes.

In some embodiments, an agent that can promote a multipotent cardiovascular progenitor cell formation is administered to a subject to stimulate endogenous regeneration activity. The agent induces the formation of multipotent cardiovascular progenitors from the subject's own cells in the heart. The agent can be any proteins, nucleic acids, or compounds as described in the present disclosure, e.g., Id1, Id2, Id3, Id4, Evx1, Mesp1, and/or Grrp1 proteins, and/or nucleic acids encoding Id1, Id2, Id3, Id4, Evx1, Mesp1, and/or Grrp. In some embodiments, the agent is a modified RNA, a small molecule, RNA, protein, or inducers of Id1, Id2, Id3, Id4, Evx1, Mesp1, and/or Grrp1. In some embodiments, the agent is delivered through viral delivery, exosomal delivery, etc.

In some embodiments, an agent that can promote a multipotent cardiovascular progenitor cell formation can induce the formation of multipotent cardiovascular progenitors from the cells (e.g., stem cells) that are delivered to the subject. Thus, the agent can be delivered prior to, during, or after the cells are delivered to a subject. In some embodiments, the cells and/or the agents are delivered directly to heart.

Methods of Screening

Included herein are methods for screening test compounds, e.g., polypeptides, polynucleotides, inorganic or organic large or small molecule test compounds, to identify agents useful in promoting multipotent cardiovascular progenitor cell formation. In some embodiments, the cells can be ventricular-like cardiac cells and/or atrial-like cardiac cells.

As used herein, "small molecules" refers to small organic or inorganic molecules of molecular weight below about 3,000 Daltons. In general, small molecules useful for the methods described herein have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. In some embodiments, the test compound is a small molecule, a nucleic acid, a peptide, a protein, an oligonucleotide, an antisense molecule, a small interfering RNA, a small hairpin RNA, an antibody or an antigen-binding fragment.

A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in some embodiments, a general library of small molecules is screened, e.g., using the methods described herein.

In some embodiments, a test compound is applied to a test sample, e.g., a mesoderm cell, a stem cell (e.g., an embryonic stem cell or an induced pluripotent stem cell), a cultured cell from a cell line. One or more effects of the test compound is evaluated. In a cultured cell for example, the ability of the test compound to generate multipotent cardiovascular progenitor cells is evaluated. The multipotent cardiovascular progenitor cells can be determined by mesoderm-specific markers (e.g., Kdr, Mesp1, Snail, Cdh11). In some embodiments, the ability of the test compound to increase expression or activity of one or more proteins selected from the group consisting of Id1, Id2, Id3, Id4, Evx1, Grrp1, and Mesp1 is evaluated. In some embodiments, the ability of the test compound to decrease expression or activity of Foxa2 and/or Tcf3 is evaluated.

In some embodiments, the test sample is, or is derived from (e.g., an induced pluripotent stem cell derived from) a subject having cardiovascular disorders (e.g., myocardial infarction, ischemic heart disease, hypertrophic cardiomyopathy, or congenital cardiomyopathy) or an in vivo model for cardiovascular disorders. The in vivo model can be an animal model, for example, a rodent such as a rat or a mouse can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect an effect on gene expression level (e.g., the expression level of Id1, Id2, Id3, Id4, Evx1, Grrp1, Mesp1, Foxa2 and/or Tcf3).

A test compound that has been screened by a method described herein and determined to promote multipotent cardiovascular progenitor cell formation, can be considered a candidate agent. Candidate agents, once screened in a clinical setting, are therapeutic agents. Therapeutic agents (e.g., small molecules) can be optionally optimized and/or derivatized, and formulated with physiologically acceptable excipients to form pharmaceutical compositions.

Thus, test compounds identified as "hits" (e.g., test compounds that can promote multipotent cardiovascular progenitor cell formation) in a first screen can be selected and systematically altered, e.g., using rational design, to optimize binding affinity, avidity, specificity, or other parameter. Such optimization can also be screened for using the methods described herein. Thus, in some embodiments, the methods include screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful for generating multipotent cardiovascular progenitor cells. A variety of techniques useful for determining the structures of "hits" can be used in the methods described herein, e.g., NMR, mass spectrometry, gas chromatography equipped with electron capture detectors, fluorescence and absorption spectroscopy. Thus, this disclosure also provides compounds identified as "hits" by the methods described herein, and methods of using the "hits" for generating multipotent cardiovascular progenitor cells.

Assessing Cardiac Toxicity

A large percentage of new drugs failing in clinical studies due to cardiac toxicity. Thus, determining cardiac toxicity is important for predicting the side effects of drugs. The multipotent cardiovascular progenitor cells can be used to assess cardiac toxicity of test compounds. In one aspect, the methods involve contacting multipotent cardiovascular progenitor cells with a test compound, analyzing a plurality of cellular metabolites, and comparing cellular metabolites from multipotent cardiovascular progenitor cells contacted with the test compound to cellular metabolites of multipotent cardiovascular progenitor cells not contacted with the test compound. If the cellular metabolites comprise a metabolic profile characteristic of multipotent cardiovascular progenitor cells in response to a cardiotoxic compound, the test compound will be determined to have cardiac toxicity.

The multipotent cardiovascular progenitor cells can further differentiate into cardiomyocytes. Many methods are known in the art to assess cardiac toxicity of test compounds in cardiomyocytes. For example, cardiac toxicity to cardiomyocytes can be determined by analyzing cellular metabolites, monitoring cardiomyocyte contractions using a calcium sensitive dye, and cardiac beating assay, etc. These methods are described, e.g., in WO2011044253, WO 2010094757, U.S. Pat. No. 9,624,471, US 20110318775, and Liang et al. "Drug screening using a library of human induced pluripotent stem cell-derived cardiomyocytes reveals disease specific patterns of cardiotoxicity," Circulation (2013): CIRCULATIONAHA-113etc, each of which is incorporated by reference herein in its entirety.

Disease Modeling and Tissue Engineering

The multipotent cardiovascular progenitor cells are useful for various purposes, e.g., therapeutic use (treating cardiovascular disorders), screening compounds for treating various disorders (e.g., cardiovascular disorders), toxicology studies, tissue engineering, and disease modeling etc. Disease models can be developed using single cell types for various diseases (e.g. channelopathies, myopathies) or multiple cell types to model more complex disease phenotypes (e.g. vasculopathies). Disease models can be used for drug screening, developing personalized medicine (i.e. developing individualized treatments) and discovering basic disease mechanisms.

Multipotent cardiovascular progenitor cells can be used in disease modeling, e.g., for various cardiovascular diseases. Cardiovascular diseases include, e.g., coronary artery diseases (CAD) such as angina and myocardial infarction (commonly known as a heart attack), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis. In some embodiments, these multipotent cardiovascular progenitor cells can be directly used in the disease modeling. In some embodiments, these multipotent cardiovascular progenitor cells can be differentiated into appropriate cell types (e.g., ventricular-like cardiac cells, atrial-like cardiac cells, cardiogenic progenitors, skeletal muscle cells, vascular cells, or fibroblasts). These disease models can also be used to screen for drugs that can be used to treat these diseases. The multipotent cardiovascular progenitor cells can also carry genetic mutations of interest. These genetic mutations can be introduced into cells by methods known in the art, e.g., CRISPR/Cas9 targeted genome editing. Screening can be performed to identify compounds that can mitigate or reverse the effects of the genetic mutations.

The multipotent cardiovascular progenitor cells can also be differentiated into appropriate cell types, and be used in tissue engineering. Appropriate cell types include, e.g., cardiogenic progenitors, skeletal muscle cells, vascular cells, fibroblasts.

Engineered tissues using such cells can be used as tools for drug screening and discovery, be used in diagnostics and prognostic tools, and be used to personalize treatment options. They can also be used for regenerative applications, as described above. In some embodiments, these cells are skeletal muscle cells and can be used in skeletal muscle regeneration. In some embodiments, these cells are cardiogenic progenitors and can be used in treating various cardiovascular diseases.

Pharmaceutical Compositions

The methods described herein include the use of pharmaceutical compositions comprising multipotent cardiovascular progenitor cells or various agents or compounds that are described in this disclosure (e.g., compounds that are identified by the screening methods or compounds that are evaluated for cardiac toxicity).

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194, 389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1: Materials and Methods

The following materials and methods were used in the following examples.
mESC Culture mESCs Kdr-eGFP (Ema et al., 2006) were maintained in DMEM High Glucose (HyClone, Logan, Utah) medium supplemented with 10% fetal bovine serum, Sodium Pyruvate 1 mM (Sigma, St. Louis, MO), MEM NEAA 1X (Gibco, Grand Island, NY), L-Glutamine 2 mM (Gibco, Grand Island, NY), Penicilin-Streptomycin 100 units/mL and 100 µg/mL (HyClone, Logan, Utah), β-mercaptoethanol 50 µM (Sigma, St. Louis, MO) and LIF 1000 units/mL (Millipore, Billerica, MA). For differentiation, mESCs were seeded in 10 cm low-attachment tissue culture dishes at a density of $10^6$ cells/dish in a chemically-defined media (CDM) (Gadue et al., 2006) where they formed embryoid bodies (EBs) over a period of 2 days. At day 2, EBs were then dissociated using 0.25% Trypsin EDTA (Gibco, Grand Island, NY), washed in PBS and replated in CDM supplemented with 50 ng/mL of Recombinant Human Activin A (338-AC-050, R&D Systems, Minneapolis, MN) in 10 cm low-attachment tissue culture dishes.
Kdr-eGFP Assay On day 3 of differentiation, EBs were collected and dissociated using 0.25% Trypsin EDTA; $10^4$ cells/well were plated in 100 µL of CDM containing Recombinant Human Activin A (50 ng/mL) into gelatin coated 384-well optical tissue culture plates (Greiner Bio-One, Kremsmunster, Austria), pre-spotted with 25 nM siRNAs in 0.2 µL Lipofectamine RNAiMax+14.8 µL OPTI-MEM I (Gibco, Grand Island, NY). Fixation was performed at day 6 using 4% Paraformaldehyde. Next, wells are imaged using HT microscope (ImageXPress, Molecular Devices, Sunnyvale, CA) and fluorescence is quantified using custom method developed in MetaXpress Analysis software (Molecular Devices, Sunnyvale, CA) to determine integrated pixel intensity of Kdr-eGFP.
hESC Culture Cells were routinely maintained in mTeSR1 media (05850, Stem Cell Technologies, Vancouver, Canada) on growth factor-reduced Matrigel (9 µg/cm2) and passaged every 4 days using ReLeSR (05872, Stem Cell Technologies, Vancouver, Canada). H9 hESC lines (WA09) were supplied by WiCell Research Institute. H9 hESCs were cultured for at least five passages before beginning differentiation. Cells were maintained with 2.5 ml medium per 9.6 cm² of surface area, or equivalent. All pluripotent cultures were routinely tested for *mycoplasma* contamination using a MycoAlert Kit (Lonza, Basel, Switzerland).
Lentivirus Preparation Large-scale lentivirus production was performed. Three plasmids including lentivector, pCMVDR8.74, and pMD2.G were co-transfected into HEK-293T cells in a ratio of 3:2:1. UltraCULTURE™ serum-free medium (Lonza, Basel, Switzerland) supplemented with 1 mM L-glutamine (Life Technologies, Carlsbad, CA) was used to re-feed transfected cells and the supernatant was collected every 24 hours from day 2 to day 4 post-transfection. All viral supernatant was pooled and filtrated through 0.22 µm pores, followed by concentration and purification using 20% sucrose gradient ultra-centrifugation at 21,000 rpm for 2 hours. The pellet containing concentrated viral particles was resuspended in PBS, aliquoted, and kept in −80° C. for long term storage.
Generation of Transgenic Cell Lines (mESCs and hESCs)

The following modifications were applied to pCDH-CMV vector (Cat #CD511B-1, System Biosciences, Palo Alto, CA): the CMV promoter driving the expression of the MCS was replaced by the Ef1α promoter to ensure robust expression in ESC stages, and the Ef1α-CopGFP cassette was replaced by a pgk-puro cassette to enrich for infected clones.

mESCs with Kdr-eGFP (Ema et al. 2006) were infected with all possible combinations of high-titer lentiviruses (modified pCDH-CMV) overexpressing Id1, Evx1, or Grrp1 and subsequently grown under continuous puromycin selection (2 µg/ml) (227420100, Acros, Geel, Belgium).

Similarly, H9 hESCs were infected with Id1-overxpressing lentivirus and selected with puromycin 6 µg/ml.
Mouse Id1-Induced MCPs Id1-overexpressing mESCs were grown and differentiated as wild type mESCs, in the presence of 2 µg/ml puromycin. At day 3, cells were collected and dissociated with 0.25% Trypsin EDTA (Gibco, Grand Island, NY), trypsin was inactivated with 10% FBS-containing media, cells were washed in PBS and resuspended in CDM supplemented with Recombinant Human Activin A (300 ng/ml)+ puromycin (2 µg/ml). $10^7$ cells were replated onto a 15 cm gelatin coated tissue culture dish into 30 ml of CDM+ Recombinant Human Activin A (300 ng/ml)+ puromycin (2 µg/ml) and cultured for 3 days. At day 6, cells were collected and frozen in freezing media (10% DMSO, 20% FBS, 70% DMEM High-glucose (HyClone, Logan, Utah)) at a density of $3-5 \times 10^6$ cells per vial and stored in liquid nitrogen.
Human Id1-Induced MCPs hESCs were dissociated using 0.5 mM EDTA (Life Technologies, Carlsbad, CA) in PBS without $CaCl_2$) or $MgCl_2$ (21-040-CV, Corning, Corning, NY) for 7 minutes at room temperature. Cells were plated at $3 \times 10^5$ cells per well of a 12 well plate in mTeSR1 media (Stem Cell Technologies, Vancouver, Canada) supplemented with 2 µM Thiazovivin (Selleck Chemicals, Houston, TX) for the first 24 h after passage. Cells were fed daily for 3-5 days until they reached ≥90% confluence, whereby they were washed with PBS and the medium was changed to basal differentiation media (BDM), consisting of RPMI 1640 medium (11875-093, Life Technologies, Carlsbad, CA) and B27 Supplement minus insulin (A1895601, Life Technologies, Carlsbad, CA). For the first 24 hour differentiation period, the BDM media was supplemented with 300 ng/ml Recombinant Human Activin A, and 2 µg/ml of Puromycin (227420100, Acros, Geel, Belgium). After 24 hours this medium was replaced with basic BDM supplemented with 6 µg/ml of puromycin.

BDM+ puromycin (2 µg/ml) was replaced every 48 hours. At day 5, cells were collected and frozen for later use.

Spontaneous of Cryopreserved Id1-Induced MCPs

Figure 1B:
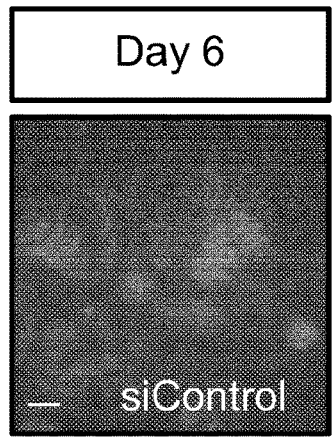
FIG. 1B. Immunostaining of Kdr-eGFP (cardiogenic mesoderm) and AlexaFluor568-Foxa2 (endoderm) showing mesoderm and endoderm differentiation in response to siControl at day 6 of differentiation. Scale bar is 50 µm.
Figure 1C:
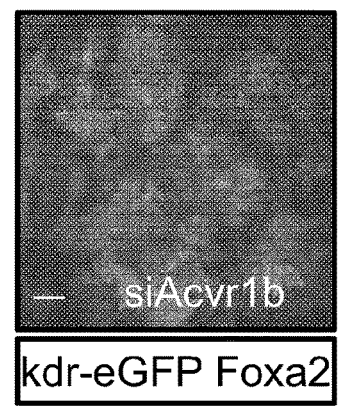
FIG. 1C. Immunostaining of Kdr-eGFP (cardiogenic mesoderm) and AlexaFluor568-Foxa2 (endoderm) showing increased mesoderm differentiation in response to siAcvr1b at day 6 of differentiation. Scale bar is 50 µm.
Figure 1D:
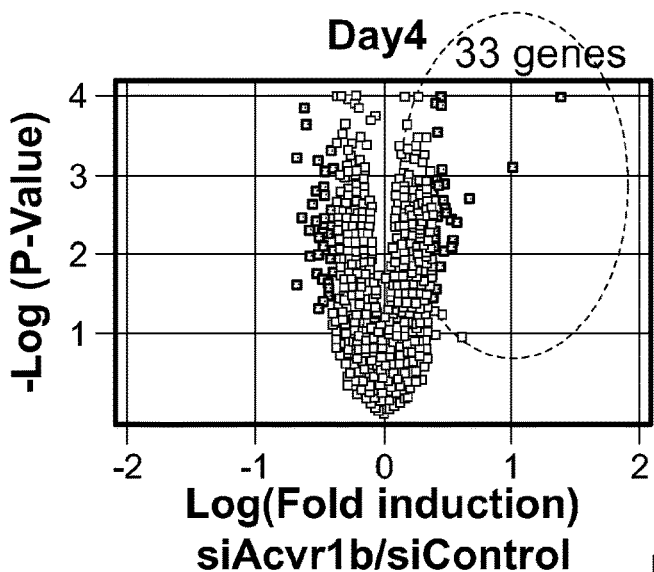
FIG. 1D. Microarray data reveals that 33 transcripts are upregulated (p<0.05) at day 4 in response to siAcvr1b as compared to siControl, 24 hours post-transfection.
Figure 1E:
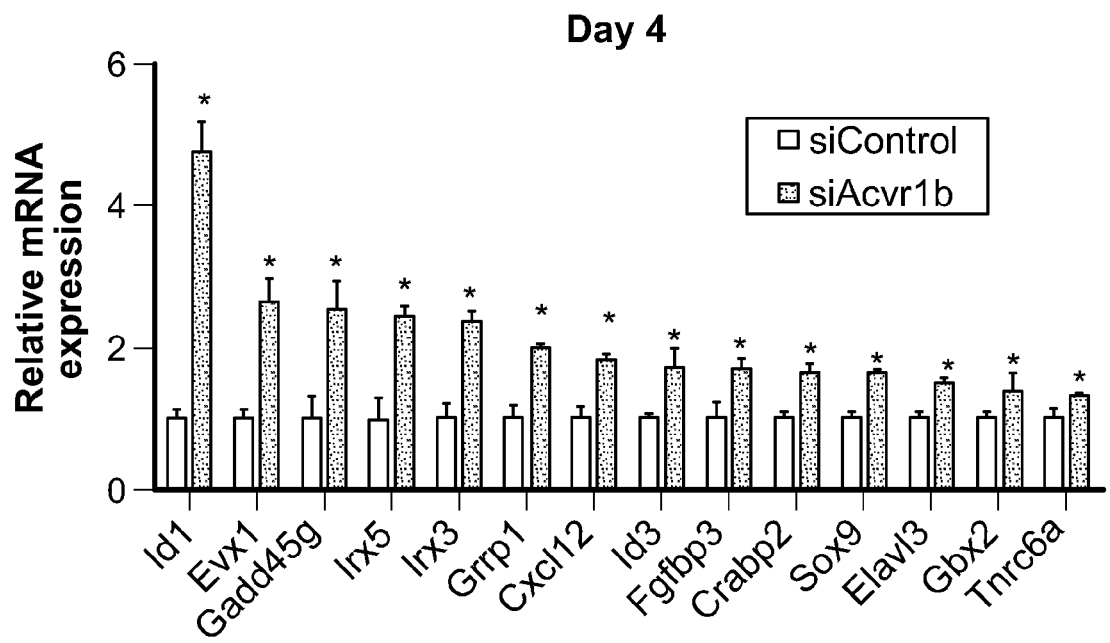
FIG. 1E. qRT-PCR confirmation of the microarray results in FIG. 1D, showing that 14 genes are robustly upregulated in response to siAcvr1b as compared to siControl. All qRT-PCR data are normalized to β-actin mRNA levels. Quantitative data are presented as means+/−SD. *p<0.05. All experiments were performed at least in biological quadruplicates.
Figure 1F:
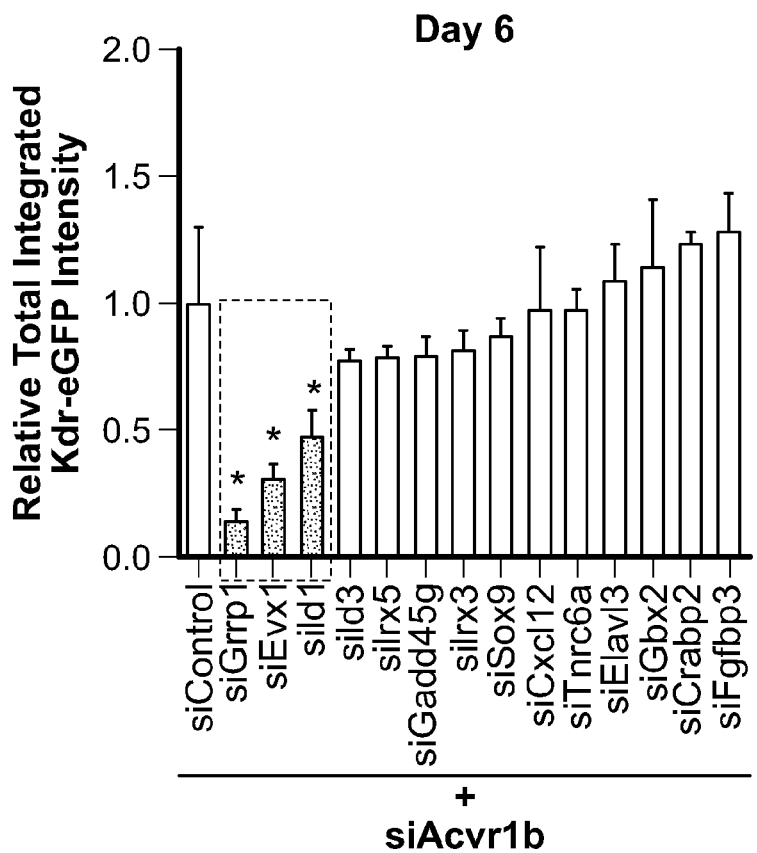
FIG. 1F. siRNA screen of the 14 candidates from FIG. 1E to evaluate their requirement for cardiogenic mesoderm formation induced by siAcvr1b. Differentiation was quantified by induction of Kdr-eGFP reporter (total integrated intensity, see material and methods for details). siGrrp1, siEvx1 and siId1 strongly repressed siAcvr1b-induced cardiogenic mesoderm.
Figure 1G:
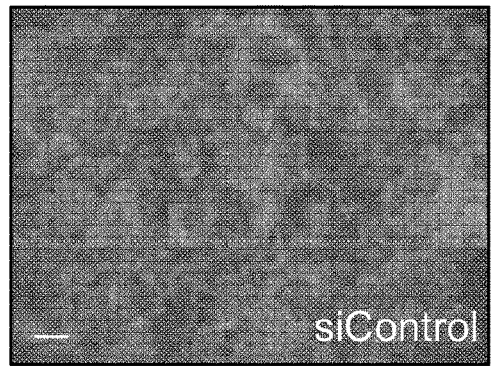
FIGS. 1G-1J. Representative images of Kdr-eGFP and AlexaFluor568-Foxa2 illustrating results presented in FIG. 1F. Scale bar is 50 µm.
Figure 1H:
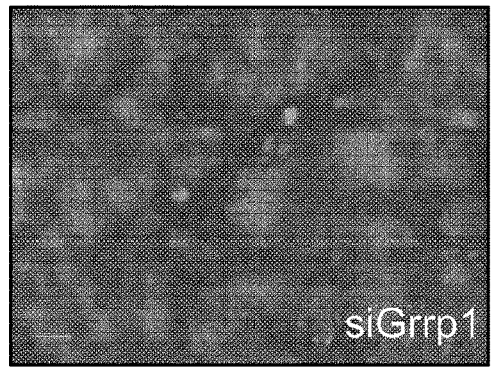
Figure 1I:
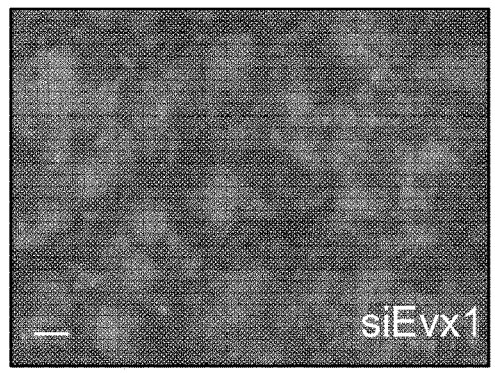
Figure 1J:
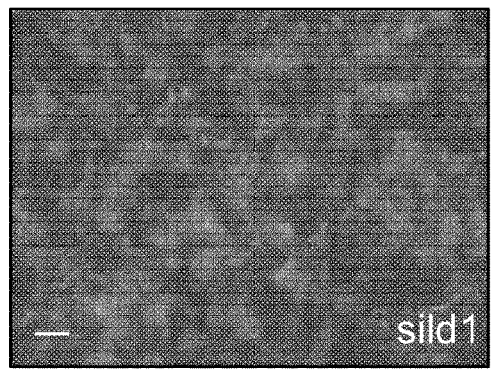
Figure 3A:
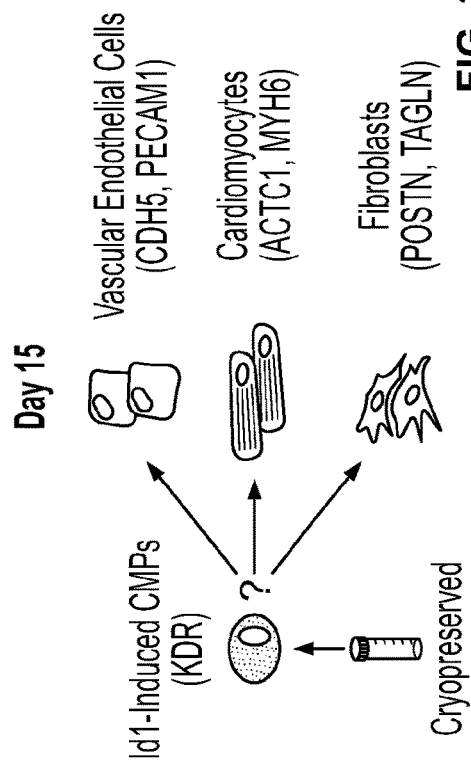
FIG. 3A. Schematic depicting prospective differentiation potential of cryopreserved Id1-induced multipotent cardiovascular progenitors to multiple cardiovascular cell types.
Figure 3B:
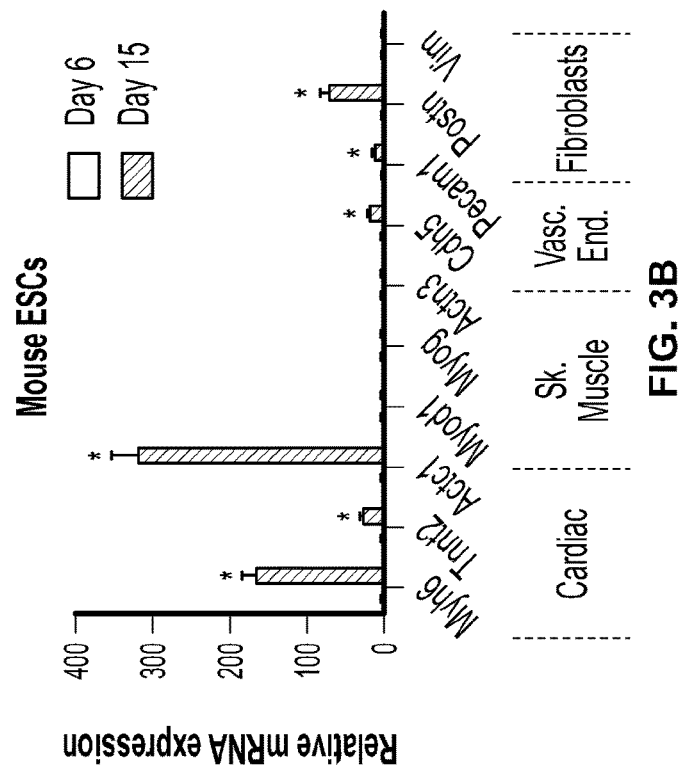
FIG. 3B. mRNA expression profiling for the spontaneous differentiation potential of mESCs stably overexpressing Id1 to cardiac (Myh6, Tnnt2, Actc1), skeletal muscle (Myod1, Myog, Actn3), vascular endothelial (Cdh5, Pecam1) and fibroblasts (Postn, Vim) markers at day 6 and day 15 of differentiation. Quantitative data are presented as means+/−SD. All experiments were performed at least in biological quadruplicates.
Figure 3C:
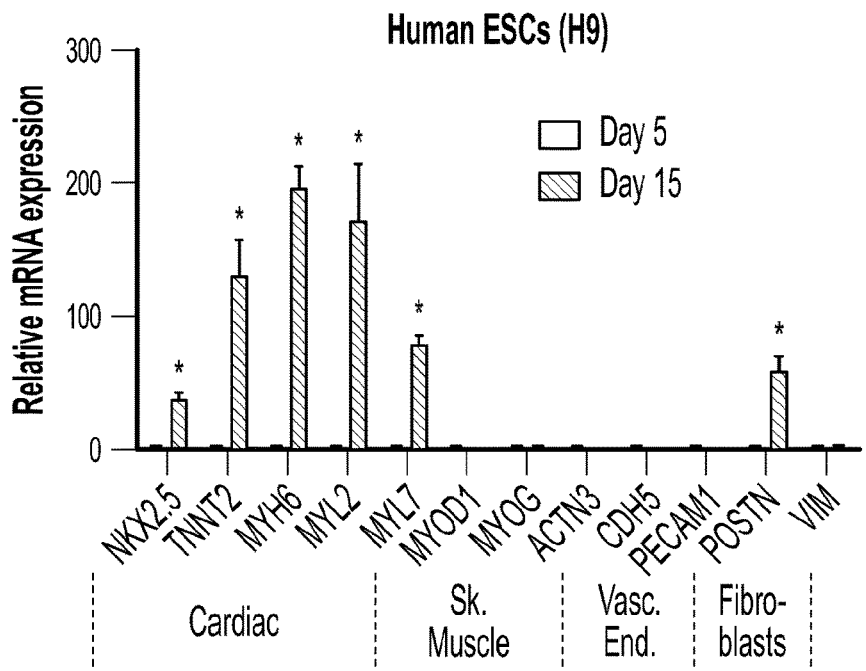
FIG. 3C. mRNA expression profiling for the spontaneous differentiation potential of h9-hESCs stably overexpressing Id1 to cardiac (NKX2.5, TNNT2, MYH6, MYL2, MYL7), skeletal muscle (MYOD1, MYOG, ACTN3), vascular endothelial (CDH5, PECAM1), and fibroblasts (POSTN, VIM) markers at day 5 and day 15 of differentiation. Quantitative data are presented as means+/−SD. All experiments were performed at least in biological quadruplicates.
Figure 3D:
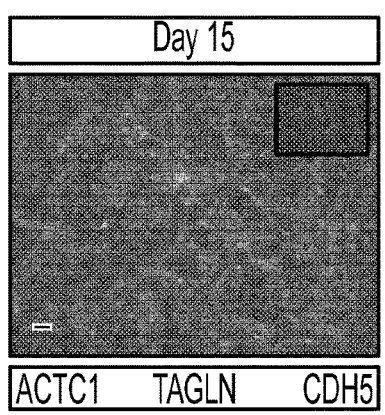
FIG. 3D. Representative immunofluorescence image cardiomyocytes (ACTC1), vascular endothelial cells (CDH5) and fibroblasts (TAGLN) at day 15 of differentiation in h9-hESCs stably overexpressing Id1. Scale bar is 50 μm.
Figure 3E:
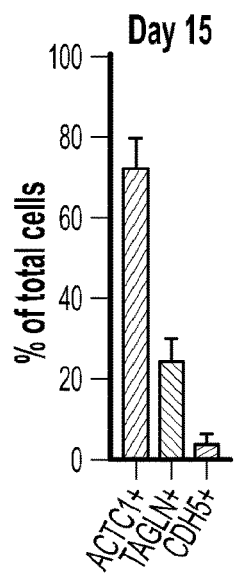
FIG. 3E. Diagram showing quantification of % of ACTC1$^+$ (cardiomyocytes), TAGLN$^+$ (fibroblasts), CDH5$^+$ (vascular endothelial cells) at day 15 of differentiation in h9-hESCs stably overexpressing Id1.
Figure 3F:
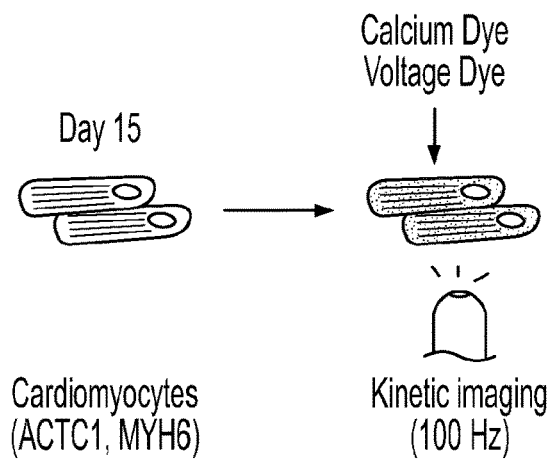
FIG. 3F. Schematic of the workflow for the physiological assessment of cardiomyocytes derived from Id1 overexpressing h9-hESCs using the calcium (Fluo-4) and voltage (VF2.1 Cl)(Miller et al., 2012) sensitive dyes.

To resume differentiation, MCPs (mouse or human) were thawed in 37° C. water bath for 3 minutes, washed and resuspended in BDM+ hES cell recovery supplement (2 µM) (Stemgent, Cambridge, MA) for human Id1-induced MCPs or CDM+ hES cell recovery supplement (2 µM) for mouse-induced MCPs and plated onto gelatin coated 384-well culture plates (Greiner Bio-One, Kremsmunster, Austria) at a cell density of 25,000 cells/well. Media (BDM or CDM) was replaced every other day until day 15 of differentiation.

siRNAs siRNAs from FIG. 1F and FIG. 3F were cherry-picked from mouse genome-wide siGENOME SMARTpool library from Dharmacon (Lafayette, CO) and were transfected at a final concentration of 12.5 nM. All remaining siRNAs were purchased from life technologies (Silencer™ select siRNAs) and transfected at a final concentration of 25 nM: siControl (AM4611), siEvx1 (s65742), siFoxa2 (s67627), siGrrp1 (s91214), siId1 (s68006), siTcf3 (s74856), siTcf4 (s74829), siTcf12 (s74811).

Immunostaining for Cell Culture and Cardiovascular Lineage Quantification

Cells grown on gelatin coated 384-well plates (Greiner Bio-One, Kremsmunster, Austria) were fixed using 4% paraformaldehyde and immunostained by incubating in block solution (10% horse serum, 0.5% Triton X100, and 0.01% gelatin in phosphate buffered saline (PBS)) for 30 minutes at room temperature followed by incubation with antibodies directed against Foxa2 (sc-6554, Santa Cruz Biotechnology, Dallas, TX), Pecam1 (sc-1506, Santa Cruz Biotechnology, Dallas, TX), Actc1 (A7811, Sigma, St. Louis, Missouri), CDH5 (AF938, R&D Systems, Minneapolis, Minnesota) for 1 hour at room temperature in the block solution. The cells were then washed 3 times with PBS and incubated with Alexa-conjugated secondary antibodies (Life Technologies, Carlsbad, California) in block solution at room temperature for 1 hour. The cells were then washed 3 times with PBS, and stored in 50% glycerol (v/v) in PBS. Next, wells were imaged using HT microscope (ImageXPress, Molecular Devices, Sunnyvale, California) and fluorescence was quantified using custom method developed in MetaXpress Analysis software (Molecular Devices, Sunnyvale, California) to determine the % of ACTC1, TAGLN and CDH5 positive cells.

Reverse Transcription Quantitative PCR Analysis (RT-qPCR)

Total RNA was extracted with miRVana isolation kit (AM1540, Ambion, Waltham, MA) and reverse transcribed to cDNA with QuantiTect Reverse Transcription Kit (Qiagen, Hilden, Germany) according to the manufacturer's instructions. cDNA samples synthesized from 1 µg of total RNA were subjected to RT-qPCR with 7900HT Fast Real-Time PCR System (Applied Biosystems, Foster City, California) using the iTaq SYBR Green Supermix with ROX (Bio-Rad). Primer sequences are listed in Table 1. The data was analyzed with the ΔΔCt method applying β-Actin as a normalization control.

TABLE 1

Quantitative PCR oligonucleotide primers

Mouse primers

| Gene Name | Gene Bank Accession | Sequence |
|---|---|---|
| Acrv1b | NM_007395 | F: TTCTTCCCCCTTGTTGTCCTC (SEQ ID NO: 25) |
|  |  | R: ACAGGTGTAGTTGGTCTGTAGG (SEQ ID NO: 26) |
| Actc1 | NM_009608 | F: CTGGATTCTGGCGATGGTGTA (SEQ ID NO: 27) |
|  |  | R: CGGACAATTTCACGTTCAGCA (SEQ ID NO: 28) |
| Actn3 | NM_013456 | F: AACAGCAGCGGAAAACCTTCA (SEQ ID NO: 29) |
|  |  | R: GGCTTTATTGACATTGGCGATTT (SEQ ID NO: 30) |
| Cdh11 | NM_009866 | F: CTGGGTCTGGAACCAATTCTTT (SEQ ID NO: 31) |
|  |  | R: GCCTGAGCCATCAGTGTGTA (SEQ ID NO: 32) |
| Cdh5 | NM_009868 | F: CACTGCTTTGGGAGCCTTC (SEQ ID NO: 33) |
|  |  | R: GGGGCAGCGATTCATTTTTCT (SEQ ID NO: 34) |
| Chst15 | NM_029935 | F: TTCCCCGAAGACACACACAAA (SEQ ID NO: 35) |
|  |  | R: CCCCAGTTTTCATTGCCCTCA (SEQ ID NO: 36) |
| Crabp2 | NM_0007759 | F: ATGCCTAACTTTTCTGGCAACT (SEQ ID NO: 37) |
|  |  | R: GCACAGTGGTGGAGGTTTTGA (SEQ ID NO: 38) |
| Cxcl12 | NM_001012477 | F: TGCATCAGTGACGGTAAACCA (SEQ ID NO: 39) |
|  |  | R: TTCTTCAGCCGTGCAACAATC (SEQ ID NO: 40) |
| Dnajc6 | NM_001164584 | F: TGAAAATAAAGGTGCCTCGTCTC (SEQ ID NO: 41) |
|  |  | R: TCAGGTTACTGAATAGCCTCCC (SEQ ID NO: 42) |
| Egr1 | NM_007913 | F: TCGGCTCCTTTCCTCACTCA (SEQ ID NO: 43) |
|  |  | R: CTCATAGGGTTGTTCGCTCGG (SEQ ID NO: 44) |
| Elavl3 | NM_010487 | F: TCCTATGCACGTCCCAGTTCT (SEQ ID NO: 45) |
|  |  | R: TCGATCCTCTTGTCAAAGCGG (SEQ ID NO: 46) |
| Evx1 | NM_007966 | F: GAGAGCCGAAAGGACATGGTT (SEQ ID NO: 47) |
|  |  | R: CTGCCTGCTAGTCCATCGAC (SEQ ID NO: 48) |

TABLE 1-continued

Quantitative PCR oligonucleotide primers

| Gene | Accession | Primers |
|---|---|---|
| Fgf8 | NM_001166361 | F: CCGAGGAGGGATCTAAGGAAC (SEQ ID NO: 49)<br>R: CTTCCAAAAGTATCGGTCTCCAC (SEQ ID NO: 50) |
| Fgfbp3 | NM_028263 | F: GGTCGCTTCGTGAGTCCAG (SEQ ID NO: 51)<br>R: AGCAGCCGTCTCCAGTAGT (SEQ ID NO: 52) |
| FoxA2 | NM_010446 | F: CCCTACGCCAACATGAACTCG (SEQ ID NO: 53)<br>R: GTTCTGCCGGTAGAAAGGGA (SEQ ID NO: 54) |
| Gadd45g | NM_011817 | F: GGGAAAGCACTGCACGAACT (SEQ ID NO: 55)<br>R: AGCACGCAAAAGGTCACATTG (SEQ ID NO: 56) |
| Gbx2 | NM_010262 | F: CAACTTCGACAAAGCCGAGG (SEQ ID NO: 57)<br>R: ACTCGTCTTTCCCTTGCCCT (SEQ ID NO: 58) |
| Gemin6 | NM_026053 | F: GCCAACATTGTCCTCGTAAACT (SEQ ID NO: 59)<br>R: TGTGGTCCCCTTCACTTATGG (SEQ ID NO: 60) |
| Grm6 | NM_173372 | F: GCAGAAACATCTGGTTTGCTG (SEQ ID NO: 61)<br>R: CCTCCTGTTCATAGGTGGAGTC (SEQ ID NO: 62) |
| Grrp1 | NM_001099296 | F: AGGGACCACTGCAACTCAG (SEQ ID NO: 63)<br>R: CCATACACAGTTAAGGACGCAC (SEQ ID NO: 64) |
| Gsc | NM_010351 | F: CAGATGCTGCCCTACATGAAC (SEQ ID NO: 65)<br>R: TCTGGGTACTTCGTCTCCTGG (SEQ ID NO: 66) |
| Id1 | NM_010495 | F: CCTAGCTGTTCGCTGAAGGC (SEQ ID NO: 67)<br>R: CTCCGACAGACCAAGTACCAC (SEQ ID NO: 68) |
| Id3 | NM_008321 | F: CGACCGAGGAGCCTCTTAG (SEQ ID NO: 69)<br>R: GGACGCGATAGGGAAGACC (SEQ ID NO: 70) |
| Irx3 | NM_001253822 | F: TCTGGGTCCCTATCCAATGTG (SEQ ID NO: 71)<br>R: GGTCCCCGAACTGGTACTG (SEQ ID NO: 72) |
| Irx5 | NM_018826 | F: TACAGCACCAGCGTCATTTCG (SEQ ID NO: 73)<br>R: GAGCCCACGTAAGAGAAGGC (SEQ ID NO: 74) |
| Kdr | NM_010612 | F: TTTGGCAAATACAACCCTTCAGA (SEQ ID NO: 75)<br>R: GCAGAAGATACTGTCACCACC (SEQ ID NO: 76) |
| Lefty1 | NM_010094 | F: CCAACCGCACTGCCCTTAT (SEQ ID NO: 77)<br>R: CGCGAAACGAACCAACTTGT (SEQ ID NO: 78) |
| Lefty2 | NM_177099 | F: CAGCCAGAATTTTCGAGAGGT (SEQ ID NO: 79)<br>R: CAGTGCGATTGGAGCCATC (SEQ ID NO: 80) |
| Mesp1 | NM_008588 | F: GTCACTCGGTCCTGGTTTAAG (SEQ ID NO: 81)<br>R: ACGATGGGTCCCACGATTCT (SEQ ID NO: 82) |
| Myh6 | NM_010856 | F: GCCCAGTACCTCCGAAAGTC (SEQ ID NO: 83)<br>R: GCCTTAACATACTCCTCCTTGTC (SEQ ID NO: 84) |
| Myog | NM_031189 | F: GAGACATCCCCCTATTTCTACCA (SEQ ID NO: 85)<br>R: GCTCAGTCCGCTCATAGCC (SEQ ID NO: 86) |
| Nodal | NM_013611 | F: TTCAAGCCTGTTGGGCTCTAC (SEQ ID NO: 87)<br>R: TCCGGTCACGTCCACATCTT (SEQ ID NO: 88) |
| Pecam1 | NM_001032378 | F: ACGCTGGTGCTCTATGCAAG (SEQ ID NO: 89)<br>R: TCAGTTGCTGCCCATTCATCA (SEQ ID NO: 90) |
| Pitx2 | NM_011098 | F: GCAGCCGTTGAATGTCTCTTC (SEQ ID NO: 91)<br>R: GTCCGTGAACTCGACCTTTTT (SEQ ID NO: 92) |
| Snail | | F: CACACGCTGCCTTGTGTCT (SEQ ID NO: 93)<br>R: GGTCAGCAAAAGCACGGTT (SEQ ID NO: 94) |
| Sox9 | NM_011448 | F: GAGCCGGATCTGAAGAGGGA (SEQ ID NO: 95)<br>R: GCTTGACGTGTGGCTTGTTC (SEQ ID NO: 96) |
| Stk4 | NM_021420 | F: TCATTCGGCTACGGAACAAGA (SEQ ID NO: 97)<br>R: GACCTGCGACTCCAAAGTCTG (SEQ ID NO: 98) |
| Tnnt2 | NM_001130181 | F: CAGAGGAGGCCAACGTAGAAG (SEQ ID NO: 99)<br>R: CTCCATCGGGGATCTTGGGT (SEQ ID NO: 100) |

TABLE 1-continued

Quantitative PCR oligonucleotide primers

| | | |
|---|---|---|
| Tnrc6a | NM_144925 | F: ATGCTCCTGAAAGCAAACCAG (SEQ ID NO: 101)<br>R: CCTTTTAGGGCAAGTCCATTGT (SEQ ID NO: 102) |
| Trim67 | NM_198632 | F: CCACTCTCTGCGAGCAATG (SEQ ID NO: 103)<br>R: GGTGGCTGAACTAGCCGAT (SEQ ID NO: 104) |
| Zfp750 | NM_178763 | F: ATGAGTCTCCTAAAGGAACGGA (SEQ ID NO: 105)<br>R: GGGAATACGATCTTGCTCTGAC (SEQ ID NO: 106) |
| Zmpste24 | NM_172700 | F: GCATCGGTGGACGCTATGT (SEQ ID NO: 107)<br>R: TGTGCTAGGAAGGTCTCCCAA (SEQ ID NO: 108) |

Human primers

| Gene Name | Gene Bank Accession | Sequence |
|---|---|---|
| ACTN3 | NM_001104 | F: GATGACCCCATCGGAAACCTG (SEQ ID NO: 109)<br>R: CTTGCAGATCCTGTTGGCAG (SEQ ID NO: 110) |
| CDH11 | NM_001797 | F: GTATCCTCGAAGGACAACCCT (SEQ ID NO: 111)<br>R: GACATCGGTCAGTGTGATCGT (SEQ ID NO: 112) |
| CDH5 | NM_001795 | F: AAGCGTGAGTCGCAAGAATG (SEQ ID NO: 113)<br>R: TCTCCAGGTTTTCGCCAGTG (SEQ ID NO: 114) |
| EVX1 | NM_001989 | F: GACCAGATGCGTCGTTACCG (SEQ ID NO: 115)<br>R: GTGGTTTCCGGCAGGTTTAG (SEQ ID NO: 116) |
| GRRP1 | NM_024869 | F: TCAAGACGCACCAGGTGATAG (SEQ ID NO: 117)<br>R: CGGTAGAAGATGAGGGAATCAGG (SEQ ID NO: 118) |
| ID1 | NM_181353 | F: CTGCTCTACGACATGAACGG (SEQ ID NO: 119)<br>R: GAAGGTCCCTGATGTAGTCGAT (SEQ ID NO: 120) |
| KDR | NM_002253 | F: GTGATCGGAAATGACACTGGAG (SEQ ID NO: 121)<br>R: CATGTTGGTCACTAACAGAAGCA (SEQ ID NO: 122) |
| MESP1 | | F: CCACCGTCCCCGCTCCTTCC (SEQ ID NO: 123)<br>R: CGGTGCTCACAGAGACGGCG (SEQ ID NO: 124) |
| MYH6 | NM_002471 | F: GCTGGTCACCAACAATCCCTA (SEQ ID NO: 125)<br>R: CGTCAAAGGCACTATCGGTGG (SEQ ID NO: 126) |
| MYOG | NM_002479 | F: GGGGAAAACTACCTGCCTGTC (SEQ ID NO: 127)<br>R: AGGCGCTCGATGTACTGGAT (SEQ ID NO: 128) |
| PECAM1 | NM_000442 | F: CCAAGGTGGGATCGTGAGG (SEQ ID NO: 129)<br>R: TCGGAAGGATAAAACGCGGTC (SEQ ID NO: 130) |
| SNAl1 | NM_005985 | F: TCGGAAGCCTAACTACAGCGA (SEQ ID NO: 131)<br>R: AGATGAGCATTGGCAGCGAG (SEQ ID NO: 132) |
| TNNT2 | NM_001001431 | F: ACAGAGCGGAAAAGTGGGAAG (SEQ ID NO: 133)<br>R: TCGTTGATCCTGTTTCGGAGA (SEQ ID NO: 134) |

Microarray Experiment and Analysis siControl or siAcvr1b were transfected in day 3 differentiating mESCs. Total RNA (500 ng) was collected at day 4 and hybridized on MouseRef-8 v2.0 Expression BeadChip (25,600 transcripts, Illumina, San Diego, California). BeadChips were subsequently washed and developed with fluorolink streptavidin-Cy3 (GE Healthcare, Marlborough, MA). BeadChips were scanned with an Illumina BeadArray Reader, and hybridization efficiency was monitored using BeadStudio software (Illumina, San Diego, California) to measure internal controls built into the Illumina system. Linear models were fitted for each gene using the Bioconductor limma package in R. Moderated t-statistics, fold-change and the associated P-values were calculated for each gene. To account for testing thousands of genes, false discovery rate (FDR)-adjusted values were calculated using the Benjamin-Hochberg method.

Flow Cytometry

For live Kdr-eGFP cells, cells were dissociated using 0.25% Trypsin EDTA, blocked with 10% FBS-containing media and resuspended in PBS containing 0.5% FBS (washing buffer) for flow sorting using LSRFortessa or FACS Aria Flow cytometers (BD Biosciences, San Jose, California). For hESCs, day 5 cells dissociated using 1×TrypLE Express (Gibco, Grand Island, New York), blocked and washed with PBS containing 0.5% FBS (washing buffer). Cells were incubated for 20 minutes with PE anti-human CD309 (cat #359903, dilution 1:100, BioLegend, San Diego, California) in PBS containing 0.5% FBS at 4° C. Next, cells were washed in washing buffer, fixed for 20 min in 1% PBS:formaldehyde at 4° C., washed and resuspended in washing buffer and processed by flow sorting.

Xenopus laevis Embryo Culture

Embryos were fertilized in vitro, dejellied in 2% cysteine-HCl, pH=7.8, and maintained in 0.1×MMR (Peng, 1991).

Embryos were staged according to Nieuwkoop and Faber (Nieuwkoop, 1967). For gene expression analysis, whole embryos were fixed in MEMFA for in situ hybridization as below.

mRNA Injection in *Xenopus laevis*

Synthetic capped mRNAs for Xid2 injection were transcribed from pSP64T plasmid using SP6 mMessage kit (Ambion, Waltham, MA). mRNAs were injected at 125 ng/blastomere at 4-cell stage embryos.

In Situ Hybridization in *Xenopus laevis* Embryos

In situ hybridization for Xbra (Colas et al., 2008), Xmespb was carried out as described, e.g., in Djiane et al., Role of frizzled 7 in the regulation of convergent extension movements during gastrulation in *Xenopus laevis*. Development 127, 3091-3100 (2000).

Mouse Embryos

Mouse embryos were dissected into DEPC-treated PBS, fixed overnight in 4% PFA, and dehydrated into MeOH. In situ hybridization used Id1, Grrp1, Evx1 (cloned into pGEM), and Mesp1 (Saga et al., 1996) probes (60° C. hybridization) as described, e.g., in Wilkinson et al., Detection of messenger RNA by in situ hybridization to tissue sections and whole mounts. Methods in enzymology 225, 361-373 (1993). For histology, embryos were embedded in paraffin, H&E stained and sectioned (5 μm thickness) following standard procedures. Sections were scanned at high magnification (40×) using Leica Aperio AT2.

CRISPR/Cas9 Id Gene Editing of Mouse Embryos

CRISPR/Cas9 gene editing to generate Id1-4 mutant embryos was performed. Eight single-guide RNAs (sgRNAs) were designed to target sites near the ATG translation initiation site and near the beginning of the HLH domain for each Id gene, using the tool at crispr.mit.edu to ensure maximum specificity. DNA templates for sgRNAs were generated by PCR amplification (Phusion DNA Polymerase; New England Biolabs, Ipswich, MA) of ssDNA ultramer oligonucleotides (Integrated DNA Technologies, Coralville, IA); sgRNAs were transcribed from these templates using HiScribe T7 High Yield RNA Synthesis Kit (New England Biolabs, Ipswich, MA) and purified using Megaclear Kit (Life Technologies, Carlsbad, CA). For mouse zygote injections, 50 ng/μl Cas9 mRNA (Life Technologies, Carlsbad, CA) and 20 ng/μl of each sgRNA was combined in nuclease free water. Fertilized oocytes were collected from 3 to 4 week-old superovulated C57Bl6 females (prepared by injecting 5 IU each of pregnant mare serum gonadotropin and human chorionic gonadotropin (Sigma-Aldrich, St. Louis, MO)), then transferred into M2 medium (Millipore, Billerica, MA), and injected with the Cas9 mRNA/sgRNA solution into the cytoplasm. Injected embryos were then re-implanted into recipient pseudo-pregnant ICR female mice. Implanted females were sacrificed 8-9 days after re-implantation; yolk sac DNA was collected for genotyping by PCR (Bioline MyTaq Extract kit) followed by DNA deep sequencing (Ilumina Nextera kit for library preparation, Illumina HiSeq 1500 for sequencing). Sequences were analyzed, and variant alleles were recorded, using IGV genome browser (Broad Institute, Cambridge, MA). For off-target analysis, the top 8 off-target sites were identified using the tool at crispr.mit.edu; these regions were PCR amplified and Sanger sequenced.

Statistics

Each experiment represents at least quadruplicate biological replicates per condition. Statistical analysis was performed with unpaired Student's T test, P<0.05.

Example 2: Identification of New Agonists of Cardiogenic Mesoderm Formation

Mouse embryonic stem cells (mESCs) form mesendodermal progenitors (Gsc$^+$, Foxa2$^+$, T$^+$) at day 3-4 of differentiation in response to Activin/Nodal signaling and subsequently differentiate into either Foxa2$^+$ definitive endoderm or Kdr$^+$ cardiogenic mesoderm (diagrammed in FIG. 1A). Attenuation of Acvr1b drives mesendodermal progenitors to form multipotent cardiovascular progenitors marked by Mesp1, Kdr, Cdh11, and Snai1 expression at day 5-6, rather than endoderm; a process robustly elicited by transfecting mesendodermal progenitors at day 3 with either let-7 or miR-18 mimics or siRNAs directed against their respective mRNA targets Acvr1b or Smad2 (day 3) (FIGS. 1A-1C).

In order to identify the downstream effectors of cardiogenic mesoderm formation, mRNA expression was analyzed 24 hours after Acvr1b siRNA (siAcvr1b) transfection (Day 4). Microarray data revealed 33 genes that were upregulated (FIG. 1D and Table 2) in response to Acvr1b siRNA relative to a scrambled sequence siRNA control, of which 14 were confirmed by qPCR (FIG. 1E). Consistent with a potential role as cell fate regulators, 8 of the candidate genes are known regulators of gene transcription, including transcription factors (Evx1, Gbx2, Irx3, Irx5, Sox9), inhibitors of bHLH transcription factors (Id1, Id3), and a mediator of DNA demethylation (Gadd45g). Of the 6 remaining candidates, 3 are signaling pathway modulators (Fgfbp3, Crabp2, Cxcl12), 2 are involved in RNA processing (Elavl3, Tnrc6a), and 1 encodes a protein with two centrosome-associated domains but no known function (Grrp1). Interestingly, none of the 14 candidates were previously shown to directly control cardiogenic mesoderm formation, suggesting that a novel molecular signature marking differentiating multipotent cardiovascular progenitors was identified.

Figure 1K:
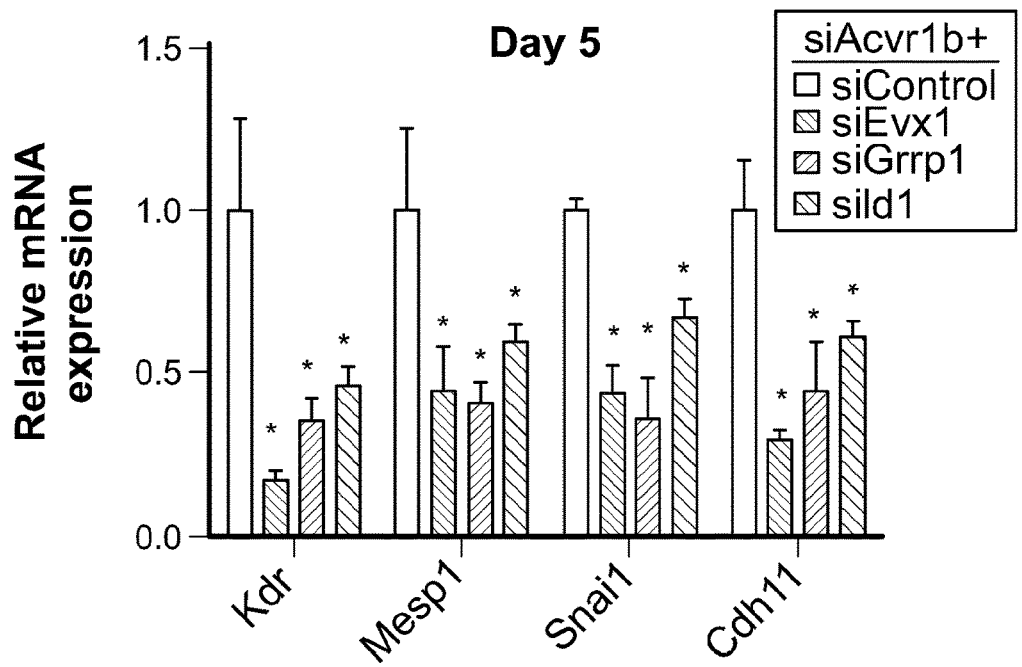
FIG. 1K. qRT-PCR results showing that siGrrp1, siEvx1 and siId1 markedly repress cardiogenic mesoderm-specific marker (Kdr, Mesp1, Snai1, Cdh11) expression. All qRT-PCR data are normalized to β-actin mRNA levels. Quantitative data are presented as means+/−SD. *p<0.05. All experiments were performed at least in biological quadruplicates.

Next, siRNA against each of the 14 candidates was assessed whether it would block cardiogenic mesoderm formation induced by siAcvr1b using a Kdr-eGFP reporter system (Colas et al., 2012). Of all the unregulated genes, only siRNAs against Grrp1, Evx1, and Id1 significantly decreased the number of Kdr$^+$-expressing cells (FIGS. 1F-1J) and blunted the induction of cardiogenic mesoderm marker genes including Kdr, Mesp1, Snai1, and Cdh11 (FIG. 1K). Thus, Grrp1, Evx1, and Id1 are needed for normal cardiogenic mesoderm differentiation in mESCs.

TABLE 2

Gene Candidates Regulated by siAcvr1b

| | Fold Upregulation P-Value < 0.05 | Gene ID | | Fold Downregulation P-Value < 0.05 | Gene ID |
| --- | --- | --- | --- | --- | --- |
| 1 | 2.609411 | Id1 | 1 | 1.6015979 | Zmpste24 |
| 2 | 2.0134268 | Gadd45g | 2 | 1.6013767 | Cdc42 |
| 3 | 1.5968683 | Irx3 | 3 | 1.5671402 | Egr1 |
| 4 | 1.4899422 | Sox9 | 4 | 1.5383662 | Fgf8 |

TABLE 2-continued

Gene Candidates Regulated by siAcvr1b

| | Fold Upregulation P-Value < 0.05 | Gene ID | | Fold Downregulation P-Value < 0.05 | Gene ID |
|---|---|---|---|---|---|
| 5 | 1.4583107 | Evx1 | 5 | 1.525815 | Leftb |
| 6 | 1.4510411 | Cxcl12 | 6 | 1.515485 | Acvr1b |
| 7 | 1.4346725 | Rgma | 7 | 1.4910644 | Zic2 |
| 8 | 1.4037634 | Tnrc6a | 8 | 1.4896251 | Ppp4r4 |
| 9 | 1.3917822 | Gadd45g | 9 | 1.467095 | Gemin6 |
| 10 | 1.3839511 | Gbx2 | 10 | 1.4522598 | Trim67 |
| 11 | 1.3793361 | BC030476 | 11 | 1.4373533 | Notch3 |
| 12 | 1.3663218 | Fus | 12 | 1.4351145 | Srprb |
| 13 | 1.365738 | Irx5 | 13 | 1.4311734 | Gsc |
| 14 | 1.3544436 | Elavl3 | 14 | 1.4305644 | Zmpste24 |
| 15 | 1.3542395 | Crabp2 | 15 | 1.4290521 | Igfbp3 |
| 16 | 1.3431355 | 1500011K16Rik | 16 | 1.4245033 | Zmpste24 |
| 17 | 1.3422825 | Tnrc6 | 17 | 1.4184229 | Grm6 |
| 18 | 1.3389522 | Ccdc85b | 18 | 1.4032689 | Ube2q |
| 19 | 1.329755 | Grrp1 | 19 | 1.3981106 | Lbr |
| 20 | 1.3260252 | Fgfbp3 | 20 | 1.3852041 | Tmem63a |
| 21 | 1.3247453 | Bcl2l11 | 21 | 1.3845202 | Pitx2 |
| 22 | 1.3216742 | Slc1a3 | 22 | 1.382626 | Npm3 |
| 23 | 1.3198931 | Gtl2 | 23 | 1.3775356 | Ttc19 |
| 24 | 1.3195066 | Id3 | 24 | 1.3773962 | Stk4 |
| 25 | 1.3176388 | Bckdha | 25 | 1.3745593 | Sgk |
| 26 | 1.3164426 | Chka | 26 | 1.3733177 | Armcx2 |
| 27 | 1.3119096 | Chd4 | 27 | 1.365576 | Tmem63a |
| 28 | 1.3110358 | Rras | 28 | 1.3652078 | Wdr82 |
| 29 | 1.3094118 | Mrg1 | 29 | 1.3617791 | Gemin6 |
| 30 | 1.3044847 | Lsm12 | 30 | 1.3600438 | Ppp4r4 |
| 31 | 1.3036366 | Cbln1 | 31 | 1.359722 | Tcn2 |
| 32 | 1.3035693 | Zfp296 | 32 | 1.3578465 | Dnajc6 |
| 33 | 1.3024908 | Klf7 | 33 | 1.3522204 | Ncoa4 |
| | | | 34 | 1.3519416 | Prpf8 |
| | | | 35 | 1.3507187 | Hdlbp |
| | | | 36 | 1.346875 | Rnf213 |
| | | | 37 | 1.3434738 | Nodal |
| | | | 38 | 1.3346514 | Slc19a2 |
| | | | 39 | 1.3340039 | Rab1 |
| | | | 40 | 1.332933 | Klhl22 |
| | | | 41 | 1.3268061 | Foxa2 |
| | | | 42 | 1.3243924 | Zfp750 |
| | | | 43 | 1.323197 | Map2k4 |
| | | | 44 | 1.3197291 | Eppk1 |
| | | | 45 | 1.3165845 | Car2 |
| | | | 46 | 1.3164321 | Smarca5-ps |
| | | | 47 | 1.3136374 | Lefty1 |
| | | | 48 | 1.3131495 | Cnn3 |
| | | | 49 | 1.3128709 | Igfbp3 |
| | | | 50 | 1.311379 | Ints5 |
| | | | 51 | 1.30427 | Tgfbr3 |
| | | | 52 | 1.3032453 | Chst15 |
| | | | 53 | 1.3031058 | Atl2 |

Figure 1X:
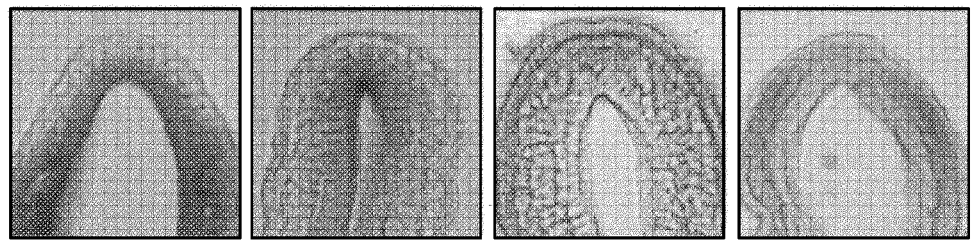
FIG. 1X. Schematic representation of an E7 embryo transverse section illustrating the different domains of expression of the 3 candidates. The gastrulating epiblast (blue) indicates the domain where Id1 and Grrp1 expression overlaps. In the primitive streak region (gray), high levels of Evx1 expression are observed with decreased Grrp1 expression. As cells exit the primitive streak and migrate laterally (purple), cells start to express Mesp1 along with Evx1. As mesoderm cells migrate more anteriorly (orange), cells resume Id1 expression.
Figure 1X:
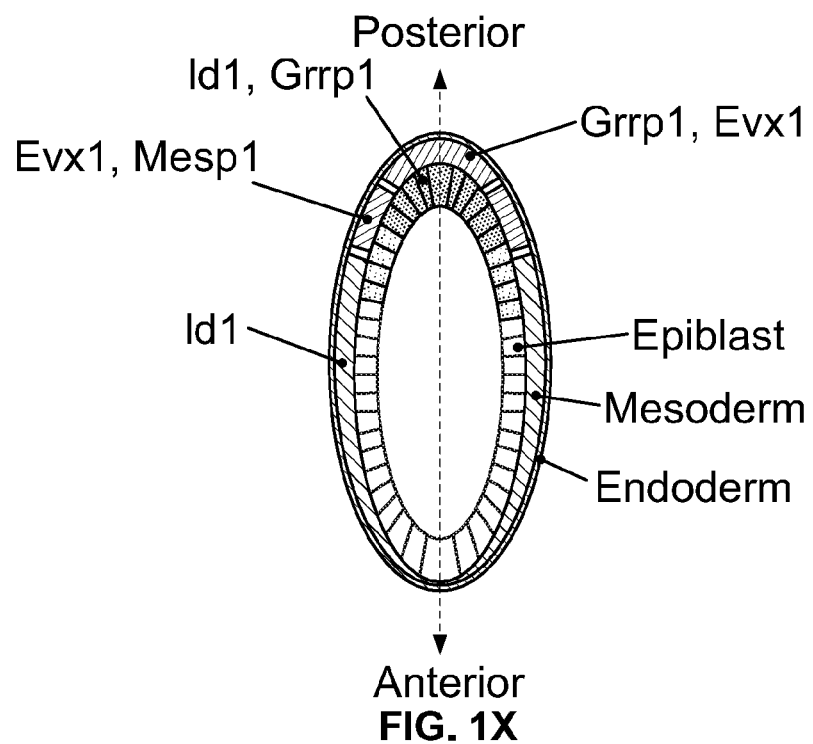

Example 3: Spatiotemporal Expression of Id1, Grrp1 and Evx1 is Consistent with Involvement in Cardiogenic Mesoderm Formation Maximal Id1 expression occurs at day 4 of mESC differentiation, preceding the peaks of Grrp1, Evx1, and Mesp1 expression (FIGS. 1L-1O). In mouse embryos, Id1 is expressed throughout the entire epiblast of the proximal region of the late gastrula-stage (E7.5) embryo near the primitive streak, and is also strongly expressed in lateral mesoderm as it migrates toward the anterior region of the embryo where early specified cardiac precursors are located (FIGS. 1P, 1T, 1T') (Devine et al 2014). Id1 transcripts are notably absent from the primitive streak, posterior mesoderm, and definitive endoderm. Grrp1 transcripts are expressed throughout the primitive streak of the embryo (FIGS. 1Q, 1U, 1U'). Transverse sections reveal that Grrp1 expression is mostly localized in gastrulating epiblast and rapidly declines as cells migrate away from the primitive streak. Evx1 expression is absent from the gastrulating epiblast while being mostly concentrated in the primitive streak and migrating mesoderm (FIGS. 1R, 1V, 1V'). Evx1 expression greatly decreases as cells migrate towards the anterior region of the embryo. Mesp1 expression marks early differentiating multipotent mesoderm, and is expressed by cells as they emerge from the primitive streak and start to migrate (FIGS. 1S, 1W, 1W'). Thus, spatiotemporal expression of candidate transcripts is consistent with their potential involvement in cardiogenic mesoderm specification, and also suggests that Id1 and Grrp1 in the gastrulating epiblast may function upstream of Evx1 in the primitive streak to ultimately direct Mesp1 expression in cells that exit the primitive streak (FIG. 1X).

Figure 2B:
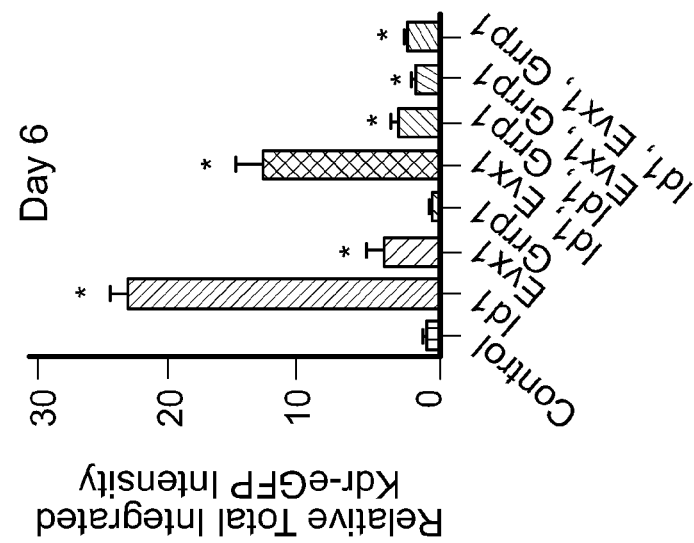
FIG. 2B. Kdr-eGFP fluorescence measurement at day 6 of differentiation in mESCs overexpressing all possible combinations of the three candidates plotted relative to uninfected control levels.
Figure 2A:
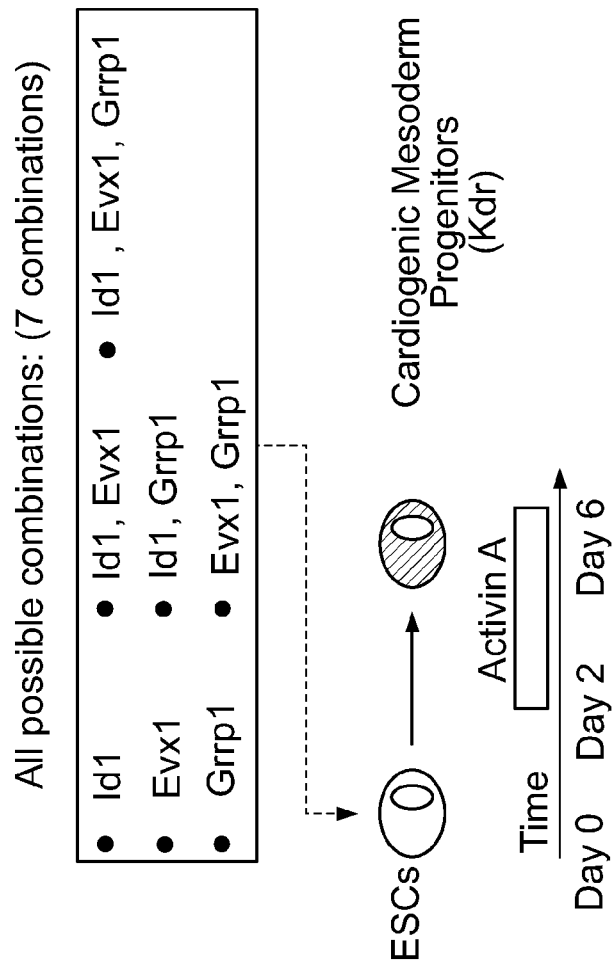
FIG. 2A. Schematic of strategy to evaluate the sufficiency (gain of function) of any of three candidates alone or in combination to promote mesoderm differentiation.
Figure 2C:
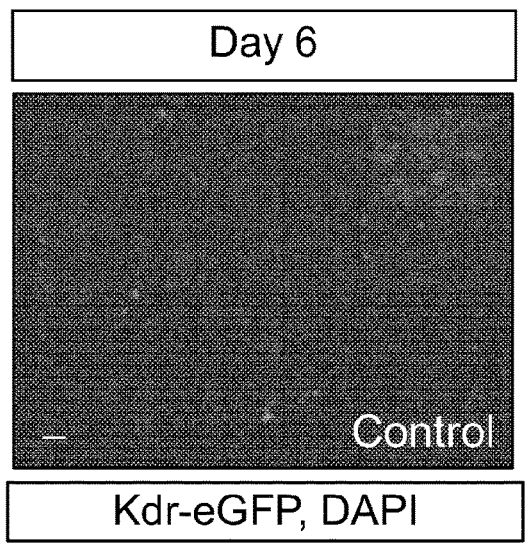
FIGS. 2C-2D. Representative images of Kdr-eGFP for Id1 overexpressing vs. control mESCs illustrating the results presented in (B). Scale bar is 50 µm.
Figure 2E:
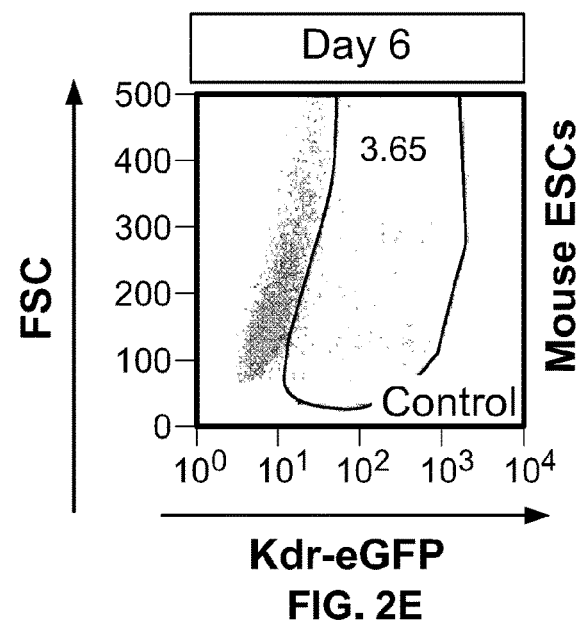
FIGS. 2E-2F. Flow cytometry analysis reveals that 61.6% of Id1-overexpressing mESCs differentiate into Kdr-eGFP+ mesoderm as compared to 3.65% for control cells at day 6.
Figure 2D:
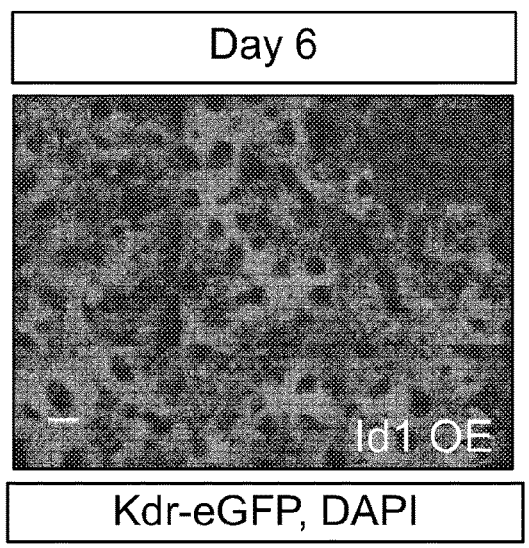
Figure 2F:
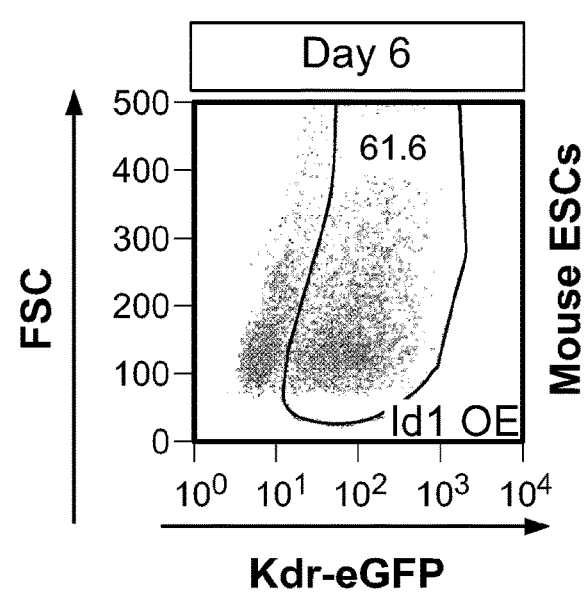
Figure 8A:
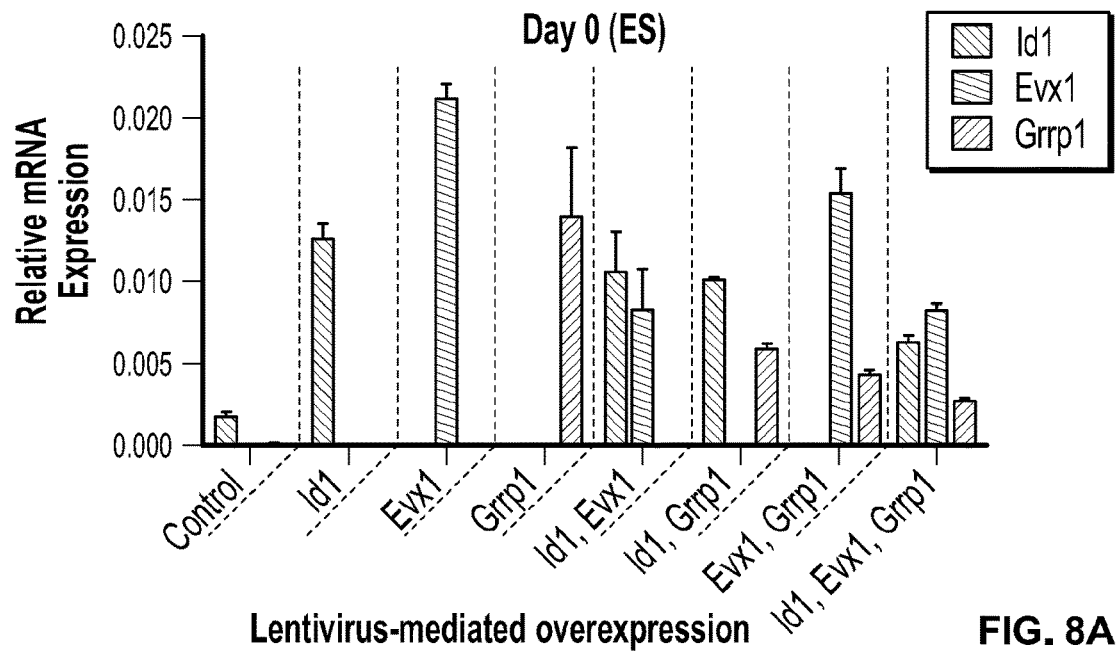
FIG. 8A. RT-qPCR analysis shows the establishment of mESC cell-line overexpressing all possible combinations of Id1, Evx1 and Grrp1 as compared to control mESCs. Quantitative data are presented as means+/−SD. All experiments were performed at least in biological quadruplicates.
Figure 8B:
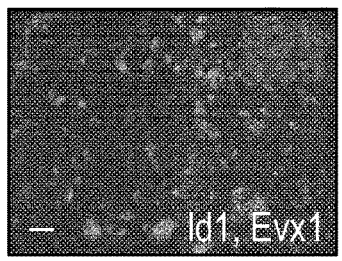
FIGS. 8B-8G. Representative images of Kdr-eGFP fluorescence at day 6 of differentiation in mESCs overexpressing all possible combinations of the three candidate genes. Scale bar is 50 µm.
Figure 8C:
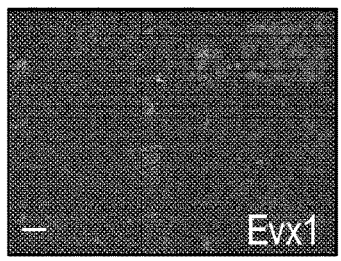
Figure 8D:
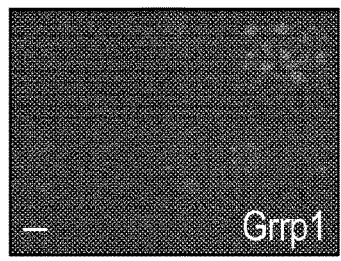
Figure 8E:
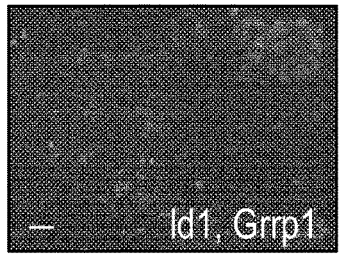
Figure 8F:
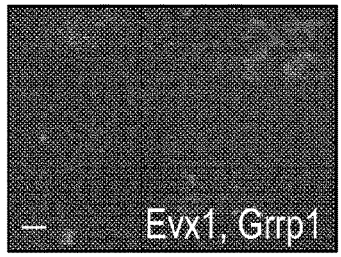
Figure 8G:
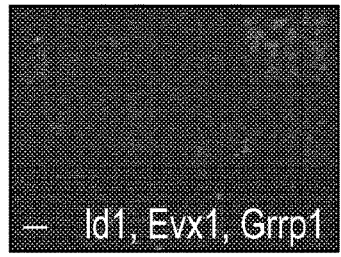

Example 4: Id1 is Sufficient to Direct Kdr+ Cardiogenic Mesoderm Formation in Mouse and Human ESCs In order to evaluate whether candidate genes, alone or in combination, are sufficient to promote cardiogenic mesoderm differentiation, mESC lines overexpressing all 7 possible combinations of the 3 candidates were generated (FIG. 2A and FIG. 8A). The cell lines were treated with Activin A (but not with Acvr1b siRNA) and the resulting differentiation was assessed on day 6. Id1 was sufficient to massively direct ESCs to differentiate towards Kdr$^+$ mesoderm without Acvr1b attenuation (~22-fold over parental mESCs), while the other genes had less potent effects (FIGS. 2B-2D and FIGS. 8B-8G). Quantitatively, the conversion rate of Id1-overexpressing mESCs into Kdr-eGFP$^+$ mesoderm is approximately 60% as compared to only 3.65% for control ESCs (FIGS. 2E, 2F).

Next, experiments were performed to determine whether Id1 functions similarly in human ESCs (hESCs) by generating a WiCell (H9) hESC line that stably overexpresses mouse Id1 since mouse and human HLH domains are identical (FIGS. 2G, 2H). Consistent with mESCs, Id1 greatly increased the incidence of KDR$^+$-mesoderm in Activin A treated cultures at day 5 from 9.1% in parental hESCs to 69.8% in hESC$^{Id1}$ (FIGS. 2I, 2J).

Figure 2S:
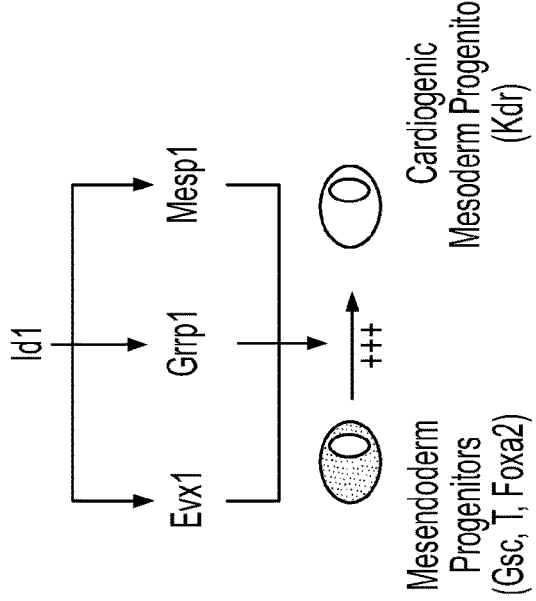
FIG. 2S. Model summarizing pro-cardiogenic role of Id1 by upregulating the expression of Evx1, Grrp1, and Mesp1 in bi-potent mesendoderm progenitors.

Remarkably, the formation of Id1-induced Kdr$^+$/KDR$^+$ mesoderm progenitors (iMPs) was consistently preceded by the upregulation of Evx1/EVX1 and Grrp1/GRRP1 (day 3/4 in mESCs (FIGS. 2K, 2L) and day 3 in hESCs (FIGS. 2O, 2P)); followed by dramatic Mesp1/MESP1 upregulation (FIGS. 2M, 2Q; ~67 fold in mESCs at day 4 and ~20 fold in hESCs at day 3); and subsequent Kdr I KDR upregulation at day 4 and day 5, respectively (FIGS. 2N, 2R). Altogether, these data show that Id1 initiates the activation of an evolutionarily conserved gene regulatory network (Evx1/EVX1, Grrp1/GRRP1 and Mesp1/MESP1) controlling the formation Kdr$^+$/KDR$^+$ mesoderm (FIG. 2S).

Figure 3G:
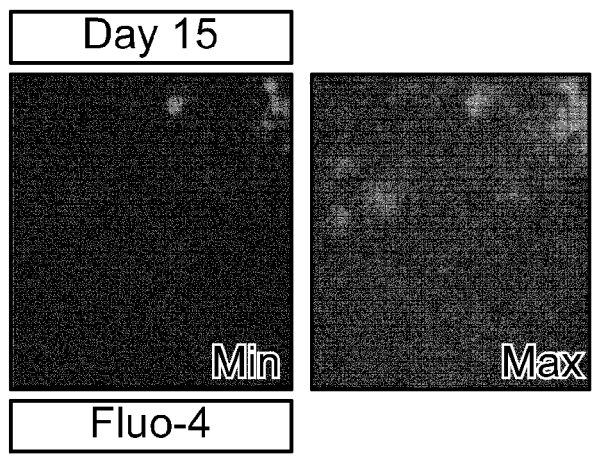
FIG. 3G. Representative images illustrating the minimum and maximum changes in fluorescence of Fluo-4 in cardiomyocytes derived from Id1 overexpressing h9-hESCs.
Figure 3H:
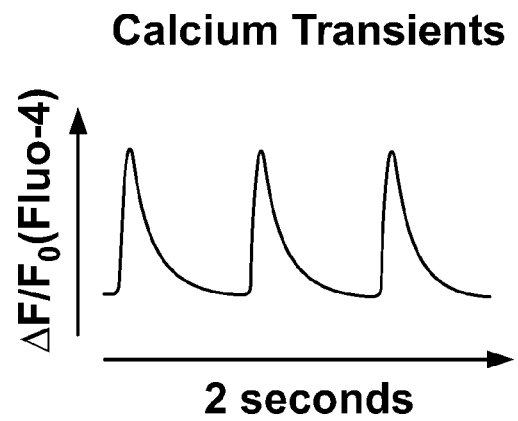
FIG. 3H. Representative calcium transient trace of day 15 cardiomyocytes derived from Id1 overexpressing h9-hESCs.
Figure 3I:
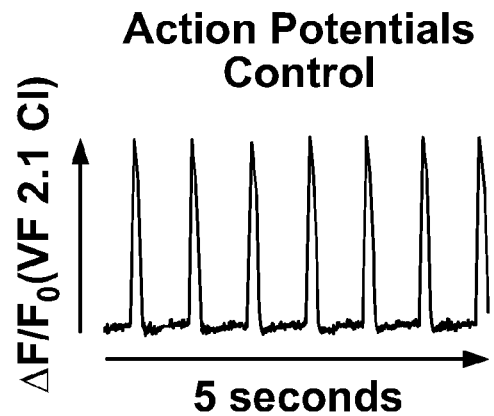
FIG. 3I. Representative action potential traces of cardiomyocytes derived from Id1 overexpressing h9-hESCs in control conditions.
Figure 3J:
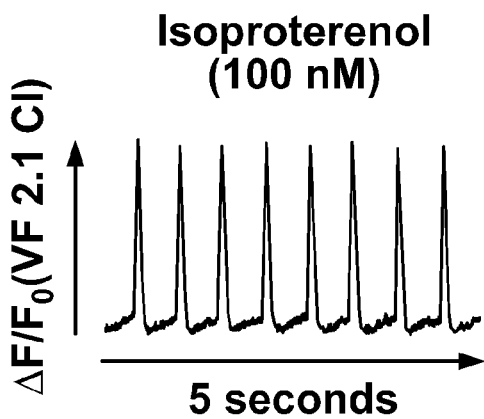
FIG. 3J. Representative action potential traces of cardiomyocytes derived from Id1 overexpressing h9-hESCs in response to isoproterenol measured optically with VF2.1 Cl.
Figure 3K:
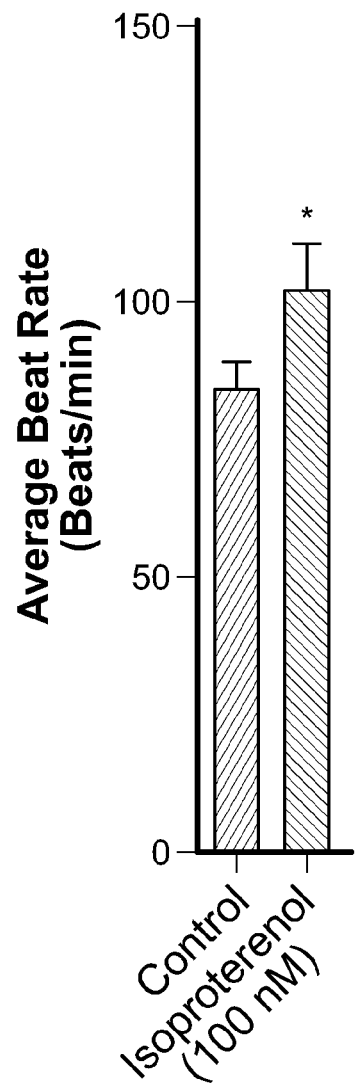
FIG. 3K. Beat rate quantification of cardiomyocytes derived from Id1 overexpressing h9-hESCs indicating an increase in beating frequency in response to isoproterenol (100 nM) treatment as compared to vehicle and measured with VF2.1 Cl.
Figure 9A:
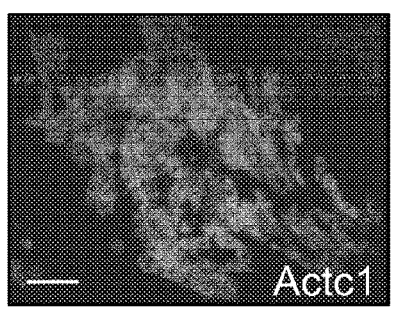
FIG. 9A. Representative immunofluorescence images for cardiomyocytes (Actc1) at day 15 of differentiation. Scale bar is 50 µm FIG. 9B. Representative immunofluorescence images for vascular endothelial cells (Pecam1) at day 15 of differentiation. Scale bar is 50 µm FIG. 10A. qRT-PCR analysis showing siTcf3-mediated knock-down efficiency as compared to siControl at day 5 of differentiation.
Figure 9B:
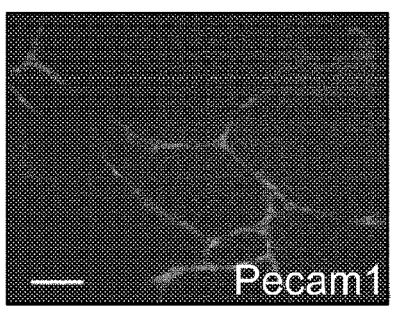

Next, experiments were performed to determine whether iMP progenitors are bona fide multipotent cardiovascular progenitors and thus able to differentiate into multiple cardiac lineages including functional cardiomyocytes. To address this question, iMPs were first produced in bulk until day 6 of differentiation for mouse, or day 5 for human. At this point, iMPs could be cryopreserved or used fresh. Spontaneous differentiation potential under basal media conditions without cytokines (FIG. 3A) was assessed by RT-qPCR (FIGS. 3B, 3C) and immunostaining (FIG. 3D and FIGS. 9A, 9B) at day 15 of differentiation. The results show that iMPs spontaneously differentiate into at least three distinct cellular lineages normally present in the heart, including cardiomyocytes (Myh6, Tnnt2, Actc1), vascular endothelial cells (Pecam1, Cdh5), and fibroblasts (Postn, Tagln) in both species. Although iMPs are multipotent progenitors, the vast majority of the cells (~70%) spontaneously differentiate into ACTC1$^+$ cardiomyocytes in hESCs (FIG. 3E). Next, we assessed whether resulting ACTC1$^+$ cells show characteristics of functional cardiomyocytes, which include the ability to contract, display intracellular calcium oscillations and action potentials, and respond to hormonal stimuli (Birket et al., 2015; Burridge et al., 2014). High-speed optical recording (100 frames per second) (FIG. 3F) reveals that in addition to expressing cardiac-specific markers, day 15 cells contract rhythmically (Movie S3), display periodic calcium transients (FIGS. 3G, 3H and Movie S4) and action potentials, (FIG. 3I and Movie S5) and show increased beat rate in response to β-adrenergic agonist, isoproterenol (FIGS. 3J, 3K and Movie S6). In summary, these observations demonstrate that iMPs represent a novel population of bona fide multipotent cardiovascular progenitors with remarkable ability to spontaneously differentiate into functional cardiomyocytes.

Example 5: Id1 Promotes Cardiogenic Mesoderm Differentiation by Inhibiting Tcf3 and Foxa2

Figure 4B:
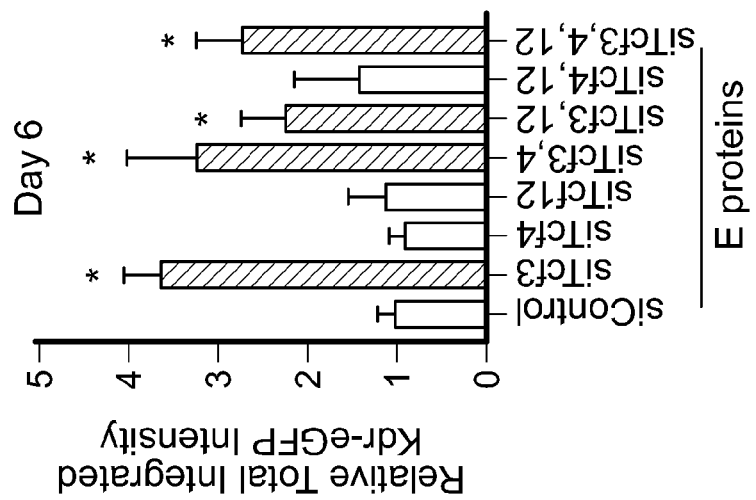
FIG. 4B. siRNA-mediated functional screen evaluating the role E proteins (Tcf3, Tcf4, Tcf12) in repressing cardiogenic mesoderm differentiation. Diagram shows fluorescence quantification of Kdr-eGFP in response to all 7 possible siRNA combinations and siControl.
Figure 4A:
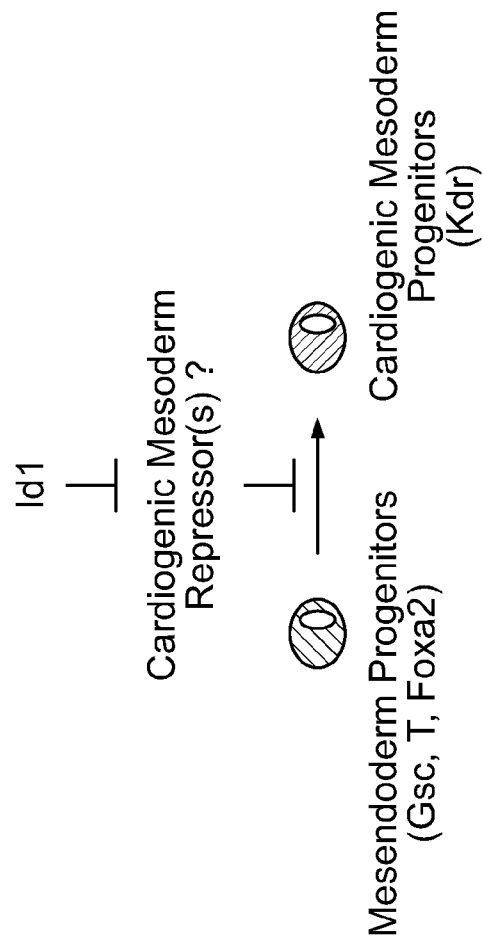
FIG. 4A. Schematic predicting that Id1 mediates its pro-cardiogenic effect by targeting and inhibiting repressors of cardiogenic mesoderm differentiation.

Id proteins do not bind DNA directly, but regulate transcription by antagonizing the function of bHLH transcription factors through their HLH domains (Kee, 2009). Their canonical partners are the ubiquitously expressed class I bHLH transcription factors (E proteins) Tcf3, Tcf4 and Tcf12 (Kee, 2009; Yang et al., 2014). Therefore, to determine if Id1 might initiate cardiogenic mesoderm formation by inhibiting E proteins (FIG. 4A), experiments were performed to test if siRNAs directed against the three E proteins, either alone or in combination (7 combinations) would inhibit Kdr-eGFP fluorescence at day 6 of differentiation as above. All combinations of siRNAs that contained siTcf3 promoted cardiogenic mesoderm differentiation (~4-fold over siControl) (FIGS. 4B-4D). Although these studies implicate Tcf3 as a relevant target of Id1, siTcf3 was significantly less potent at inducing Kdr-eGFP$^+$ cells than either Id1 overexpression or siAcvr1b transfection, suggesting that additional targets are involved. Therefore, all 104 members of the class II family of bHLH transcription factors were screened (e.g. MyoD, NeuroD, myogenin, etc.) by an analogous approach, but none had any effect on cardiogenic mesoderm formation.

Figure 4F:
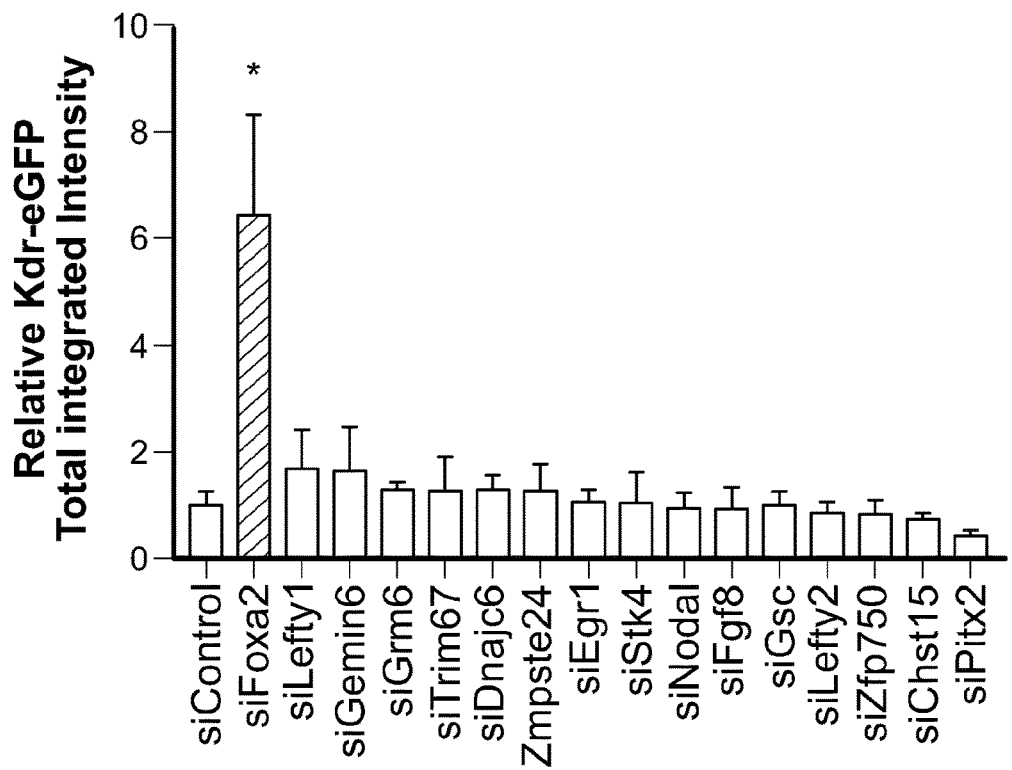
FIGS. 4F-4G. siRNA-mediated functional screen evaluating if downstream targets of Acvr1b signaling are involved in the repression of cardiogenic mesoderm differentiation. Diagram shows fluorescence quantification of Kdr-eGFP where only a siRNA directed against siFoxa2 is able to promote cardiogenic mesoderm differentiation (FIG. 4F). Representative Kdr-eGFP immunofluorescence images of siFoxa2 (FIG. 4G). Scale bar is 50 μm.
Figure 4G:
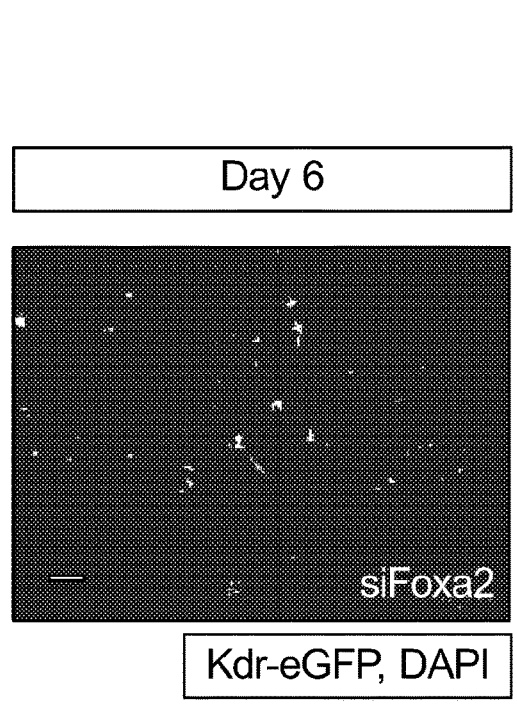
Figure 4H:
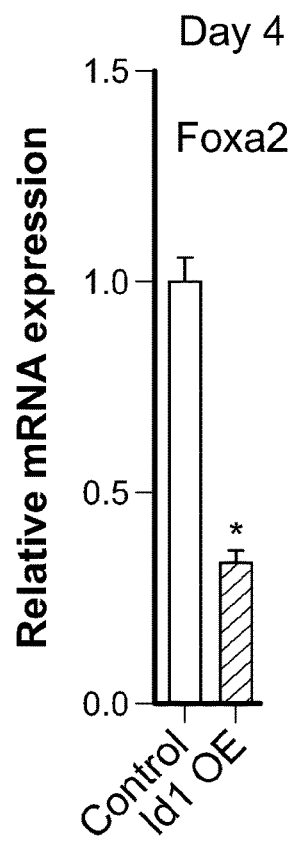
FIG. 4H. qRT-PCR shows that Foxa2 expression is downregulated in Id1-overexpressing mESCs as compared to control.

Next, experiments were performed to test whether Id1 might mediate part of its pro-cardiogenic mesoderm activity by downregulating antagonists of cardiogenic mesoderm formation. Such genes should be among those downregulated in response to the pro-cardiogenic mesoderm actions of siAcvr1b at day 4 of differentiation. Out of the 53 genes identified in the microarray (Table 2), 17 were confirmed by RT-qPCR to be robustly downregulated by siAcvr1b (FIG. 4E). Next, experiments were performed to test whether siRNA-mediated knockdown of any of these 17 genes would be sufficient to promote Kdr-eGFP$^+$ cardiogenic mesoderm formation. Strikingly, siRNA to only one gene, encoding the forkhead transcription factor, Foxa2, was sufficient to induce Kdr-eGFP$^+$ mesoderm (FIGS. 4F, 4G). Although Id1 is not known to physically interact with forkhead transcription factors, overexpression of Id1 strongly decreased the abundance of Foxa2 transcripts in the cells relative to controls (FIG. 4H), suggesting that Id1 indirectly inhibits Foxa2 gene expression.

Figure 4I:
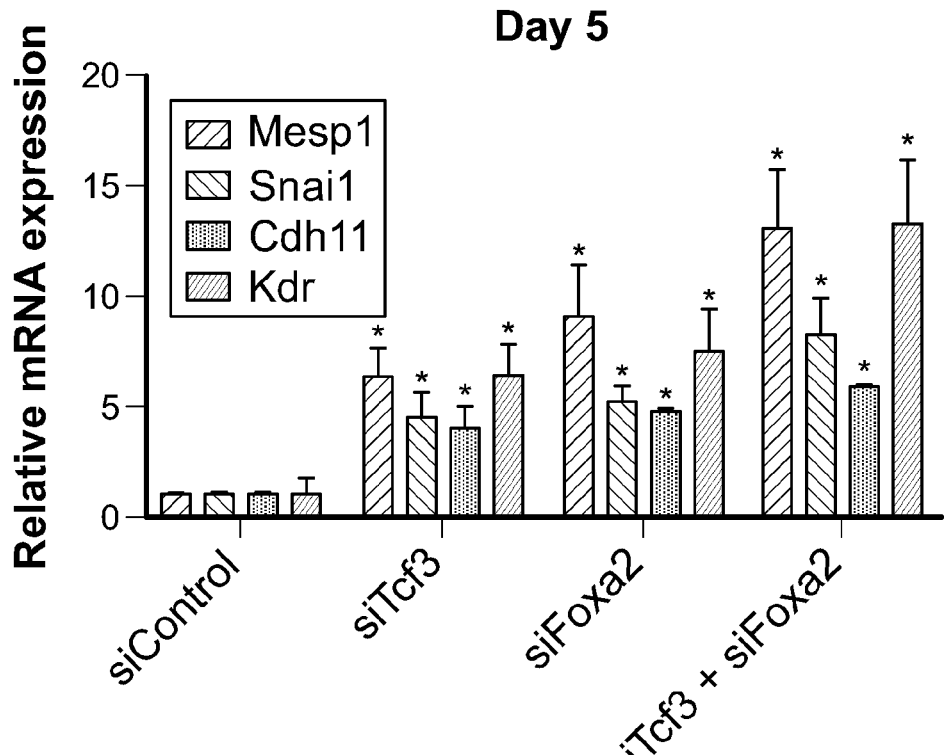
FIGS. 4I-4K. qRT-PCR for cardiogenic mesoderm markers (Mesp1, Snai1, Cdh11 and Kdr) shows that the co-transfection of siFoxa2 and siTcf3 further enhances cardiogenic mesoderm differentiation as compared to siTcf3 or siFoxa2 alone (FIG. 4I). Diagram showing fluorescence quantification of Kdr-eGFP (FIG. 4J) and representative image (FIG. 4K) of siTcf3+siFoxa2 condition. Scale bar is 50 μm.
Figure 4J:
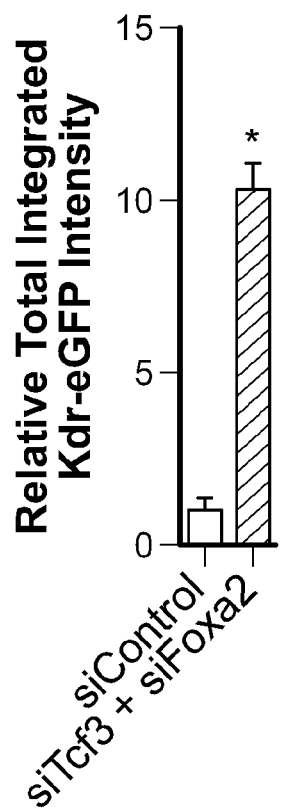
Figure 4K:
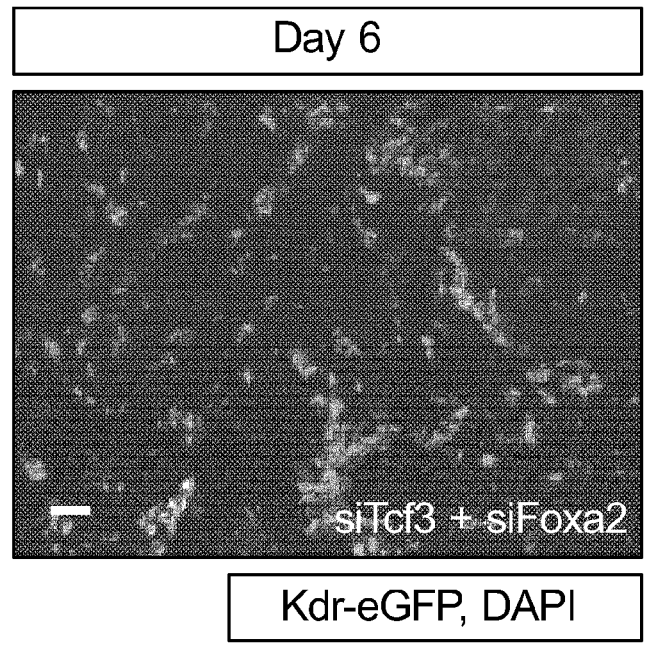
Figure 4L:
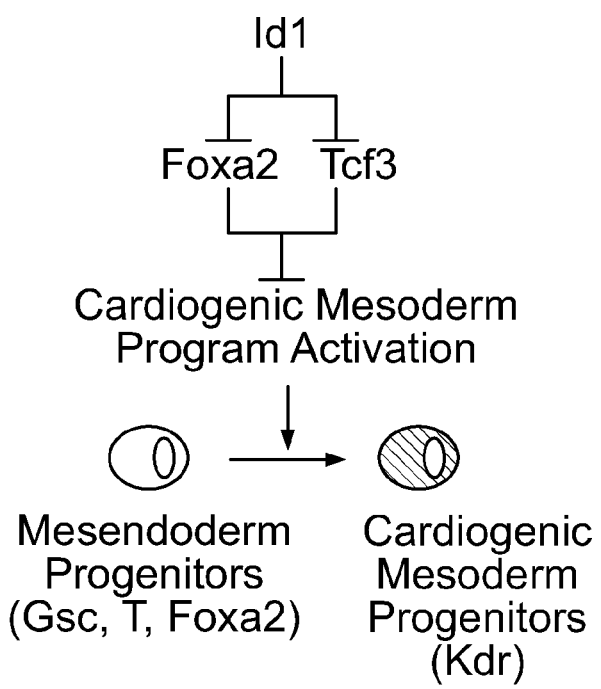
FIG. 4L. Model showing Id1 repressive role on Tcf3 and Foxa2 activity to promote cardiogenic mesoderm differentiation.
Figure 10A:
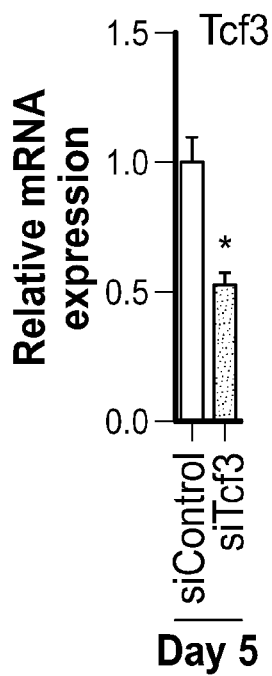
FIG. 10B. qRT-PCR analysis showing siFoxa2-mediated knock-down efficiency as compared to siControl at day 5 of differentiation.
Figure 10B:
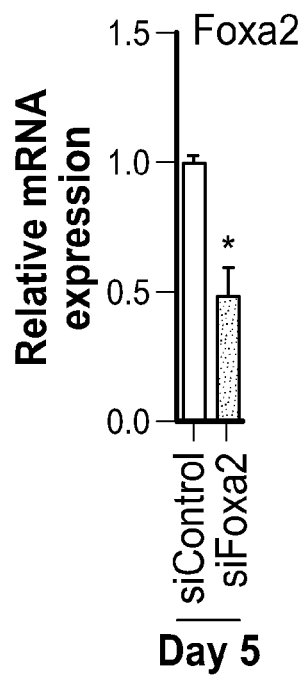

Moreover and consistent with the hypothesis, Tcf3 and Foxa2 knockdowns (FIGS. 10A, 10B) each de-repressed cardiogenic mesoderm gene expression (Mesp1, Snai1, Cdh11, and Kdr) (FIG. 4I). In addition, combined knockdown of Tcf3 and Foxa2 further enhanced cardiogenic mesoderm differentiation efficiency, suggesting that both genes act in a non-redundant manner during this process (FIGS. 4I-4K). Thus, Id1 activates the cardiogenic program by inhibiting Tcf3 protein activity while suppressing Foxa2 transcription (FIG. 4L).

Example 6: Id Proteins Promote Cardiogenic Mesoderm Formation In Vivo

Figure 5C:
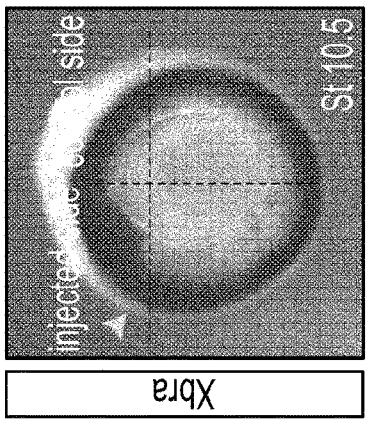
FIGS. 5C-5F. Unilaterally injected embryos (as in FIG. 5A) cultured to gastrula stage (stage 10.5) in whole mount (FIGS. 5C and 5E) or transversely bisected (FIGS. 5D and 5F) and probed for mesoderm marker Xbra (FIGS. 5C and 5D) and cardiogenic mesodermXmespb (FIGS. 5E and 5F) expression. Yellow arrows indicate expansions of both the Xbra and Xmespb domains in the Xid1 injected side.
Figure 5D:
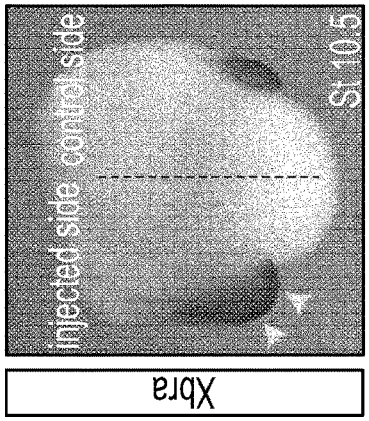
Figure 5E:
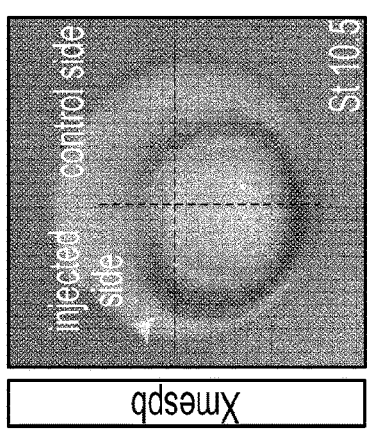
Figure 5F:
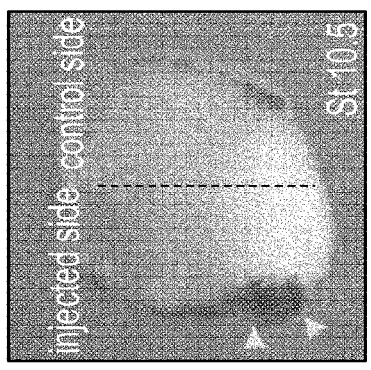
Figure 5G:
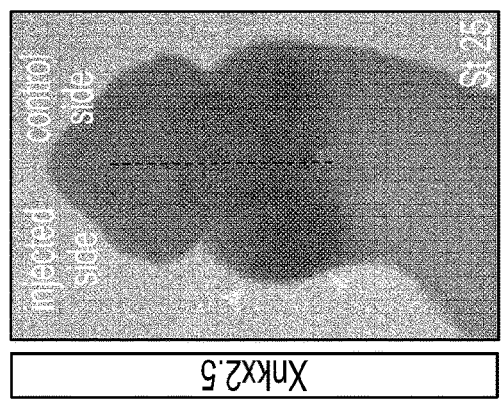
FIGS. 5G-5I. Unilaterally injected embryos cultured to early tailbud stage (stage 25) in whole mount and probed for Xnkx2.5 expression. Yellow arrows indicated an expansion of the Xnkx2.5 domain in the Xid2 injected side of the embryo.
Figure 5H:
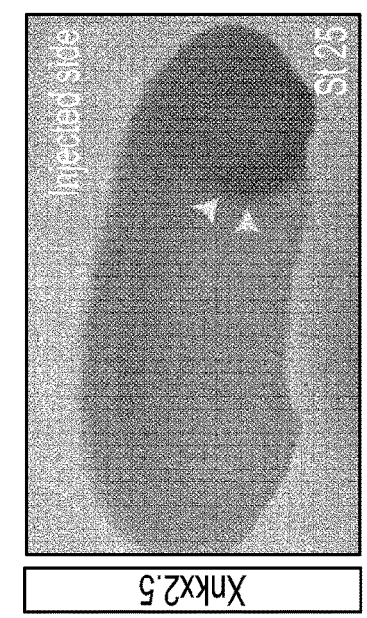
Figure 5I:
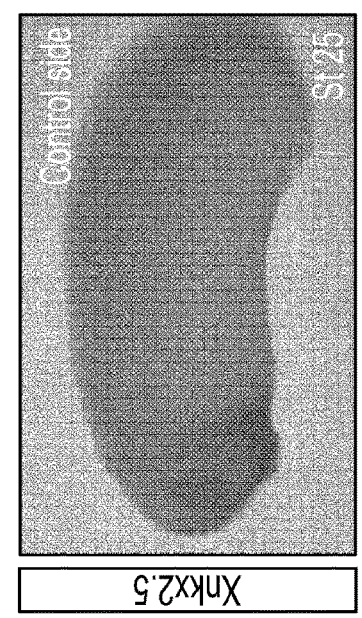
Figure 11A:
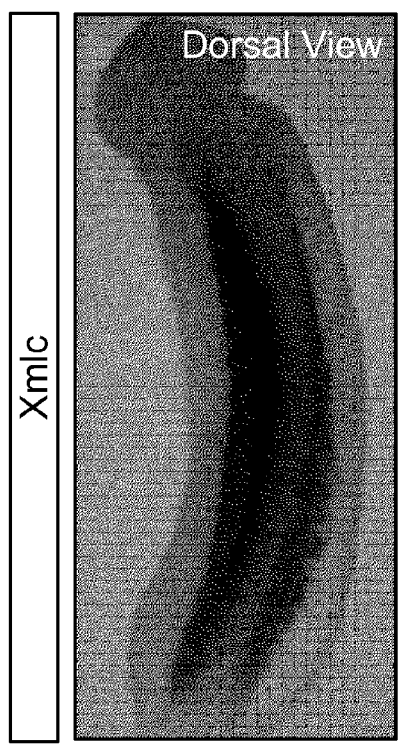
FIG. 11A. Dorsal view of the embryos. Embryos were hemilaterally injected at 4-cell stage as in FIG. 5 and cultured to early tailbud stage (stage 25). Whole mount in situ hybridization probes for skeletal muscle marker Xmlc expression.
Figure 11B:
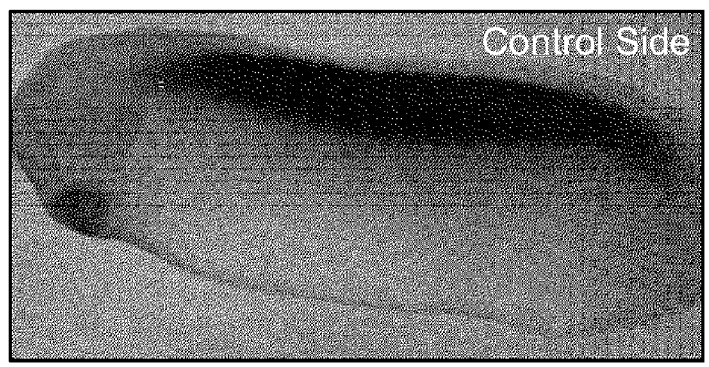
FIG. 11B. Control side of the embryos.
Figure 11C:
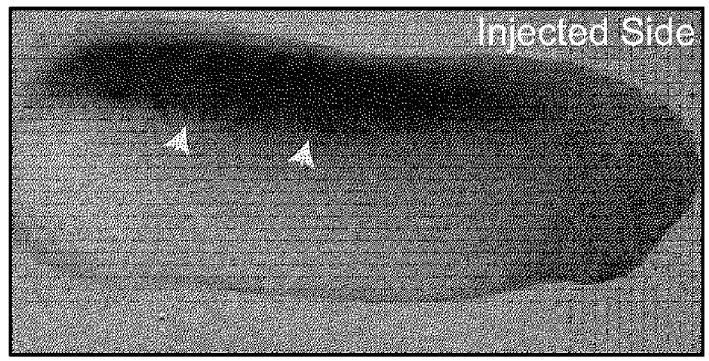
FIG. 11C. Injected side of the embryos. Yellow arrows indicate decreased and disorganized pattern of expression in the injected side as compared to control side.

Next, *Xenopus* embryos were used to test if Id genes can promote cardiogenic mesoderm formation in vivo. Equatorial and hemilateral injection of Xid2 mRNA (FIG. 5A), which is the closest orthologue to mouse Id1 (FIG. 5B), causes a dramatic expansion of Xbra (FIGS. 5C, 5E; 74%, n=105) and Xmespb (FIGS. 5D, 5F; 78%, n=132) expression domains (marking mesoderm) in gastrula-stage embryos (Nieuwekoop and Faber stage 10.5). To determine if the expanded Xbra$^+$, Xmespb$^+$ domains correlate with a subsequent increase in cardiogenesis, tailbud stage (stage 25) embryos were examined for Xnkx2.5 expression that marks the cardiac primordium (Raffin et al., 2000). Strikingly, Xid2 overexpression caused an expansion of Xnkx2.5 expression domain (FIGS. 5G-5I; 68%, n=88) while in contrast, it diminished expression of the skeletal muscle marker, Xmlc (FIG. 11A-11C; 66%, n=30)). Taken together, Xid2, like mammalian Id1, promotes the formation of mesoderm progenitors that are primed to differentiate towards cardiogenic lineages.

Example 7: Id Genes are Essential for Early Mammalian Heart Formation In Vivo

Figure 6A:
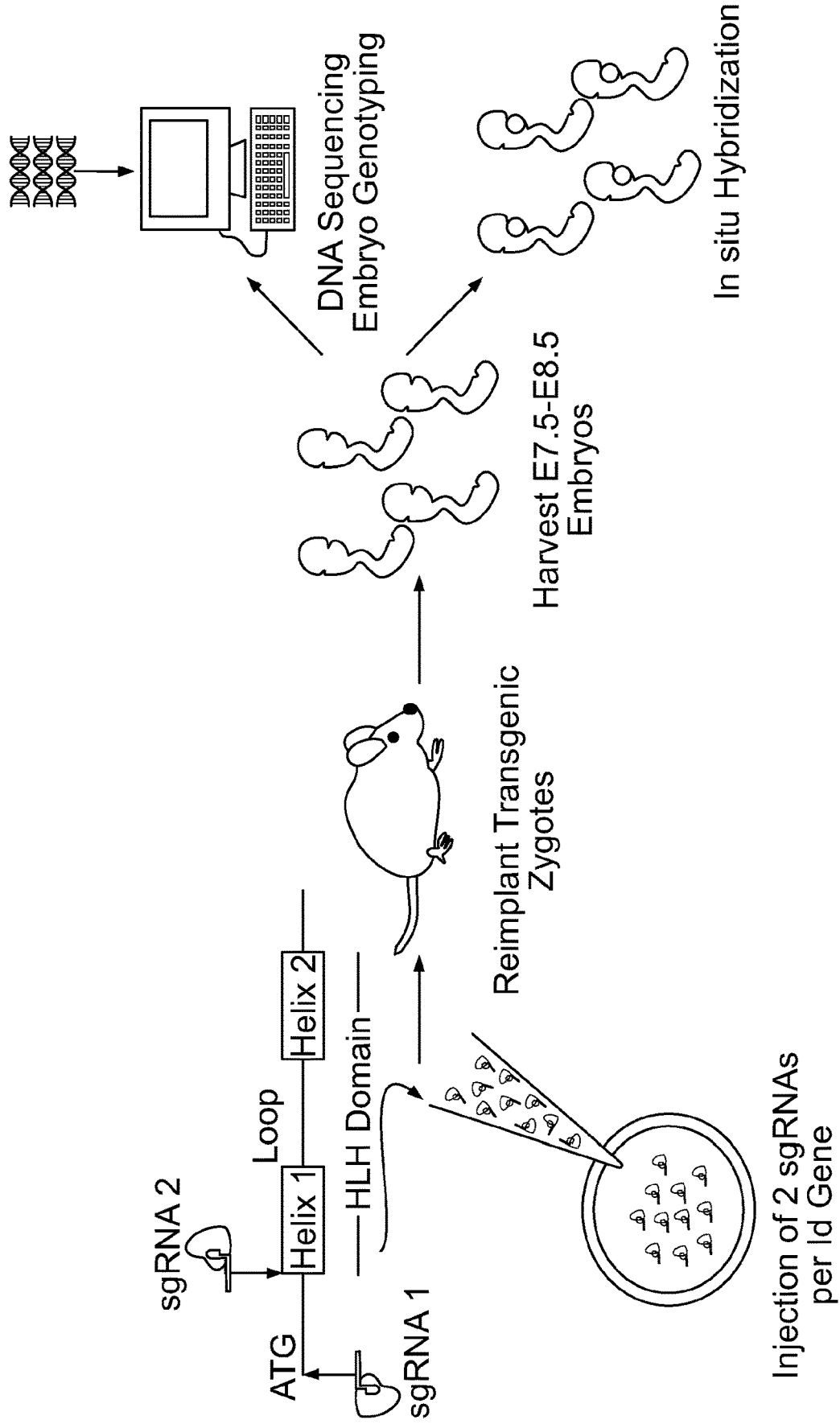
FIG. 6A. Schematic illustrating the generation and analysis of Id1-4 mutant embryos using CRISPR/Cas9 technology. Two sgRNAs per gene (targeting the translational start site and the HLH domain) were injected into single cell mouse zygotes alongside Cas9 mRNA. Zygotes were reimplanted and harvested at stages E7.5-E8.5. Resulting embryos were genotyped by DNA deep sequencing and cardiac gene expression was assessed via whole mount in situ hybridization.
Figure 12:
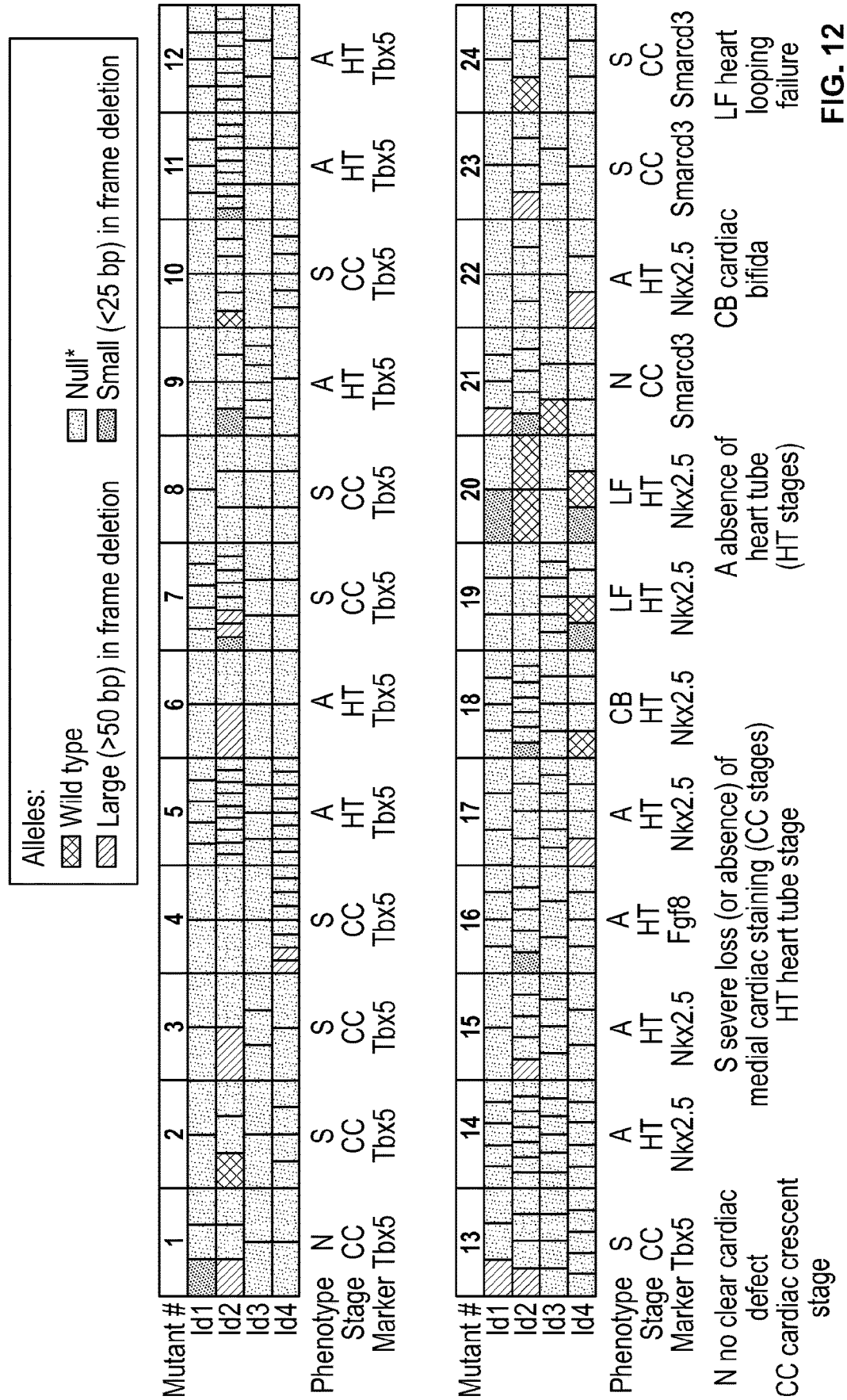
FIG. 12. Summary of genotype information of mouse embryos analyzed in loss of function study. DNA sequences of 24 mutant embryos were analyzed, and variant alleles were recorded using IGV genome browser (Broad Institute). Blue box marks wild type allele, red box marks null alleles, orange box marks large (>50 bp) in-frame deletion, yellow box marks small (<25 bp) in-frame deletion. Phenotypes are annotated as follows: N: no cardiac defect, S: severe loss (or absence) of medial staining in cardiac crescent, A: absence of heart tube, CB: cardiac bifida, LF: looping failure. Two embryo stages are reported: CC: cardiac crescent stage and HT: heart tube stage. Four cardiac markers were tested: Smarcd3, Tbx5, Nkx2.5, and Fgf8.

The gain of function experiments show that Id proteins are sufficient to direct the formation of multipotent cardiac progenitors both in vitro and in vivo, so the next question is whether Id proteins are normally required for this process. A previous study (Fraidenraich et al., 2004) found that deleting 3 out of the 4 Id genes (Id1,2,3 triple gene knockout) caused complex cardiac defects, but did not ablate the heart in these embryos, thereby indicating that earlier cardiac specification could still occur. Given the functional similarity of Id family members (Fraidenraich et al., 2004; Kee and Bronner-Fraser, 2005; Lyden et al., 1999; Niola et al., 2012; Niola et al., 2013), it was hypothesized that either redundant or compensatory activity of Id4 might allow heart formation to occur in triple knockout embryos. To test this hypothesis, all four Id gene members were genetically ablated using a CRISPR/Cas9 gene editing strategy in mouse embryos. To increase the probability of null allele generation, each Id gene was targeted by two sgRNAs, directed against the ATG and the beginning of the HLH domain, respectively. 24 embryos (ranging from E7.75-E8.75), collected from three independent zygote injection sessions, were subjected to genotyping by DNA sequencing and cardiac phenotype assessment by in situ hybridization (FIG. 6A). DNA sequencing results show that despite widespread mosaicism, 320 (90.7%) of the 353 alleles detected were null (elimination of the HLH-domain reading frame), 24 (6.8%) were in-frame mutations, and only 9 (2.5%) were wild-type. Only 7/24 embryos harbored one or more wild-type alleles while 17/24 embryos harbored no wild-type alleles (FIG. 12). Importantly, no off-target mutagenesis was detected in the top 8 predicted off-target sites.

The phenotypic assessment at E7.75 showed that two markers of early cardiac precursors, Smarcd3 and Tbx5, were absent from the most anterior and medial region of the cardiac crescent that gives rise to the heart tube (FIGS. 6B-6I; n=9/11; embryos #21,23,24 (Smarcd3) and #1-3,4, 7,8,10,13 (Tbx5); see FIG. 12 for genotype information). In contrast, expression of these markers was maintained in two lateral domains of mesoderm posterior to the heart tube-forming region suggesting that these posterior cardiac progenitors could differentiate and migrate appropriately. At E8.25, when the heart tube has normally formed, the cardiac marker Nkx2.5 revealed an absence of heart tube formation in Id1-4 mutants (FIGS. 6K-6N). Histological sectioning confirmed the absence of anatomical heart tube formation (FIGS. 6L', 6N'). At E8.75, when the heart begins to loop, analysis of Nkx2.5 (FIGS. 6O, 6Q, 6R) and the first heart field marker Tbx5, (FIGS. 6S-6V) confirmed the absence of hearts in quadruple knockout embryos (FIGS. 6M, 6N, 6Q, 6R, 6U, 6V; n=10/13; embryos #14,15,17,22 (Nkx2.5) and #5,6,9,11,12,13 (Tbx5)). Finally, and consistent with the initial hypothesis of functional redundancy between Id family members, embryos harboring at least one Id4 wild-type allele can still form a heart tube that loops, albeit abnormally, as compared to controls (FIGS. 6O, 6P; n=3/13; embryo #18,19,20). Collectively, these results demonstrate that the Id family of genes is required for the specification of heart tube-forming multipotent cardiovascular progenitors and its subsequent assembly.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Benezra, R., Davis, R. L., Lockshon, D., Turner, D. L., and Weintraub, H. (1990). The protein Id: a negative regulator of helix-loop-helix DNA binding proteins. Cell 61, 49-59.

Beppu, H., Kawabata, M., Hamamoto, T., Chytil, A., Minowa, O., Noda, T., and Miyazono, K. (2000). BMP type II receptor is required for gastrulation and early development of mouse embryos. Developmental biology 221, 249-258.

Birket, M. J., Ribeiro, M. C., Verkerk, A. O., Ward, D., Leitoguinho, A. R., den Hartogh, S. C., Orlova, V. V., Devalla, H. D., Schwach, V., Bellin, M., et al. (2015). Expansion and patterning of cardiovascular progenitors derived from human pluripotent stem cells. Nature biotechnology 33, 970-979.

Bondue, A., Lapouge, G., Paulissen, C., Semeraro, C., Iacovino, M., Kyba, M., and Blanpain, C. (2008). Mesp1 acts as a master regulator of multipotent cardiovascular progenitor specification. Cell stem cell 3, 69-84.

Bruneau, B. G. (2013). Signaling and transcriptional networks in heart development and regeneration. Cold Spring Harb Perspect Biol 5, a008292.

Buckingham, M., Meilhac, S., and Zaffran, S. (2005). Building the mammalian heart from two sources of myocardial cells. Nature reviews Genetics 6, 826-835.

Burridge, P. W., Matsa, E., Shukla, P., Lin, Z. C., Churko, J. M., Ebert, A. D., Lan, F., Diecke, S., Huber, B., Mordwinkin, N. M., et al. (2014). Chemically defined generation of human cardiomyocytes. Nature methods 11, 855-860.

Cai, C. L., Liang, X., Shi, Y., Chu, P. H., Pfaff, S. L., Chen, J., and Evans, S. (2003). Isl1 identifies a cardiac progenitor population that proliferates prior to differentiation and contributes a majority of cells to the heart. Developmental cell 5, 877-889.

Chan, S. S., Shi, X., Toyama, A., Arpke, R. W., Dandapat, A., Iacovino, M., Kang, J., Le, G., Hagen, H. R., Garry, D. J., et al. (2013). Mesp1 patterns mesoderm into cardiac, hematopoietic, or skeletal myogenic progenitors in a context-dependent manner. Cell stem cell 12, 587-601.

Chiapparo, G., Lin, X., Lescroart, F., Chabab, S., Paulissen, C., Pitisci, L., Bondue, A., and Blanpain, C. (2016).

Mesp1 controls the speed, polarity, and directionality of cardiovascular progenitor migration. J Cell Biol 213, 463-477.

Colas, A., Cartry, J., Buisson, I., Umbhauer, M., Smith, J. C., and Riou, J. F. (2008). Mix. 1/2-dependent control of FGF availability during gastrulation is essential for pronephros development in *Xenopus*. Developmental biology 320, 351-365.

Colas, A R., McKeithan, W. L., Cunningham, T. J., Bushway, P. J., Garmire, L. X., Duester, G., Subramaniam, S., and Mercola, M. (2012). Whole-genome microRNA screening identifies let-7 and mir-18 as regulators of germ layer formation during early embryogenesis. Genes & development 26, 2567-2579.

Collop, A. H., Broomfield, J. A., Chandraratna, R. A., Yong, Z., Deimling, S. J., Kolker, S. J., Weeks, D. L., and Drysdale, T. A. (2006). Retinoic acid signaling is essential for formation of the heart tube in *Xenopus*. Developmental biology 291, 96-109.

Costello, I., Pimeisl, I. M., Drager, S., Bikoff, E. K., Robertson, E. J., and Arnold, S. J. (2011). The T-box transcription factor Eomesodermin acts upstream of Mesp1 to specify cardiac mesoderm during mouse gastrulation. Nature cell biology 13, 1084-1091.

David, R., Brenner, C., Stieber, J., Schwarz, F., Brunner, S., Vollmer, M., Mentele, E., Muller-Hocker, J., Kitajima, S., Lickert, H., et al. (2008). MesP1 drives vertebrate cardiovascular differentiation through Dkk-1-mediated blockade of Wnt-signalling. Nature cell biology 10, 338-345.

Djiane, A., Riou, J., Umbhauer, M., Boucaut, J., and Shi, D. (2000). Role of frizzled 7 in the regulation of convergent extension movements during gastrulation in *Xenopus laevis*. Development 127, 3091-3100.

Ema, M., Takahashi, S., and Rossant, J. (2006). Deletion of the selection cassette, but not cis-acting elements, in targeted Flk1-lacZ allele reveals Flk1 expression in multipotent mesodermal progenitors. Blood 107, 111-117.

Foley, A. C., Korol, O., Timmer, A. M., and Mercola, M. (2007). Multiple functions of Cerberus cooperate to induce heart downstream of Nodal. Developmental biology 303, 57-65.

Fraidenraich, D., Stillwell, E., Romero, E., Wilkes, D., Manova, K., Basson, C. T., and Benezra, R. (2004). Rescue of cardiac defects in id knockout embryos by injection of embryonic stem cells. Science 306, 247-252.

Gadue, P., Huber, T. L., Paddison, P. J., and Keller, G. M. (2006). Wnt and TGF-beta signaling are required for the induction of an in vitro model of primitive streak formation using embryonic stem cells. Proc Natl Acad Sci USA 103, 16806-16811.

Galvin, K. E., Travis, E. D., Yee, D., Magnuson, T., and Vivian, J. L. (2010). Nodal signaling regulates the bone morphogenic protein pluripotency pathway in mouse embryonic stem cells. The Journal of biological chemistry 285, 19747-19756.

Hollnagel, A., Oehlmann, V., Heymer, J., Ruther, U., and Nordheim, A. (1999). Id genes are direct targets of bone morphogenetic protein induction in embryonic stem cells. The Journal of biological chemistry 274, 19838-19845.

Huang, P., He, Z., Ji, S., Sun, H., Xiang, D., Liu, C., Hu, Y., Wang, X., and Hui, L. (2011). Induction of functional hepatocyte-like cells from mouse fibroblasts by defined factors. Nature 475, 386-389.

Katagiri, T., Imada, M., Yanai, T., Suda, T., Takahashi, N., and Kamijo, R. (2002). Identification of a BMP-responsive element in Id1, the gene for inhibition of myogenesis. Genes to cells: devoted to molecular & cellular mechanisms 7, 949-960.

Kaltman, S. J., Huber, T. L., and Keller, G. M. (2006). Multipotent flk-1+ cardiovascular progenitor cells give rise to the cardiomyocyte, endothelial, and vascular smooth muscle lineages. Developmental cell 11, 723-732.

Kee, B. L. (2009). E and ID proteins branch out. Nature reviews Immunology 9, 175-184.

Kee, Y., and Bronner-Fraser, M. (2005). To proliferate or to die: role of Id3 in cell cycle progression and survival of neural crest progenitors. Genes & development 19, 744-755.

Kelly, R. G., Brown, N. A., and Buckingham, M. E. (2001). The arterial pole of the mouse heart forms from Fgf10-expressing cells in pharyngeal mesoderm. Developmental cell 1, 435-440.

Kelly, R. G., Buckingham, M. E., and Moorman, A. F. (2014). Heart fields and cardiac morphogenesis. Cold Spring Harb Perspect Med 4.

Korchynskyi, O., and ten Dijke, P. (2002). Identification and functional characterization of distinct critically important bone morphogenetic protein-specific response elements in the Id1 promoter. The Journal of biological chemistry 277, 4883-4891.

Laflamme, M. A., Chen, K. Y., Naumova, A. V., Muskheli, V., Fugate, J. A., Dupras, S. K., Reinecke, H., Xu, C., Hassanipour, M., Police, S., et al. (2007). Cardiomyocytes derived from human embryonic stem cells in pro-survival factors enhance function of infarcted rat hearts. Nature biotechnology 25, 1015-1024.

Lescroart, F., Chabab, S., Lin, X., Rulands, S., Paulissen, C., Rodolosse, A., Auer, H., Achouri, Y., Dubois, C., Bondue, A., et al. (2014). Early lineage restriction in temporally distinct populations of Mesp1 progenitors during mammalian heart development. Nature cell biology 16, 829-840.

Lian, X., Zhang, J., Azarin, S. M., Zhu, K., Hazeltine, L. B., Bao, X., Hsiao, C., Kamp, T. J., and Palecek, S. P. (2013). Directed cardiomyocyte differentiation from human pluripotent stem cells by modulating Wnt/beta-catenin signaling under fully defined conditions. Nature protocols 8, 162-175.

Lopez-Rovira, T., Chalaux, E., Massague, J., Rosa, J. L., and Ventura, F. (2002). Direct binding of Smad1 and Smad4 to two distinct motifs mediates bone morphogenetic protein-specific transcriptional activation of Id1 gene. The Journal of biological chemistry 277, 3176-3185.

Lyden, D., Young, A. Z., Zagzag, D., Yan, W., Gerald, W., O'Reilly, R., Bader, B. L., Hynes, R. O., Zhuang, Y., Manova, K., et al. (1999). Id1 and Id3 are required for neurogenesis, angiogenesis and vascularization of tumour xenografts. Nature 401, 670-677.

Marvin, M. J., Di Rocco, G., Gardiner, A., Bush, S. M., and Lassar, A. B. (2001). Inhibition of Wnt activity induces heart formation from posterior mesoderm. Genes & development 15, 316-327.

McKeithan, W. L., Colas, A. R., Bushway, P. J., Ray, S., and Mercola, M. (2012). Serum-free generation of multipotent mesoderm (Kdr+) progenitor cells in mouse embryonic stem cells for functional genomics screening. Current protocols in stem cell biology Chapter 1, Unit IF 13.

Meilhac, S. M., Esner, M., Kelly, R. G., Nicolas, J. F., and Buckingham, M. E. (2004). The clonal origin of myocardial cells in different regions of the embryonic mouse heart. Developmental cell 6, 685-698.

Meilhac, S. M., Lescroart, F., Blanpain, C., and Buckingham, M. E. (2015). Cardiac cell lineages that form the heart. Cold Spring Harb Perspect Med 5, a026344.

Menasche, P., Vanneaux, V., Fabreguettes, J. R., Bel, A., Tosca, L., Garcia, S., Bellamy, V., Farouz, Y., Pouly, J., Damour, O., et al. (2015). Towards a clinical use of human embryonic stem cell-derived cardiac progenitors: a translational experience. Eur Heart J 36, 743-750.

Mercola, M., Colas, A., and Willems, E. (2013). Induced pluripotent stem cells in cardiovascular drug discovery. Circulation research 112, 534-548.

Miller, E. W., Lin, J. Y., Frady, E. P., Steinbach, P. A., Kristan, W. B., Jr., and Tsien, R. Y. (2012). Optically monitoring voltage in neurons by photo-induced electron transfer through molecular wires. Proceedings of the National Academy of Sciences of the United States of America 109, 2114-2119.

Moretti, A., Laugwitz, K. L., Dorn, T., Sinnecker, D., and Mummery, C. (2013). Pluripotent stem cell models of human heart disease. Cold Spring Harb Perspect Med 3.

Nieuwkoop, P. D. (1967). The "organization centre". 3. Segregation and pattern formation in morphogenetic fields. Acta Biotheor 17, 178-194.

Niola, F., Zhao, X., Singh, D., Castano, A., Sullivan, R., Lauria, M., Nam, H. S., Zhuang, Y., Benezra, R., Di Bernardo, D., et al. (2012). Id proteins synchronize stemness and anchorage to the niche of neural stem cells. Nature cell biology 14, 477-487.

Niola, F., Zhao, X., Singh, D., Sullivan, R., Castano, A., Verrico, A., Zoppoli, P., Friedmann-Morvinski, D., Sulman, E., Barrett, L., et al. (2013). Mesenchymal high-grade glioma is maintained by the ID-RAP1 axis. The Journal of clinical investigation 123, 405-417.

Olson, E. N. (2006). Gene regulatory networks in the evolution and development of the heart. Science 313, 1922-1927.

Paige, S. L., Thomas, S., Stoick-Cooper, C. L., Wang, H., Maves, L., Sandstrom, R., Pabon, L., Reinecke, H., Pratt, G., Keller, G., et al. (2012). A temporal chromatin signature in human embryonic stem cells identifies regulators of cardiac development. Cell 151, 221-232.

Pandur, P., Lasche, M., Eisenberg, L. M., and Kuhl, M. (2002). Wnt-11 activation of a non-canonical Wnt signalling pathway is required for cardiogenesis. Nature 418, 636-641.

Peng, H. B. (1991). *Xenopus laevis*: Practical uses in cell and molecular biology. Solutions and protocols. Methods Cell Biol 36, 657-662.

Raffin, M., Leong, L. M., Rones, M. S., Sparrow, D., Mohun, T., and Mercola, M. (2000). Subdivision of the cardiac Nkx2.5 expression domain into myogenic and nonmyogenic compartments. Developmental biology 218, 326-340.

Roschger, C., and Cabrele, C. (2017). The Id-protein family in developmental and cancer-associated pathways. Cell Commun Signal 15, 7.

Saga, Y., Hata, N., Kobayashi, S., Magnuson, T., Seldin, M. F., and Taketo, M. M. (1996). MesP1: a novel basic helix-loop-helix protein expressed in the nascent mesodermal cells during mouse gastrulation. Development 122, 2769-2778.

Saga, Y., Kitajima, S., and Miyagawa-Tomita, S. (2000). Mesp1 expression is the earliest sign of cardiovascular development. Trends in cardiovascular medicine 10, 345-352.

Schneider, V. A., and Mercola, M. (2001). Wnt antagonism initiates cardiogenesis in *Xenopus laevis*. Genes & development 15, 304-315.

Schultheiss, T. M., Burch, J. B., and Lassar, A. B. (1997). A role for bone morphogenetic proteins in the induction of cardiac myogenesis. Genes & development 11, 451-462.

Sekiya, S., and Suzuki, A. (2011). Direct conversion of mouse fibroblasts to hepatocyte-like cells by defined factors. Nature 475, 390-393.

Stainier, D. Y. (2002). A glimpse into the molecular entrails of endoderm formation. Genes & development 16, 893-907.

Viotti, M., Nowotschin, S., and Hadjantonakis, A. K. (2014). SOX17 links gut endoderm morphogenesis and germ layer segregation. Nature cell biology 16, 1146-1156.

Wilkinson, D. G., and Nieto, M. A. (1993). Detection of messenger RNA by in situ hybridization to tissue sections and whole mounts. Methods in enzymology 225, 361-373.

Yang, J., Li, X., and Morrell, N. W. (2014). Id proteins in the vasculature: from molecular biology to cardiopulmonary medicine. Cardiovascular research 104, 388-398.

Yang, L., Soonpaa, M. H., Adler, E. D., Roepke, T. K., Kattman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.

Yoshida, T., Vivatbutsiri, P., Morriss-Kay, G., Saga, Y., and Iseki, S. (2008). Cell lineage in mammalian craniofacial mesenchyme. Mech Dev 125, 797-808.

Zhao, R., Watt, A. J., Battle, M. A., Li, J., Bondow, B. J., and Duncan, S. A. (2008). Loss of both GATA4 and GATA6 blocks cardiac myocyte differentiation and results in acardia in mice. Developmental biology 317, 614-619.

---

What is claimed is:

1. A method of generating a multipotent cardiovascular progenitor cell, the method comprising:
   (i) overexpressing one or more proteins selected from the group consisting of Id1 (Inhibitor of DNA binding 1, HLH protein), Id2 (Inhibitor of DNA Binding 2, HLH Protein), Id3 (Inhibitor of DNA Binding 3, HLH Protein), Id4 (Inhibitor of DNA Binding 4, HLH Protein), Evx1 (Even-Skipped Homeobox 1), and Grrp1 (glycine/arginine rich protein 1) in a stem cell, thereby generating a multipotent cardiovascular progenitor cell; or
   (ii) inhibiting the expression or activity of one or both of Foxa2 (Forkhead Box A2) and Tcf3 (Transcription Factor 3) in a stem cell, thereby generating a multipotent cardiovascular progenitor cell.

2. The method of claim 1, further comprising transfecting the stem cell with a nucleic acid comprising a sequence encoding one or more proteins selected from the group consisting of Id1, Id2, Id3, Id4, Evx1, and Grrp1.

3. The method of claim 1, wherein the method further comprises overexpressing Mesp1 (Mesoderm posterior protein 1).

4. The method of claim 1, wherein the method comprises inhibiting Tcf3.

5. The method of claim 1, wherein the method comprises inhibiting Foxa2.

6. The method of claim 1, wherein the method comprises contacting the stem cell with siTcf3.

7. The method of claim 1, wherein the method comprises contacting the stem cell with siFoxa2.

* * * * *